(12) United States Patent
Kim et al.

(10) Patent No.: US 11,877,508 B2
(45) Date of Patent: Jan. 16, 2024

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicants: DUK SAN NEOLUX CO., LTD., Cheonan-si (KR); SAMSUNG DISPLAY CO., LTD., Yongin-si (KR)

(72) Inventors: Ki Won Kim, Cheonan-si (KR); Kyung Hwan Oh, Cheonan-si (KR); Bu Yong Yun, Cheonan-si (KR); Hyung Dong Lee, Cheonan-si (KR); Jin Woo Shin, Cheonan-si (KR); Soung Yun Mun, Cheonan-si (KR); Jae Duk Yoo, Cheonan-si (KR); Jung Geun Lee, Cheonan-si (KR); Joon Gu Lee, Yongin-si (KR); Yeon Hwa Lee, Yongin-si (KR); Mi Kyung Kim, Yongin-si (KR); Ji Hyun Seo, Yongin-si (KR); Kwan Hee Lee, Yongin-si (KR)

(73) Assignees: DUK SAN NEOLUX CO., LTD., Cheonan-si (KR); SAMSUNG DISPLAY CO., LTD., Yongin-si (KR)

( * ) Notice: Subject to any disclaimer, the term of this patent is extended or adjusted under 35 U.S.C. 154(b) by 0 days.

(21) Appl. No.: 18/169,541

(22) Filed: Feb. 15, 2023

(65) Prior Publication Data
US 2023/0200214 A1    Jun. 22, 2023

Related U.S. Application Data

(62) Division of application No. 17/995,065, filed as application No. PCT/KR2022/009054 on Jun. 24, 2022.

(30) Foreign Application Priority Data

Jul. 5, 2021  (KR) .................. 10-2021-0088124
Jul. 21, 2021 (KR) .................. 10-2021-0095913
(Continued)

(51) Int. Cl.
  *H01L 51/50*   (2006.01)
  *H10K 85/60*   (2023.01)
  (Continued)

(52) U.S. Cl.
  CPC ........... *H10K 85/622* (2023.02); *C07C 22/08* (2013.01); *C07C 43/29* (2013.01); *C07C 211/56* (2013.01);
  (Continued)

(58) Field of Classification Search
  CPC ........ H10K 85/622; C07C 22/08; C07C 43/29
  See application file for complete search history.

(56) References Cited

U.S. PATENT DOCUMENTS

2002/0103385 A1   8/2002   Yoon et al.
2008/0154036 A1   6/2008   Terada et al.
(Continued)

FOREIGN PATENT DOCUMENTS

CN   105985364 A   10/2016
CN   109942361 A   6/2019
(Continued)

OTHER PUBLICATIONS

Alameddine et al., "Synthesis of Perfluoroalkylated Bulky Triarylamines", Synthesis, 2007, vol. 2, pp. 271-276.
(Continued)

*Primary Examiner* — Anthony Ho
(74) *Attorney, Agent, or Firm* — Vorys, Sater, Seymour and Pease LLP; Mih Suhn Koh

(57) ABSTRACT

Provided are a fluorinated compound for patterning a metal or an electrode (cathode), an organic electronic element
(Continued)

using the same, and an electronic device thereof, wherein a fine pattern of the electrode is formed by using the fluorinated compound as a material for patterning a metal or an electrode (cathode), without using a shadow mask, and it is possible to more easily apply UDC since it is easy to manufacture a transparent display having high light transmittance.

12 Claims, 15 Drawing Sheets

(30) Foreign Application Priority Data

Feb. 22, 2022 (KR) ............ 10-2022-0022719
Feb. 22, 2022 (KR) ............ 10-2022-0022998

(51) Int. Cl.

| | |
|---|---|
| C09K 11/06 | (2006.01) |
| C07D 213/26 | (2006.01) |
| C07D 251/24 | (2006.01) |
| C07C 211/56 | (2006.01) |
| C07D 333/76 | (2006.01) |
| C07D 307/77 | (2006.01) |
| C07C 43/29 | (2006.01) |
| C07C 323/09 | (2006.01) |
| C07F 7/08 | (2006.01) |
| H10K 85/40 | (2023.01) |
| C07D 209/86 | (2006.01) |
| C07D 307/91 | (2006.01) |
| C07D 311/96 | (2006.01) |
| C07D 487/04 | (2006.01) |
| H10K 50/816 | (2023.01) |
| C07C 22/08 | (2006.01) |

(52) U.S. Cl.
CPC .......... *C07C 323/09* (2013.01); *C07D 209/86* (2013.01); *C07D 213/26* (2013.01); *C07D 251/24* (2013.01); *C07D 307/77* (2013.01); *C07D 307/91* (2013.01); *C07D 311/96* (2013.01); *C07D 333/76* (2013.01); *C07D 487/04* (2013.01); *C07F 7/081* (2013.01); *C07F 7/0816* (2013.01); *C09K 11/06* (2013.01); *H10K 50/816* (2023.02); *H10K 85/40* (2023.02); *H10K 85/60* (2023.02); *H10K 85/615* (2023.02); *H10K 85/631* (2023.02); *H10K 85/636* (2023.02); *H10K 85/654* (2023.02); *H10K 85/6572* (2023.02); *H10K 85/6574* (2023.02); *H10K 85/6576* (2023.02); *C07C 2603/18* (2017.05); *C07C 2603/24* (2017.05); *C07C 2603/42* (2017.05); *C09K 2211/1007* (2013.01); *C09K 2211/1011* (2013.01); *C09K 2211/1014* (2013.01)

(56) References Cited

U.S. PATENT DOCUMENTS

| | | |
|---|---|---|
| 2014/0221655 A1 | 8/2014 | Strauss et al. |
| 2015/0166561 A1 | 6/2015 | Kitamura et al. |
| 2015/0221876 A1 | 8/2015 | Kitamura et al. |
| 2020/0062778 A1 | 2/2020 | Cui et al. |

FOREIGN PATENT DOCUMENTS

| | | |
|---|---|---|
| CN | 111377977 A | 7/2020 |
| CN | 112135808 A | 12/2020 |
| JP | 2011-153276 A | 8/2011 |
| JP | 2014-82247 A | 5/2014 |
| KR | 10-2007-0068092 A | 6/2007 |
| KR | 10-2012-0095927 A | 8/2012 |
| KR | 10-2020-0125941 A | 11/2020 |
| WO | 2011/050048 A2 | 4/2011 |
| WO | 2021/036683 A1 | 3/2021 |

OTHER PUBLICATIONS

The International Search Report for PCT/KR2022/009054, dated Nov. 29, 2022, 9 pages including translation.
The Notice of Allowance issued for corresponding KR Patent Application No. 10-2022-0022998, dated Jun. 13, 2022, 5 pages including translation.
The Notice of Result of Preliminary Examination issued for corresponding KR Patent Application No. 10-2022-0022998, dated Apr. 14, 2022, 10 pages including translation.
Pommerehne et al., "Electron Tunneling in Organic Bilayer Light-Emitting Diodes with a Novel Electron-Transporting Polymer", Macromolecules, 1997, vol. 30, pp. 8270-8277.
Stapff et al., "Preliminary communication—Multilayer light emitting diodes based on columnar discotics", Liquid Crystals, 1997, vol. 23, No. 4, pp. 613-617.
Schnitte et al., "Uniform shape monodisperse single chain nanocrystals by living aqueous catalytic polymerization", Nature Communications, (2019) 10:2592, 6 pages.
Garcia-Lopez et al., "Use of 2-Bromophenylboronic Esters as Benzyne Precursors in the Pd-Catalyzed Synthesis of Triphenylenes,", Org. Lett., 2014, 16, 2338-2341.
Hu et al., "Two-in-One Strategy for the Pd(II)-Catalyzed Tandem C—H Arylation/Decarboxylative Annulation Involved with Cyclic Diaryliodonium Salts", Org. Lett., 2019, 7233-7237.
Kuvychko et al., "Taming Hot CF3 Radicals: Incrementally Tuned Families of Polyarene Electron Acceptors for Air-Stable Molecular Optoelectronics", Angew. Chem. Int. Ed., 2013, 52, 4871-4874.
Zhu et al., "Bottom-up Construction on π-Extended Arenes by a Palladium-Catalyzed Annulative Dimerization of o-Iodobiaryl Compunds", Angew. Chem. Int. Ed. 2018, 57, 8848-8853.

[FIG. 1]
100
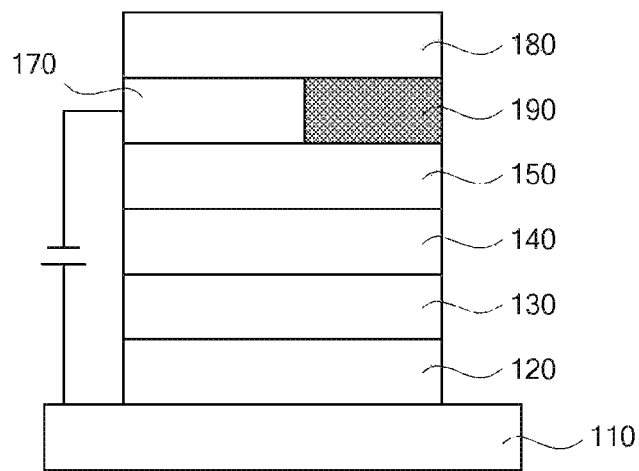
[FIG. 2]
200
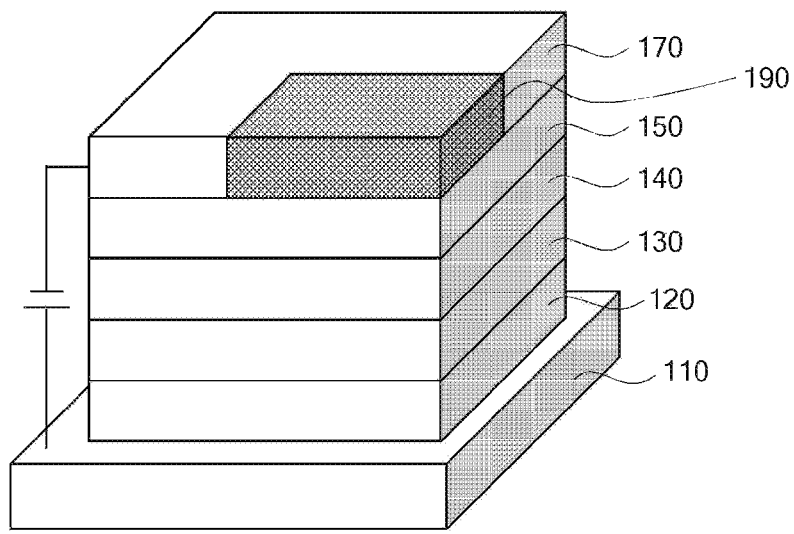

[FIG. 3]
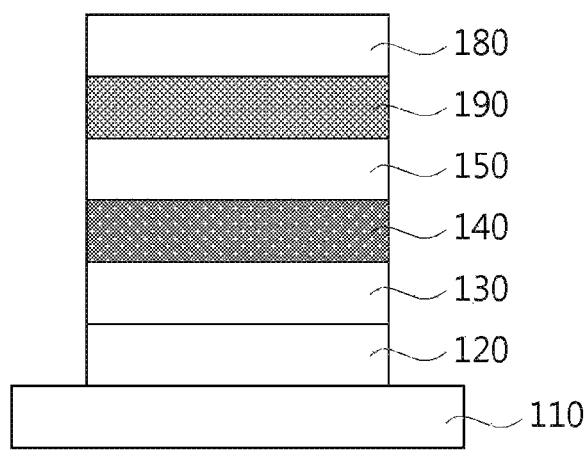
[FIG. 4a]
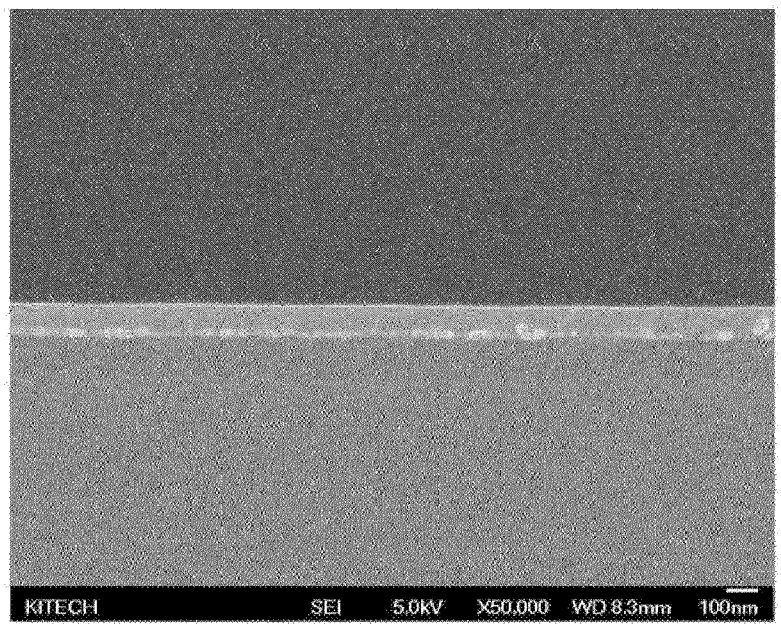

[FIG. 4b]
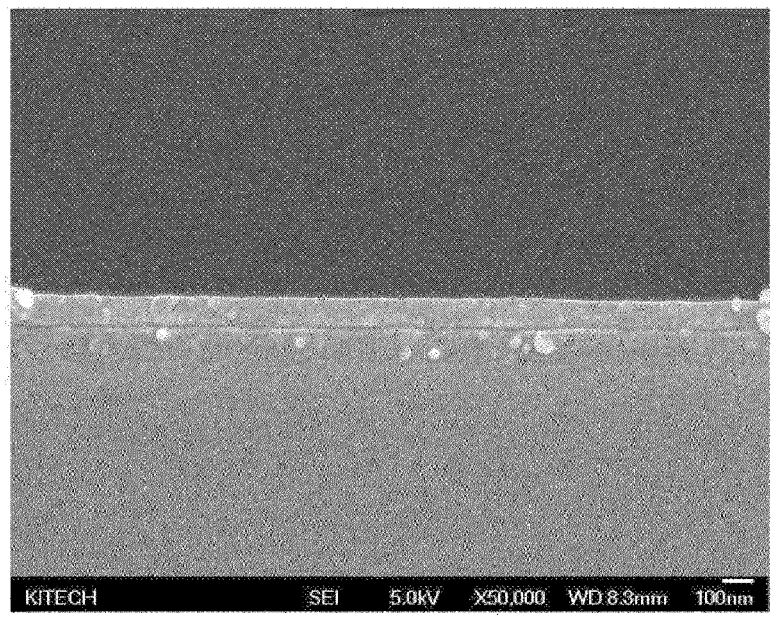
[FIG. 5a]
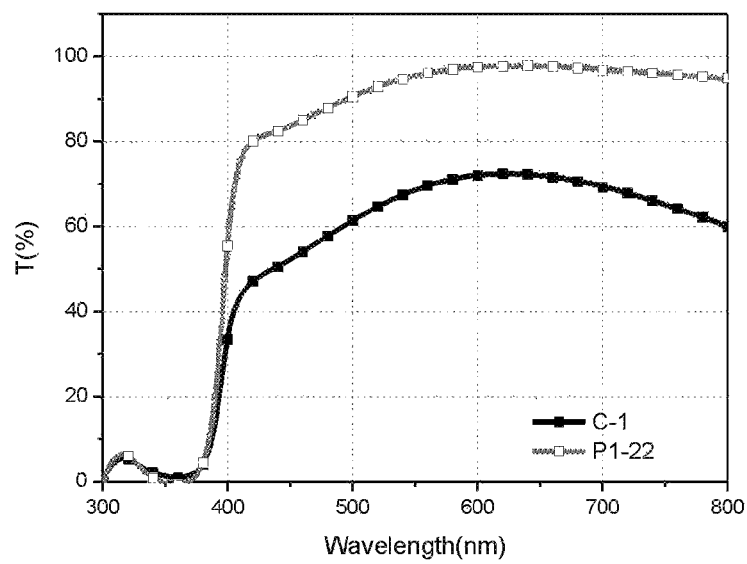

[FIG. 5b]
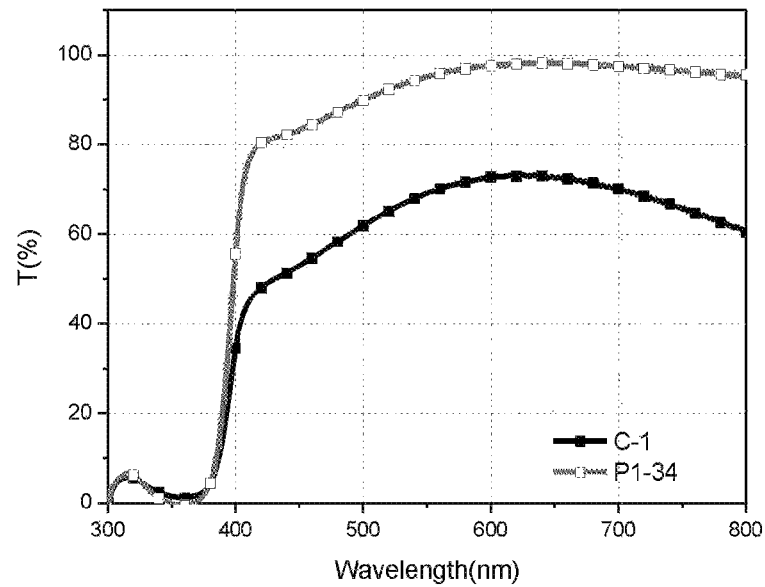
[FIG. 5c]
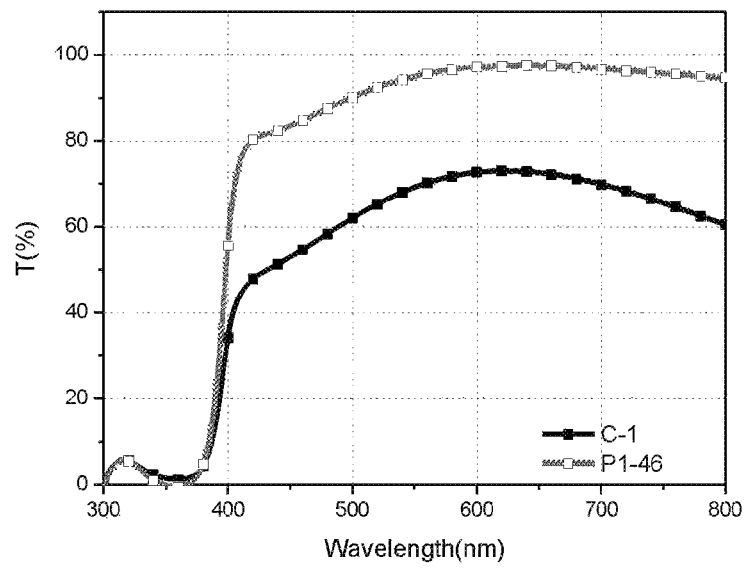

[FIG. 5d]
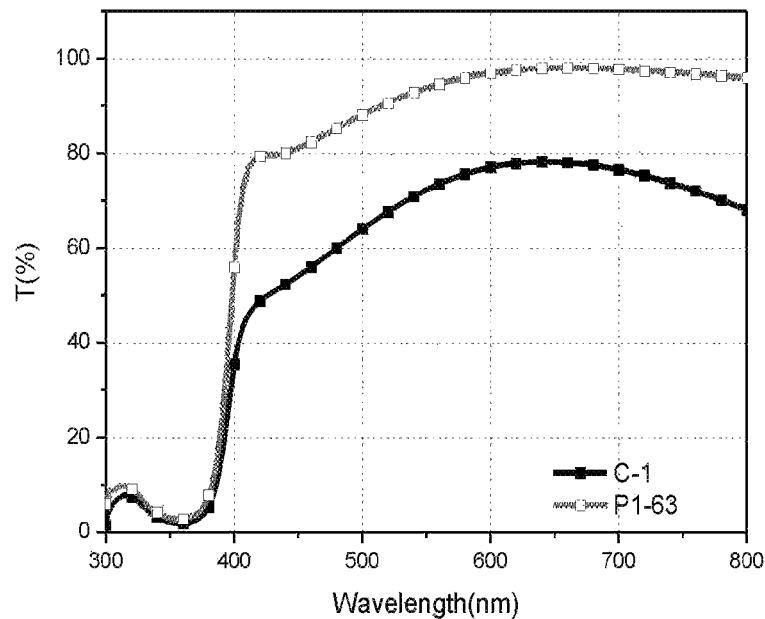
[FIG. 5e]
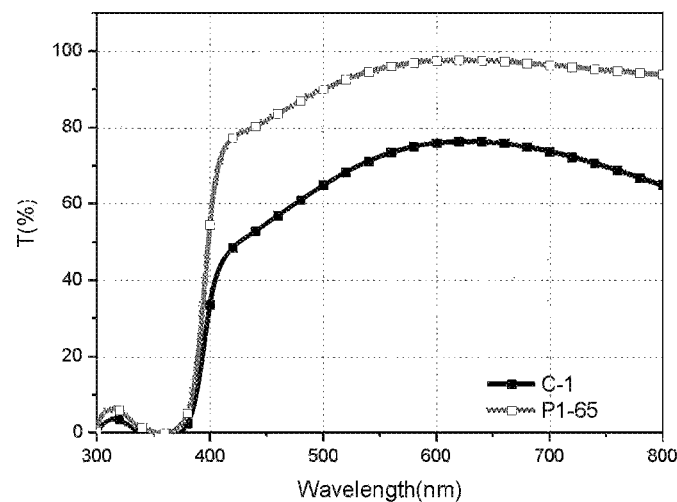

[FIG. 5f]
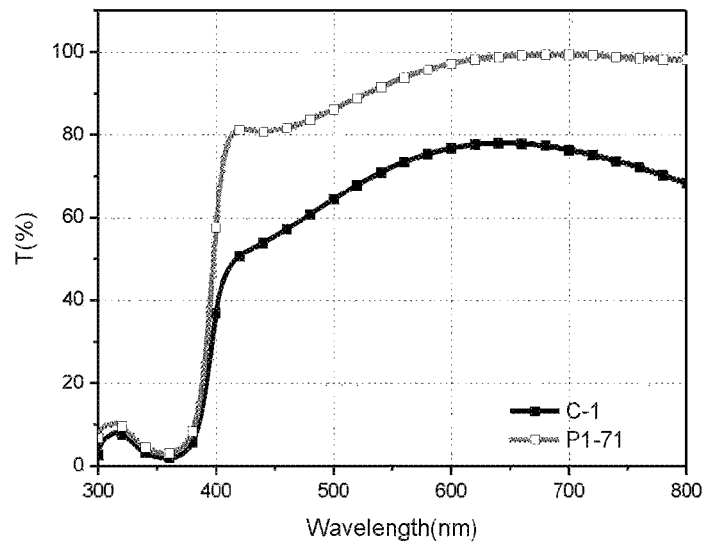
[FIG. 5g]
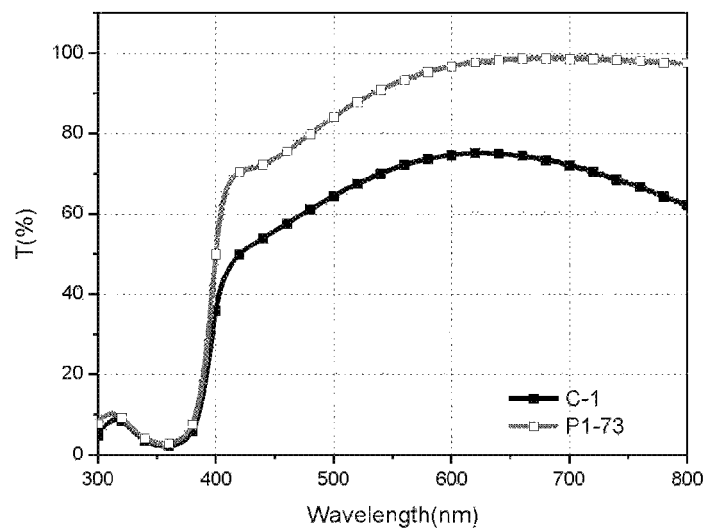

[FIG. 5h]
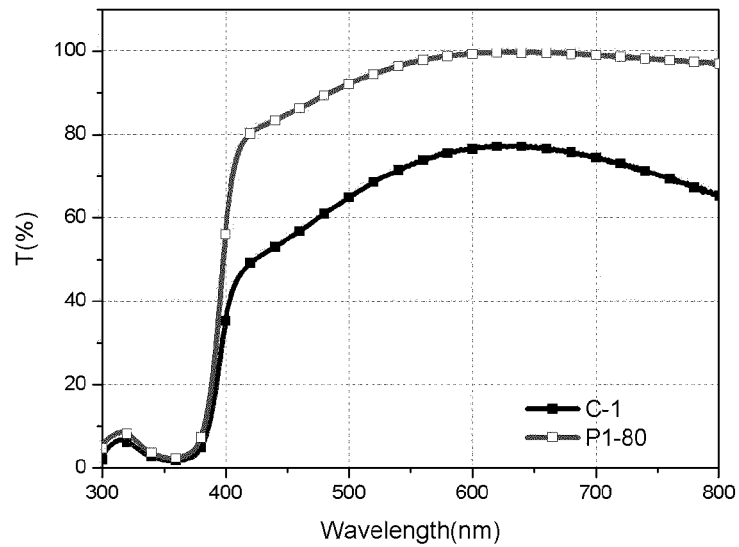
[FIG. 5i]
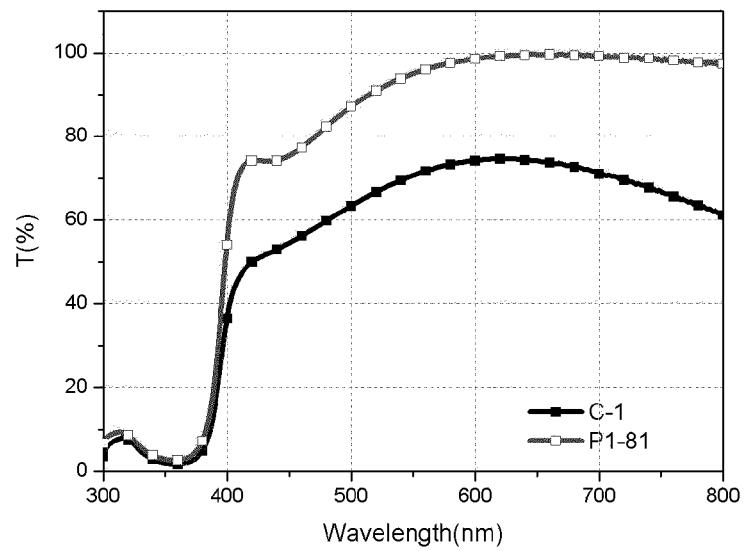

[FIG. 5j]
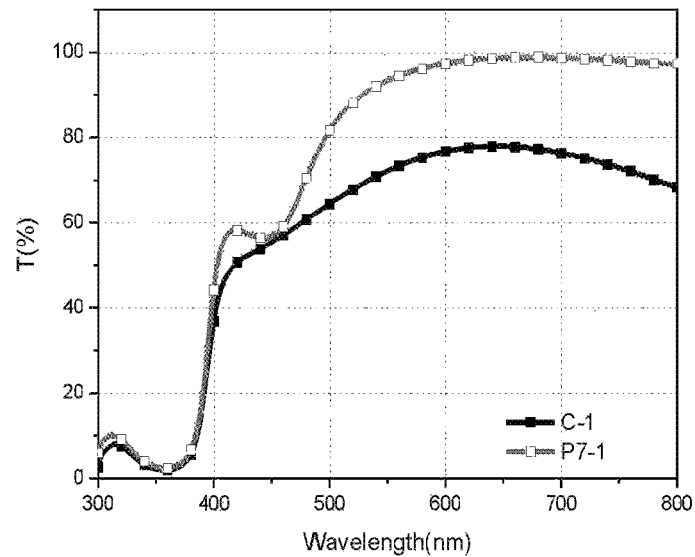
[FIG. 6a]
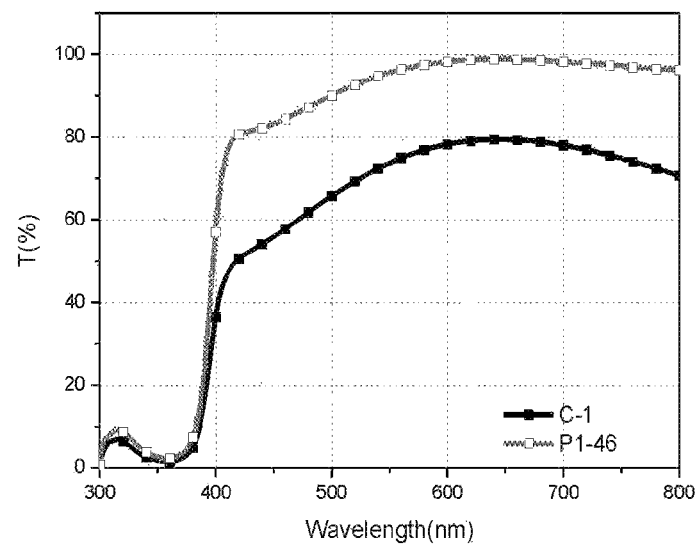

[FIG. 6b]
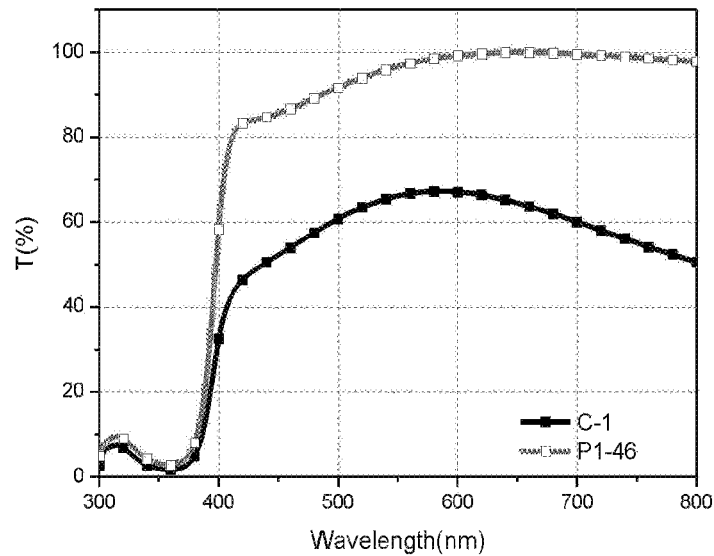
[FIG. 6c]
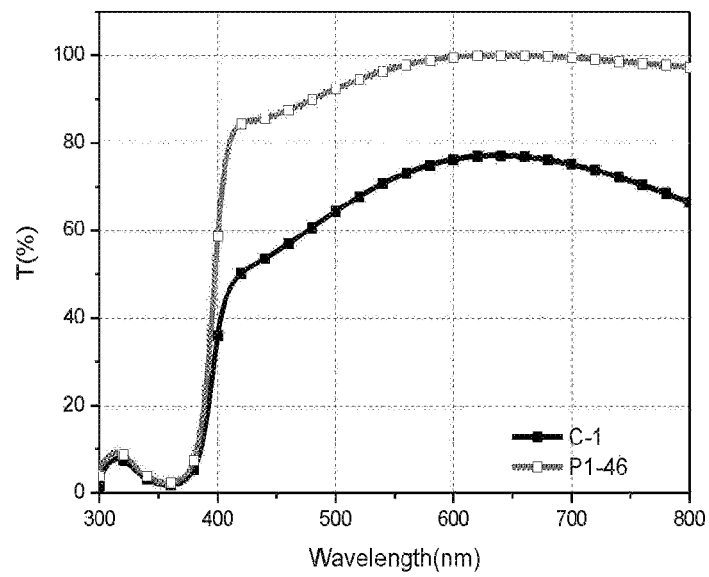

[FIG. 7a]
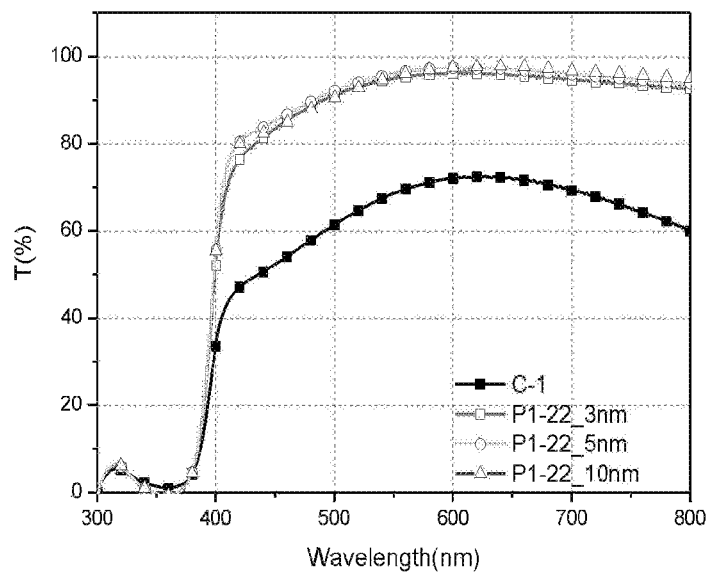
[FIG. 7b]
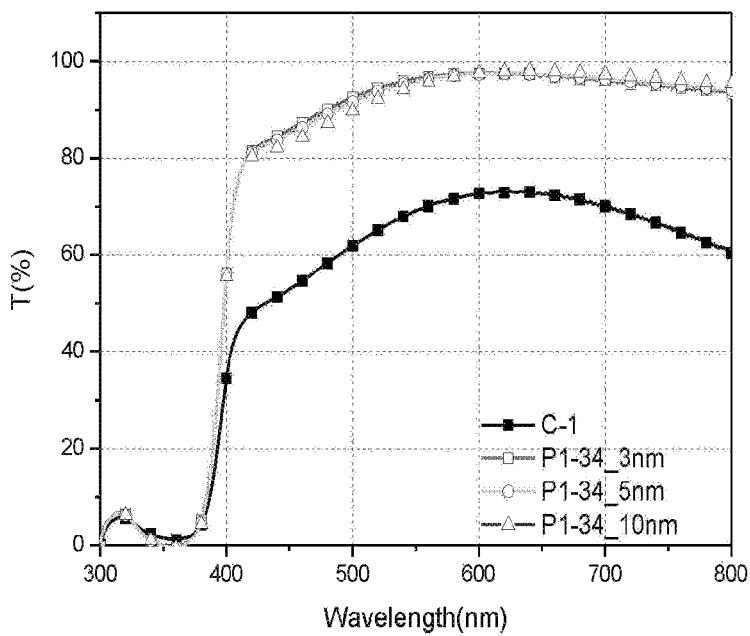

[FIG. 7c]
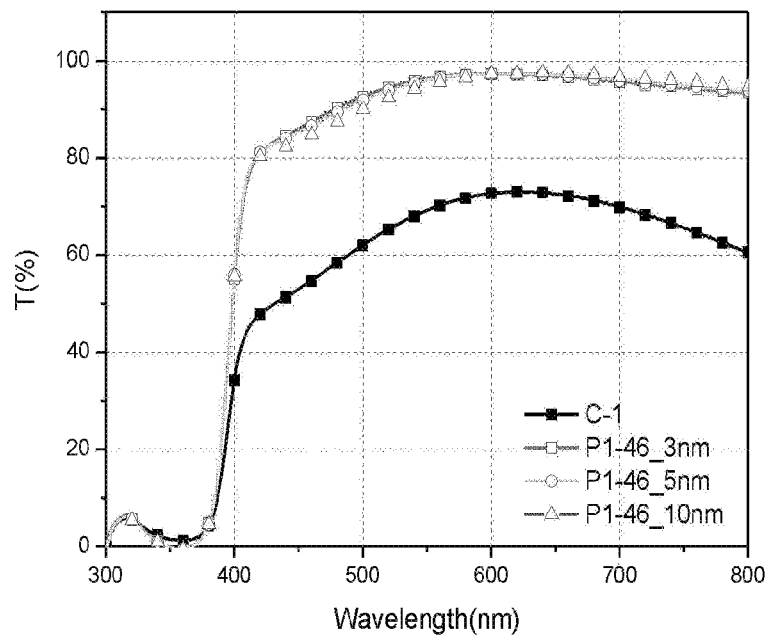
[FIG. 7d]
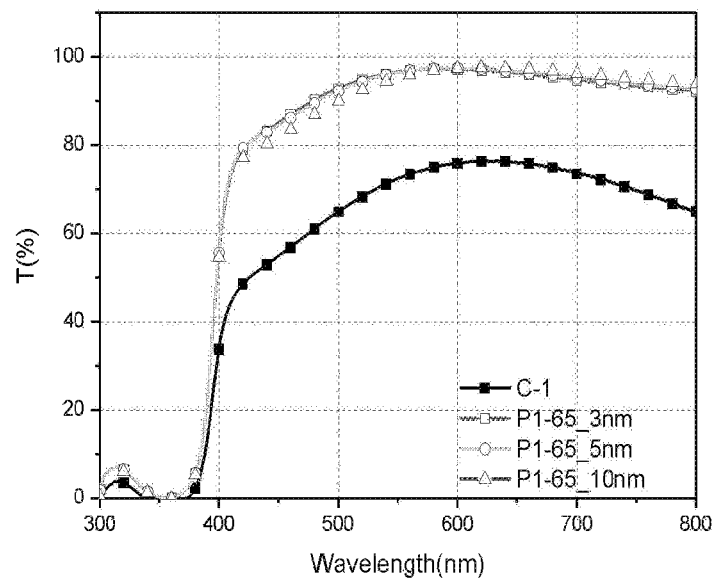

[FIG. 8a]
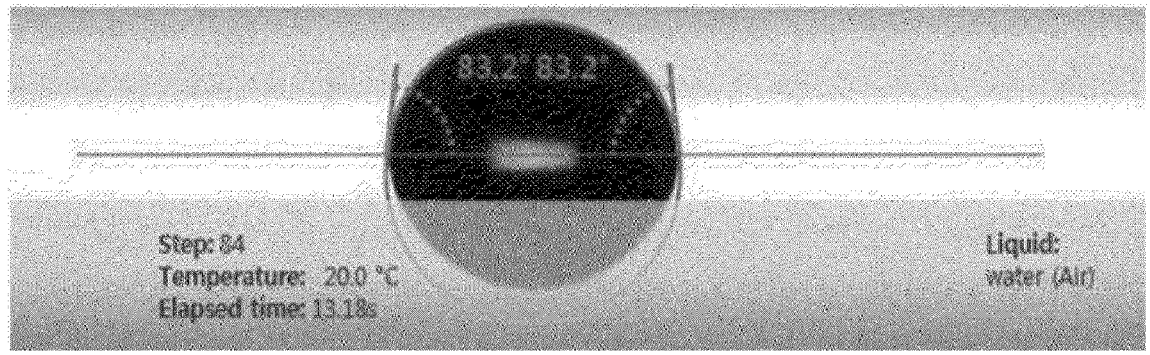
[FIG. 8b]
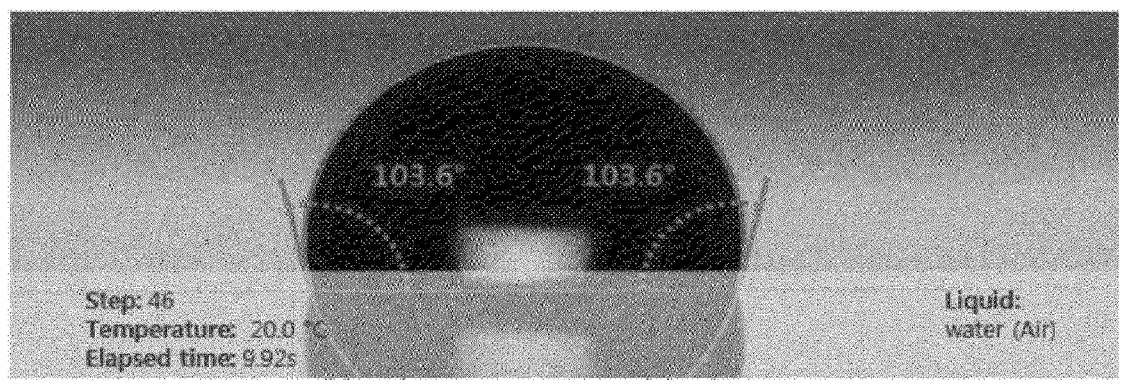
[FIG. 8c]
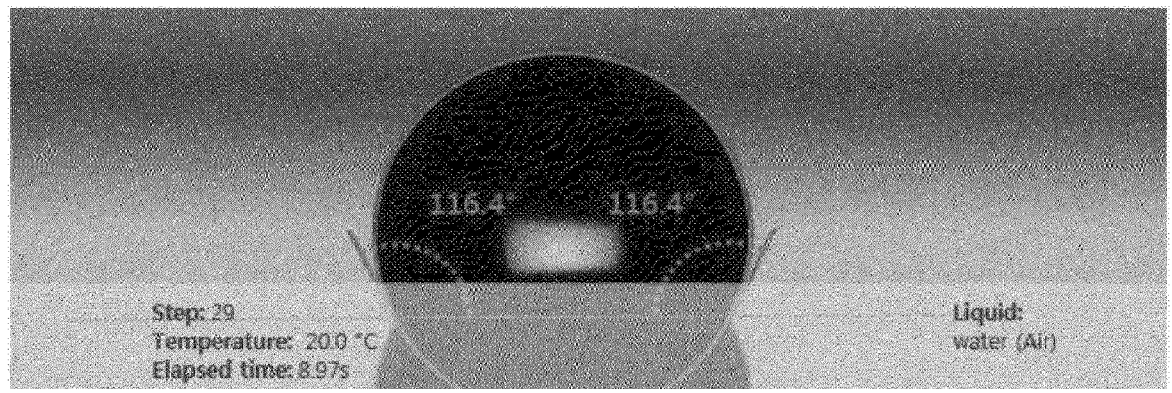

[FIG. 8d]
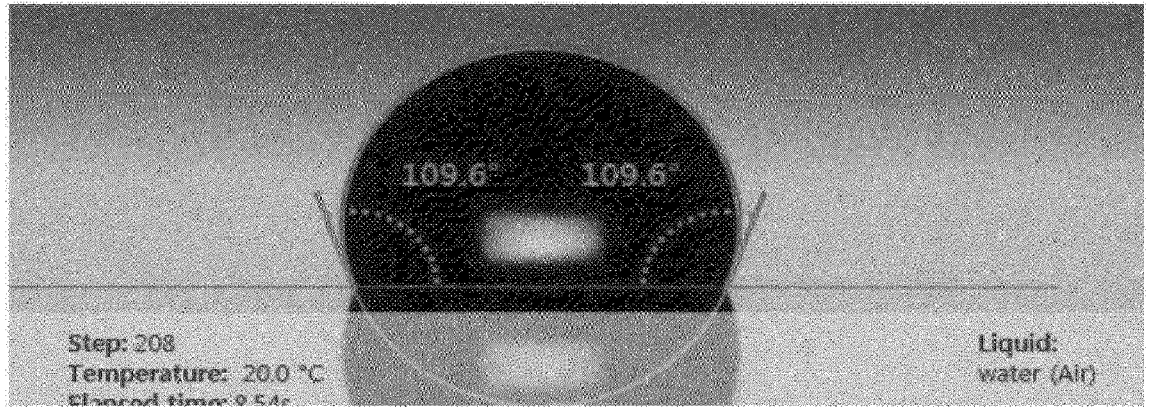
[FIG. 8e]
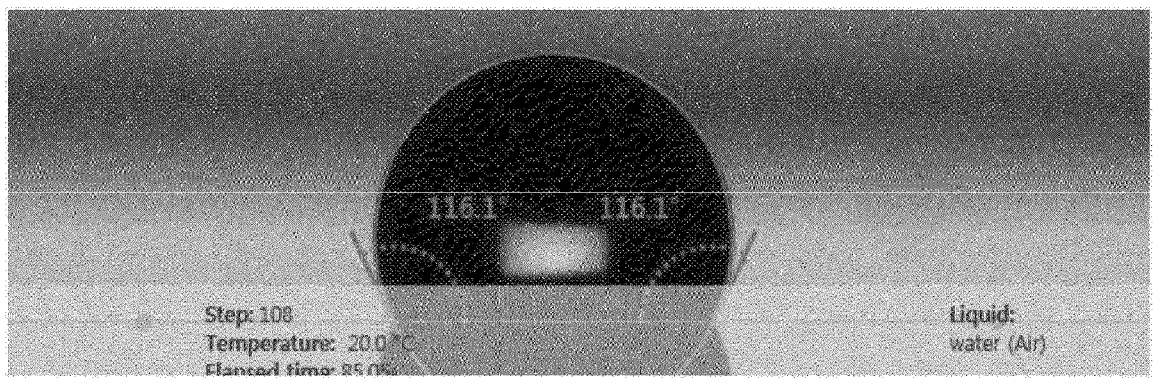
[FIG. 8f]
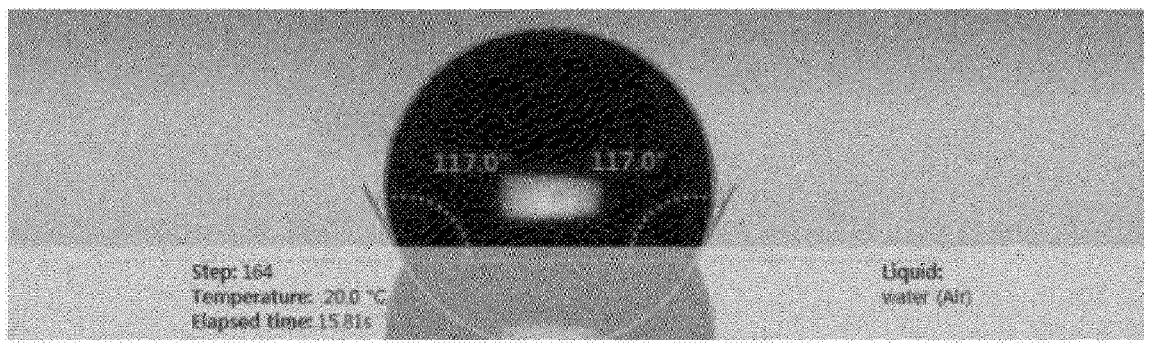

[FIG. 8g]
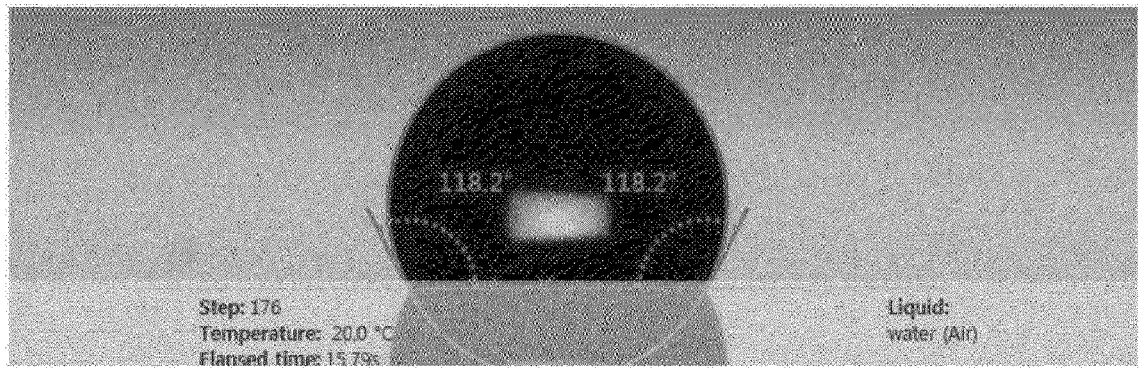
[FIG. 8h]
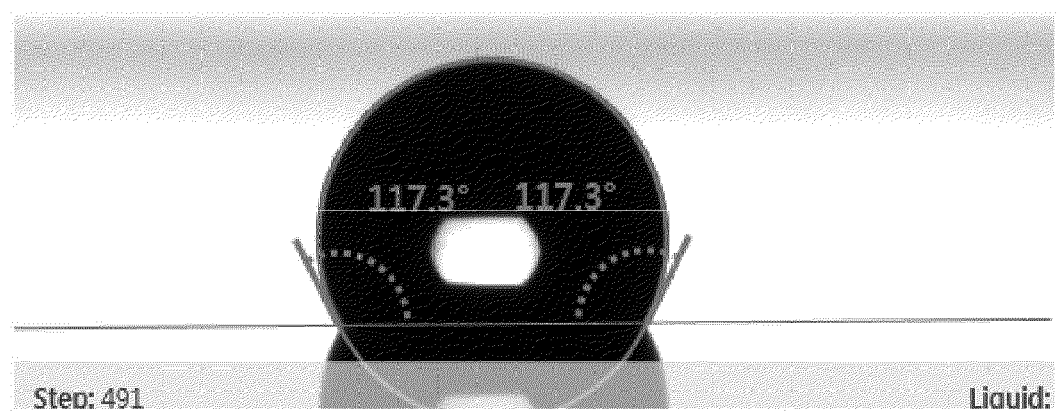
[FIG. 8i]
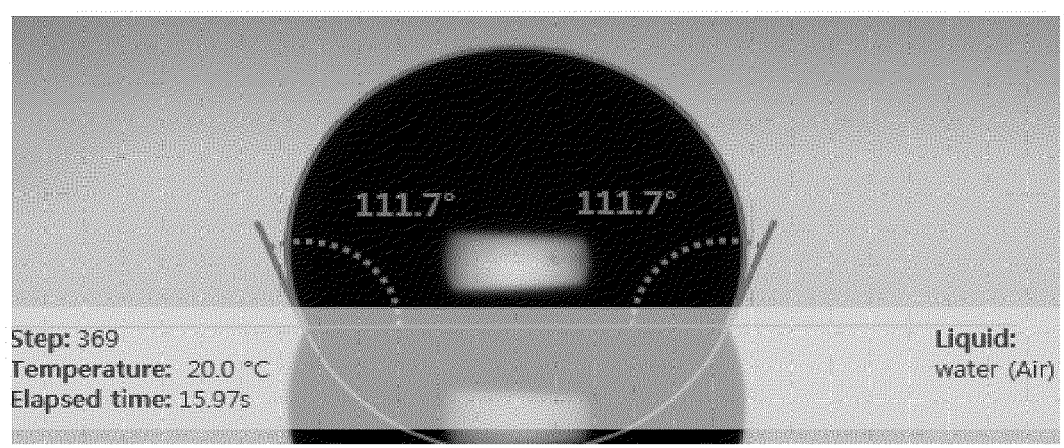

[FIG. 8j]
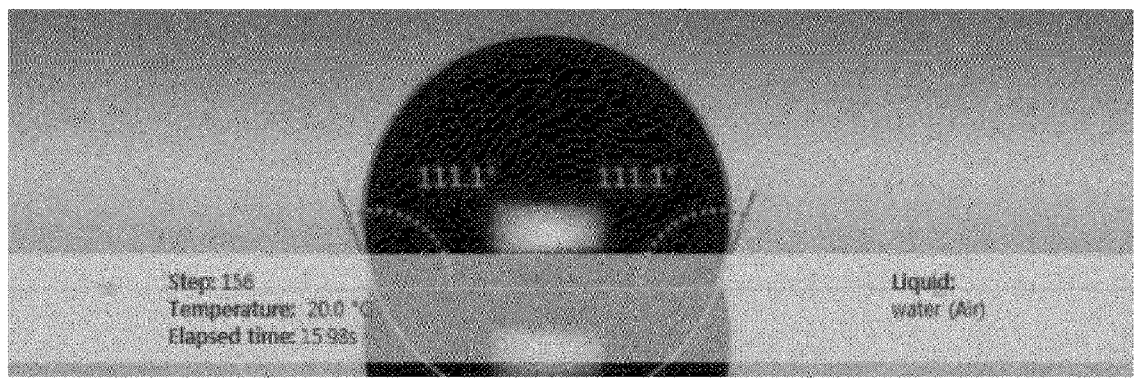

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE OF RELATED APPLICATIONS

This application is a divisional of U.S. patent application Ser. No. 17/995,065 filed on Sep. 29, 2022, which is a 371 of PCT/KR2022/009054 filed on Jun. 24, 2022, which claims the benefit of priority from Korean Patent Application Nos. 10-2021-0088124, 10-2021-0095913, 10-2022-0022719, and 10-2022-0022998 filed on Jul. 5, 2021, Jul. 21, 2021, Feb. 22, 2022, and Feb. 22, 2022, respectively, the contents of each of which are incorporated herein by reference in its entirety.

BACKGROUND

Technical Field

The present invention relates to a fluorinated compound for patterning a metal or an electrode (cathode), and a transparent display device using the same.

Background Art

With the continuous development of display technology, user demands for display devices are increasing, and terminal display devices (especially, smart phones) are required to develop in the direction of flexibility, full screen, and high integration.

In particular, in the case of smart phone displays, efforts have been made to make the screen as large as possible even for a smart phone of the same size according to the development of technology. As a result, the bezel size of the smartphone was developed to be as small as possible according to the increase in the screen size. In the process, the physical button on the front of the smartphone disappeared into the screen, and the location of the smartphone's camera is constantly changing in a way such as a notch, a hole, or a slide.

In recent years, the development of a Bezel-less Under Display is progressing rapidly, and for this reason, the development of transparent display technology is also rapidly progressing.

With the development of such display devices, recently, the implementation of next-generation smartphone display technologies such as UDC (Under Display Camera) and UPS (Under Panel Sensor) is receiving a lot of attention.

In particular, since the UDC camera can operate normally only when high transmittance of the display is guaranteed, precise patterning of the cathode is essential to increase transmittance.

In general, 2 methods are mainly used as electrode patterning methods. First, an electrode is patterned on a desired part using a shadow mask, or second, a pattern is made by irradiating a laser to the cathode.

However, in the method for patterning an electrode using the shadow mask, a bending phenomenon occurs during a high-temperature deposition process due to the typical material characteristics of the metal mask, which causes a problem in that the mask shape and the electrode pattern are distorted. Accordingly, since time and cost for maintaining the mask are inevitably required, it is not commercially suitable for mass production of the device.

Also, the method for patterning an electrode using the laser causes the inconvenience of determining the type and intensity of the laser so that the substrate is not damaged in the manner in which the electrode is patterned due to the inherent properties of the laser.

Meanwhile, organic fluorinated compound materials are being used for various purposes in organic electronic elements. For example, Japanese Patent Laid-Open No. 1992-206386, in the organic EL device having a laminated structure in which an emitting layer composed of a fluorescent organic solid is interposed between 2 electrodes facing each other, discloses compounds that serve as a sealant by depositing at least one polymer from the group consisting of a chlorotrifluoroethylene homopolymer, a dichlorofluoroethylene homopolymer, and a copolymer of chlorotrifluoroethylene and dichlorodifluoreneethylene to more fully prevent the penetration of moisture or oxygen into the emitting layer.

Also, Japanese Patent Laid-Open No. 2001-247498 and J. Am. Chem. Soc., 2000, Vol. 122, 1832. disclose that a fluorinated material has high chemical and thermal stability and can improve the transport of electrons, so it can be used as an electron transport layer of an organic EL device and exhibits a hole blocking function and it can be used as a hole blocking layer as well as a protective film, thereby improving the lifespan of the device.

Korean Patent Publication No. KR2000-0000628 also discloses that a florinated material can be used as a material for the emitting layer in addition to the electron transport layer, and Korean Patent Application Laid-Open No. 2000-0000628 discloses a green light-emitting polymer with improved electroluminescence efficiency by introducing a fluorinated aryl with strong electron affinity, that is, a pentafluoro aryl or an octafluorobiphenyl group into poly (p-phenylenevinylene) to induce balanced electron and hole meetings. Korean Patent Application Laid-Open No. 2005-0115069 discloses a light-emitting compound including a fluorinated branch having an AIEE (Aggregation Induced Enhanced Emission) characteristic, which is particularly excellent in luminous efficiency in a solid state. Korean Patent No. 10-0846597 discloses an organic light emitting device comprising a first electrode; hole transport layer; emitting layer; a second electrode; wherein an aromatic fluorocarbon compound of $C_{6y}F_{6y-2n}$ substituted with fluorine is between the first electrode and the hole transport layer, and further comprising the same between the emitting layer and the second electrode. This discloses providing an organic light emitting device of low power consumption by strengthening the driving voltage by inserting a thin film containing a fluorinated compound at the interface between the first electrode (anode) and the hole injection (hole transport layer) in order to control the interface of the organic light emitting device with an aromatic fluorinated carbon compound.

DETAILED DESCRIPTION OF THE INVENTION

Summary

An object of the present invention is to provide a fluorinated material for patterning a metal or an electrode (cathodes) that can reduce time and cost required for a patterning method while forming a precise electrode pattern in a display device.

Technical Solution

The present invention provides a fluorinated compound represented by Formula (1), a composition for patterning metals comprising the same, and an organic electronic element including the same.

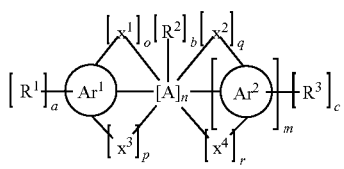

Formula (1)

Effects of the Invention

In the present invention, by using the compound represented by Formula (1) as a material for patterning a metal or an electrode (cathode), it is possible to form a fine pattern of the electrode without the use of a shadow mask, and easy to manufacture a transparent display having a high light transmittance, thereby making it easier to apply UDC.

BRIEF DESCRIPTION OF THE DRAWINGS

FIG. 1 to FIG. 3 are exemplary views of a display stacked structure including a fluorine compound.

FIG. 4*a* is an SEM cross-sectional view of Comparative Example 1.

FIG. 4*b* is an SEM cross-sectional view of Comparative Example 3.

FIG. 5*a* is a graph of light transmittance measurement results of Comparative Example 1 and Example 1.

FIG. 5*b* is a graph of light transmittance measurement results of Comparative Example 1 and Example 2.

FIG. 5*c* is a graph of light transmittance measurement results of Comparative Example 1 and Example 3.

FIG. 5*d* is a graph of light transmittance measurement results of Comparative Example 1 and Example 4.

FIG. 5*e* is a graph of light transmittance measurement results of Comparative Example 1 and Example 5.

FIG. 5*f* is a graph of light transmittance measurement results of Comparative Example 1 and Example 6.

FIG. 5*g* is a graph of light transmittance measurement results of Comparative Example 1 and Example 7.

FIG. 5*h* is a graph of light transmittance measurement results of Comparative Example 1 and Example 8.

FIG. 5*i* is a graph of light transmittance measurement results of Comparative Example 1 and Example 9.

FIG. 5*j* is a graph of light transmittance measurement results of Comparative Example 1 and Example 10.

FIG. 6*a* is a graph of light transmittance measurement results of Comparative Example 3 and Example 11.

FIG. 6*b* is a graph of light transmittance measurement results of Comparative Example 4 and Example 12.

FIG. 6*c* is a graph of light transmittance measurement results of Comparative Example 5 and Example 13.

FIG. 7*a* is a graph of light transmittance measurement results of Comparative Example 6 and Examples 14~16.

FIG. 7*b* is a graph of light transmittance measurement results of Comparative Example 6 and Examples 17~19.

FIG. 7*c* is a graph of light transmittance measurement results of Comparative Example 6 and Examples 20~22.

FIG. 7*d* is a graph of light transmittance measurement results of Comparative Example 6 and Examples 23~25.

FIG. 8*a* shows a contact angle measurement result of Comparative Example 7.

FIG. 8*b* shows a contact angle measurement result of Comparative Example 26.

FIG. 8*c* shows a contact angle measurement result of Comparative Example 27.

FIG. 8*d* shows a contact angle measurement result of Comparative Example 28.

FIG. 8*e* shows a contact angle measurement result of Comparative Example 29.

FIG. 8*f* shows a contact angle measurement result of Comparative Example 30.

FIG. 8*g* shows a contact angle measurement result of Comparative Example 31.

FIG. 8*h* shows a contact angle measurement result of Comparative Example 32.

FIG. 8*i* shows a contact angle measurement result of Comparative Example 33.

FIG. 8*j* shows a contact angle measurement result of Comparative Example 34.

| 100, 200, 300: | organic electronic element |
|---|---|
| 110: | the first electrode |
| 120: | hole injection layer |
| 130: | hole transport layer |
| 140: | emitting layer |
| 150: | electron transport layer |
| 170: | second electrode |
| 180: | light efficiency enhancing Layer |
| 190: | metal pattering layer |

DETAILED DESCRIPTION

As used in the specification and the accompanying claims, unless otherwise stated, the following is the meaning of the term as follows.

As used herein, the term "halo" or "halogen" refers to fluorine (F), bromine (Br), chlorine (Cl) or iodine (I), unless otherwise specified.

As used herein, the term "alkyl" or "alkyl group" has a single bond of 1 to 60 carbon atoms, unless otherwise specified, and means saturated aliphatic functional radicals including a linear alkyl group, a branched chain alkyl group, a cycloalkyl group (alicyclic), an cycloalkyl group substituted with an alkyl or an alkyl group substituted with a cycloalkyl.

As used herein, the terms "alkenyl group" or "alkynyl group" have a double or triple bond of 2 to 60 carbon atoms, respectively, unless otherwise specified, and include a straight or branched chain group, but not limited thereto.

As used herein, the term "cycloalkyl" refers to an alkyl forming a ring having 3 to 60 carbon atoms unless otherwise specified, but is not limited thereto.

As used herein, the term "alkoxyl group", "alkoxy group", or "alkyloxy group" refers to an alkyl group to which an oxygen radical is attached, and has 1 to 60 carbon atoms, unless otherwise specified, but is not limited thereto.

As used herein, the term "aryloxyl group" or "aryloxy group" refers to an aryl group to which an oxygen radical is attached, and has 6 to 60 carbon atoms unless otherwise specified, but is not limited thereto.

As used herein, the term "alkylthio group" refers to an alkyl group to which a sulfur radical is attached, and has 1 to 60 carbon atoms unless otherwise specified, but is not limited thereto.

As used herein, the term "arylthio group" refers to an aryl group to which a sulfur radical is attached, and has 1 to 60 carbon atoms unless otherwise specified, but is not limited thereto.

As used herein, the terms "aryl group" and "arylene group" each have 6 to 60 carbon atoms, and are not limited thereto, unless otherwise specified. In the present invention, an aryl group or an arylene group means a single ring or multiple ring aromatic, and includes an aromatic ring formed by a neighboring substituent joining or participating in a reaction. For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein. Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

As used herein, the term "heterocyclic group" includes one or more heteroatoms unless otherwise specified, has 2 to 60 carbon atoms, includes any one of a single ring or multiple ring, and may include heteroaliphadic ring and heteroaromatic ring. The heterocyclic group may also be formed in conjunction with an adjacent functional groups.

As used herein, the term "heteroatom" refers to N, O, S, P or Si unless otherwise specified.

In addition, 'heterocyclic group' refers to a monocyclic type containing a hetero atom, a ring aggregate, a fused multiple ring system, a spiro compound, and the like. Also, a compound including a heteroatom group such as $SO_2$, $P=O$, etc., as in the following compound instead of carbon forming a ring, may also be included in the heterocyclic group.

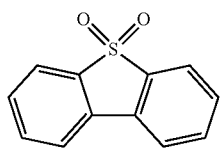 [SMILES: O=S1(=O)c2ccccc2-c2ccccc21]

The term "aliphatic ring group" used in the present invention refers to a cyclic hydrocarbon other than an aromatic hydrocarbon, and includes a single ring type, a ring aggregate, a fused multiple ring system, a spiro compound, etc., and unless otherwise specified, means the number of carbon atoms 3 to 60 rings, but is not limited thereto. For example, even when benzene, which is an aromatic ring, and cyclohexane, which is a non-aromatic ring, are fused, it corresponds to an aliphatic ring.

The term "fluorenyl group", "fluorenylene group", and "fluorentriyl group" used in the present invention means a monovalent, divalent or trivalent functional group in which R, R' and R" in each of the following structures are all hydrogen, unless otherwise specified, and "substituted fluorenyl group", "substituted fluorenylene group" or "substituted fluorentriyl group" means that at least one of the substituents R, R' and R" is a substituent other than hydrogen, and includes cases in which R and R' are bonded to each other to form a spiro compound together with the carbon to which they are attached. In the present specification, the fluorenyl group, fluorenylene group, and fluorentriyl group may all be referred to as fluorene groups regardless of the valence.

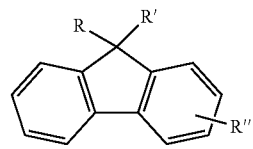

In the present specification, the 'group name' corresponding to the aryl group, arylene group, heterocyclic group, etc. exemplified as examples of each symbol and its substituents may be described as 'the name of the group reflecting the valence', but is described as the 'name of the parent compound'.

For example, in the case of 'phenanthrene', which is a kind of aryl group, the monovalent 'group' is 'phenanthryl', and the divalent group can be described by distinguishing the valency such as 'phenanthrylene', but regardless of the valence, can also be described as 'phenanthrene', which is the name of the parent compound. Similarly, in the case of pyrimidine, regardless of the valence, it can be described as 'pyrimidine', or in the case of monovalent, as a pyrimidinyl group, in the case of divalent, as the 'name of the group' of the corresponding valence, such as pyrimidinylene. In addition, in the present specification, in describing the name of the compound or the name of a substituent, numbers or alphabets indicating positions may be omitted. For example, pyrido[4,3-d]pyrimidine to pyridopyrimidine, benzofuro[2,3-d]pyrimidine to benzofuropyrimidine, 9,9-dimethyl-9H-fluorene can be described as dimethylfluorene and the like. Therefore, both benzo[g]quinoxaline and benzo[f]quinoxaline can be described as benzoquinoxaline.

In addition, unless there is an explicit explanation, the formula used in the present invention is the same as the definition of the substituent by the exponent definition of the following formula.

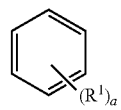

Here, when a is an integer of 0, the substituent $R^1$ is absent, when a is an integer of 1, the sole substituent $R^1$ is linked to any one of the carbon constituting the benzene ring, when a is an integer of 2 or 3, each is bonded as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

(a=2)

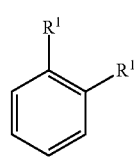

-continued

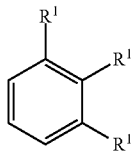
(a=3)

In addition, unless otherwise stated herein, when representing a condensed ring, the number in 'number-condensed ring' indicates the number of rings to be condensed. For example, a form in which 3 rings are condensed with each other, such as anthracene, phenanthrene, benzoquinazoline, etc., may be expressed as a 3-condensed ring.

In addition, unless otherwise stated herein, when a ring is expressed in the form of a 'numeric-atom', such as a 5-membered ring, a 6-membered ring, etc., the number in 'number-atom' indicates the number of elements forming the ring. For example, thiophene or furan may correspond to a 5-membered ring, and benzene or pyridine may correspond to a 6-membered ring.

In addition, unless otherwise stated herein, a ring formed by bonding adjacent groups to each other may be selected from the group consisting of a $C_6$-$C_{60}$ aromatic ring group; fluorenyl group; $C_2$~$C_{60}$ heterocyclic group containing at least one heteroatom of O, N, S, Si or P; and $C_3$~$C_{60}$ aliphatic ring group;

At this time, unless otherwise stated herein, the term 'adjacent groups' refers to the following formula as an example, includes not only $R^1$ and $R^2$, $R^2$ and $R^3$, $R^3$ and $R^4$, $R^5$ and $R^6$, but also $R^7$ and $R^8$ that share one carbon, and may include substituents bonded to non-adjacent ring constituent elements (such as carbon or nitrogen), such as $R^1$ and $R^7$, $R^1$ and $R^8$, or $R^4$ and $R^5$. That is, when there is a substituent on a ring constituent element such as carbon or nitrogen immediately adjacent to it, they may be adjacent groups, but if no substituent is bonded to a ring component at the immediately adjacent position, it may be a group adjacent to the substituent bonded to the next ring component, and also, substituents bonded to the same ring constituent carbons can be said to be adjacent groups.

When substituents bonded to the same carbon as $R^7$ and $R^8$ in the following formulas are bonded to each other to form a ring, a compound including a spiro moiety may be formed.

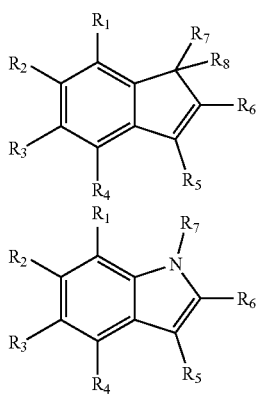

In addition, in the present specification, the expression 'adjacent groups may be bonded to each other to form a ring' is used in the same meaning as 'adjacent groups are bonded to each other to selectively form a ring', and means to a case in which at least one pair of adjacent groups are bonded to each other to form a ring.

Hereinafter, the compound according to an aspect of the present invention will be described.

According to one aspect of the present invention, a fluorinated compound represented by Formula (1) is provided.

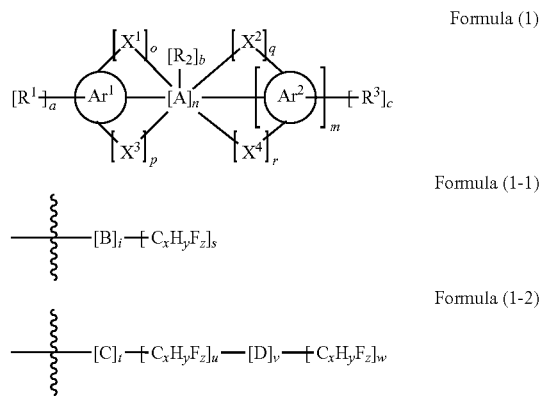

Formula (1)

Formula (1-1)

Formula (1-2)

Wherein, each symbol may be defined as follows.

1) $Ar^1$ and $Ar^2$ are each independently selected from the group consisting of a $C_6$-$C_{60}$ aryl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

In case $Ar^1$ and $Ar^2$ are aryl groups, preferably a $C_6$-$C_{30}$ aryl group, more preferably a $C_6$-$C_{20}$ aryl group, even more preferably a $C_6$-$C_{18}$ aryl group, such as phenyl, biphenyl, naphthyl, terphenyl, etc.

In case $Ar^1$ and $Ar^2$ are a heterocyclic group, preferably a $C_2$-$C_{30}$ heterocyclic group, and more preferably a $C_2$-$C_{20}$ heterocyclic group, even more preferably a $C_2$-$C_{16}$ heterocyclic group, for example, pyridine, pyrimidine, quinoline, quinazoline, quinoxaline, dibenzofuran, dibenzothiophene, naphthobenzothiophene, naphthobenzofuran, benzofuran, benzothiophene, etc.

2) A, B, C and D are each independently selected from the group consisting of —$CR^aR^b$—; —$NR^c$—; —O—; —S—; —$SiR^dR^e$—; a $C_6$-$C_{60}$ arylene group; a fluorenylene group; a $C_2$-$C_{60}$ heterocyclic group including at least one heteroatom of O, N, S, Si or P;

In case A, B, C and D are an arylene group, preferably a $C_6$-$C_{30}$ arylene group, more preferably a $C_6$-$C_{20}$ arylene group, even more preferably a $C_6$-$C_{18}$ arylene group, for example, phenylene, biphenylene, naphthylene, terphenylene, etc.

In case A, B, C and D are a fluorenylene group, 9,9-dimethyl-9H-fluorenylene, 9,9-diphenyl-9H-fluorenylene, 9,9'-spirobifluorenylene, etc.

In case A, B, C and D are a heterocyclic group, preferably a $C_2$-$C_{30}$ heterocyclic group, more preferably a $C_2$-$C_{20}$ heterocyclic group, and even more preferably a $C_2$-$C_{16}$ heterocyclic group, for example, pyridine, pyrimidine, quinoline, quinazoline, quinoxaline, dibenzofuran, dibenzothiophene, naphthobenzothiophene, naphthobenzofuran, benzofuran, benzothiophene etc.

However, in case m is 0, A is a $C_6$-$C_{60}$ aryl group; or a $C_2$-$C_{60}$ heterocyclic group including at least one heteroatom of O, N, S, Si or P;

In case A is an aryl group, preferably a $C_6$-$C_{30}$ aryl group, more preferably a $C_6$-$C_{20}$ aryl group, and even more preferably a $C_6$-$C_{18}$ aryl group, for example, phenyl, biphenyl, naphthyl, terphenyl, etc.

In case A is a heterocyclic group, preferably a $C_2$-$C_{30}$ heterocyclic group, more preferably a $C_2$-$C_{20}$ heterocyclic group, and even more preferably a $C_2$-$C_{16}$ heterocyclic group for example, pyridine, pyrimidine, quinoline, quinazoline, quinoxaline, dibenzofuran, dibenzothiophene, naphthobenzothiophene, naphthobenzofuran, benzofuran, benzothiophene etc.

3) $R^1$, $R^2$ and $R^3$ are the same or different from each other independently, and each independently selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_6$ aromatic ring; a $C_1$-$C_{50}$ alkyl group; a $C_1$-$C_{50}$ alkoxyl group; a $C_6$-$C_{60}$ aryloxy group; -L-NR'R''; a substituent represented by Formula (1-1); and a substituent represented by Formula (1-2); or $R^1$, $R^2$ and $R^3$ may be bonded to each other to form a ring.

In case $R^1$, $R^2$ and $R^3$ are an aryl group, preferably a $C_6$-$C_{30}$ aryl group, more preferably a $C_6$-$C_{20}$ aryl group, and even more preferably a $C_6$-$C_{18}$ aryl group, for example, phenyl, biphenyl, naphthyl, terphenyl, etc.

In case $R^1$, $R^2$ and $R^3$ are a fluorenyl group, 9,9-dimethyl-9H-fluorenyl, 9,9-diphenyl-9H-fluorenyl group, 9,9'-spirobifluorenyl, etc.

In case $R^1$, $R^2$ and $R^3$ are a heterocyclic group, preferably a $C_2$-$C_{30}$ heterocyclic group, more preferably a $C_2$-$C_{20}$ heterocyclic group, and even more preferably a $C_2$-$C_{16}$ heterocyclic group, for example, pyridine, pyrimidine, quinoline, quinazoline, quinoxaline, dibenzofuran, dibenzothiophene, naphthobenzothiophene, naphthobenzofuran, benzofuran, benzothiophene etc.

In case $R^1$, $R^2$ and $R^3$ are an alkyl group, preferably a $C_1$-$C_{20}$ alkyl group, and more preferably a $C_1$-$C_{10}$ alkyl group, for example, methyl, t-butyl, etc.

When $R^1$, $R^2$ and $R^3$ are an alkoxy group, preferably a $C_1$-$C_{20}$ alkoxyl group, more preferably a $C_1$-$C_{10}$ alkoxyl group, such as methoxy, t-butoxy, etc.

In case $R^1$, $R^2$ and $R^3$ are an aryloxy group, preferably a $C_6$-$C_{30}$ aryloxy group, preferably an $C_6$-$C_{20}$ aryloxy group.

However, at least one of $R^1$, $R^2$ and $R^3$ are a substituent represented by Formula (1-1) or a substituent represented by Formula (1-2).

4) a, b and c are each independently an integer of 0 to 10, with the proviso that a+b+c is 1 or more, 5) m and n are each independently an integer of 0 to 50. wherein, when n is 0, $R^2$ is absent, where a+c is 1 or more, when m is 0, $R^3$ is not present, where, a+b is 1 or more, when both n and m are 0, $R^2$ and $R^3$ are absent, where a is an integer from 1 to 10.

6) $X^1$, $X^2$, $X^3$ and $X^4$ are each independently $CR^fR^g$, $NR^h$, O, S or $SiR^iR^j$, 7) R' and R'' are each independently selected from the group consisting of a $C_6$-$C_{60}$ aryl group; a $C_2$-$C_{60}$ heterocyclic group including at least one heteroatom of O, N, S, Si or P; a fused ring group of a $C_3$-$C_{60}$ aliphatic ring and a $C_6$-$C_6$ aromatic ring; or R' and R'' may be bonded to each other to form a ring.

In case R' and R'' are aryl groups, preferably a $C_6$-$C_{30}$ aryl group, more preferably a $C_6$-$C_{20}$ aryl group, and even more preferably a $C_6$-$C_{18}$ aryl group, such as phenyl, biphenyl, naphthyl, terphenyl, etc.

In case R' and R'' are a heterocyclic group, preferably a $C_2$-$C_{30}$ heterocyclic group, more preferably a $C_2$-$C_{20}$ heterocyclic group, and even more preferably a $C_2$-$C_{16}$ heterocyclic group, for example, pyridine, pyrimidine, quinoline, quinazoline, quinoxaline, dibenzofuran, dibenzothiophene, naphthobenzothiophene, naphthobenzofuran, benzofuran, benzothiophene, etc.

8) $R^a$, $R^b$, $R^c$, $R^d$, $R^e$, $R^f$, $R^g$, $R^h$, $R^i$ and $R^j$ are each independently selected from the group consisting of hydrogen; deuterium; halogen; a $C_6$-$C_{60}$ aryl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a substituent represented by Formula (1-1); or a substituent represented by Formula (1-2); or $R^a$, $R^b$, $R^c$, $R^d$, $R^e$, $R^f$, $R^g$, $R^h$, $R^i$ and $R^j$ may be bonded to each other to form a ring.

In case $R^a$, $R^b$, $R^c$, $R^d$, $R^e$, $R^f$, $R^g$, $R^h$, $R^i$ and $R^j$ are an aryl group, preferably a $C_6$-$C_{30}$ aryl group, more preferably a $C_6$-$C_{20}$ aryl group, and even more preferably a $C_6$-$C_{18}$ aryl group, for example, phenyl, biphenyl, naphthyl, terphenyl, etc.

In case $R^a$, $R^b$, $R^c$, $R^d$, $R^e$, $R^f$, $R^g$, $R^h$, $R^i$ and $R^j$ are a heterocyclic group, preferably a $C_2$-$C_{30}$ heterocyclic group, more preferably a $C_2$-$C_{20}$ heterocyclic group, and even more preferably a $C_2$-$C_{16}$ heterocyclic group, for example, pyridine, pyrimidine, quinoline, quinazoline, quinoxaline, dibenzofuran, dibenzothiophene, naphthobenzothiophene, naphthobenzofuran, benzofuran, benzothiophene etc.

In case $R^a$, $R^b$, $R^c$, $R^d$, $R^e$, $R^f$, $R^g$, $R^h$, $R^i$ and $R^j$ are an alkyl group, preferably a $C_1$-$C_{20}$ alkyl group, and more preferably a $C_1$-$C_{10}$ alkyl group, for example, methyl, t-butyl, etc.

9) o, p, q and r are each independently an integer of 0 or 1. Wherein, when o is 0, $X^1$ is absent, when p is 0, $X^2$ is absent, when q is 0, $X^3$ does is absent, and when r is 0, $X^4$ is absent.

10) x is an integer from 1 to 50. Also, y+z is an integer of 2x+1, 2x, or 2x−2. For example, y may be 0 and z may be 2x+1, 2x or 2x−2.

Wherein, x is preferably an integer of 3 to 20, more preferably an integer of 5 to 15, and still more preferably an integer of 5 to 12. When x exceeds the above range, there is a problem that Td may be increased during vacuum deposition, and if it is less than the above range, the compound is highly likely to become a liquid.

11) i, t and v are independently integers from 0 to 20, and s, u and w are independently integers from 1 to 20. Here, when i or t is 0, B and C mean a single bond, wherein s or u is 1.

12) L is selected from the group consisting of a single bond; a $C_6$-$C_6$ arylene group; a fluorenylene group; a $C_2$-$C_{60}$ heterocyclic group including at least one heteroatom of O, N, S, Si or P; a $C_1$-$C_{50}$ alkylene group; a fused ring group of a $C_3$-$C_{60}$ aliphatic ring and a $C_6$-$C_{60}$ aromatic ring;

In case L is an arylene group, preferably a $C_6$-$C_{30}$ arylene group, more preferably a $C_6$-$C_{20}$ arylene group, and still more preferably a $C_6$-$C_{18}$ arylene group, for example, phenylene, biphenylene, naphthylene, terphenylene, etc.

In case L is a fluorenylene group, 9,9-dimethyl-9H-fluorenylene, 9,9-diphenyl-9H-fluorenylene, 9,9'-spirobifluorenylene, etc.

In case L is a heterocyclic group, preferably a $C_2$-$C_{30}$ heterocyclic group, more preferably a $C_2$-$C_{20}$ heterocyclic group, and even more preferably a $C_2$-$C_{16}$ heterocyclic group, for example, pyridine, pyrimidine, quinoline, quinazoline, quinoxaline, dibenzofuran, dibenzothiophene, naphthobenzothiophene, naphthobenzofuran, benzofuran, benzothiophene etc.

In case L is an alkylene group, preferably a $C_1$-$C_{20}$ alkylene group, more preferably a $C_1$-$C_{10}$ alkylene group, for example, methylene, butylene, etc.

13) wherein the aryl group, arylene group, heterocyclic group, fluorenyl group, fluorenylene group, fused ring group, alkyl group, alkoxyl group, aryloxy group and a ring formed by bonding adjacent groups to each other may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_6$-$C_{20}$ aryloxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; $C_6$-$C_{20}$ aryl group substituted with halogen; fluorenyl group; a $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Formula (1) is represented by Formula (2)

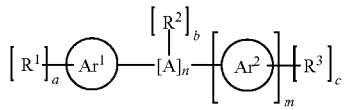

Formula (2)

Wherein $Ar^1$, $Ar^2$, $R^1$, $R^2$, $R^3$, A, a, b, c, m and n are the same as defined in Formula (1).

Preferably, Formula (1) may be represented by any one of Formulas (2-1) to (2-5).

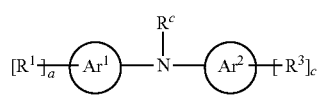

Formula (2-1)

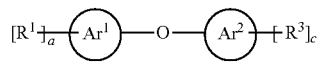

Formula (2-2)

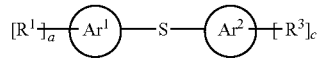

Formula (2-3)

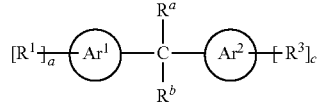

Formula (2-4)

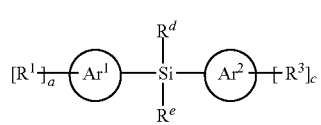

Formula (2-5)

Wherein $Ar^1$, $Ar^2$, $R^1$, $R^3$, $R^a$, $R^b$, $R^c$, $R^d$, $R^e$, a and c are the same as defined in Formula (1).

Also, preferably, Formula (1) is represented by Formula (2-6).

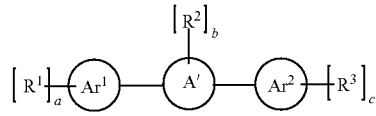

Formula (2-6)

Wherein each symbol may be defined as follows.
1) $Ar^1$, $Ar^2$, $R^1$, $R^2$, $R^3$, a, b and c are the same as defined in Formula (1),
2) A' is a $C_6$-$C_{60}$ arylene group; or $C_2$-$C_{60}$ heterocyclic group containing at least one heteroatom of O, N, S, Si or P;

In case A' is an arylene group, preferably a $C_6$-$C_{30}$ arylene group, more preferably a $C_6$-$C_{20}$ arylene group, and still more preferably a $C_6$-$C_{18}$ arylene group, for example, phenylene, biphenylene, naphthylene, terphenylene, triphenylenylene, etc.

In case A' is a heterocyclic group, preferably a $C_2$-$C_{30}$ heterocyclic group, more preferably a $C_2$-$C_{20}$ heterocyclic group, and even more preferably a $C_2$-$C_{16}$ heterocyclic group, for example, pyridine, pyrimidine, quinoline, quinazoline, quinoxaline, benzofuran, benzothiophene, etc.

Also, preferably, Formula (1) is represented by Formula (2-12).

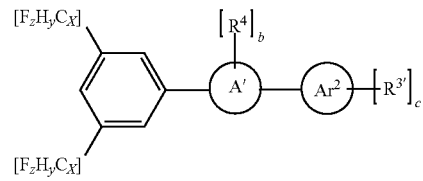

Formula (2-12)

Wherein, each symbol may be defined as follows.
1) b, c, x, y, z and $Ar^2$ are the same as defined in Formula (1),
2) A' is the same as defined in Formula (2-6),
3) $R^4$ is selected from the group consisting of a $C_6$-$C_{60}$ aryl group; a fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring; a $C_1$-$C_{50}$ alkyl group; a $C_1$-$C_{50}$ alkoxyl group; a $C_6$-$C_{60}$ aryloxy group; and -L-NR'R"; or $R^4$ may be bonded to each other to form a ring, Wherein L, R' and R" are the same as defined in Formula (1).

Wherein, when $R^4$ is an aryl group, preferably a $C_6$-$C_{30}$ aryl group, more preferably a $C_6$-$C_{20}$ aryl group, and even more preferably a $C_6$-$C_{18}$ aryl group, for example, phenyl, biphenyl, naphthyl, terphenyl, etc.

In case $R^4$ is a fluorenyl group, 9,9-dimethyl-9H-fluorenyl, 9,9-diphenyl-9H-fluorenyl, 9,9'-spirobifluorenyl, etc.

In case $R^4$ is a heterocyclic group, preferably a $C_2$-$C_{30}$ heterocyclic group, more preferably a $C_2$-$C_{20}$ heterocyclic group, and even more preferably a $C_2$-$C_{16}$ heterocyclic group, for example, pyridine, pyrimidine, quinoline, quinazoline, quinoxaline, dibenzofuran, dibenzothiophene, naphthobenzothiophene, naphthobenzofuran, benzofuran, benzothiophene etc.

In case $R^4$ is an alkyl group, preferably a $C_1$-$C_{20}$ alkyl group, and more preferably a $C_1$-$C_{10}$ alkyl group, for example, methyl, t-butyl, etc. In case $R^4$ is an alkoxy group, preferably a $C_1$-$C_{20}$ alkoxyl group, more preferably a $C_1$-$C_{10}$ alkoxyl group, such as methoxy, t-butoxy, etc.

In case $R^4$ is an aryloxy group, preferably a $C_6$-$C_{30}$ aryloxy group, more preferably a $C_6$-$C_{20}$ aryloxy group.

4) $R^{3'}$ is each independently selected from the group consisting of hydrogen; deuterium; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_1$-$C_{50}$ alkoxyl group; a $C_6$-$C_{60}$ aryloxy group; and -L-NR'R"; or $R^{3'}$ may be bonded to each other to form a ring, In case $R^{3'}$ is an aryl group, preferably a $C_6$-$C_{30}$ aryl group, more preferably a $C_6$-$C_{20}$ aryl group, and even more preferably a $C_6$-$C_{18}$ aryl group, for example, phenyl, biphenyl, naphthyl, terphenyl, etc.

In case $R^{3'}$ is a heterocyclic group, preferably a $C_2$-$C_{30}$ heterocyclic group, more preferably a $C_2$-$C_{20}$ heterocyclic group, and even more preferably a $C_2$-$C_{16}$ heterocyclic group, for example, pyridine, pyrimidine, quinoline, quinazoline, quinoxaline, dibenzofuran, dibenzothiophene, naphthobenzothiophene, naphthobenzofuran, benzofuran, benzothiophene etc.

In case $R^{3'}$ is an alkyl group, preferably a $C_1$-$C_{20}$ alkyl group, and more preferably a $C_1$-$C_{10}$ alkyl group, for example, methyl, t-butyl, etc.

In case $R^{3'}$ is an alkoxy group, preferably a $C_1$-$C_{20}$ alkoxyl group, more preferably a $C_1$-$C_{10}$ alkoxyl group, such as methoxy, t-butoxy, etc.

In case $R^{3'}$ is an aryloxy group, preferably a $C_6$-$C_{30}$ aryloxy group, more preferably a $C_6$-$C_{20}$ aryloxy group.

More preferably, Formula (1) may be represented by Formula (2-7).

Formula (2-7)

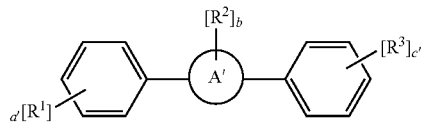

Wherein,
1) $R^1$, $R^2$, $R^3$ and b are the same as defined in Formula (1),
2) A' is the same as defined in Formula (2-6),
3) a' and c' are each independently an integer of 0 to 5.

More preferably, Formula (1) may be represented by Formula (2-8) or (2-9).

Formula (2-8)

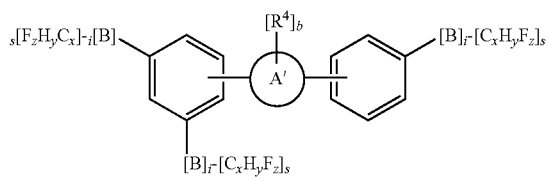

Formula (2-9)

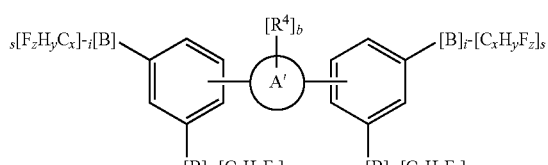

Wherein, each symbol may be defined as follows.
1) b, B, i, x, y, z and s are the same as defined in Formula (1),
2) A' is the same as defined in Formula (2-6),
3) $R^4$ is the same as defined in Formula (2-12), Most preferably, Formula (1) is represented by Formula (2-10) or Formula (2-11).

Formula (2-10)

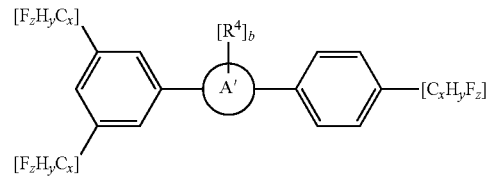

Formula (2-11)

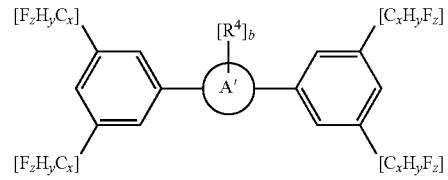

Wherein
1) b, x, y and z are the same as defined in Formula (1),
2) A' is the same as defined in Formula (2-6),
3) $R^4$ is the same as defined in Formula (2-12), Also, Formula (1) is represented by Formula (3).

Formula (3)

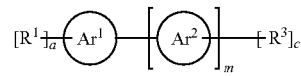

Wherein $Ar^1$, $Ar^2$, $R^1$, $R^3$, a, c and m are the same as defined in Formula (1).

Preferably, Formula (1) is represented by Formula (3-1).

Formula (3-1)

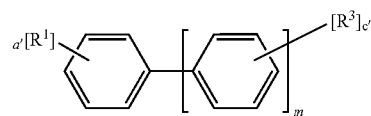

Wherein
1) $R^1$, $R^3$ and m are the same as defined in Formula (1),
2) a' and c' are each independently an integer of 0 to 5.

Also, Formula (1) is represented by Formula (4).

Formula (4)

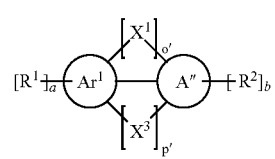

Wherein, each symbol may be defined as follows.
1) $Ar^1$, $X^1$, $X^3$, $R^1$, $R^2$, a and b are the same as defined in Formula (1),
2) o' and p' are each independently 0 or 1, o'+p' are 1 or more,
3) A" is a $C_6$-$C_{60}$ aryl group; or a $C_2$-$C_{60}$ heterocyclic group including at least one heteroatom of O, N, S, Si or P;

In case A" is an aryl group, preferably a $C_6$-$C_{30}$ aryl group, more preferably a $C_6$-$C_{20}$ aryl group, and even more preferably a $C_6$-$C_{18}$ aryl group, for example, phenyl, biphenyl, naphthyl, terphenyl, etc.

In case A" is a heterocyclic group, preferably a $C_2$-$C_{30}$ heterocyclic group, more preferably a $C_2$-$C_{20}$ heterocyclic group, and even more preferably a $C_2$-$C_{16}$ heterocyclic group, for example, pyridine, pyrimidine, quinoline, quinazoline, quinoxaline, dibenzofuran, dibenzothiophene, etc.

Preferably, Formula (1) may be represented by Formula (4-1).

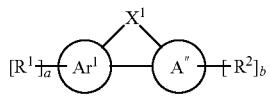

Formula (4-1)

Wherein
1) $Ar^1$, $R^1$, $R^2$, $X^1$, a and b are the same as defined in Formula (1),
2) A" is the same as defined in Formula (4).

More preferably, Formula (1) is represented by any one of Formulas (4-2) to (4-6)

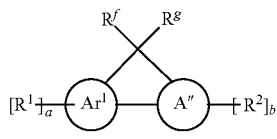

Formula (4-2)

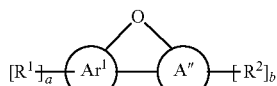

Formula (4-3)

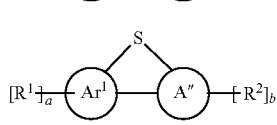

Formula (4-4)

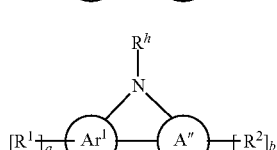

Formula (4-5)

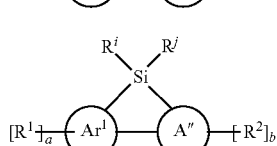

Formula (4-6)

Wherein
1) $Ar^1$, $R^1$, $R^2$, $R^f$, $R^g$, $R^h$, $R^i$, $R^j$, a and b are the same as defined in Formula (1),
2) A" is the same as defined in Formula (4).

Also, more preferably, Formula (1) may be represented by Formula (4-7).

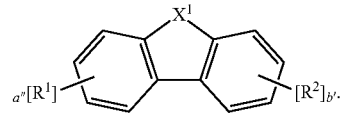

Formula (4-7)

Wherein
1) $X^1$, $R^1$ and $R^2$ are the same as defined in Formula (1),
2) a" and b' are each independently an integer of 0 to 4.

Also, Formula (1) is represented by Formula (5) or Formula (6).

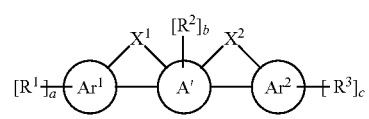

Formula (5)

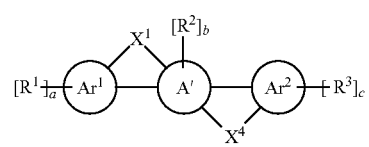

Formula (6)

Wherein
1) $Ar^1$, $Ar^2$, $X^1$, $X^2$, $X^4$, $R^1$, $R^2$, $R^3$, a, b and c are the same as defined in Formula (1),
2) A' is the same as defined in Formula (2-6).

Preferably, Formula (1) is represented by any one of Formulas (5-1) to (5-3).

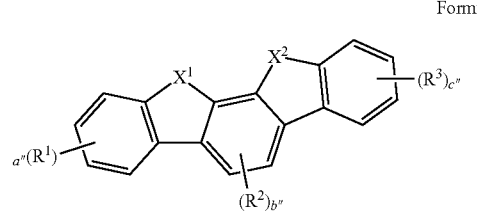

Formula (5-1)

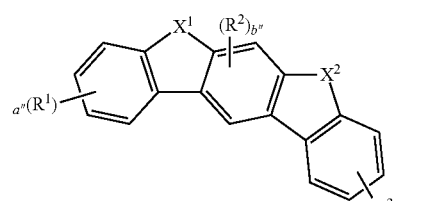

Formula (5-2)

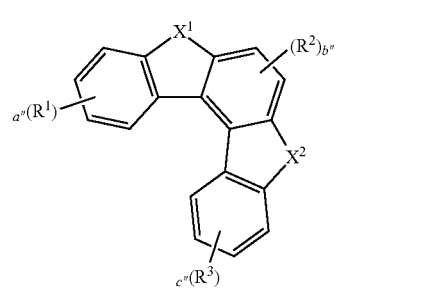

Formula (5-3)

Wherein
1) $X^1$, $X^2$, $R^1$, $R^2$ and $R^3$ are the same as defined in Formula (1),
2) a" and c" are each independently an integer of 0 to 4, b" is an integer of 0 to 2.

Also, preferably, Formula (1) is represented by Formula (6-1) or Formula (6-2).

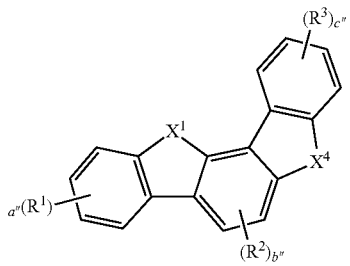

Formula (6-1)

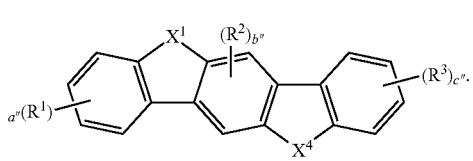

Formula (6-2)

Wherein
1) $X^1$, $X^4$, $R^1$, $R^2$ and $R^3$ are the same as defined in Formula (1),
2) a" and c" are each independently an integer of 0 to 4, b" is an integer of 0 to 2.

Also, Formula (1-1) is represented by Formula (1-1-a) or Formula (1-1-b).

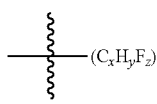

Formula (1-1-a)

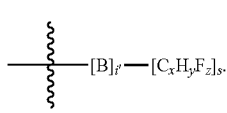

Formula (1-1-b)

Wherein
1) x, y, z, s and B are the same as defined in Formula (1),
2) i' is an integer of 1 to 20.

Meanwhile, Formula (1-1-b) is represented by Formula (1-1-c).

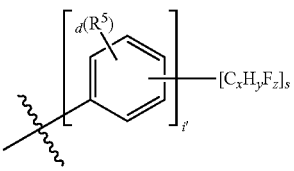

Formula (1-1-c)

Wherein
1) x, y, z and s are the same as defined in Formula (1),
2) i' is an integer of 1 to 20, d is an integer of 0 to 4,
3) $R^5$ is selected from the group consisting of deuterium; halogen; a $C_6$-$C_{20}$ aryl group; a $C_2$-$C_{20}$ heterocyclic group including at least one heteroatom of O, N, S, Si or P; a fused ring group of a $C_3$-$C_{20}$ aliphatic ring and a $C_6$-$C_{20}$ aromatic ring; a $C_1$-$C_{20}$ alkyl group; or $R^5$ may be bonded to each other to form a ring.

Also, Formula (1-2) is represented by Formula (1-2-a) or Formula (1-2-b).

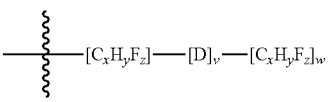

Formula (1-2-a)

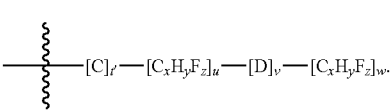

Formula (1-2-b)

Wherein
1) x, y, z, C, D, u, v and w are the same as defined in Formula (1),
2) t' is an integer of 1 to 20.

Specifically, Formulas (1-1) and (1-2) may be one of the following compounds, but are not limited thereto.

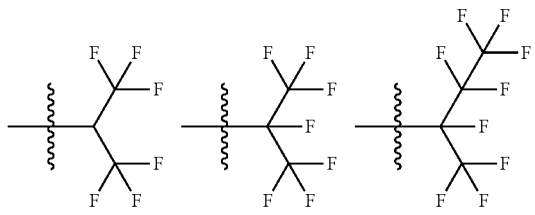

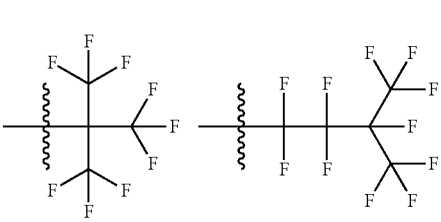

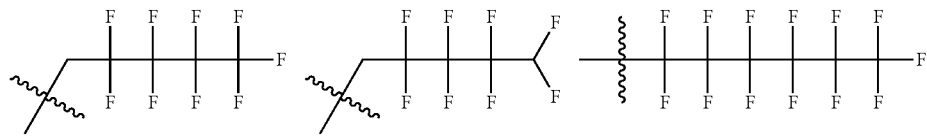

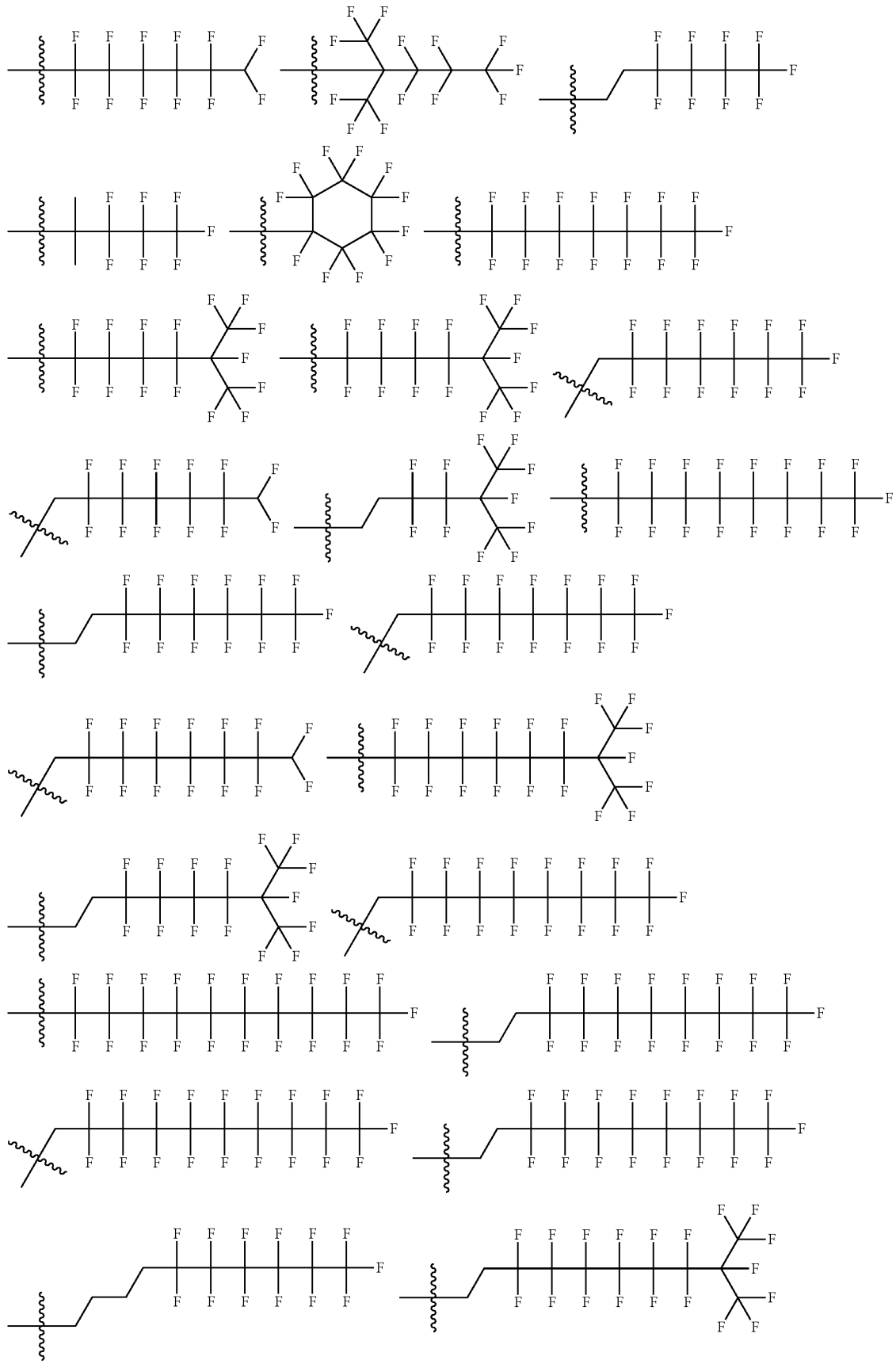
-continued

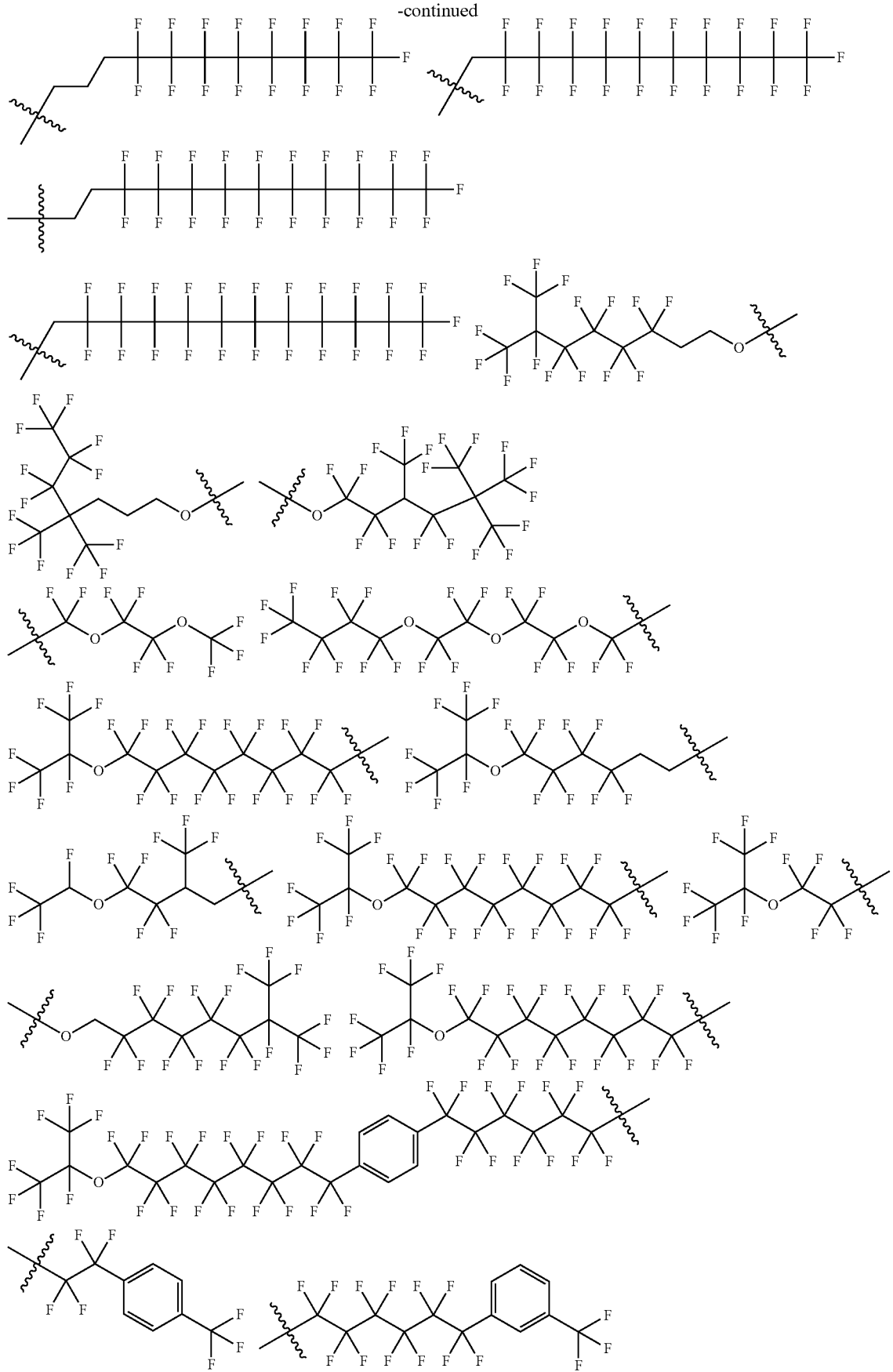

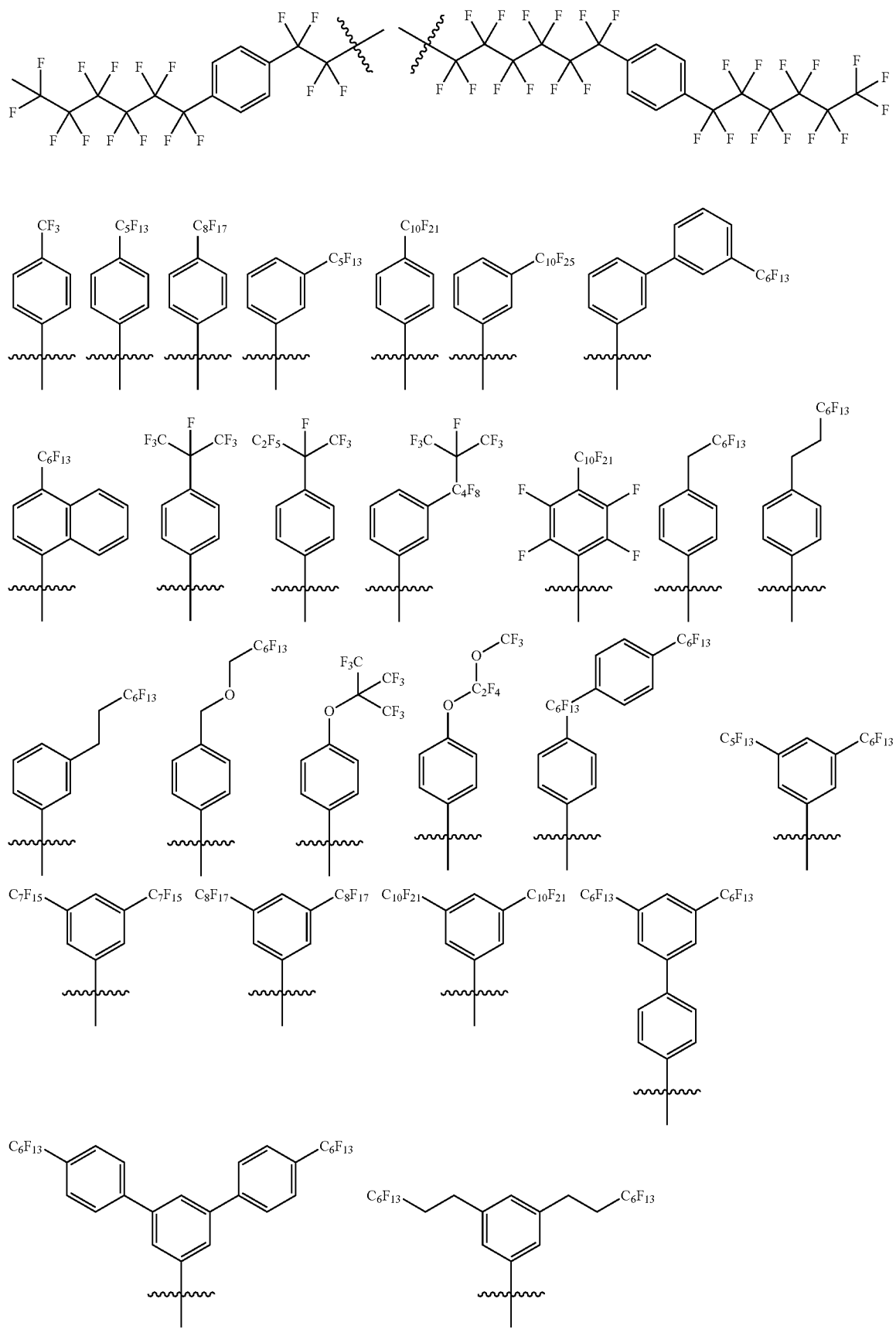

-continued
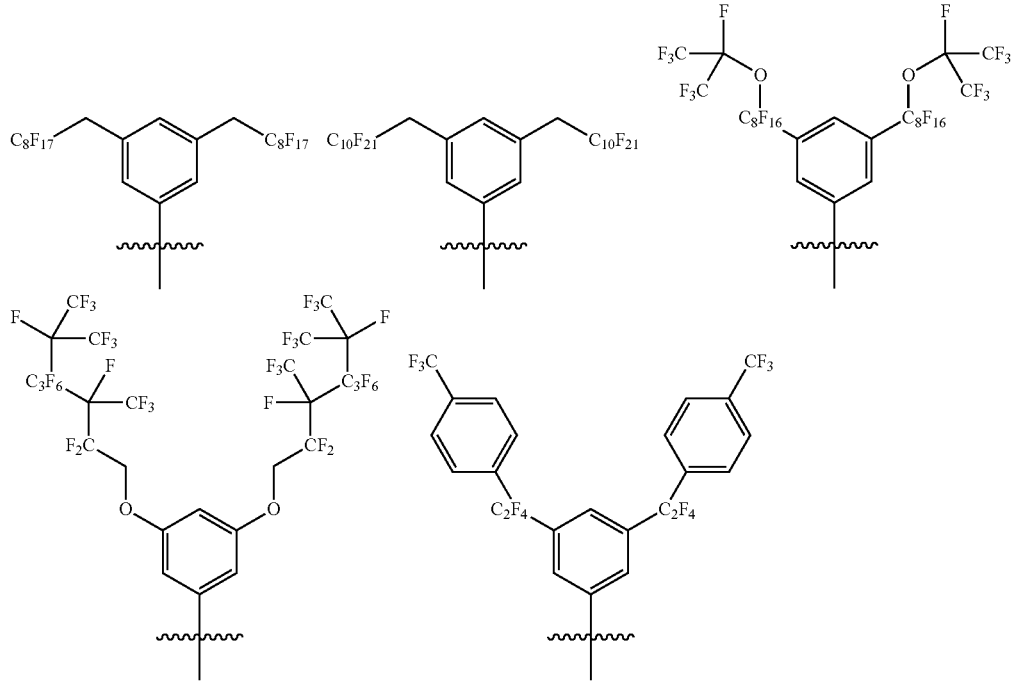
Otherwise, specifically, the compound represented by Formula (1) may be any one of the following compounds, but is not limited thereto.
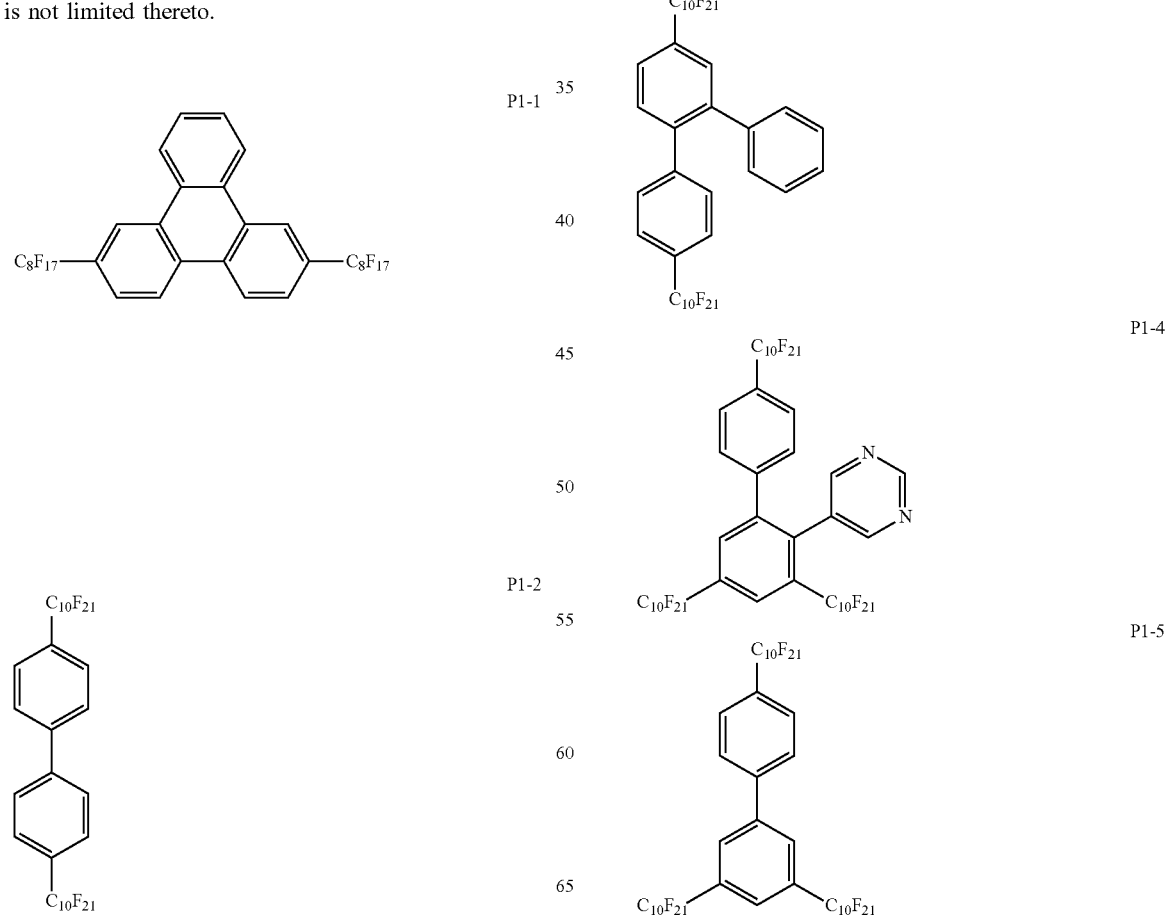

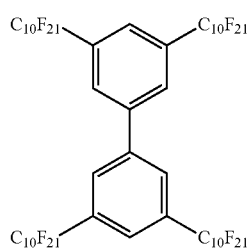 P1-6
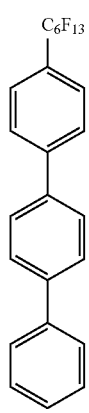 P1-7
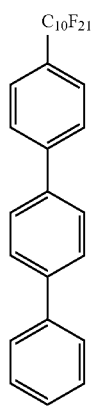 P1-8
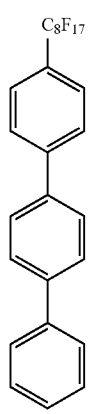 P1-9
 P1-10
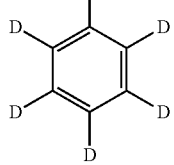
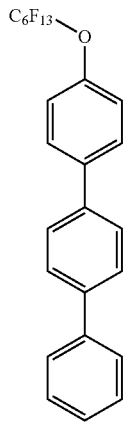 P1-11
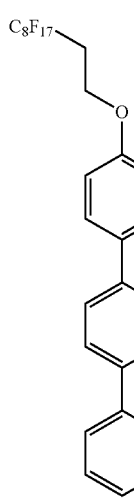 P1-12

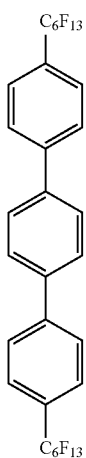
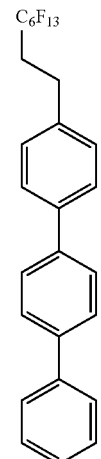

-continued
P1-19
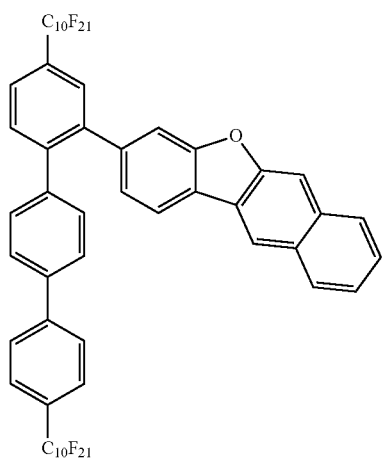
P1-20
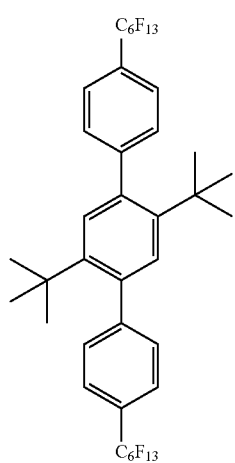
P1-21
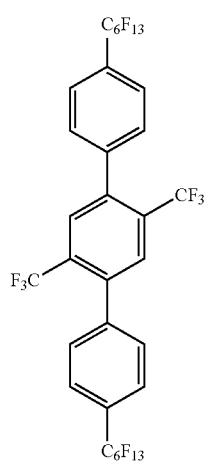
-continued
P1-22
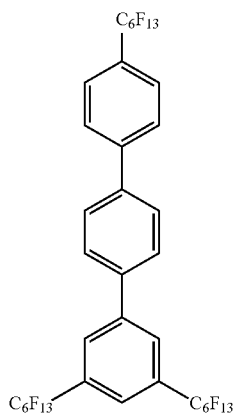
P1-23
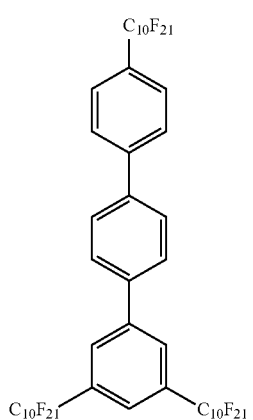
P1-24
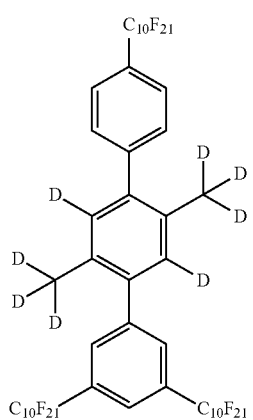
P1-25
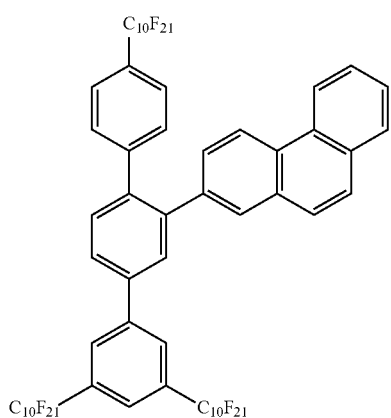

-continued
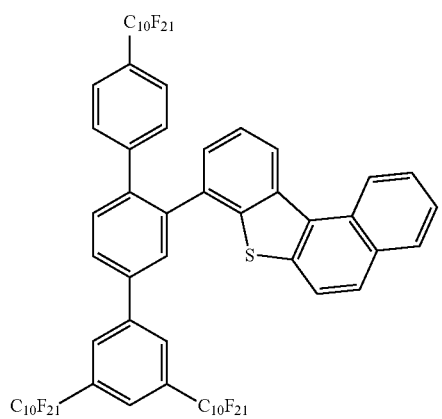
P1-26
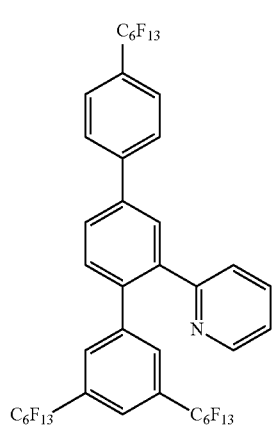
P1-27
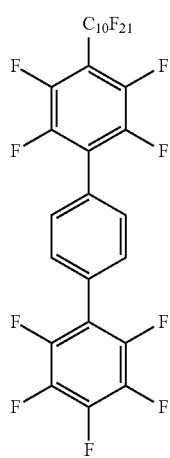
P1-28
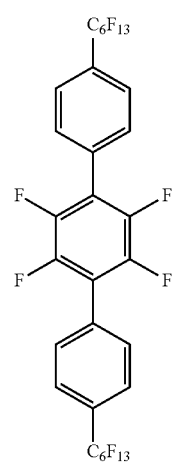
P1-29
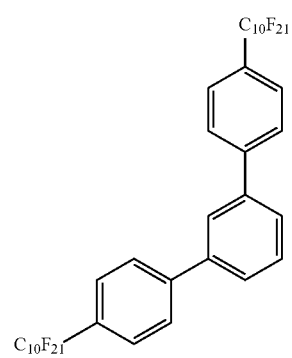
P1-30
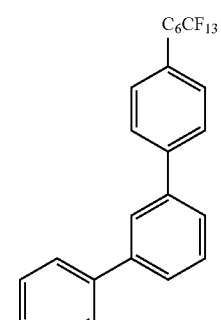
P1-31
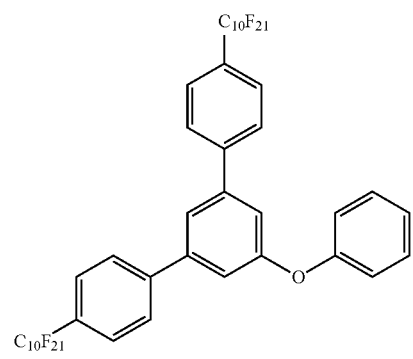
P1-32

P1-33 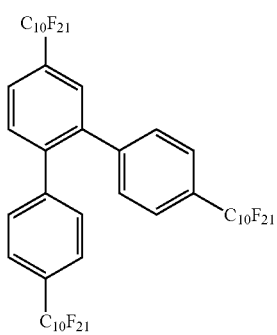
P1-37 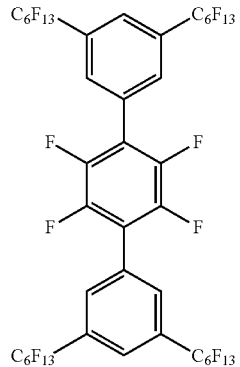
P1-34 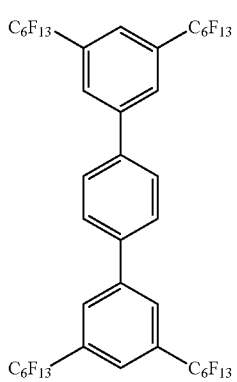
P1-38 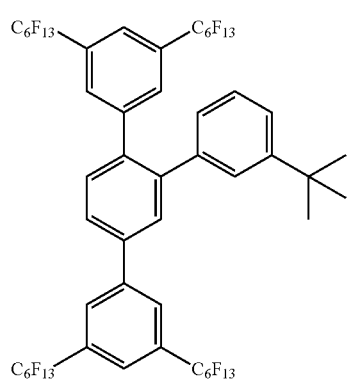
P1-35 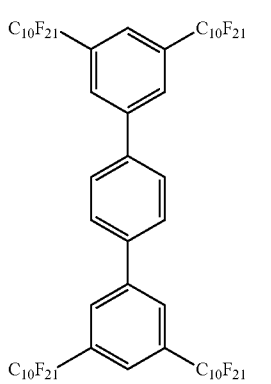
P1-39 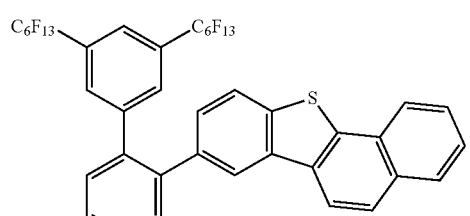
P1-36 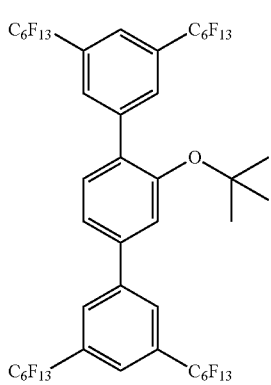
P1-40 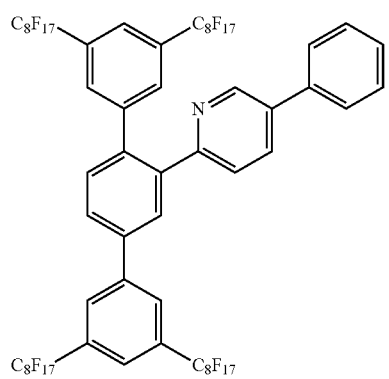

P1-41 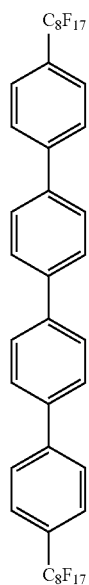
P1-42 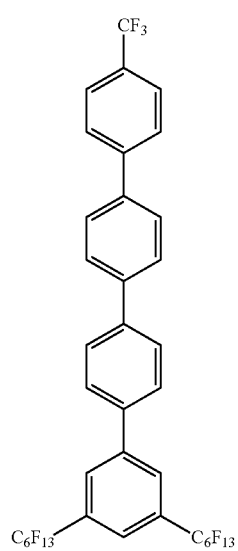
P1-43 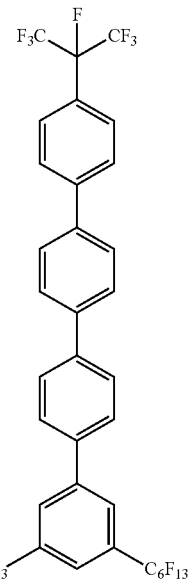
P1-44 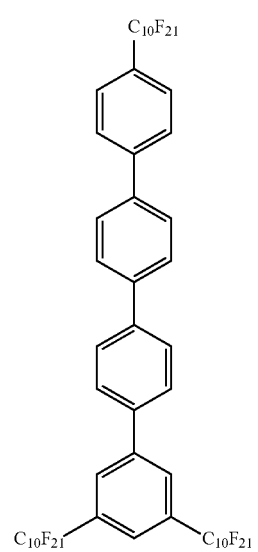
P1-45 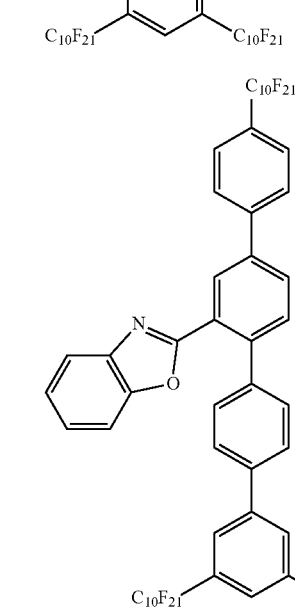

P1-46
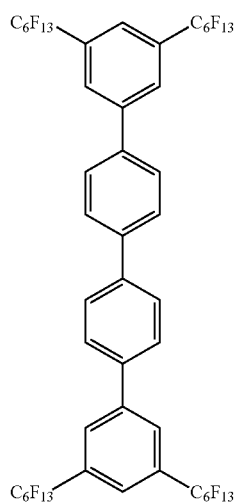
P1-49
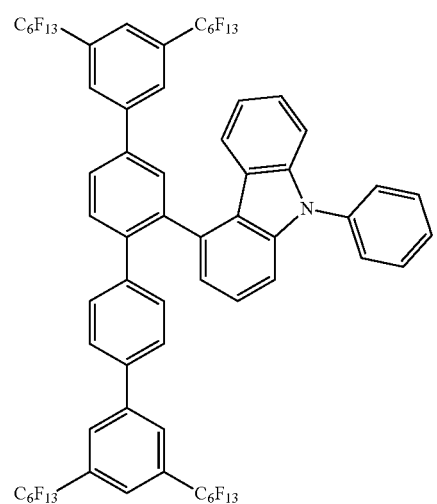
P1-47
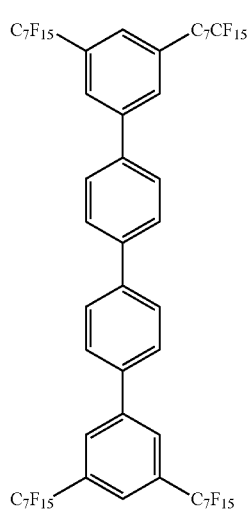
P1-50
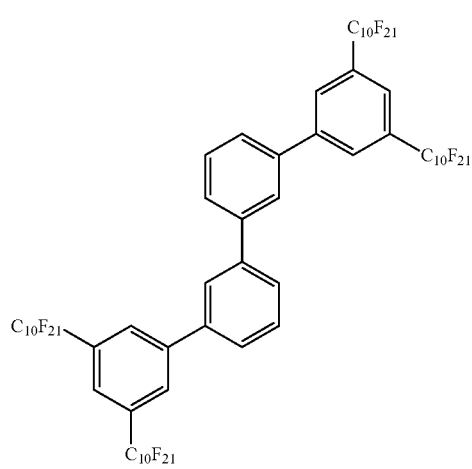
P1-48
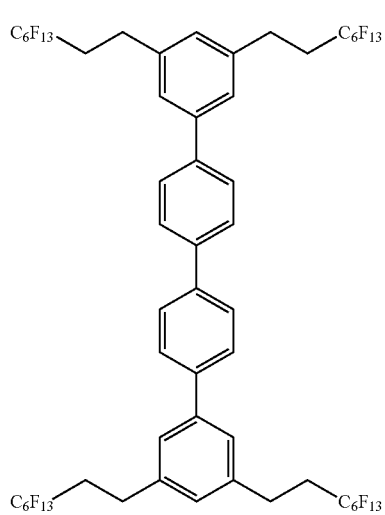
P1-51
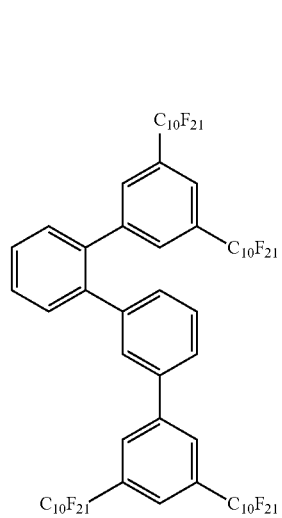

P1-52
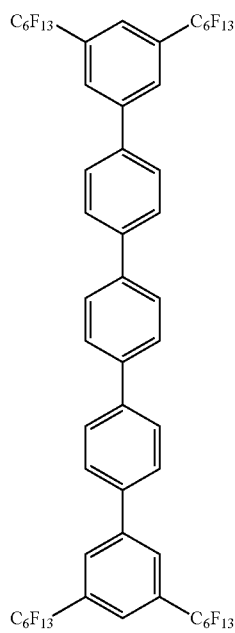
P1-53
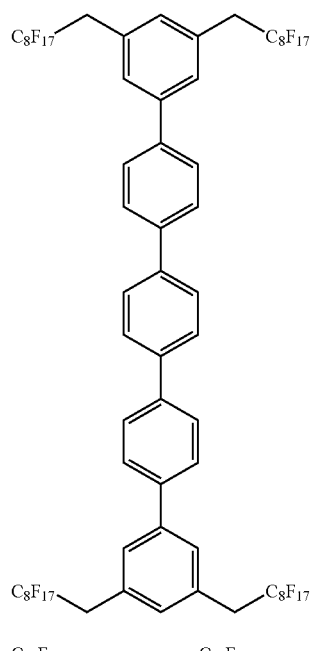
P1-54
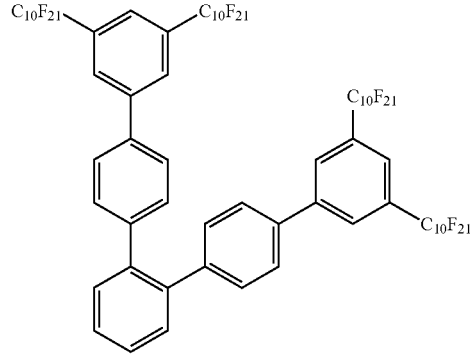
P1-55
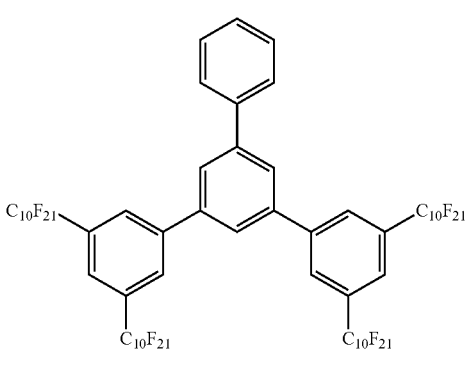
P1-56
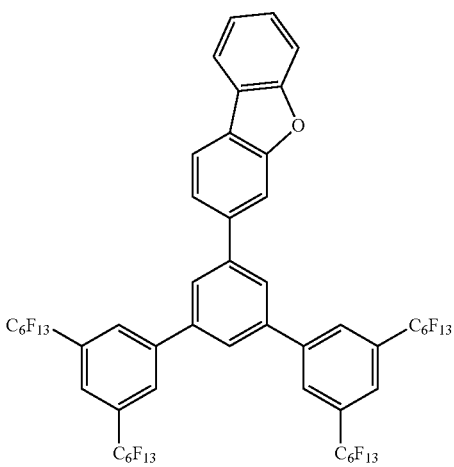
P1-57
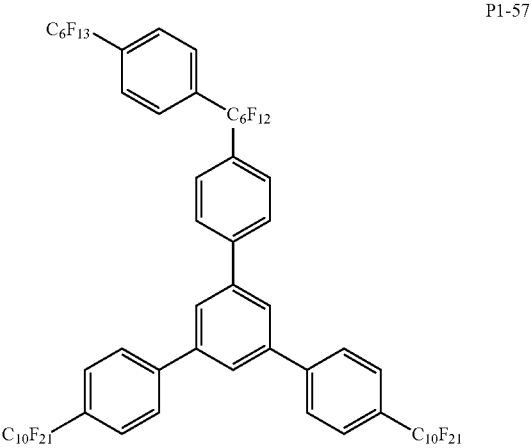

P1-58
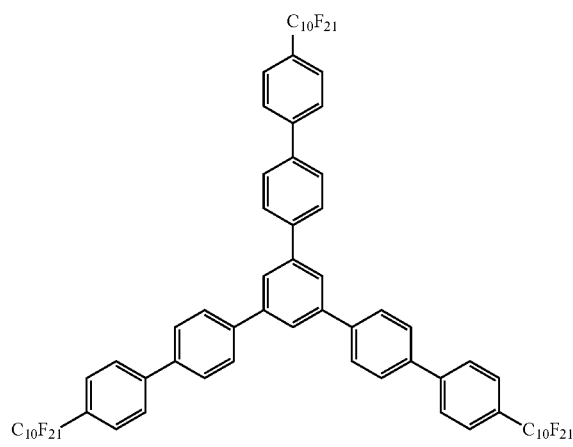
P1-59
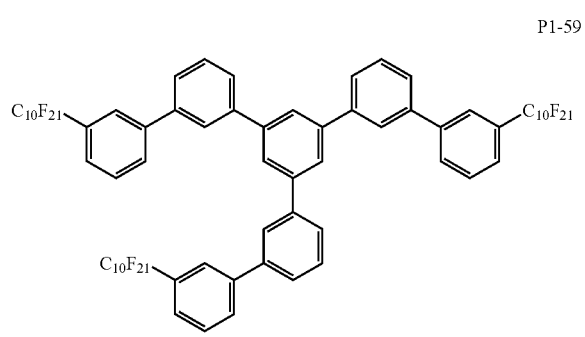
P1-60
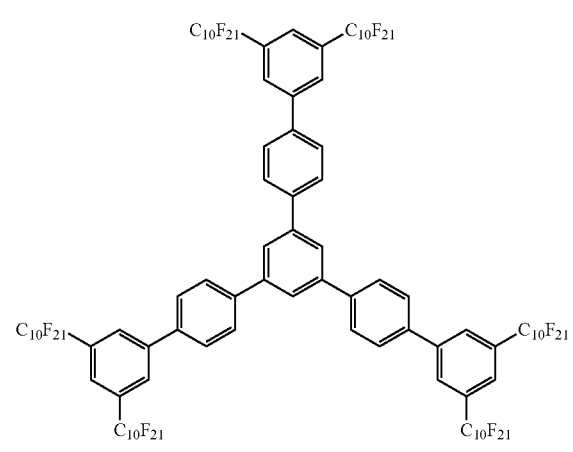
P1-61
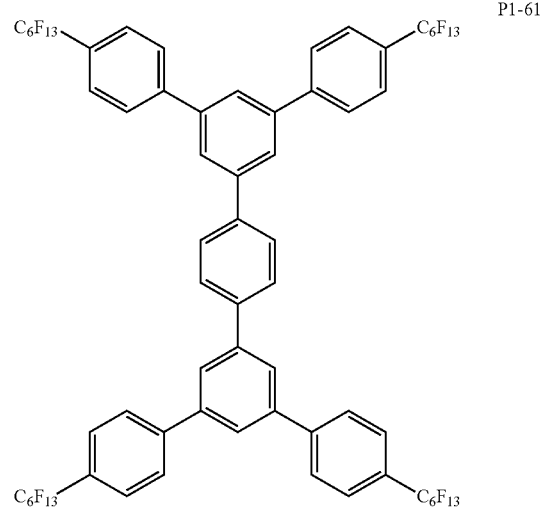
P1-62
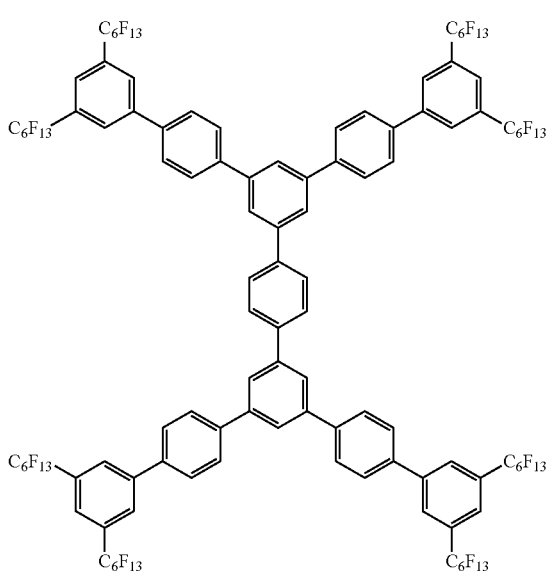
P1-63
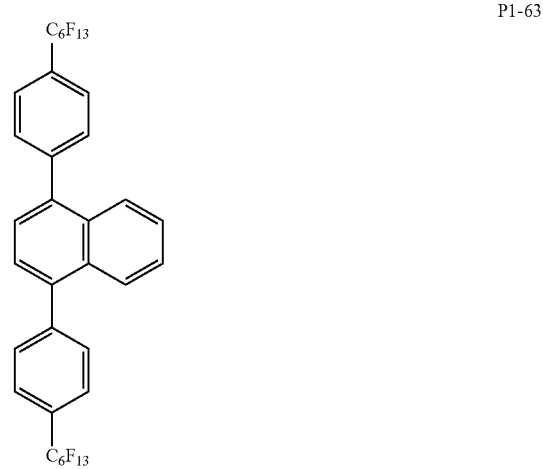

P1-64
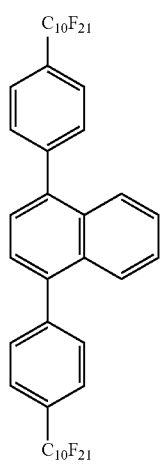
P1-65
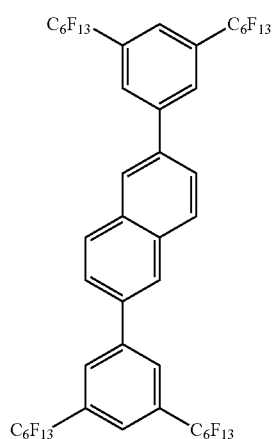
P1-66
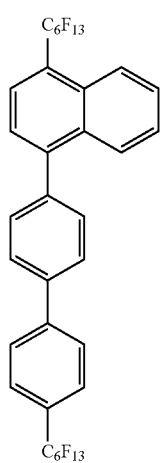
P1-67
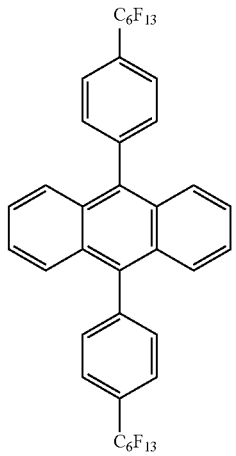
P1-68
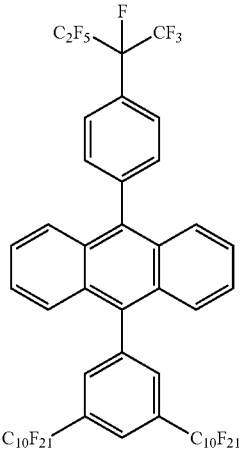
P1-69
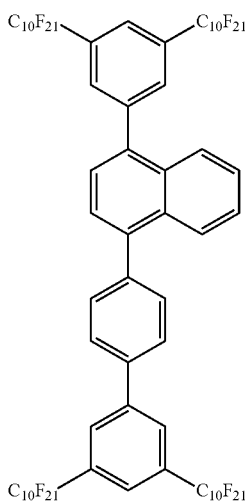

P1-70 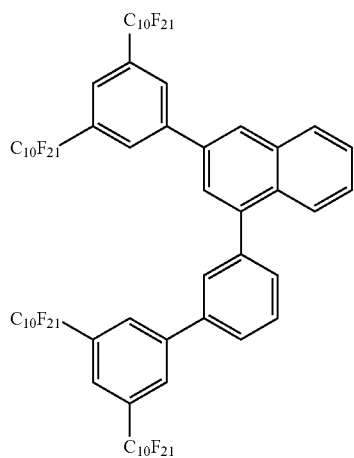
P1-71 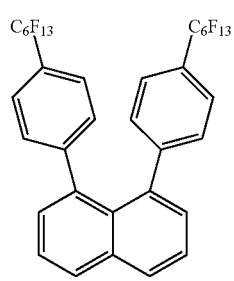
P1-72 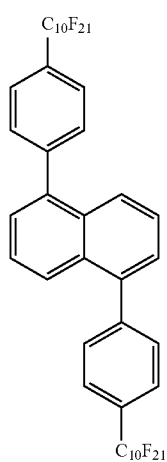
P1-73 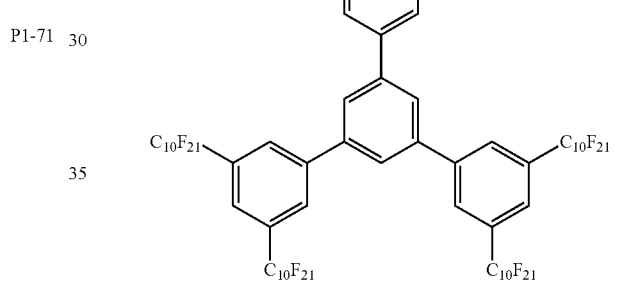
P1-74 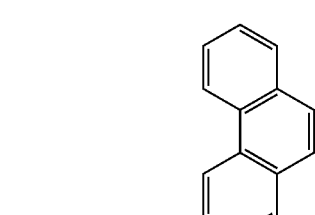
P1-75 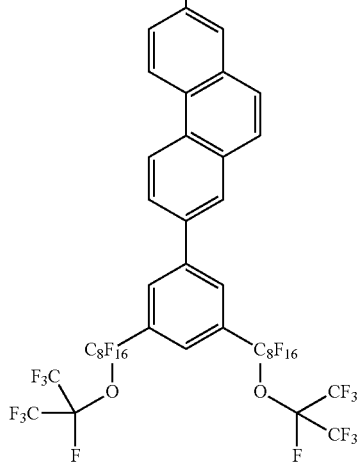

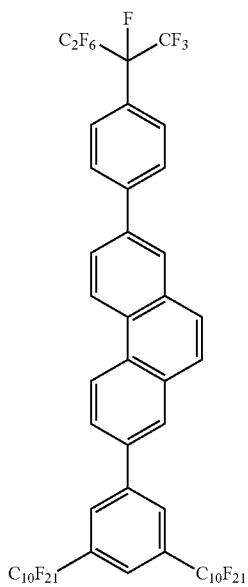
P1-76
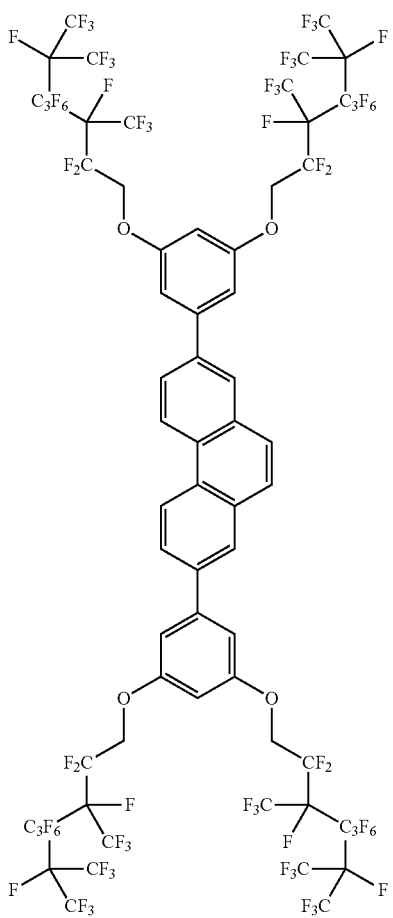
P1-77
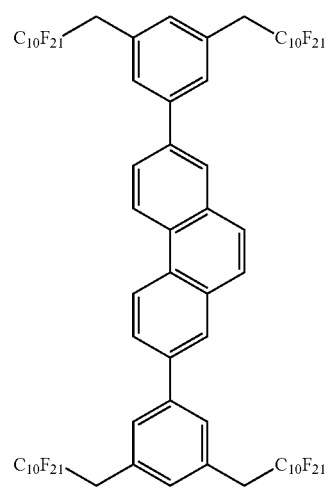
P1-78
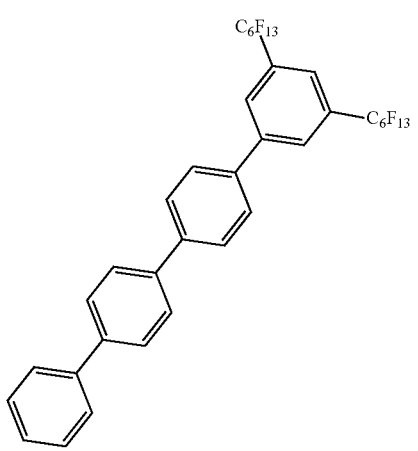
P1-79
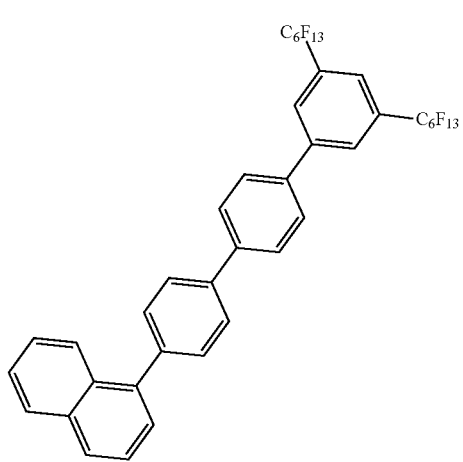
P1-80

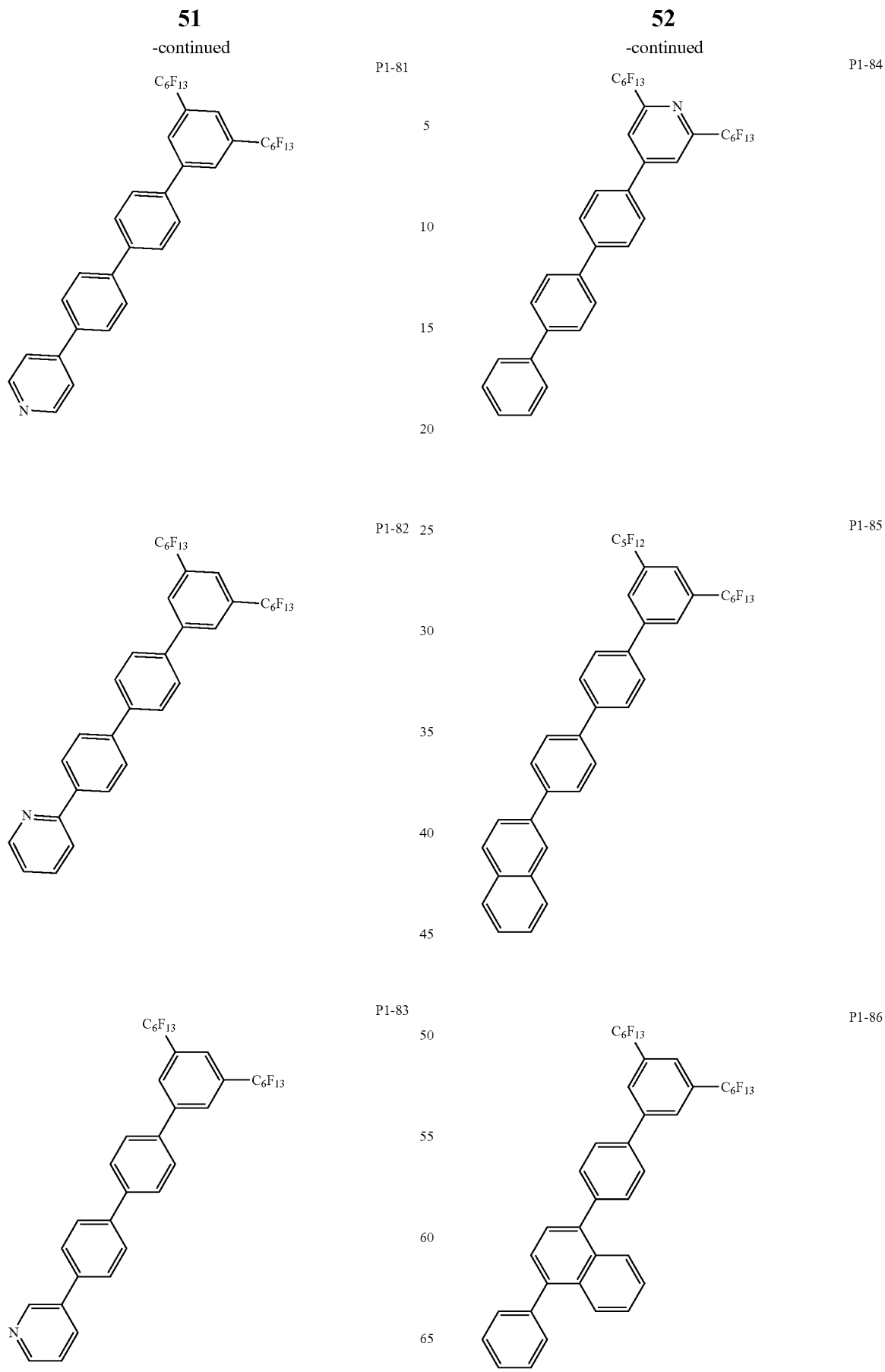

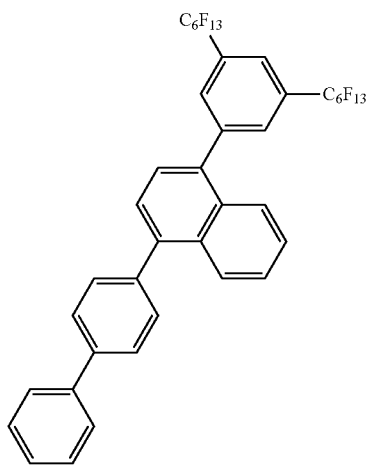
P1-87
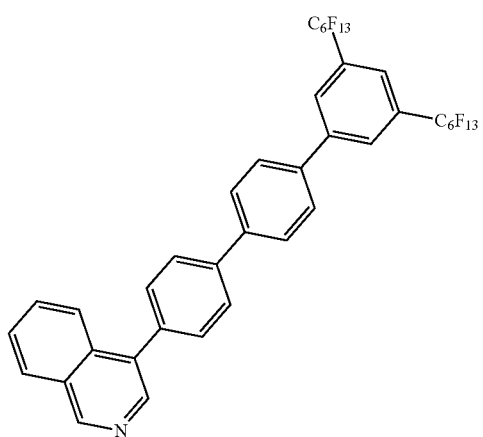
P1-90
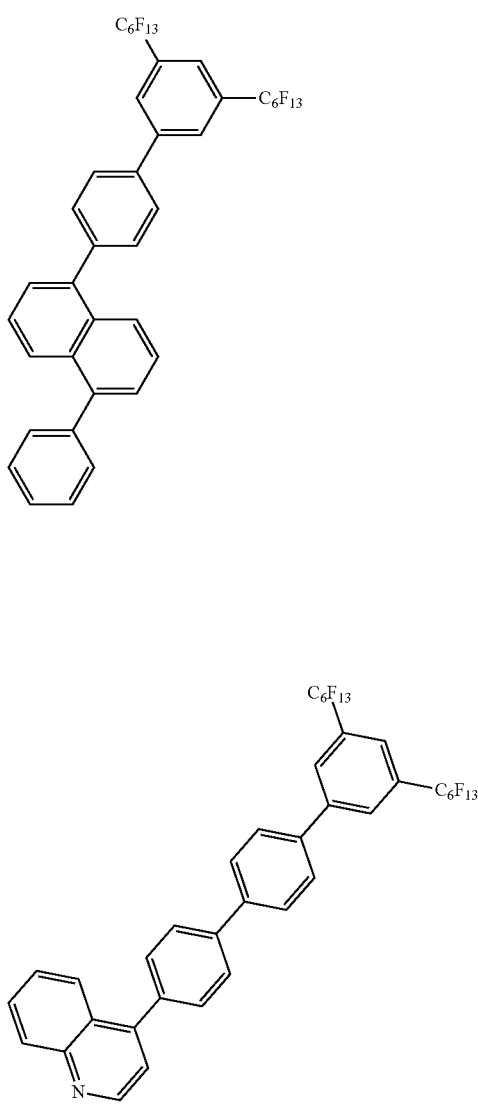
P1-88
P1-89
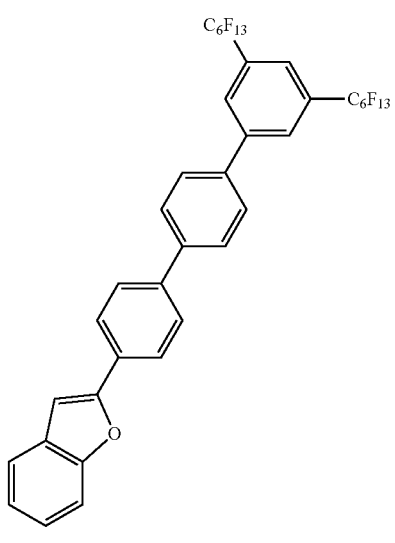
P1-91
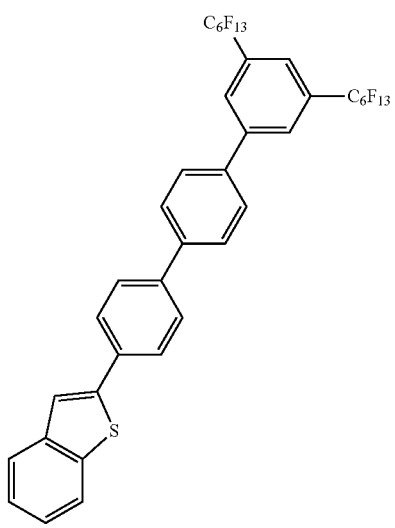
P1-92

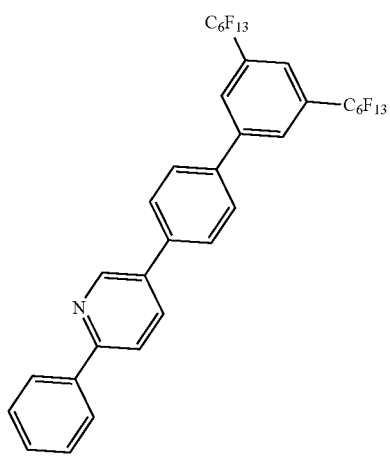
P1-93
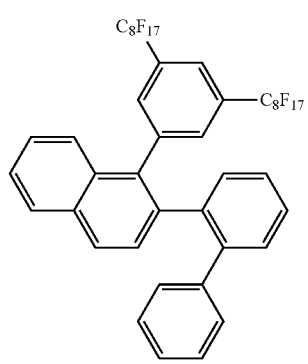
P1-96
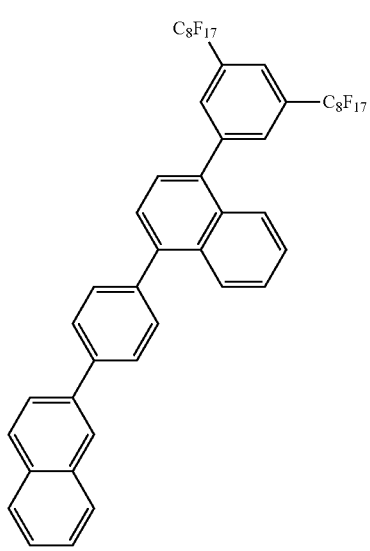
P1-94
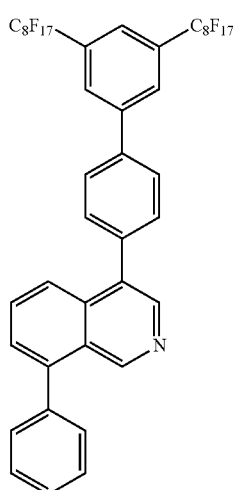
P1-97
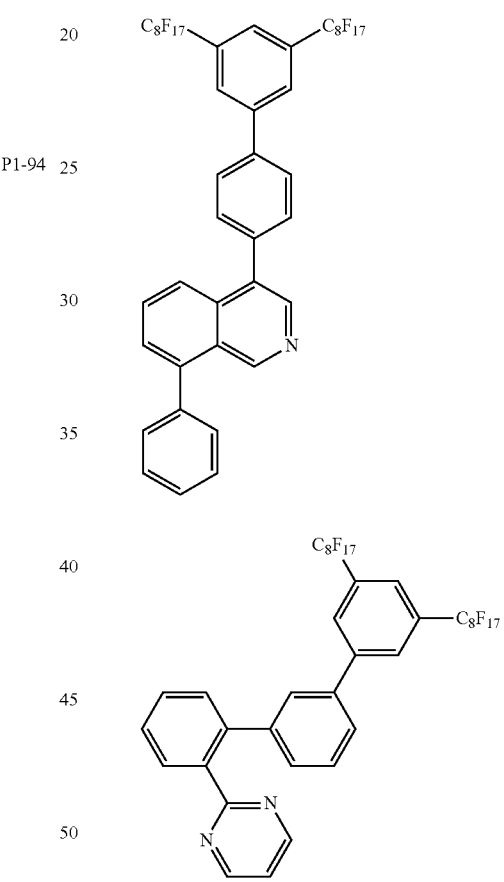
P1-98
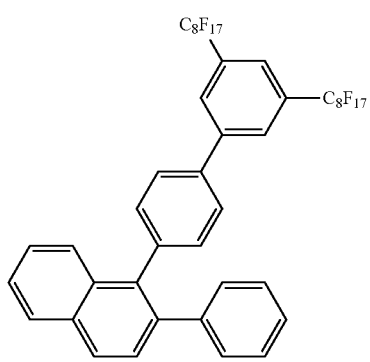
P1-95
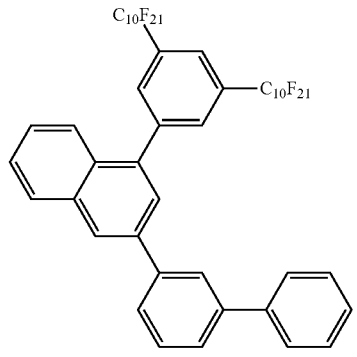
P1-99

-continued
P1-100
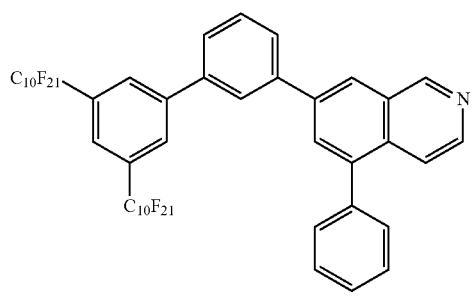
P1-103
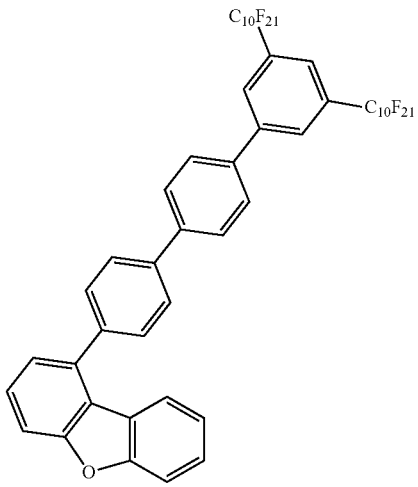
P1-101
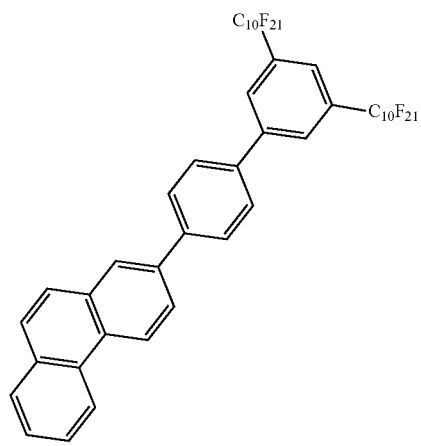
P1-104
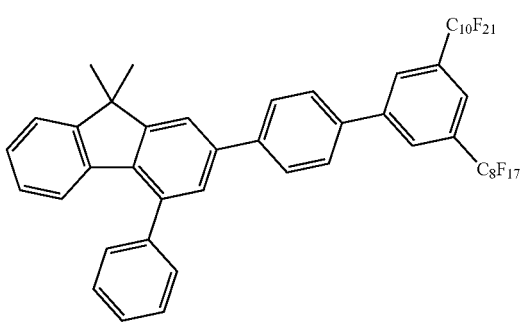
P1-102
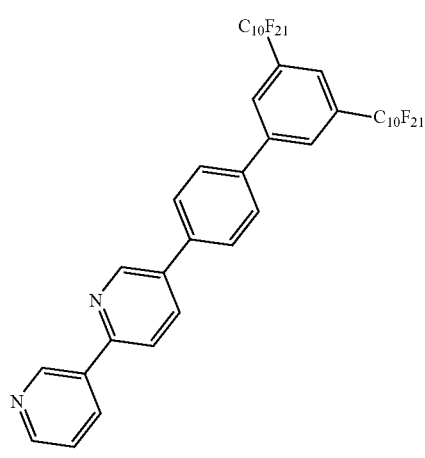
P1-105
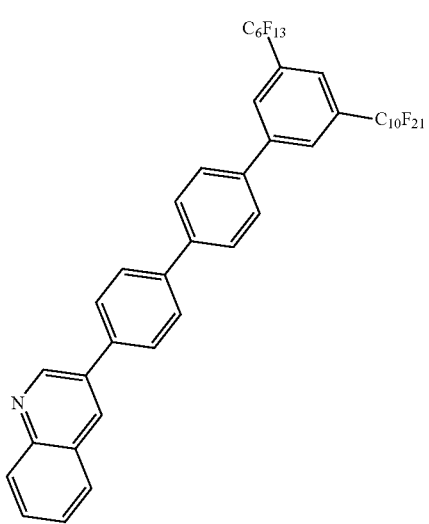

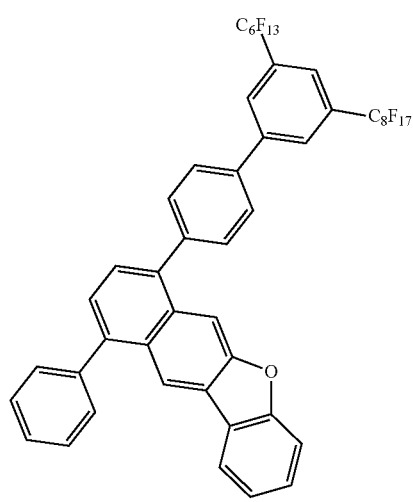
P1-106
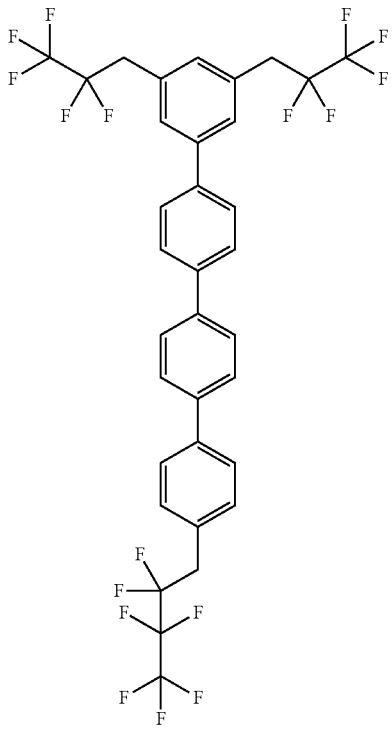
P1-108
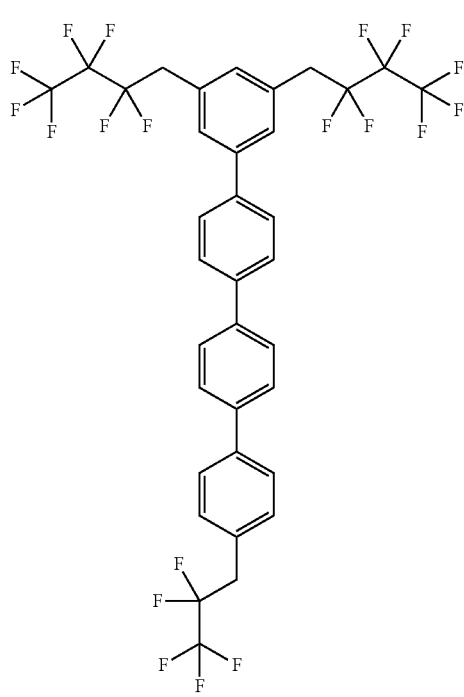
P1-107
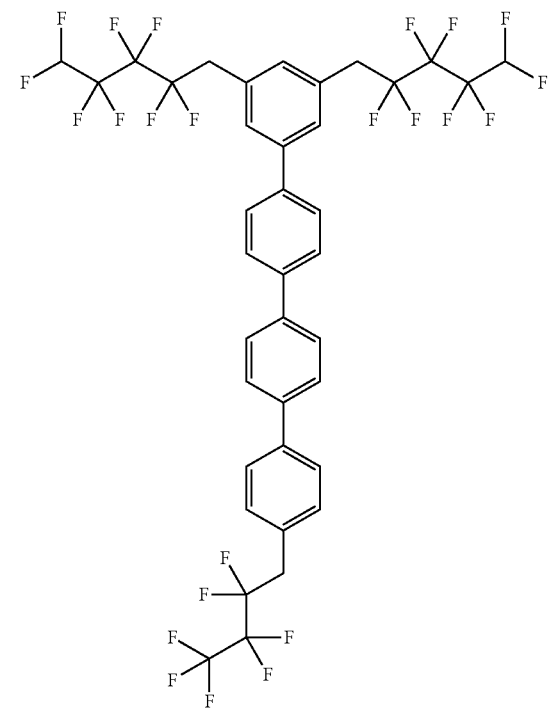
P1-109

-continued
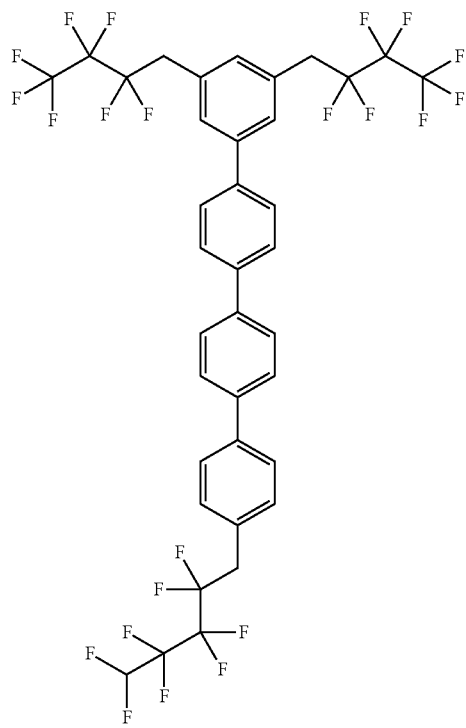
P1-110
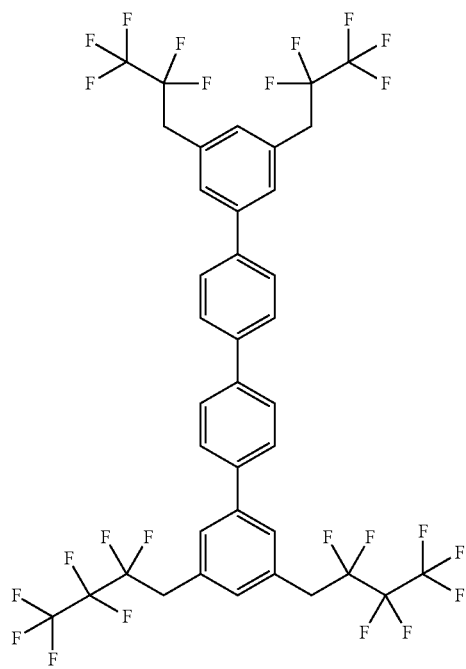
P1-111
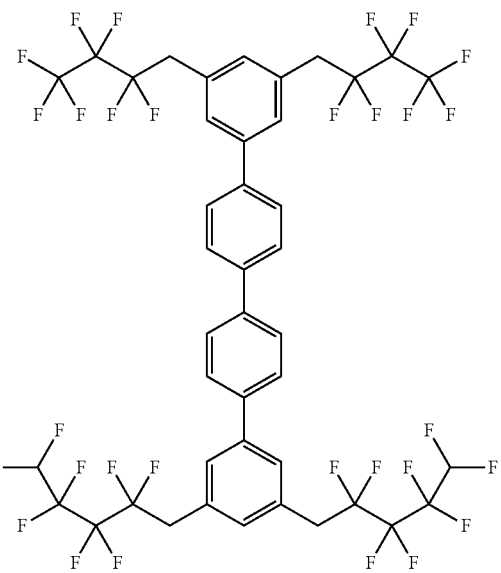
P1-112

-continued
P1-113
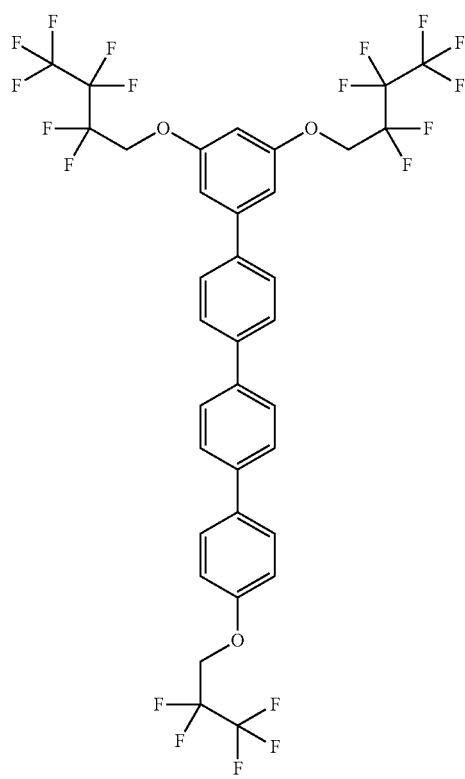
P1-114
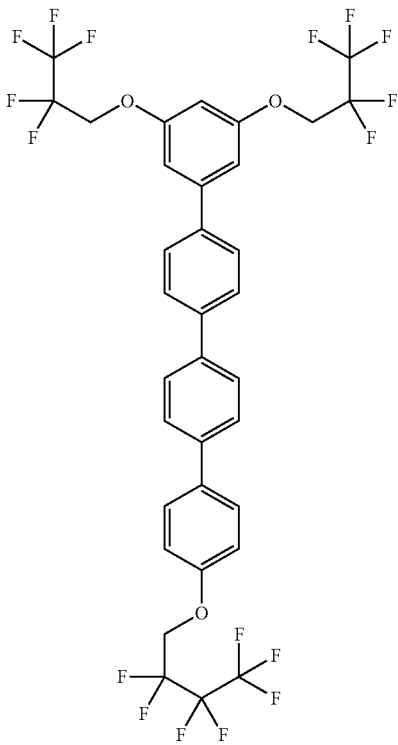
P1-115
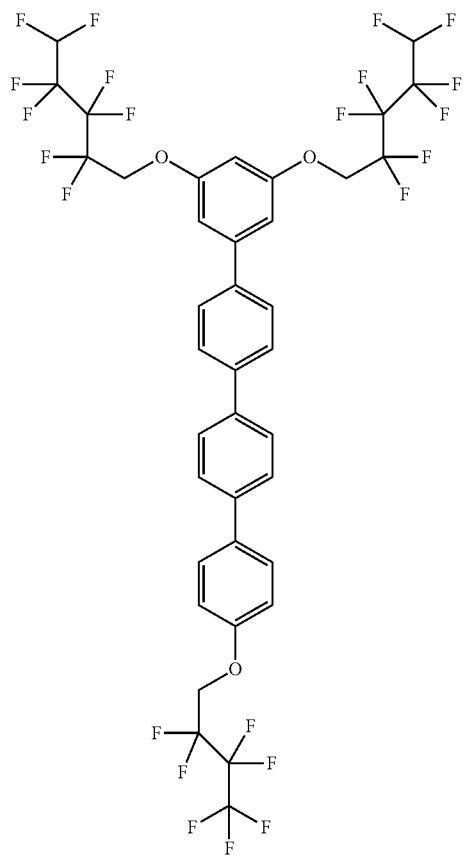
P1-116
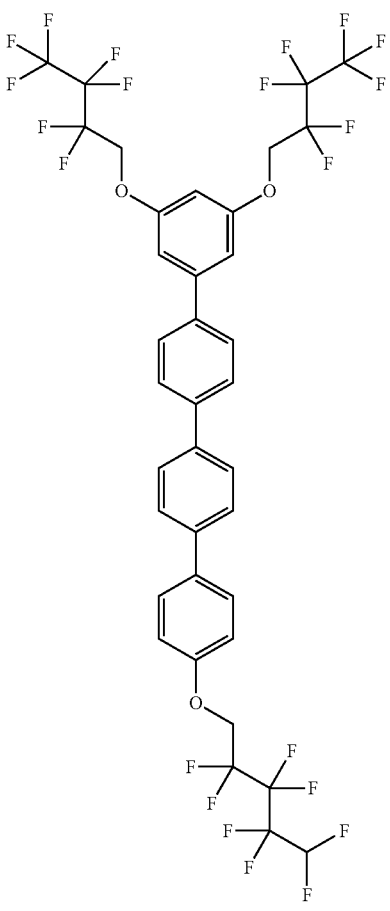

-continued
P1-117
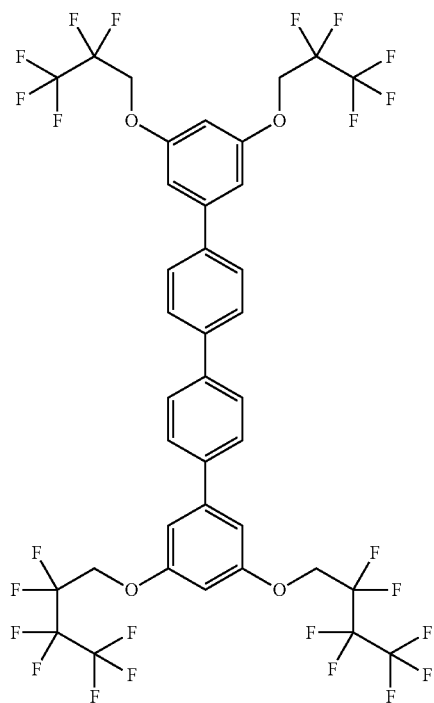
P1-118
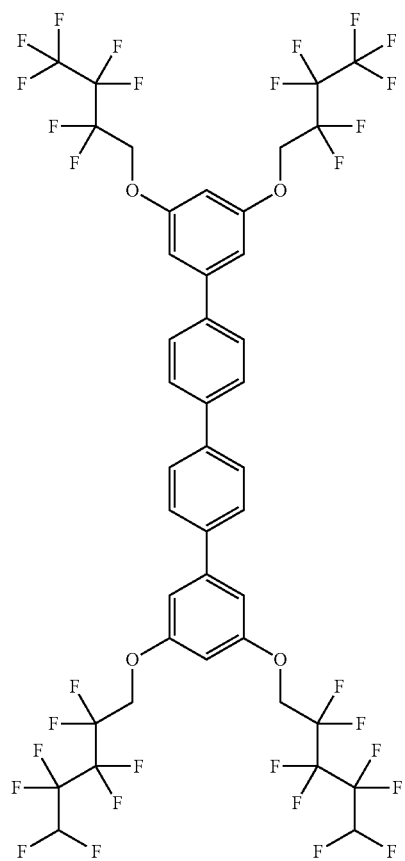
P1-119
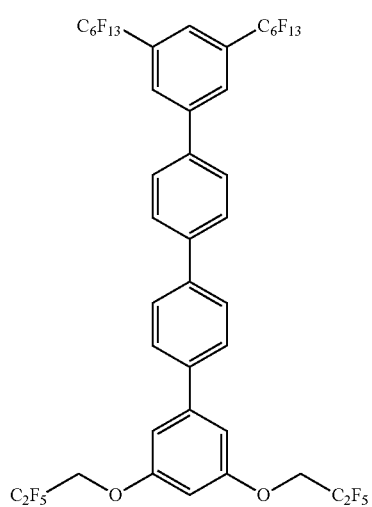
P1-120
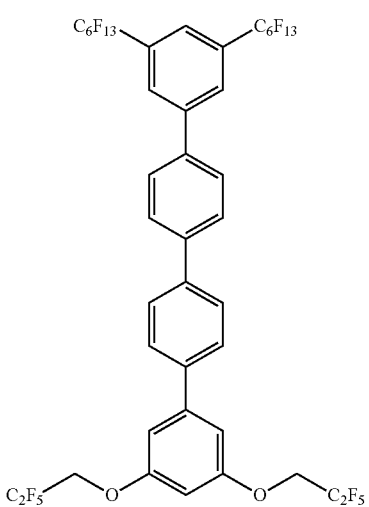

-continued
P1-121 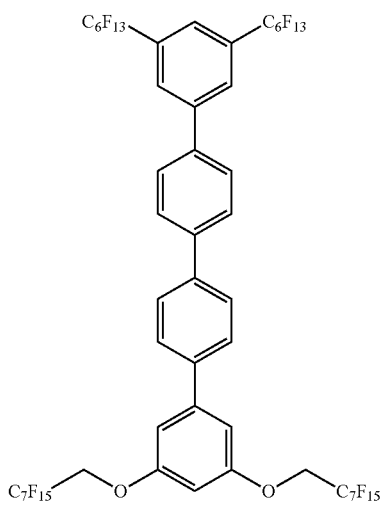
P1-122 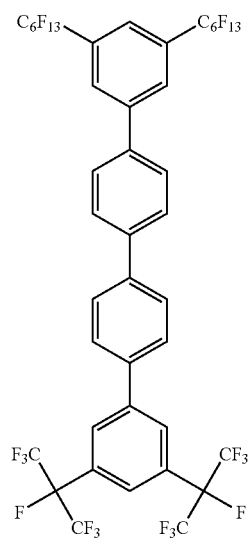
P2-1 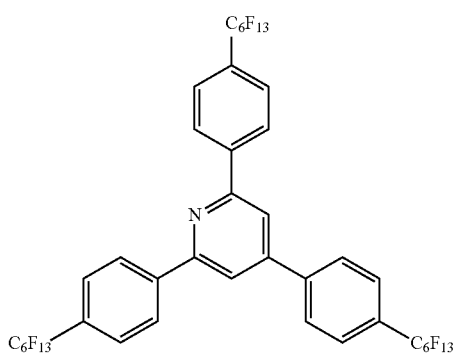
P2-2 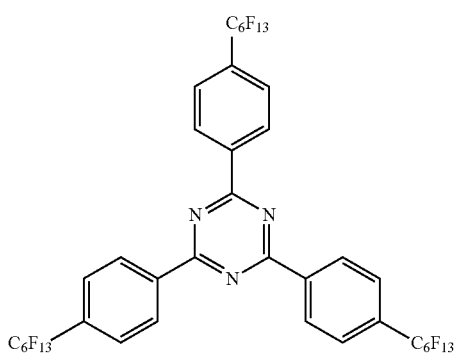
P2-3 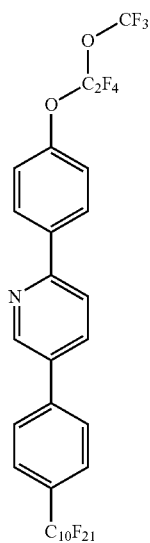
P3-1 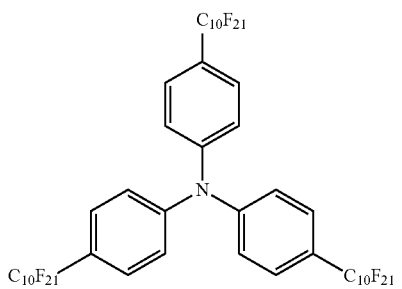

-continued
P3-2
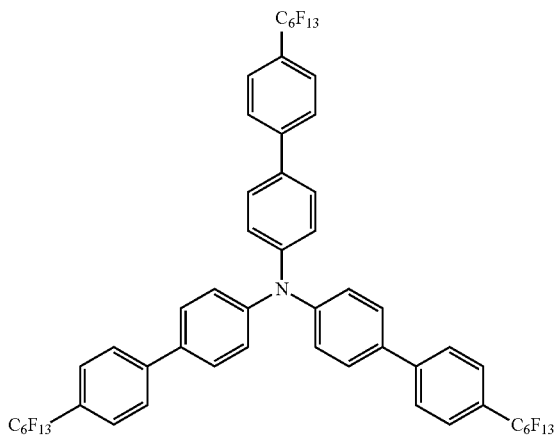
P3-3
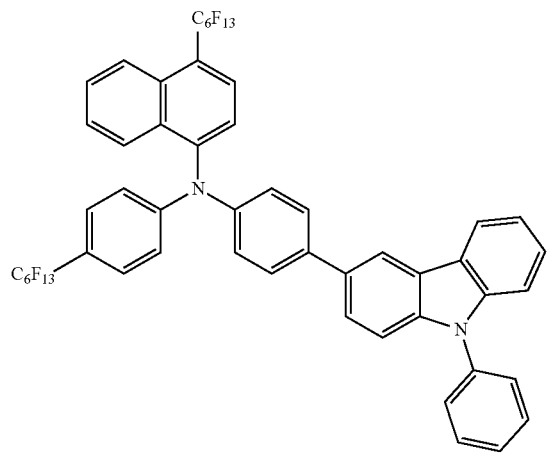
P3-4
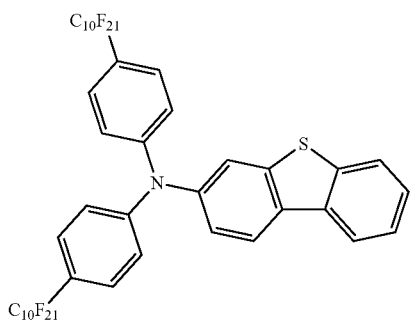
P3-5
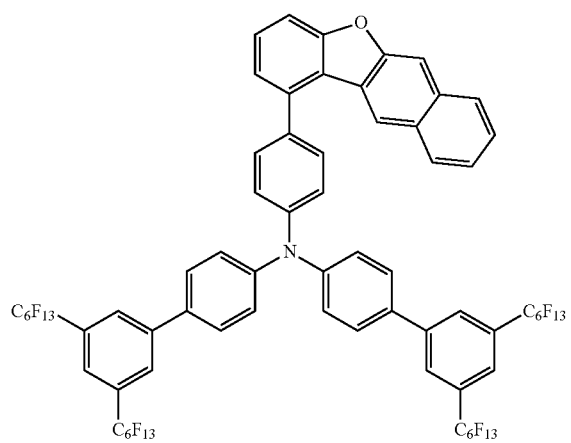
P3-6
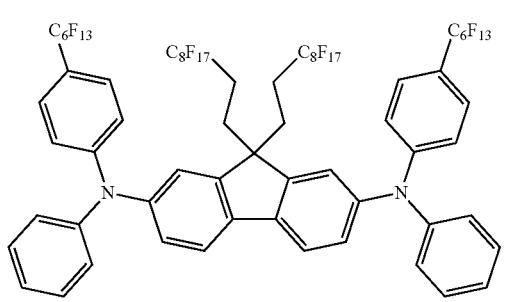
P3-7
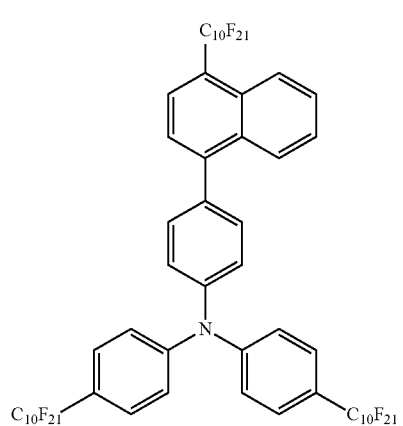

-continued
P3-8
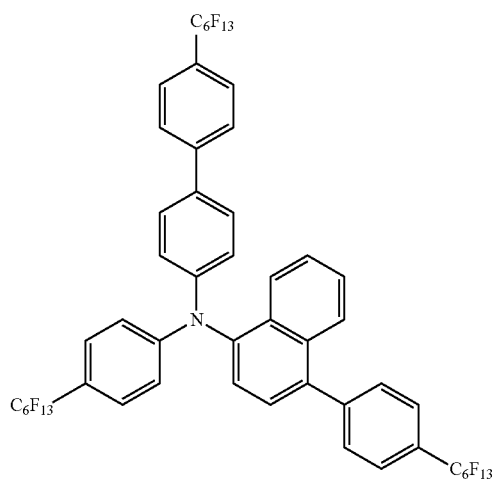
P4-1
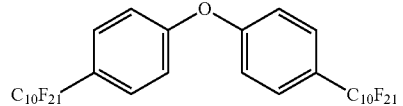
P4-2
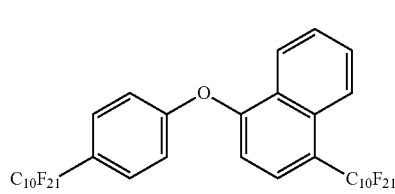
P4-3
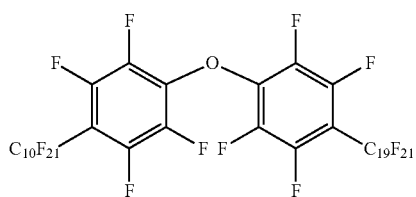
P4-4
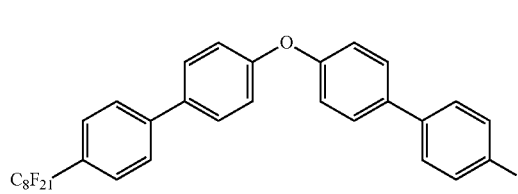
P4-5
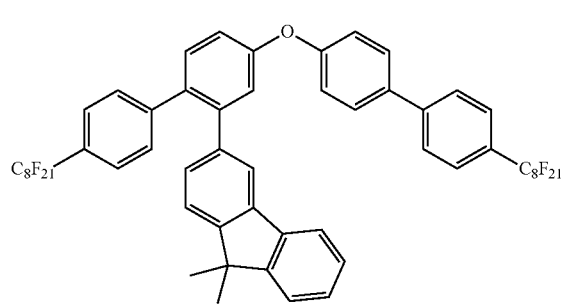
P4-6
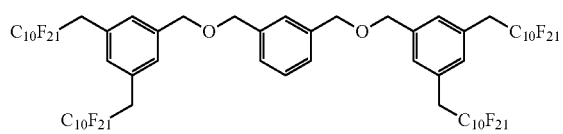
P5-1
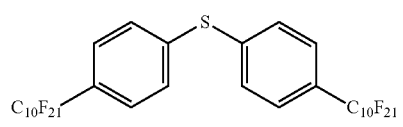
P5-2
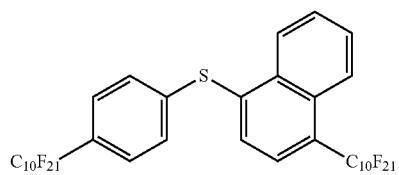
P5-3
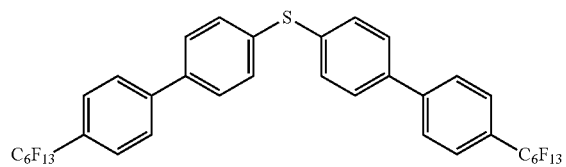
P5-4
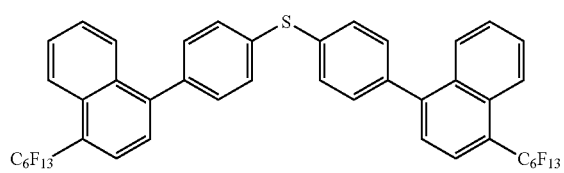
P5-5
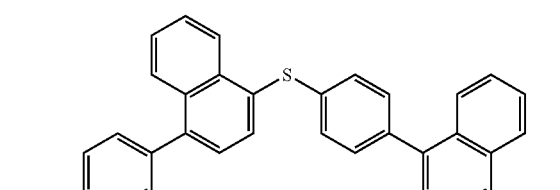

P5-6
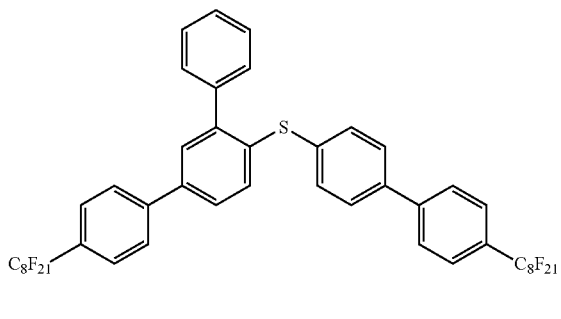
P6-1
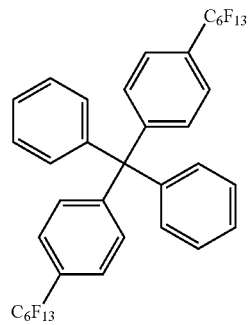
P6-3
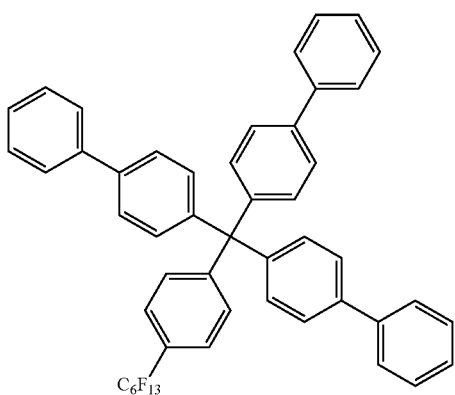
P6-2
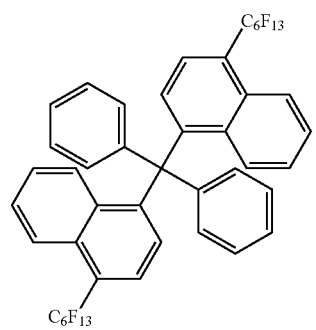
P6-4
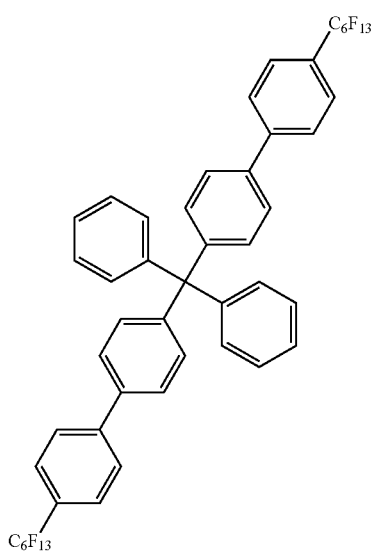
P6-5
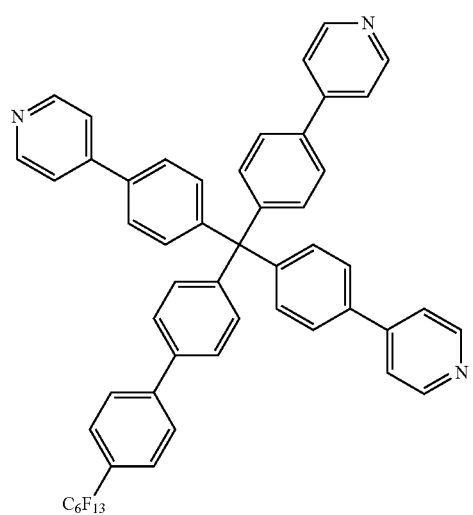

P7-1 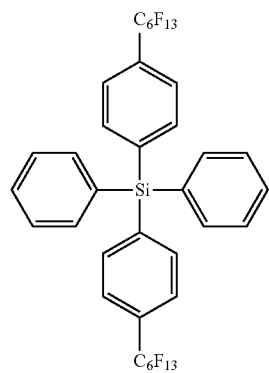
P7-2 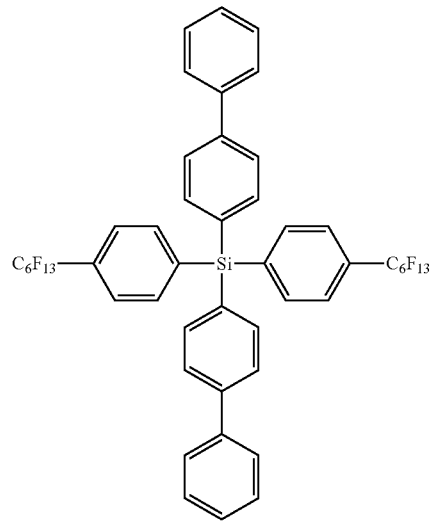
P7-4 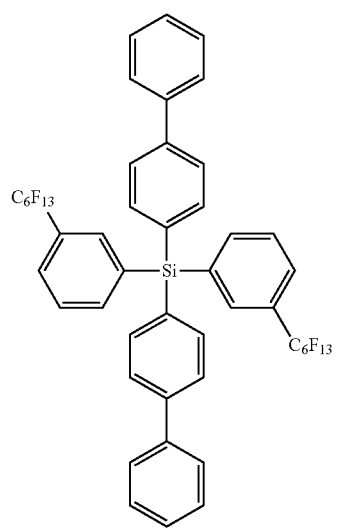
P7-3 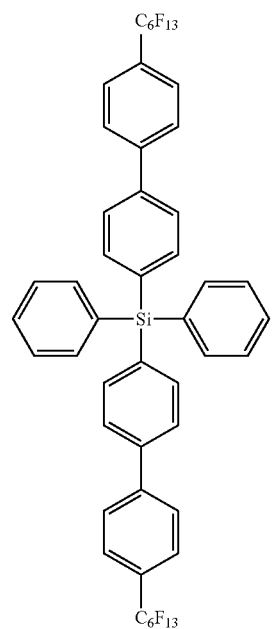

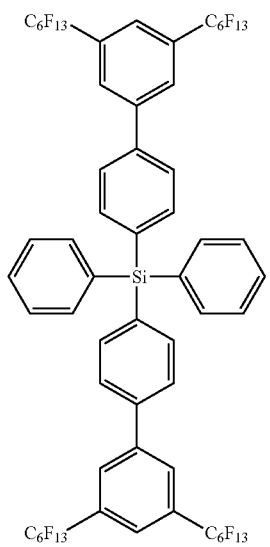
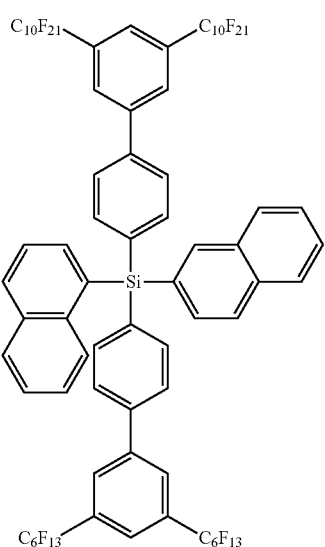
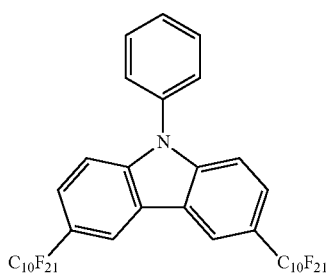
P7-5
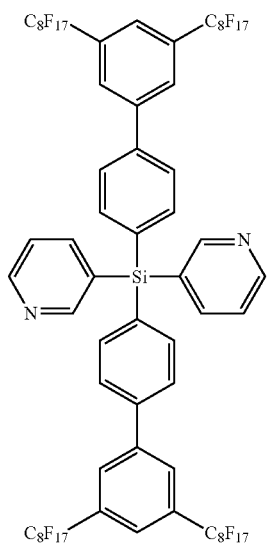
P7-6
P7-7
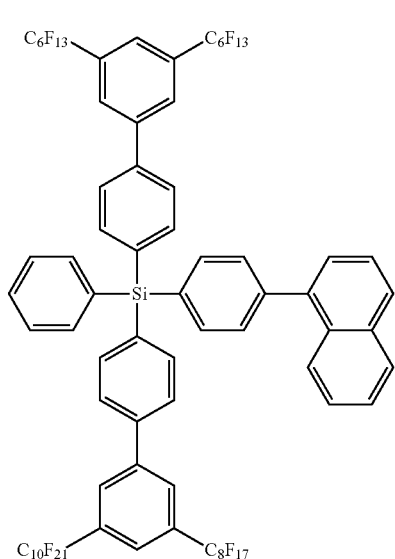
P7-8
P8-1
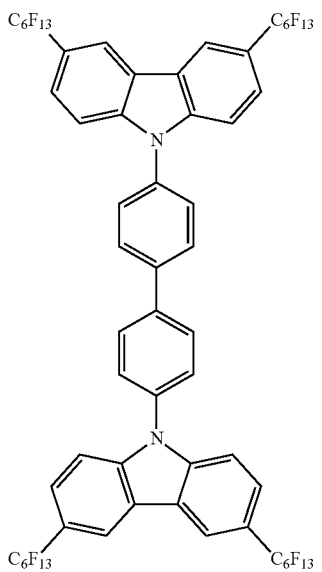
P8-2

-continued
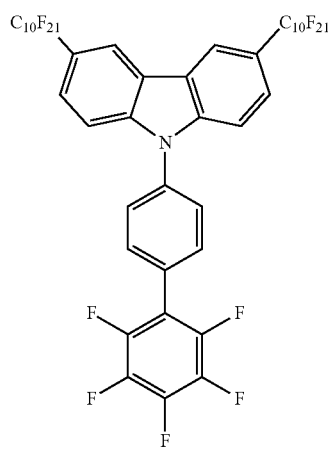
P8-3
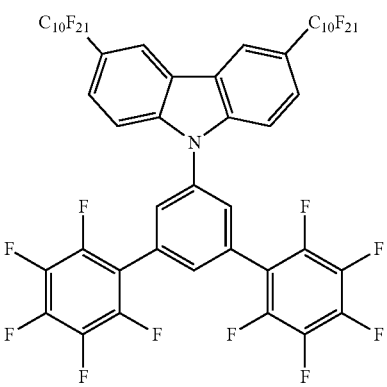
P8-4
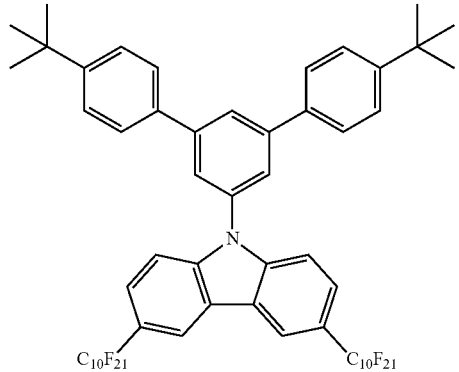
P8-5
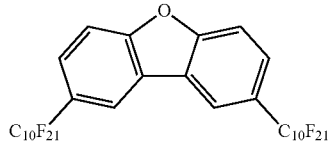
P9-1
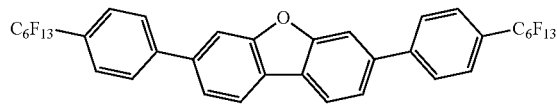
P9-2
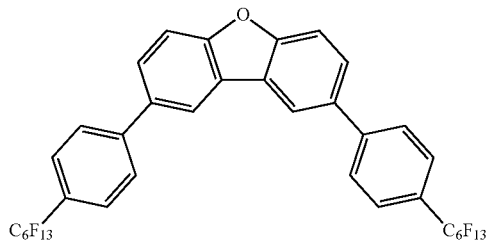
P9-3
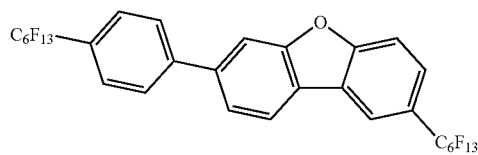
P9-4
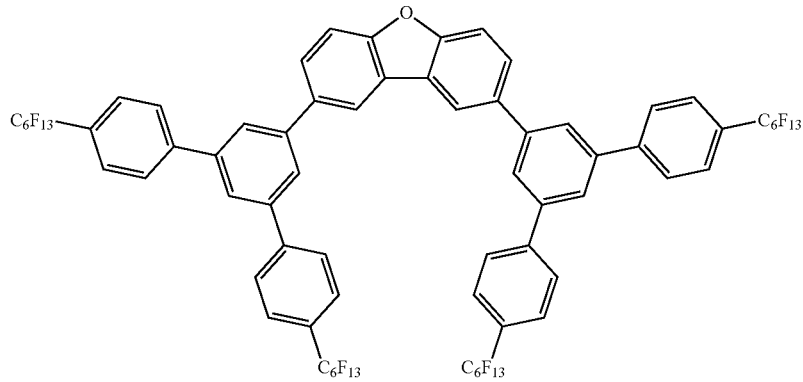
P9-5

-continued
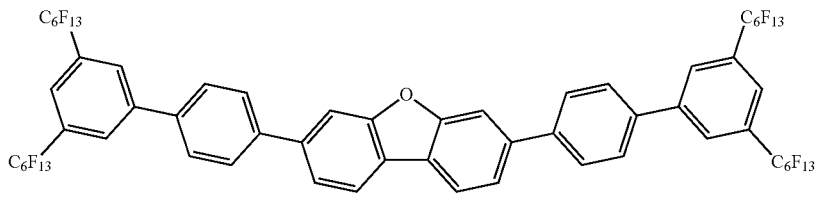
P9-6
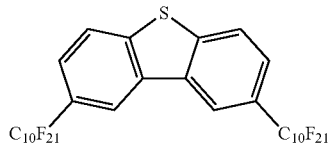
P9-7
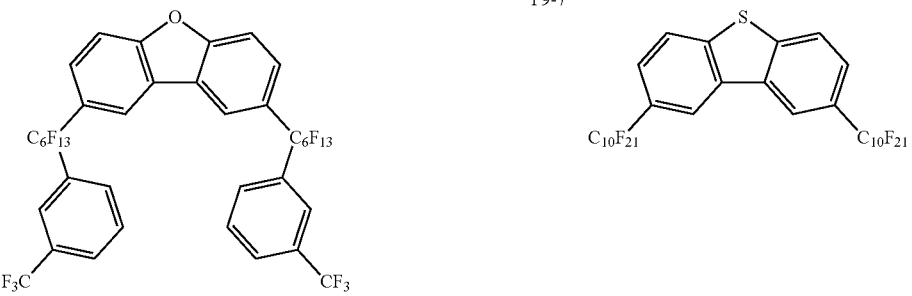
P10-1
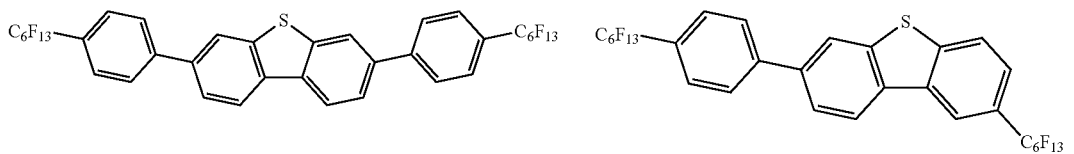
P10-2
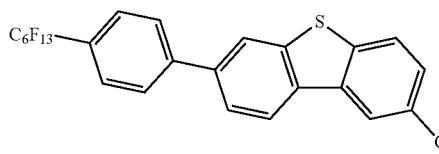
P10-3
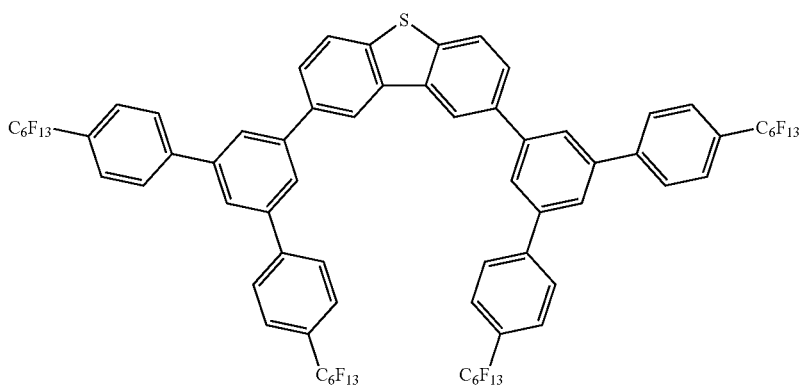
P10-4
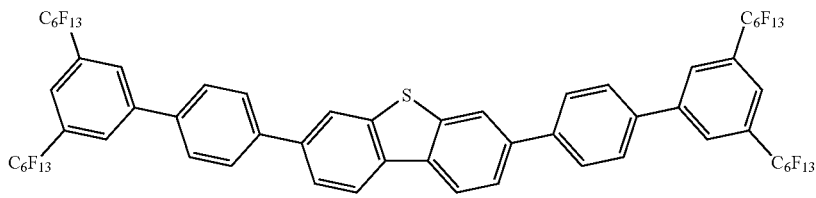
P10-5
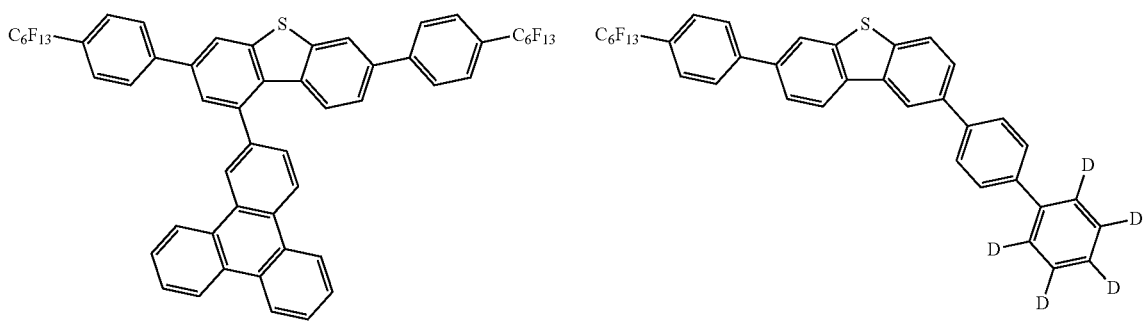
P10-6
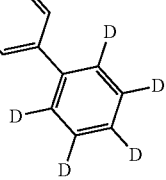
P10-7

-continued
P11-1
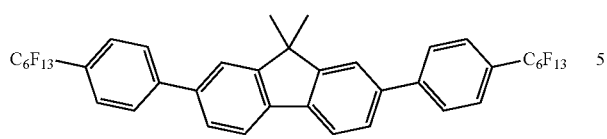
P11-2
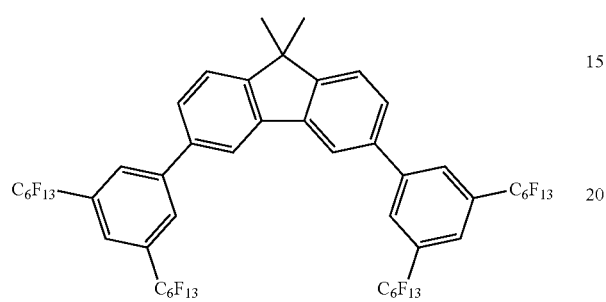
P11-3
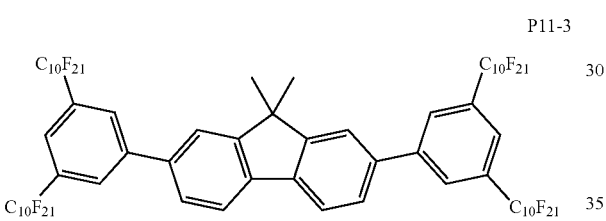
P11-4
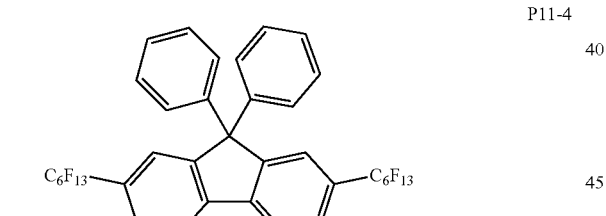
P11-5
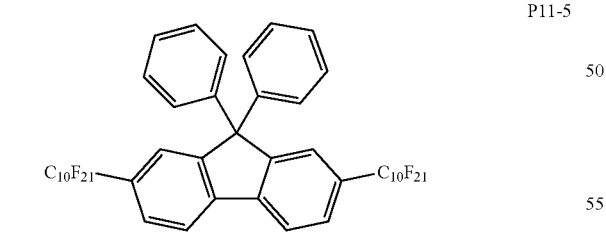
P11-6
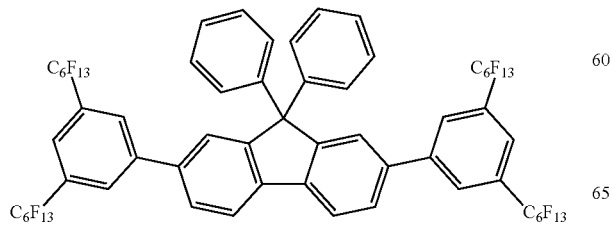
P11-7
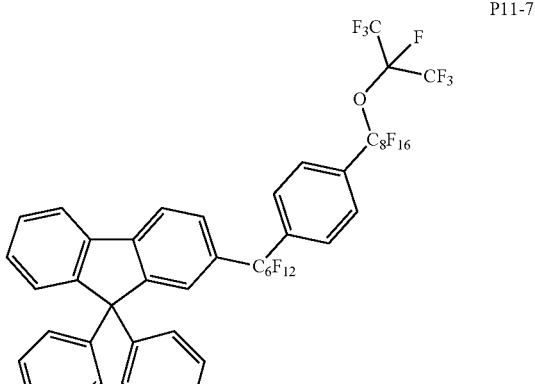
P11-8
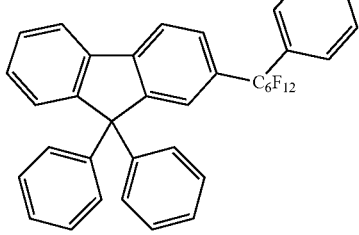
P11-9
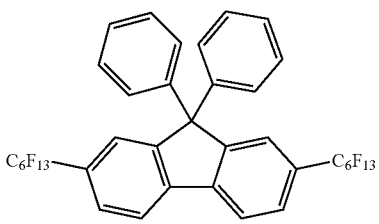
P11-10
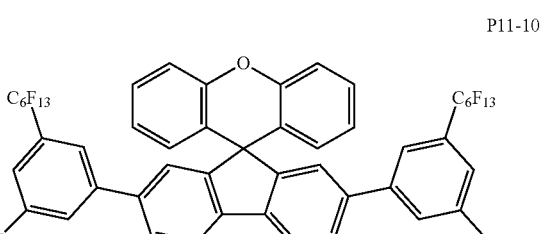
P11-11
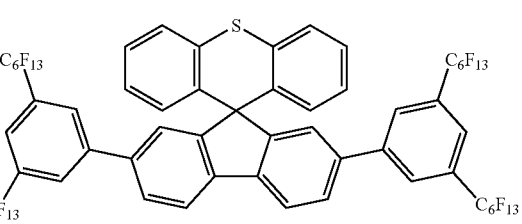

P11-12
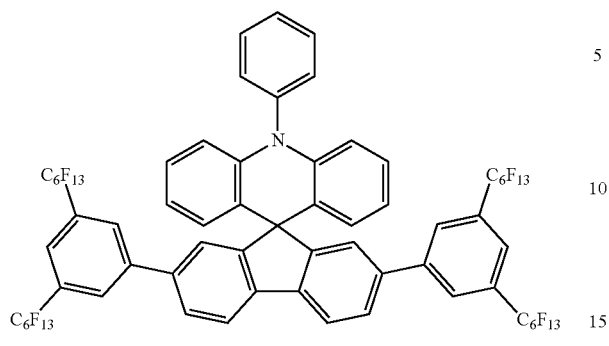
P13-2
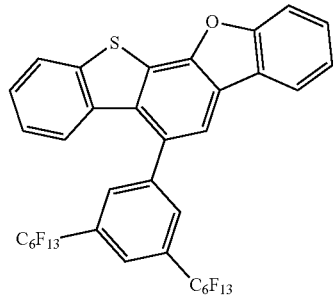
P12-1
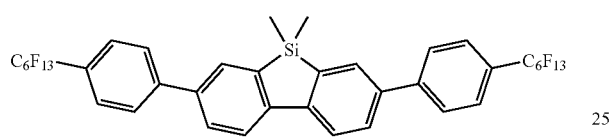
P13-3
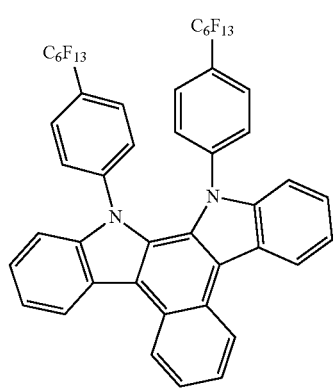
P12-2
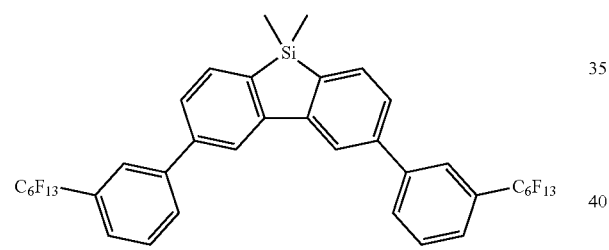
P13-4
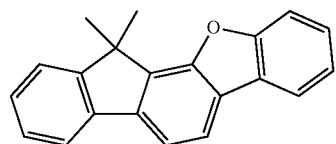
p12-3
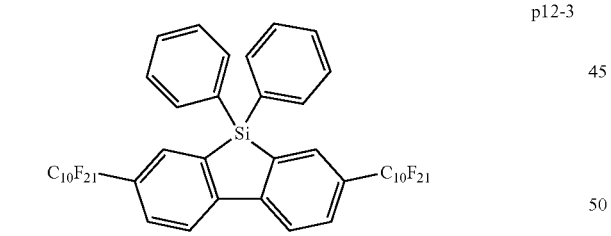
P13-1
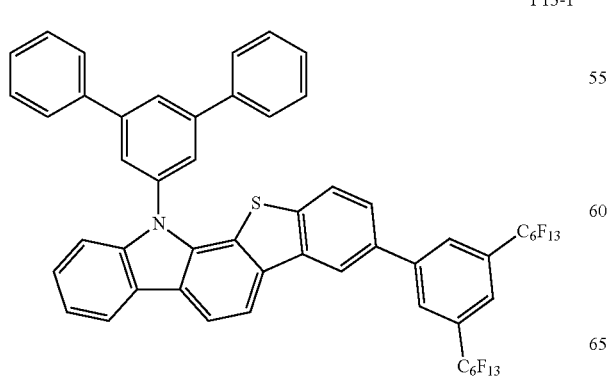
P14-1
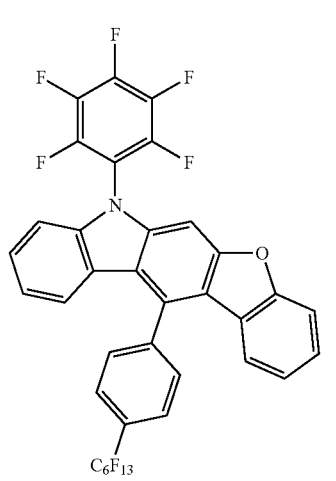
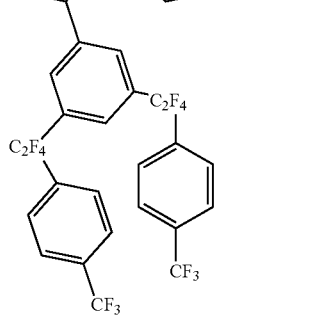

-continued
P14-2
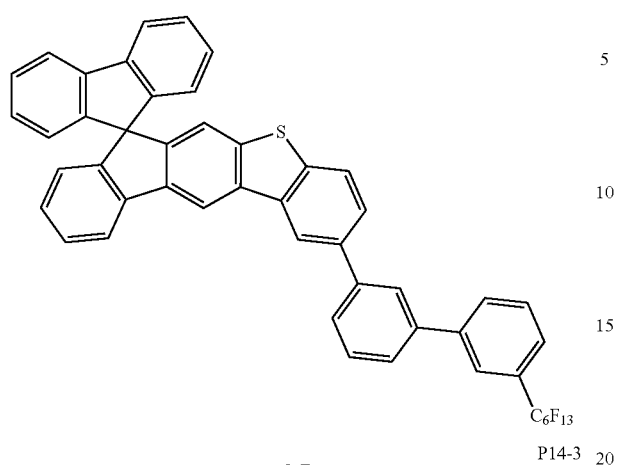
P14-3
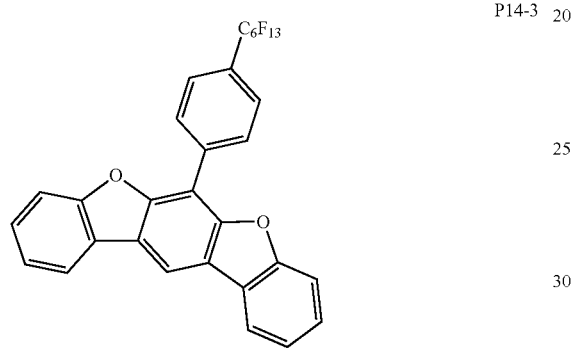
P14-4
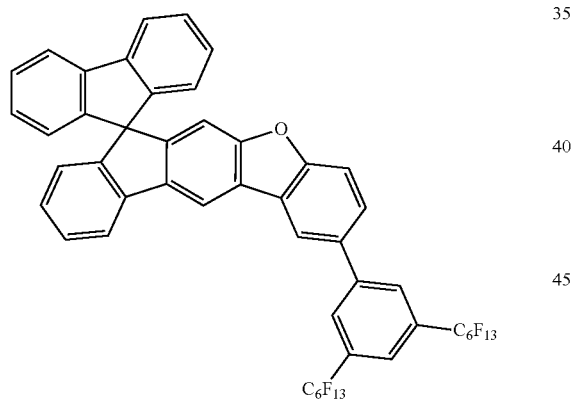
P15-1
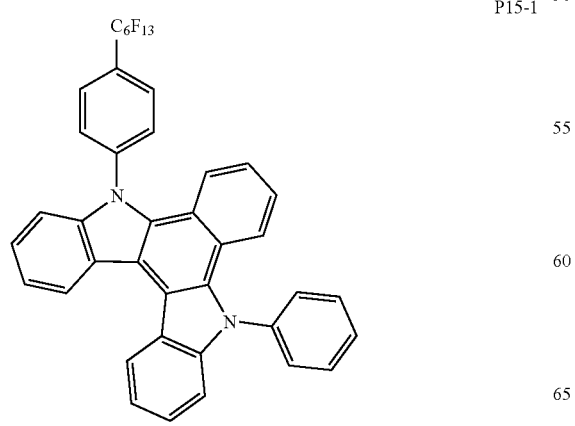
-continued
P15-2
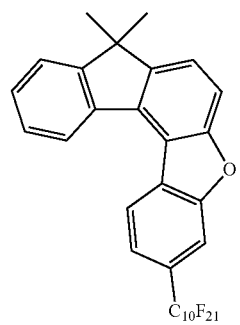
P15-3
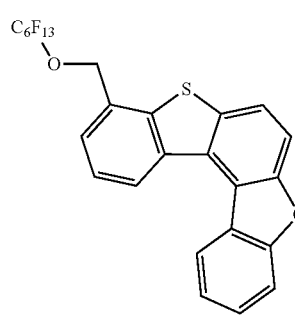
P15-4
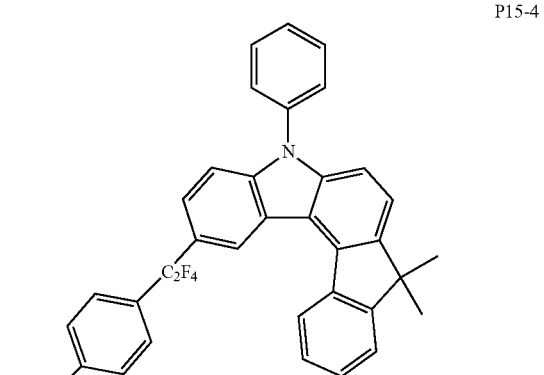
P16-1
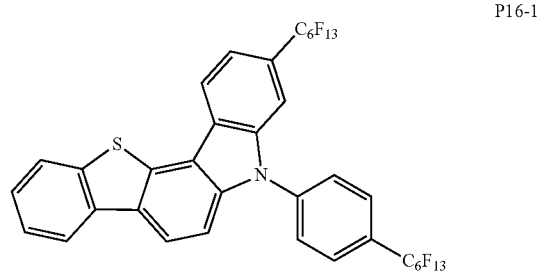
P16-2
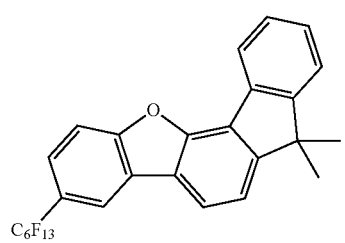

-continued

P16-3 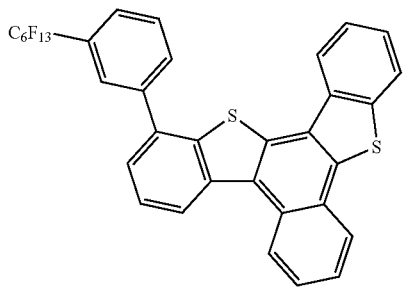

P16-4 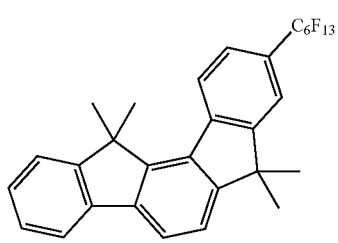

P17-1 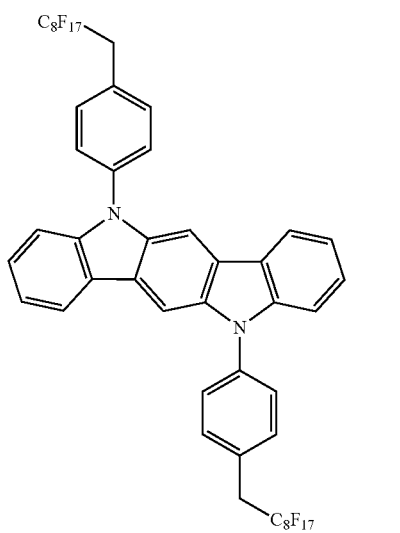

P17-2 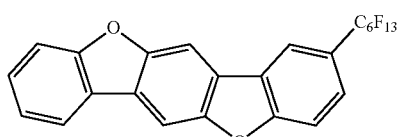

P17-3 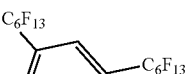

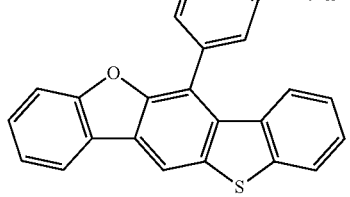

-continued

P17-4 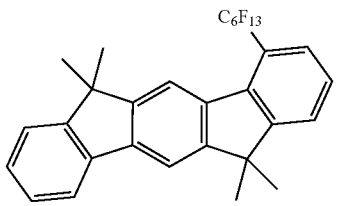

Here, the fluorine content of the compound represented by Formula (1) may be 20% or more. Preferably 20% to 80%, and more preferably 30% to 60%.

The fluorine content of the compounds described herein is represented by Equation (A).

Fluorine content=number of fluorine atoms in compound/total number of atoms in compound×100 [Equation (A)]

Here, the number of fluorine atoms in the compound means the number of fluorine atoms contained in the compound, and the total number of atoms in the compound means the total number of atoms in the compound including fluorine.

In another aspect of the present invention, the present invention provides an organic electronic element comprising an anode, an organic material layer formed on the anode, and a metal patterning layer formed on the organic material layer, wherein the metal patterning layer includes one single compound or 2 or more compounds represented by Formula (1).

The organic material layer may comprise at least one of a hole injection layer, a hole transport layer, an emitting auxiliary layer, an electron transport auxiliary layer, an electron transport layer, and an electron injection layer. In another aspect of the present invention, the present invention provides an electronic device comprising a display device including the organic electronic element represented by Formula (1), and a control unit for driving the display device.

Hereinafter, the laminated structure of the organic electronic element containing the compound of the present invention will be described with reference to FIG. 1 to 3.

In adding reference numerals to the components of each drawing, it should be noted that the same components are given the same reference numerals as much as possible even though they are indicated on different drawings. Also, in describing the present invention, if it is determined that a detailed description of a related known configuration or function may obscure the gist of the present invention, the detailed description thereof will be omitted.

When "comprises", "includes", "consisting of", etc. mentioned in this specification are used, other parts may be added unless "only" is used. When a component is expressed in a singular, it may include a case in which the plural is included unless otherwise explicitly stated.

Also, in describing the components of the present invention, terms such as first, second, A, B, (a), (b), etc. may be used. These terms are only for distinguishing the components from other components, and the essence, order, or order of the components are not limited by the terms. When a component is described as being "connected", "bonded" or "connected" to another component, the component may be directly connected or connected to the other component, but it should be understood that another component may be "connected", "bonded" or "contacted" between each component.

Also, it should be understood that cases may be included when a component, such as a layer, membrane, region, plate, etc., is said to be "on" or "upon" another component, this means not only when it is "directly above" another component, but also when another component is in between. Conversely, it should be understood that when an element is said to be "on top of" another part, it means that there is no other part in between.

FIGS. 1, 2 and 3 are exemplary views of an organic electronic element according to an embodiment of the present invention.

Referring to FIG. 1, an organic electronic element (100) according to an embodiment of the present invention includes a first electrode (110) formed on a substrate (not shown) and organic material layers (120, 130, 140, 150) formed on the first electrode (110), and a metal patterning layer (190) formed on the organic material layer.

The organic material layer may sequentially comprise a hole injection layer (120), a hole transport layer (130), an emitting layer (140), and an electron transport layer (150) on the first electrode (110). A hole blocking layer, an electron blocking layer, an emitting auxiliary layer (220), a buffer layer (210), an electron injection layer, etc. may be further included, and the electron transport layer (150) and the like may serve as a hole blocking layer. An electron injection layer may be formed on the electron transport layer (150) and may be excluded as necessary, but is not limited thereto.

The metal patterning layer (190) including the compound represented by Formula (1) is formed on the organic material layer, and the second electrode (170) is not formed on the portion where the metal patterning layer is formed. That is, by using the compound represented by Formula (1) according to the present invention as a material for the metal patterning layer (190), only a portion or a selective portion to be formed of the second electrode material can be formed. Alternatively, the formation of the second electrode may be suppressed by forming the metal patterning layer on the organic material layer as shown in FIG. 3

When the metal patterning layer is coated, the cathode is suppressed from being spread on the metal patterning layer depending on the structure of the compound and the content of fluorine comprising the metal patterning layer, and finally the cathode is spread in a very small amount or not.

At this time, the light transmittance is used to determine the amount of the electrode material present on a certain surface in relation to the coating of the electrode (electrically conductive material). This is because the electrode material contains a metal, and an electrically conductive material such as a metal attenuates and/or absorbs light. Therefore, when the light transmittance exceeds 90% in the visible light region of the electromagnetic spectrum, the surface can be considered to be substantially free of an electrically conductive material.

Through this, the pixel of the organic electronic element including metal patterning has high transmittance and does not emit light, so it acts as a blank, and due to its high transmittance, it is possible to transmit light to various optical sensors (optical sensors) under the substrate (TFT substrate) without optical noise. Therefore, in the organic electronic element including the metal patterning layer (see FIG. 3), the emitting layer (140) may or may not be present in forming the organic layer on the substrate ITO, and since there is no second electrode (cathode) on the metal patterning layer, electricity does not pass through and light is not emitted.

Otherwise, the present invention provides a composition for metal patterning comprising 2 or more compounds of the same type or structure different from each other of the compound represented by Formula (1). Also, the present invention provides an organic electronic element comprising a metal patterning layer including the compound represented by Formula (1).

Also, the organic material layer may be manufactured with a smaller number of layers by using various polymer materials, not by a deposition method, but by a solution process or a solvent process, such as a spin coating process or a nozzle printing process, inkjet printing process, slot coating process, dip coating process, roll-to-roll process, doctor blading process, screen printing process, or thermal transfer method, etc. Since the organic material layer according to the present invention can be formed by various methods, the scope of the present invention is not limited by the formation method.

Also, the organic electronic element according to an embodiment of the present invention may be selected from the group consisting of an organic electroluminescent device, an organic solar cell, an organic photoreceptor, an organic transistor, a device for monochromatic lighting, and a device for a quantum dot display.

Another embodiment of the present invention may include a display device including the organic electronic element of the present invention described above, and an electronic device including a control unit for controlling the display device. In this case, the electronic device may be a current or future wired/wireless communication terminal, and includes all electronic devices such as a mobile communication terminal such as a mobile phone, a PDA, an electronic dictionary, a PMP, a remote control, a navigation system, a game machine, various TVs, and various computers.

Hereinafter, a synthesis example of the compound represented by Formula (1) of the present invention and a preparation example of the organic electronic element of the present invention will be described in detail with reference to Examples, but the present invention is not limited to the following Examples.

SYNTHESIS EXAMPLE

The compound (Final Product) represented by Formula (1) according to the present invention is synthesized as shown in Reaction Scheme 1, but is not limited thereto.

Reaction Scheme 1

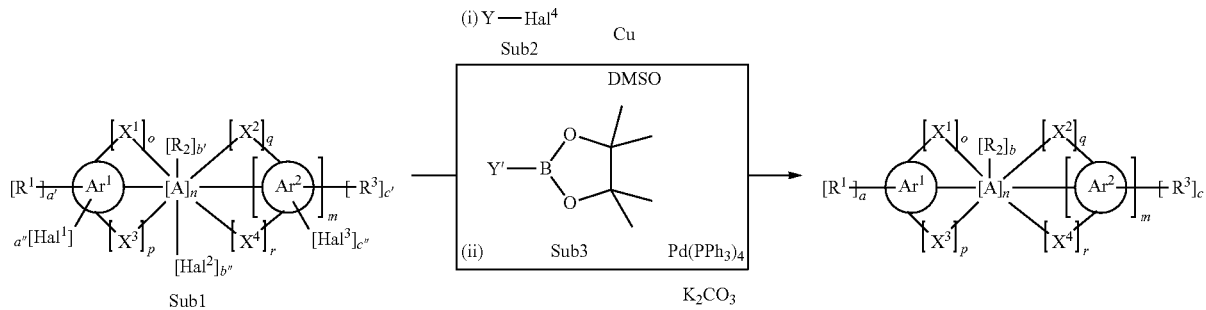

Final Product

Wherein

1) Hal$^1$, Hal$^2$, Hal$^3$ and Hal$^4$ are each independently Cl, Br or I,
2) a'+a" is a, b'+b" is b, c'+c" is c,
   provided that at least one of a", b" and c" is 1 or more,
3) Y is —[$C_xH_yF_z$] or —[$C_xH_yF_z$]-[D]v-[$C_xH_yF_z$]$_w$,
4) Y' is —[B]$_{i'}$—[$C_xH_yF_z$]$_s$ or —[C]$_{t'}$—[$C_xH_yF_z$]$_u$-[D]$_v$—[$C_xH_yF_z$]$_w$.
5) X$^1$, X$^2$, X$^3$, X$^4$, o, p, q, r, R$^1$, R$^2$, R$^3$, a, b, c, Ar$^1$, Ar$^2$, A, D, m, n, i', t', u, v, w, x, y, z are the same as defined above.

I. Synthesis of Sub1

1. Synthesis Example of Sub1-9

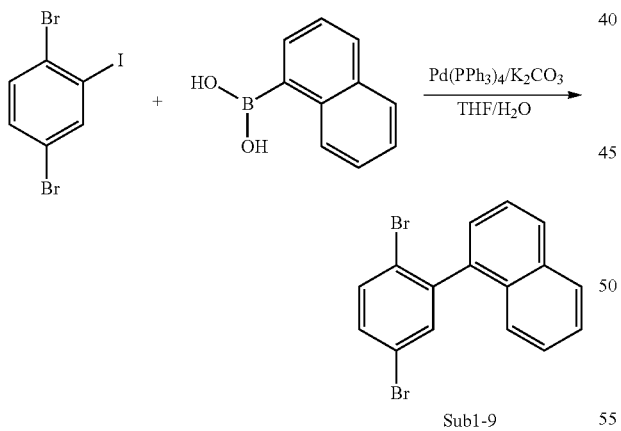

Sub1-9

After dissolving 1,4-dibromo-2-iodobenzene (10.0 g, 27.6 mmol) in THF (Tetrahydrofuran) (138 mL) in a round-bottom flask, naphthalen-1-ylboronic acid (5.2 g, 30.4 mmol), K$_2$CO$_3$ (11.5 g, 82.9 mmol), Pd(PPh$_3$)$_4$ (1.92 g, 1.66 mmol) and water (69 mL) were added and stirred at 80° C. When the reaction was completed, the mixture was extracted with CH$_2$Cl$_2$ and water, and the organic layer was dried over MgSO$_4$ and concentrated. Then, the resulting compound was recrystallized after applying a silica gel column to obtain 7.5 g (yield: 75%) of the product.

2. Synthesis Example of Sub1-12

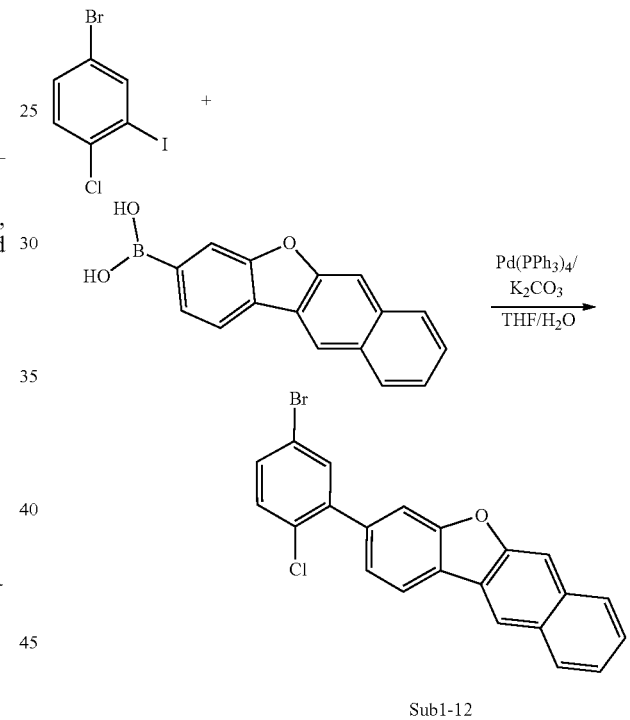

Sub1-12

4-bromo-1-chloro-2-iodobenzene (5.0 g, 15.8 mmol), THF (79 mL), naphtho[2,3-b]benzofuran-3-ylboronic acid (4.5 g, 17.3 mmol), K$_2$CO$_3$ (6.5 g, 47.3 mmol), Pd(PPh$_3$)$_4$ (1.09 g, 0.95 mmol) and water (39 mL) were used for the synthesis of Sub1-9 to obtain 4.9 g (yield: 77%) of the product.

3. Synthesis Example of Sub1-46

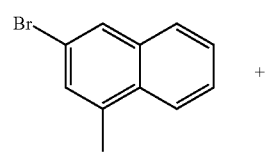

+

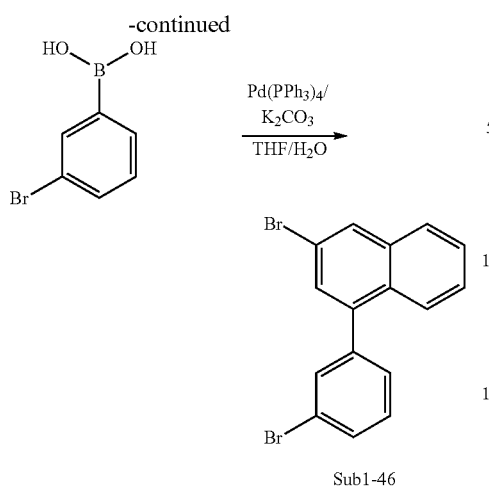

Sub1-46

3-bromo-1-iodonaphthalene (5.0 g, 15.0 mmol), THF (75 mL), (3-bromophenyl)boronic acid (3.3 g, 16.5 mmol), $K_2CO_3$ (6.2 g, 45.0 mmol), $Pd(PPh_3)_4$ (1.04 g, 0.90 mmol) and water (38 mL) were used for the synthesis of Sub1-9 to obtain 4.4 g (yield: 81%) of the product.

4. Synthesis Example of Sub1-58

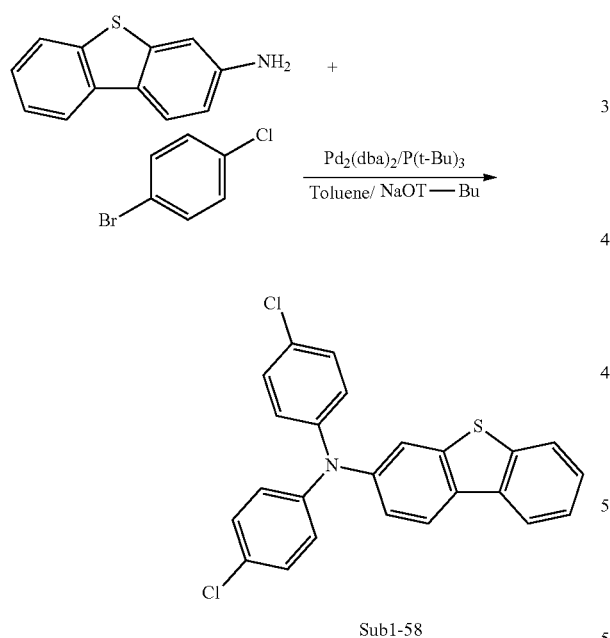

Sub1-58

Dibenzo[b,d]thiophen-3-amine (5.0 g, 25.1 mmol), Toluene (250 mL), 1-bromo-4-chlorobenzene (10.6 g, 55.2 mmol), $Pd_2(dba)_3$ (1.38 g, 1.51 mmol), P(t-Bu)$_3$ (0.61 g, 3.01 mmol) and NaOt-Bu (9.6 g, 100 mmol) were added and stirred at 100° C. When the reaction was completed, the mixture was extracted with $CH_2Cl_2$ and water, and the organic layer was dried over $MgSO_4$ and concentrated. Then, the resulting compound was recrystallized after applying a silica gel column to obtain 7.5 g (yield: 71%) of the product.

5. Synthesis Example of Sub1-63

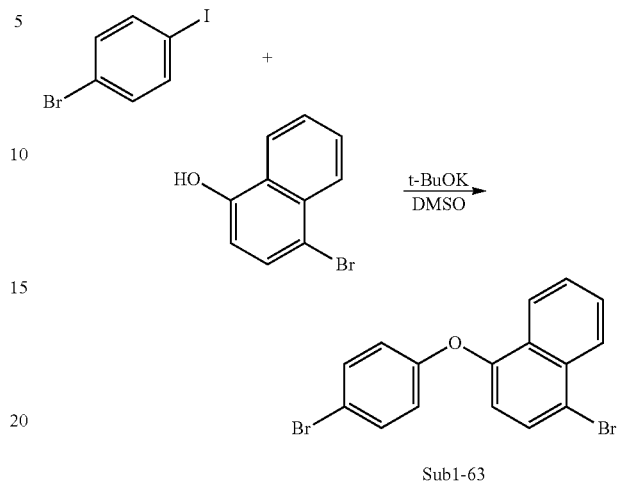

Sub1-63

4-bromonaphthalen-1-ol (5.0 g, 22.4 mmol), 1-bromo-4-iodobenzene (12.7 g, 44.8 mmol) and DMSO (22 mL) were added to a round bottom flask and stirred for 5 minutes. Then, t-BuOK (6.29 g, 56.0 mmol) was slowly added dropwise, followed by stirring at 45° C. for 8 hours. When the reaction was completed, the mixture was extracted with EA (ethyl acetate) and water, and the organic layer was dried over $MgSO_4$ and concentrated. Then, the resulting compound was recrystallized after applying a silica gel column to obtain 4.9 g (yield: 53%) of the product.

6. Synthesis Example of Sub1-69

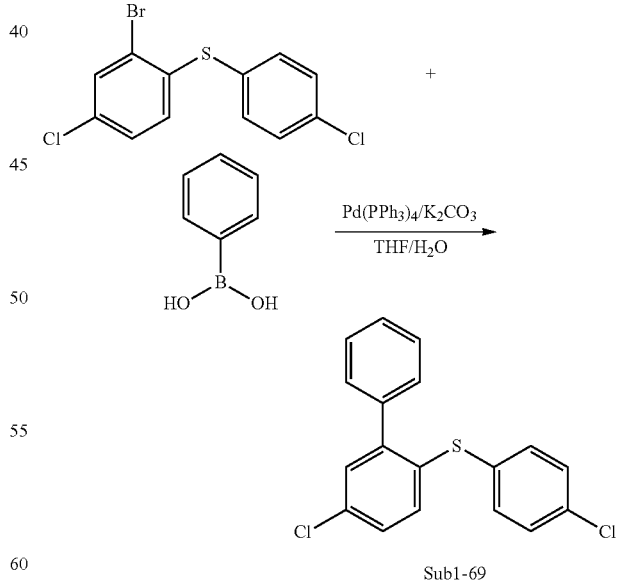

Sub1-69

(2-bromo-4-chlorophenyl)(4-chlorophenyl)sulfane (6.0 g, 18.0 mmol), THF (90 mL), phenylboronic acid (2.4 g, 19.8 mmol), $K_2CO_3$ (7.4 g, 53.9 mmol), $Pd(PPh_3)_4$ (1.25 g, 1.08 mmol) and water (45 mL) were used for the synthesis of Sub1-9 to obtain 4.4 g (yield: 74%) of the product.

7. Synthesis Example of Sub1-78

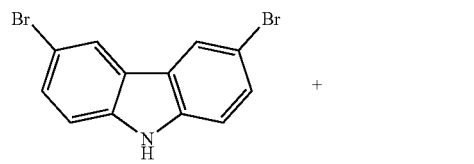

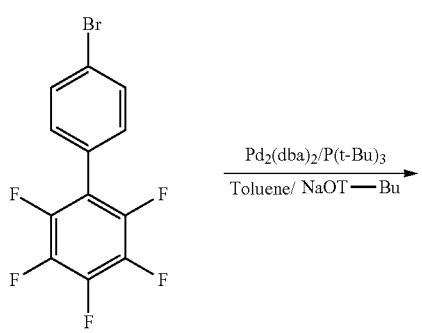

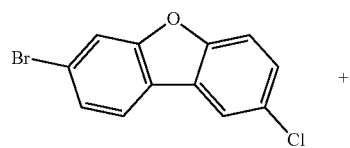

3,6-dibromo-9H-carbazole (5.0 g, 15.4 mmol), Toluene (154 mL), 4'-bromo-2,3,4,5,6-pentafluoro-1,1'-biphenyl (10.9 g, 33.8 mmol), Pd$_2$(dba)$_3$ (0.85 g, 0.92 mmol), P(t-Bu)$_3$ (0.37 g, 1.85 mmol), NaOt-Bu (5.9 g, 61.5 mmol) were used for the synthesis of Sub1-58 to obtain 6.8 g (yield: 78%) of the product.

8. Synthesis Example of Sub1-83

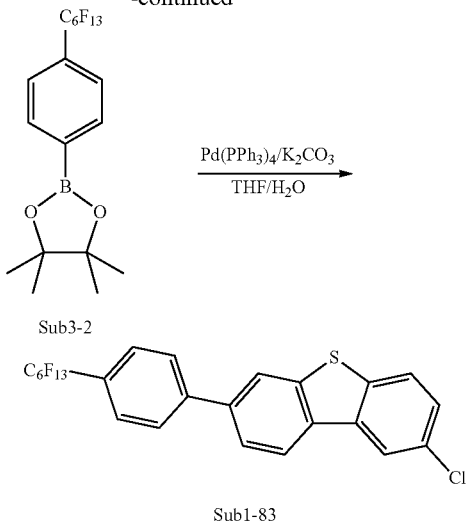

7-bromo-2-chlorodibenzo[b,d]furan (5.0 g, 17.8 mmol), THF (89 mL), Sub3-2 (10.2 g, 19.5 mmol), K$_2$CO$_3$ (7.4 g, 53.3 mmol), Pd(PPh$_3$)$_4$ (1.23 g, 1.07 mmol), water (44 mL) were used for the synthesis of Sub1-9 to obtain 8.3 g (yield: 78%) of the product.

9. Synthesis Example of Sub1-112

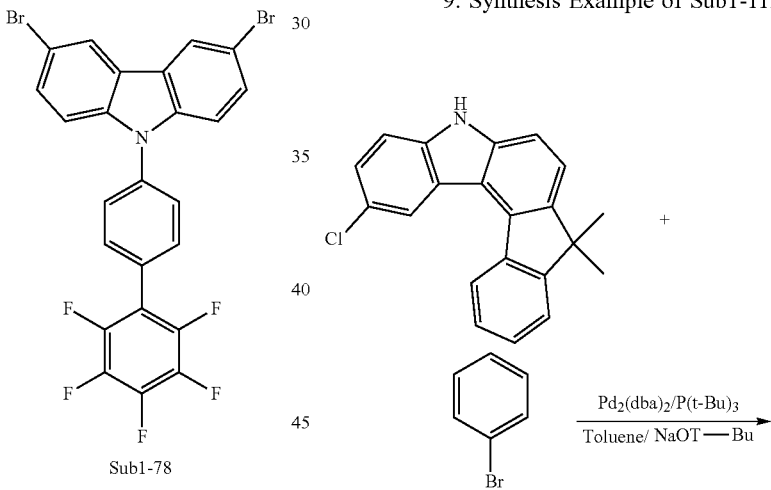

2-chloro-8,8-dimethyl-5,8-dihydroindeno[2,1-c]carbazole (5.0 g, 15.7 mmol, CAS #: 2376527-04-5), Toluene (79 mL), bromobenzene (2.7 g, 17.3 mmol), Pd$_2$(dba)$_3$ (0.43 g, 0.47 mmol), P(t-Bu)$_3$ (0.19 g, 0.94 mmol), NaOt-Bu (3.0 g, 31.5 mmol) were used for the synthesis of Sub1-58 to obtain 4.7 g (yield: 76%) of the product. Otherwise, the compound belonging to Sub1 may be a compound as follows, but is not limited thereto, Table 1 shows FD-MS (Field Desorption-Mass Spectrometry) values or CAS numbers (hereinafter, denoted as CAS #) of the following compounds. In the case of known compounds in Table 1, it is indicated by CAS #, and in the case of unknown compounds, it is indicated by FD-MS.

TABLE 1

| compound | CAS# or FD-MS |
| --- | --- |
| Sub1-1 | CAS#: 106-39-8 |
| Sub1-2 | CAS#: 106-37-6 |
| Sub1-3 | CAS#: 108-37-2 |
| Sub1-4 | CAS#: 108-36-1 |
| Sub1-5 | CAS#: 22875-47-4 |
| Sub1-6 | CAS#: 103431-11-4 |
| Sub1-7 | CAS#: 2375-96-4 |
| Sub1-8 | CAS#: 344-03-6 |
| Sub1-9 | m/z = 359.91($C_{16}H_{10}Br_2$ = 362.06) |
| Sub1-10 | m/z = 365.98($C_{20}H_{12}BrCl$ = 367.67) |
| Sub1-11 | m/z = 365.96($C_{16}H_{16}Br_2$ = 368.11) |
| Sub1-12 | m/z = 405.98($C_{22}H_{12}BrClO$ = 407.69) |
| Sub1-13 | CAS#: 1161501-90-1 |
| Sub1-14 | m/z = 421.95($C_{22}H_{12}BrClS$ = 423.75) |
| Sub1-15 | m/z = 465.90($C_{22}H_{12}Br_2S$ = 468.21) |
| Sub1-16 | m/z = 386.93($C_{17}H_{11}Br_2N$ = 389.09) |
| Sub1-17 | CAS#: 1656247-96-9 |
| Sub1-18 | CAS#: 1369931-75-8 |
| Sub1-19 | CAS#: 46438-88-4 |
| Sub1-20 | CAS#: 14862-52-3 |
| Sub1-21 | CAS#: 18282-59-2 |
| Sub1-22 | CAS#: 23055-77-8 |
| Sub1-23 | CAS#: 92-86-4 |
| Sub1-24 | CAS#: 16400-51-4 |
| Sub1-25 | CAS#: 49602-90-6 |
| Sub1-26 | CAS#: 16372-96-6 |
| Sub1-27 | CAS#: 72416-87-6 |
| Sub1-28 | CAS#: 16400-50-3 |
| Sub1-29 | CAS#: 2162961-53-5 |
| Sub1-30 | m/z = 465.83($C_{16}H_9Br_3N_2$ = 468.97) |
| Sub1-31 | m/z = 382.97($C_{19}H_{11}BrClNO$ = 384.66) |
| Sub1-32 | m/z = 507.04($C_{30}H_{19}BrClN$ = 508.84) |
| Sub1-33 | CAS#: 29510-41-6 |
| Sub1-34 | CAS#: 1762-84-1 |
| Sub1-35 | CAS#: 1290039-62-1 |
| Sub1-36 | CAS#: 17788-94-2 |
| Sub1-37 | CAS#: 24253-43-8 |
| Sub1-38 | CAS#: 1612879-37-4 |
| Sub1-39 | CAS#: 7511-49-1 |
| Sub1-40 | CAS#: 96761-85-2 |
| Sub1-41 | CAS#: 83-53-4 |
| Sub1-42 | CAS#: 17135-74-9 |
| Sub1-43 | CAS#: 7351-74-8 |
| Sub1-44 | CAS#: 13720-06-4 |
| Sub1-45 | CAS#: 952604-26-1 |
| Sub1-46 | m/z = 359.91($C_{16}H_{10}Br_2$ = 362.06) |
| Sub1-47 | CAS#: 523-27-3 |
| Sub1-48 | CAS#: 359435-47-5 |
| Sub1-49 | CAS#: 1821394-50-6 |
| Sub1-50 | CAS#: 62325-30-8 |
| Sub1-51 | CAS#: 1316311-32-6 |
| Sub1-52 | CAS#: 888041-37-0 |
| Sub1-53 | CAS#: 53939-30-3 |
| Sub1-54 | CAS#: 2408-70-0 |
| Sub1-55 | CAS#: 14921-00-7 |
| Sub1-56 | CAS#: 4316-58-9 |
| Sub1-57 | m/z = 604.15($C_{40}H_{26}Cl_2N_2$ = 605.56) |
| Sub1-58 | m/z = 419.03($C_{24}H_{15}Cl_2NS$ = 420.35) |
| Sub1-59 | m/z = 617.00($C_{34}H_{21}Br_2NO$ = 619.36) |
| Sub1-60 | m/z = 737.06($C_{26}H_{12}F_{21}N$ = 737.36) |
| Sub1-61 | m/z = 537.08($C_{22}H_{12}F_{13}N$ = 537.32) |
| Sub1-62 | CAS#: 2050-47-7 |
| Sub1-63 | m/z = 375.91($C_{16}H_{10}Br_2O$ = 378.06) |
| Sub1-64 | CAS#: 25147-71-1 |

TABLE 1-continued

| | |
| --- | --- |
| Sub1-65 | m/z = 430.09($C_{27}H_{20}Cl_2O$ = 431.36) |
| Sub1-66 | m/z = 454.01($C_{22}H_{18}Cl_4O_2$ = 456.18) |
| Sub1-67 | CAS#: 3393-78-0 |
| Sub1-68 | m/z = 391.89($C_{16}H_{10}Br_2S$ = 394.12) |
| Sub1-69 | m/z = 330.00($C_{18}H_{12}Cl_2S$ = 331.25) |
| Sub1-70 | CAS#: 906069-09-8 |
| Sub1-71 | CAS#: 1186383-49-2 |
| Sub1-72 | CAS#: 1931951-30-2 |
| Sub1-73 | CAS#: 18733-91-0 |
| Sub1-74 | CAS#: 1111070-90-6 |
| Sub1-75 | CAS#: 2448385-13-3 |
| Sub1-76 | CAS#: 57103-20-5 |
| Sub1-77 | CAS#: 597570-70-2 |
| Sub1-78 | m/z = 564.91($C_{24}H_{10}Br_2F_5N$ = 567.15) |
| Sub1-79 | m/z = 643.00($C_{30}H_9Cl_2F_{10}N$ = 644.29) |
| Sub1-80 | m/z = 575.21($C_{38}H_{35}Cl_2N$ = 576.61) |
| Sub1-81 | CAS#: 10016-52-1 |
| Sub1-82 | CAS#: 67019-91-4 |
| Sub1-83 | m/z = 596.02($C_{24}H_{10}ClF_{13}O$ = 596.77) |
| Sub1-84 | CAS#: 31574-87-5 |
| Sub1-85 | CAS#: 83834-10-0 |
| Sub1-86 | m/z = 612.00($C_{24}H_{10}ClF_{13}S$ = 612.83) |
| Sub1-87 | m/z = 478.03($C_{30}H_{16}Cl_2S$ = 479.42) |
| Sub1-88 | m/z = 375.09($C_{24}H_{10}D_5ClS$ = 375.92) |
| Sub1-89 | CAS#: 28320-32-3 |
| Sub1-90 | CAS#: 865702-19-8 |
| Sub1-91 | CAS#: 186259-63-2 |
| Sub1-92 | CAS#: 474918-32-6 |
| Sub1-93 | CAS#: 128406-10-0 |
| Sub1-94 | CAS#: 171408-84-7 |
| Sub1-95 | CAS#: 198142-65-3 |
| Sub1-96 | CAS#: 1637301-23-5 |
| Sub1-97 | CAS#: 880800-04-4 |
| Sub1-98 | CAS#: 1228595-79-6 |
| Sub1-99 | CAS#: 1315321-81-3 |
| Sub1-100 | CAS#: 1262507-19-6 |
| Sub1-101 | m/z = 535.12($C_{36}H_{22}ClNS$ = 536.09) |
| Sub1-102 | CAS#: 2416751-27-2 |
| Sub1-103 | CAS#: 885318-49-0 |
| Sub1-104 | CAS#: 1882117-91-0 |
| Sub1-105 | m/z = 500.98($C_{24}H_9BrF_5NO$ = 502.24) |
| Sub1-106 | CAS#: 1959627-18-9 |
| Sub1-107 | CAS#: 1199616-46-0 |
| Sub1-108 | CAS#: 2129175-93-3 |
| Sub1-109 | CAS#: 1627726-96-8 |
| Sub1-110 | CAS#: 2489751-47-3 |
| Sub1-111 | CAS#: 2403759-27-1 |
| Sub1-112 | m/z = 393.13($C_{27}H_{20}ClN$ = 393.91 ) |
| Sub1-113 | CAS#: 1350842-19-1 |
| Sub1-114 | CAS#: 1639155-80-8 |
| Sub1-115 | CAS#: 2491751-07-4 |
| Sub1-116 | CAS#: 2341893-65-8 |
| Sub1-117 | CAS#: 6336-32-9 |
| Sub1-118 | CAS#: 2125489-31-6 |
| Sub1-119 | CAS#: 2125520-08-1 |
| Sub1-120 | CAS#: 2299231-59-5 |
| Sub1-121 | m/z = 358.04($C_{22}H_{15}Br$ = 359.27) |
| Sub1-122 | m/z = 309.02($C_{17}H_{12}BrN$ = 310.19) |
| Sub1-123 | m/z = 309.02($C_{17}H_{12}BrN$ = 310.19) |
| Sub1-124 | m/z = 309.02($C_{17}H_{12}BrN$ = 310.19) |
| Sub1-125 | m/z = 358.04($C_{22}H_{15}Br$ = 359.27) |
| Sub1-126 | m/z = 358.04($C_{22}H_{15}Br$ = 359.27) |
| Sub1-127 | m/z = 358.04($C_{22}H_{15}Br$ = 359.27) |
| Sub1-128 | m/z = 358.04($C_{22}H_{15}Br$ = 359.27) |
| Sub1-129 | m/z = 359.03($C_{21}H_{14}BrN$ = 360.25) |
| Sub1-130 | m/z = 359.03($C_{21}H_{14}BrN$ = 360.25) |
| Sub1-131 | m/z = 348.01($C_{20}H_{13}BrO$ = 349.23) |
| Sub1-132 | m/z = 363.99($C_{20}H_{13}BrS$ = 365.29) |
| Sub1-133 | m/z = 309.02($C_{17}H_{12}BrN$ = 310.19) |
| Sub1-134 | m/z = 408.05($C_{26}H_{17}Br$ = 409.33) |
| Sub1-135 | m/z = 358.04($C_{22}H_{15}Br$ = 359.27) |
| Sub1-136 | m/z = 358.04($C_{22}H_{15}Br$ = 359.27) |
| Sub1-137 | m/z = 359.03($C_{21}H_{14}BrN$ = 360.25) |
| Sub1-138 | m/z = 310.01($C_{16}H_{11}BrN_2$ = 311.18) |
| Sub1-139 | m/z = 358.04($C_{22}H_{15}Br$ = 359.27) |
| Sub1-140 | m/z = 359.03($C_{21}H_{14}BrN$ = 360.25) |
| Sub1-141 | m/z = 332.02($C_{20}H_{13}Br$ = 333.23) |
| Sub1-142 | m/z = 310.01($C_{16}H_{11}BrN_2$ = 311.18) |
| Sub1-143 | m/z = 398.03($C_{24}H_{15}BrO$ = 399.29) |
| Sub1-144 | m/z = 424.08($C_{27}H_{21}Br$ = 425.37) |

TABLE 1-continued
| | |
|---|---|
| Sub1-145 | m/z = 359.03(C$_{21}$H$_{14}$BrN = 360.25) |
| Sub1-146 | m/z = 448.05(C$_{28}$H$_{17}$BrO = 449.35) |
| Sub1-147 | m/z = 493.94(C$_{22}$H$_{16}$Br$_2$N$_2$Si = 496.28) |
| Sub1-148 | m/z = 591.99(C$_{32}$H$_{22}$Br$_2$Si = 594.42) |
| Sub1-149 | m/z = 618.0(C$_{34}$H$_{24}$Br$_2$Si = 620.46) |
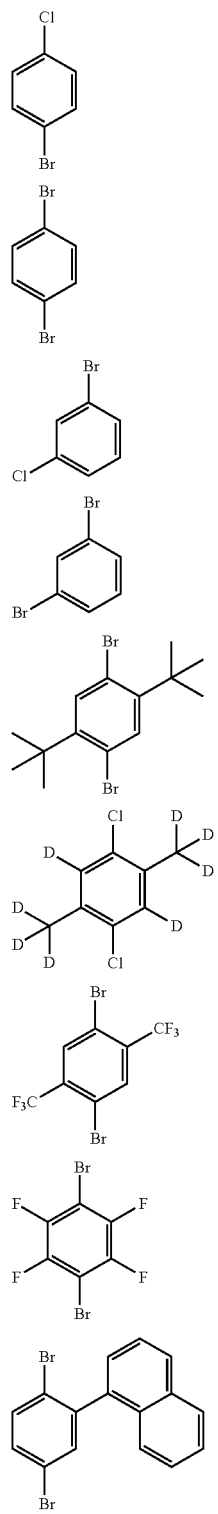
Sub1-1
Sub1-2
Sub1-3
Sub1-4
Sub1-5
Sub1-6
Sub1-7
Sub1-8
Sub1-9
TABLE 1-continued
Sub1-10
Sub1-11
Sub1-12
Sub1-13
Sub1-14
Sub1-15
Sub1-16

TABLE 1-continued
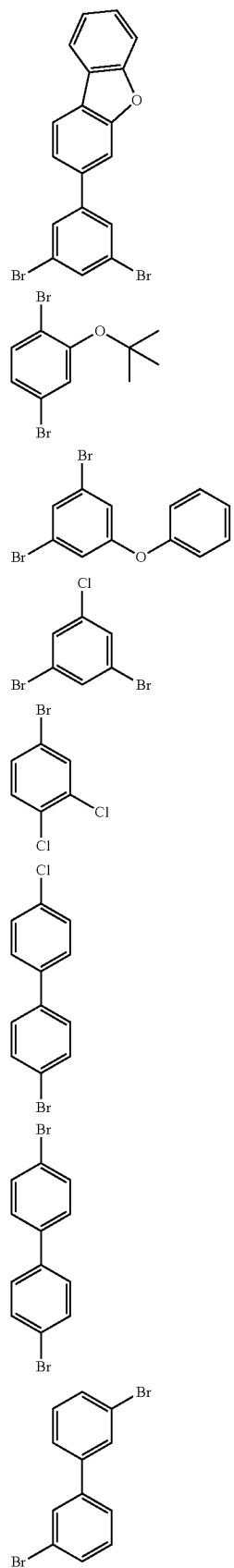
Sub1-17
Sub1-18
Sub1-19
Sub1-20
Sub1-21
Sub1-22
Sub1-23
Sub1-24
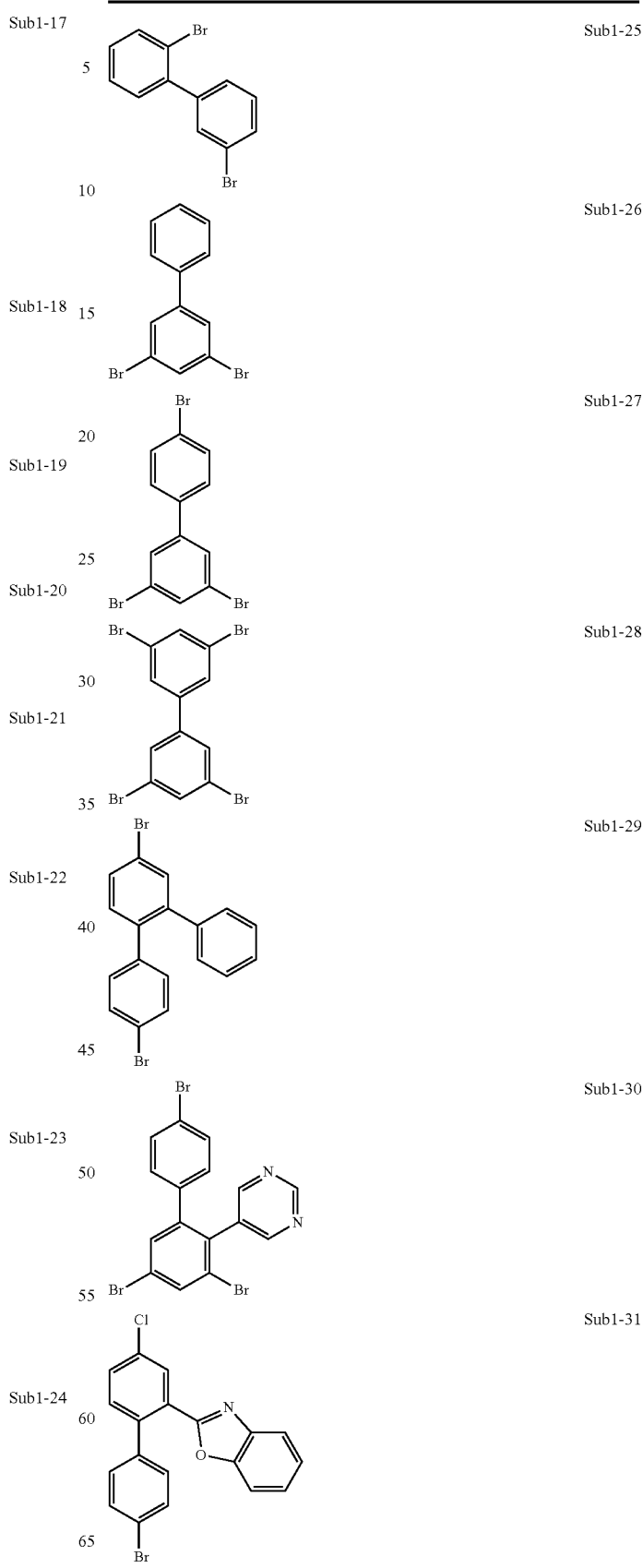
Sub1-25
Sub1-26
Sub1-27
Sub1-28
Sub1-29
Sub1-30
Sub1-31

TABLE 1-continued
Sub1-32 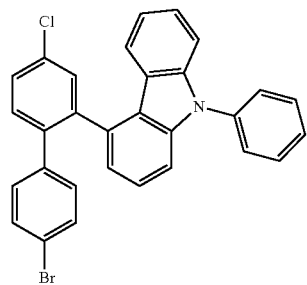 [SMILES: Clc1ccc(-c2ccc(Br)cc2)c(-c2cccc3c2c2ccccc2n3-c2ccccc2)c1]
Sub1-33 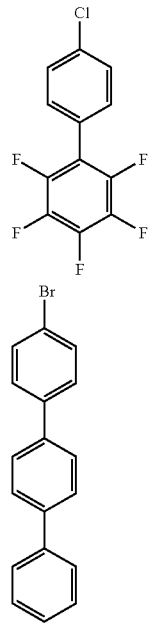
Sub1-34 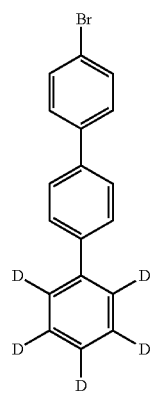 [SMILES: [2H]c1c([2H])c([2H])c(-c2ccc(-c3ccc(Br)cc3)cc2)c([2H])c1[2H]]
Sub1-35 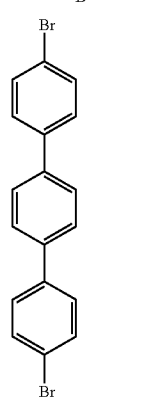
Sub1-36
Sub1-37 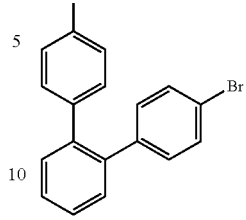
Sub1-38 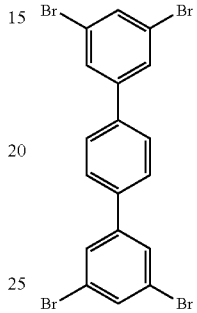
Sub1-39 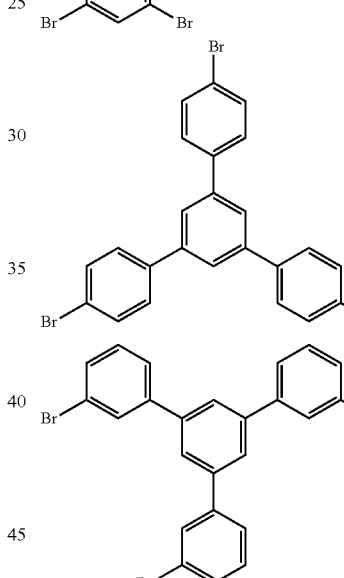
Sub1-40 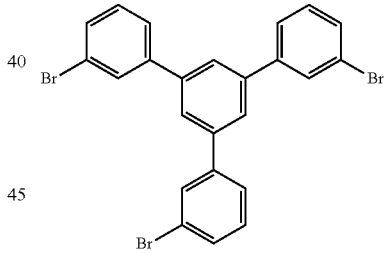
Sub1-41
Sub1-42 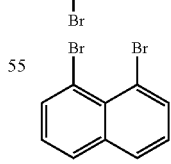
Sub1-43 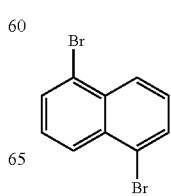

TABLE 1-continued
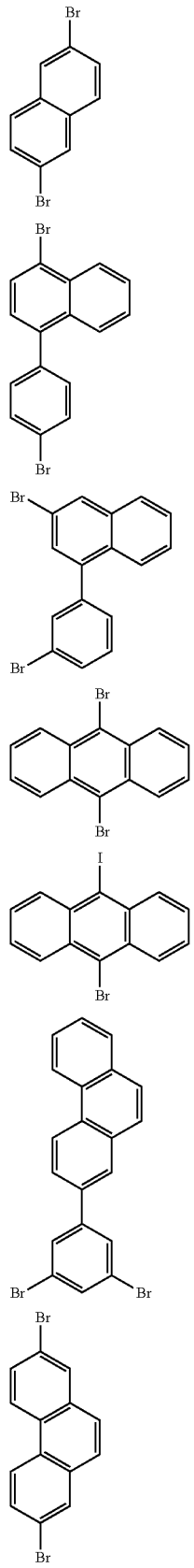
Sub1-44
Sub1-45
Sub1-46
Sub1-47
Sub1-48
Sub1-49
Sub1-50
TABLE 1-continued
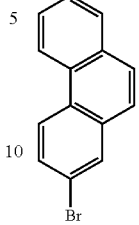
Sub1-51
Sub1-52
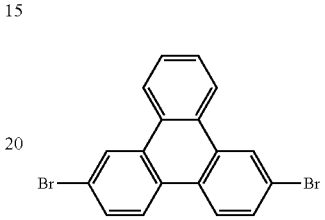
Sub1-53
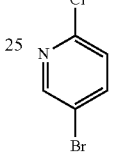
Sub1-54
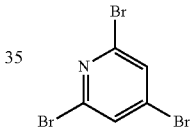
Sub1-55
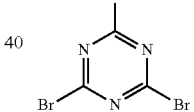
Sub1-56
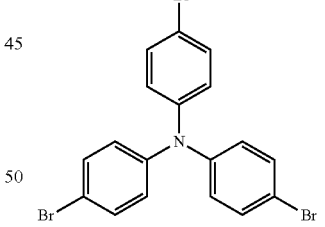
Sub1-57
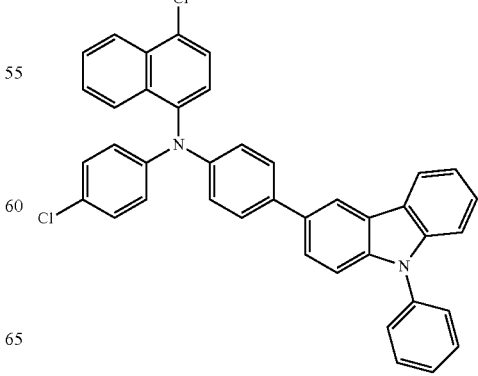

TABLE 1-continued
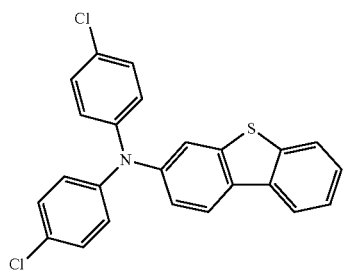 [SMILES: Clc1ccc(N(c2ccc(Cl)cc2)c2ccc3c(c2)sc2ccccc23)cc1]
Sub1-58
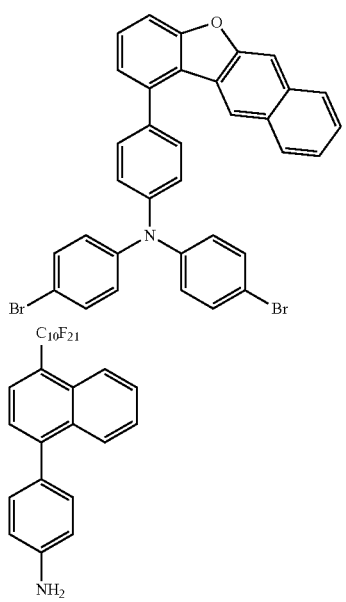
Sub1-59
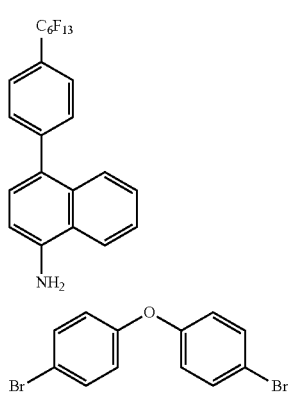
Sub1-60
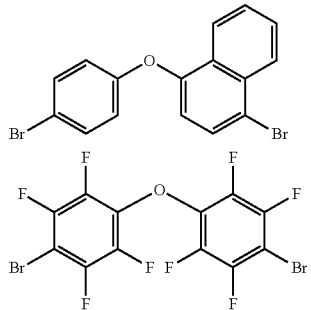
Sub1-61
Sub1-62
Sub1-63
Sub1-64
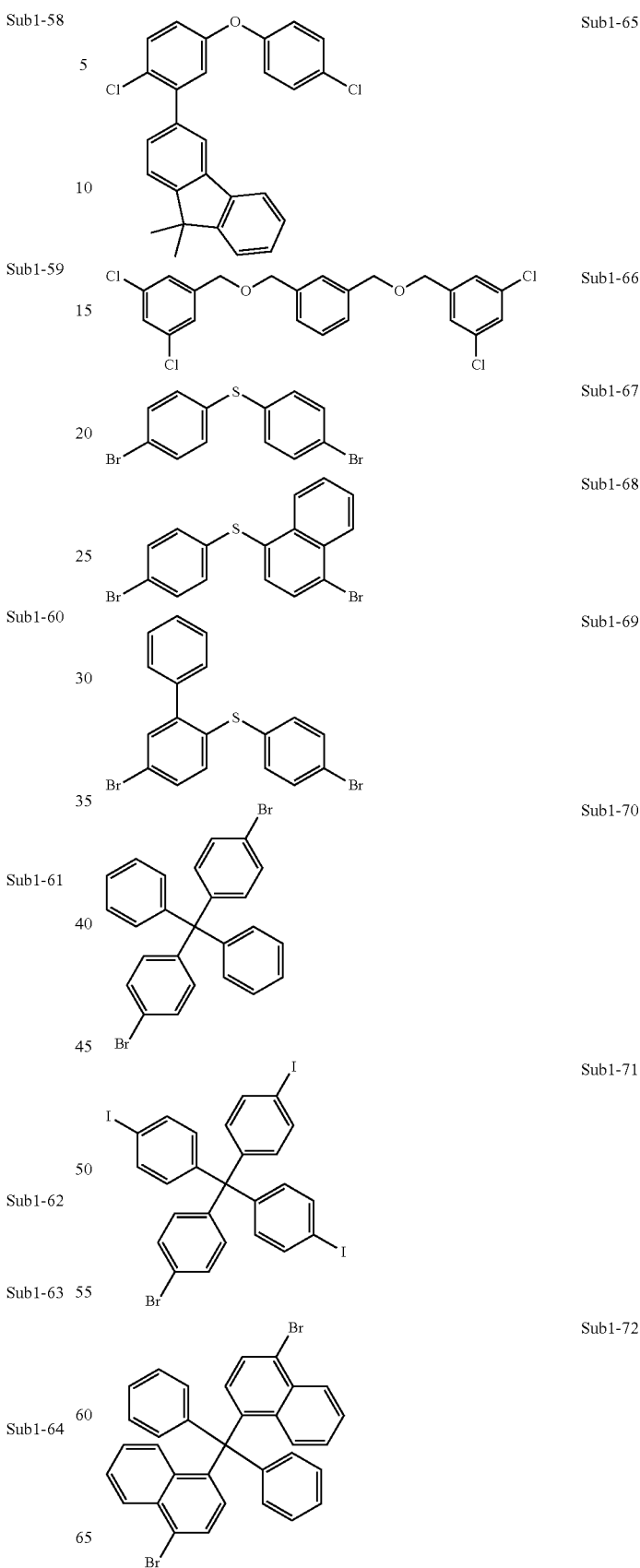
Sub1-65
Sub1-66
Sub1-67
Sub1-68
Sub1-69
Sub1-70
Sub1-71
Sub1-72

TABLE 1-continued
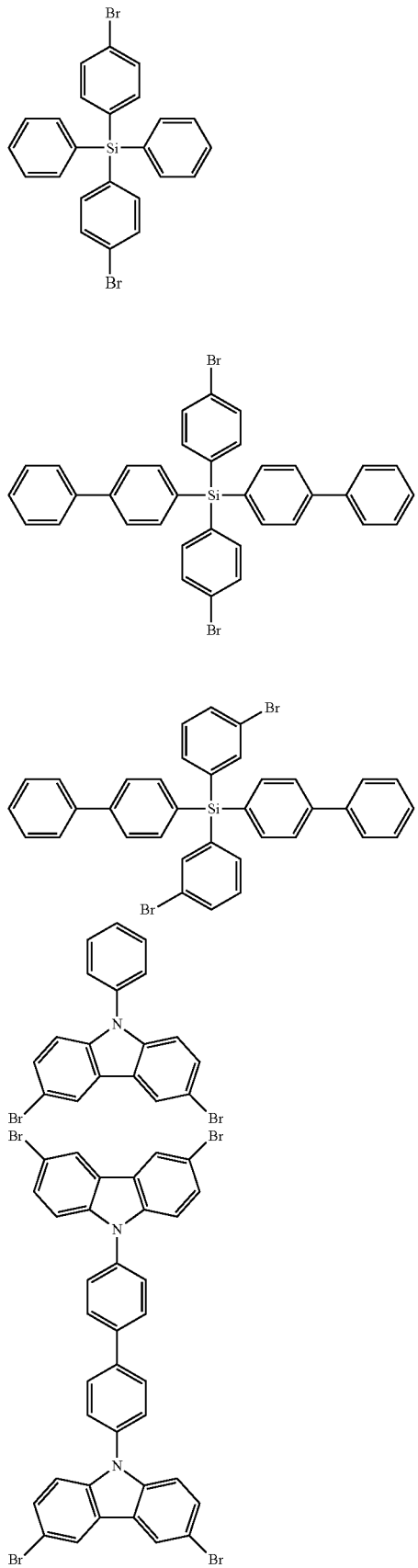
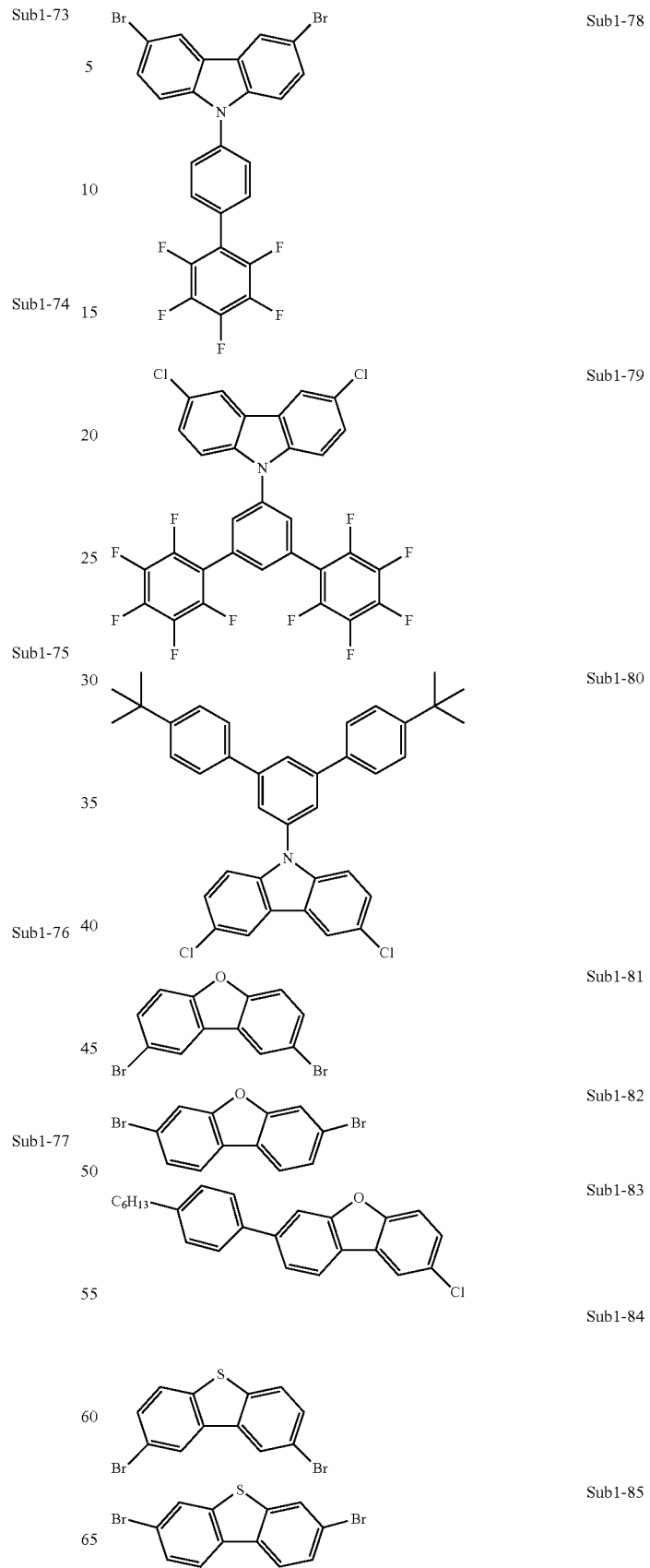

TABLE 1-continued
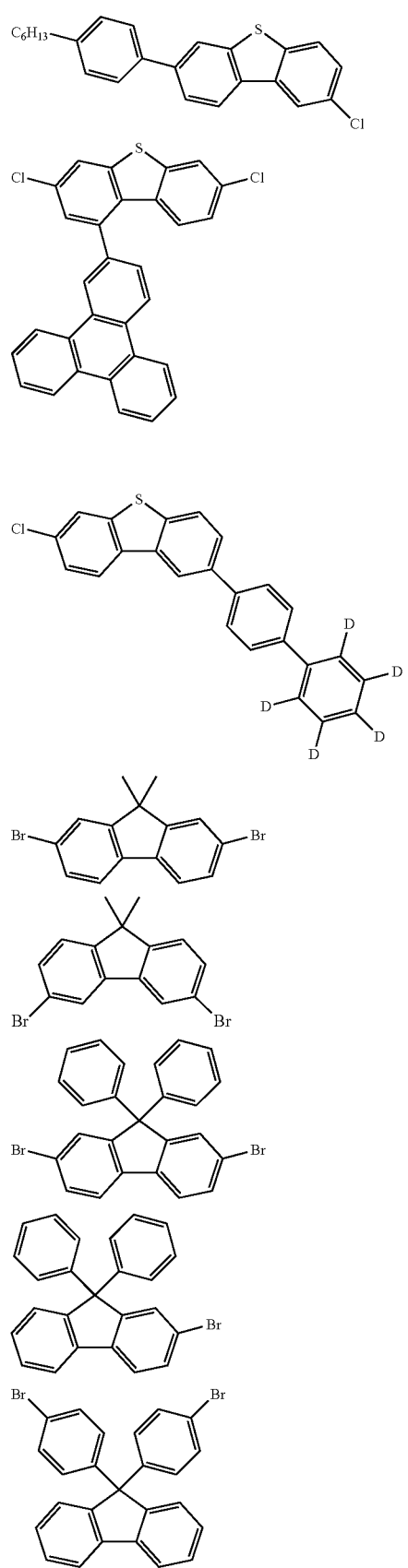
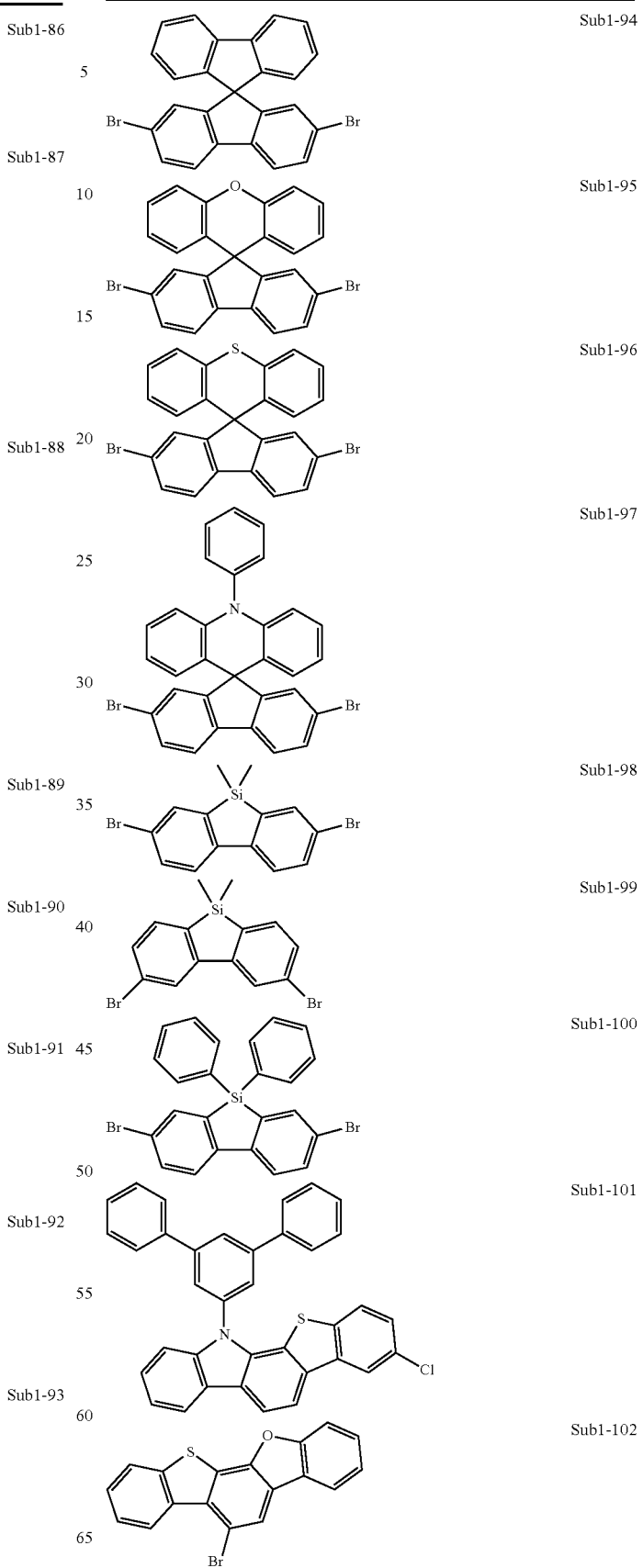

TABLE 1-continued
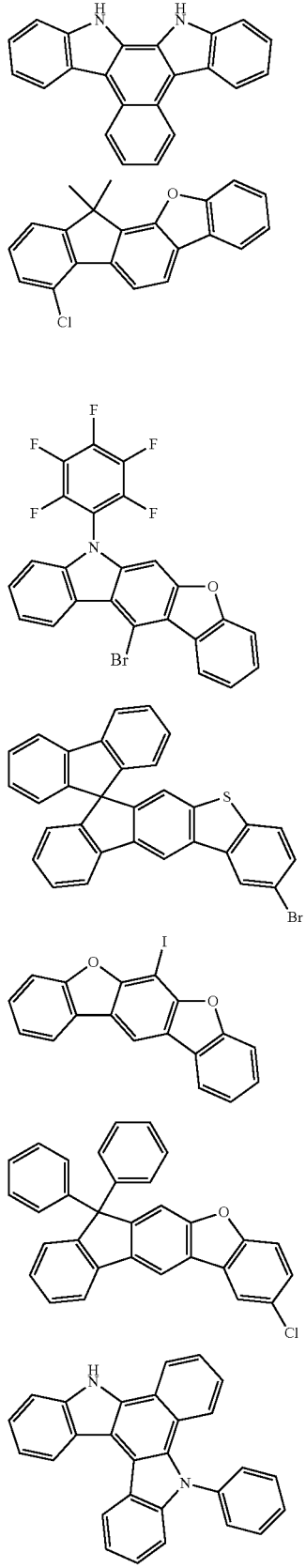
Sub1-103
Sub1-104
Sub1-105
Sub1-106
Sub1-107
Sub1-108
Sub1-109
TABLE 1-continued
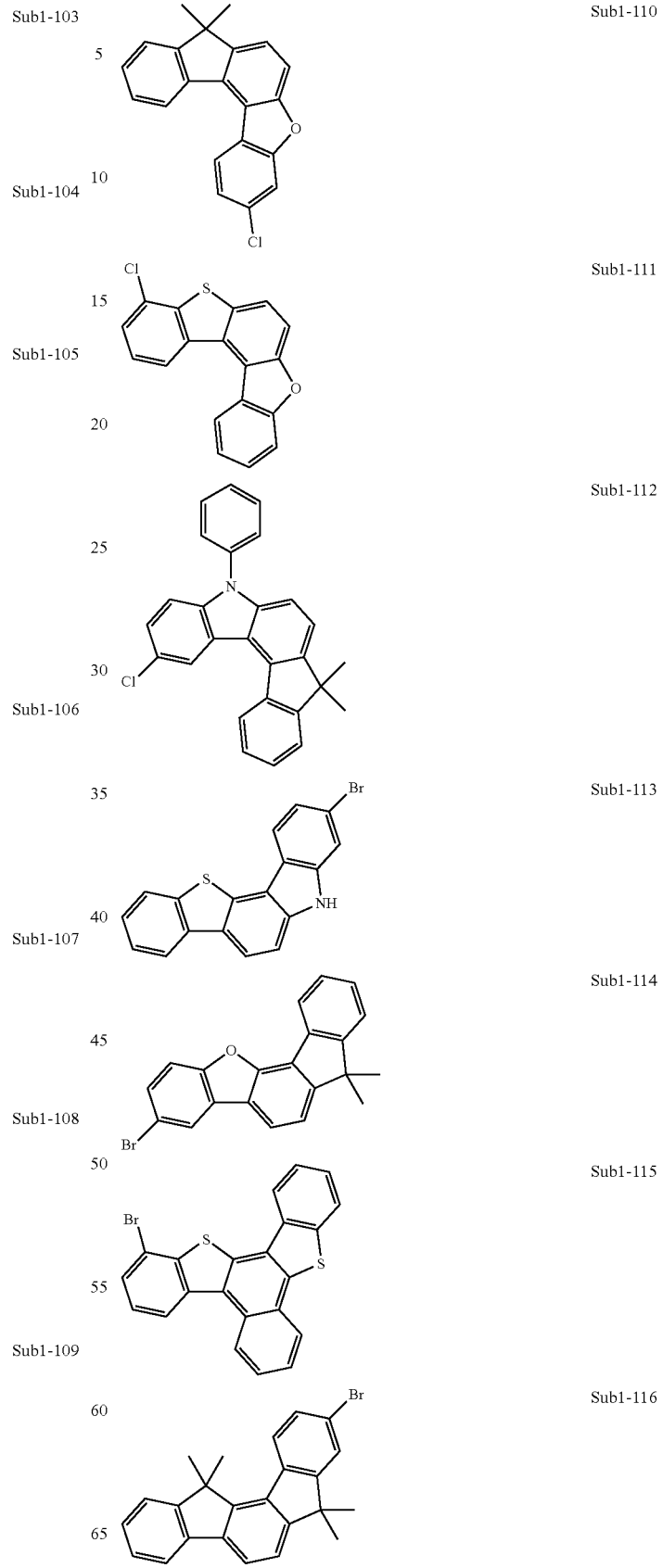
Sub1-110
Sub1-111
Sub1-112
Sub1-113
Sub1-114
Sub1-115
Sub1-116

TABLE 1-continued
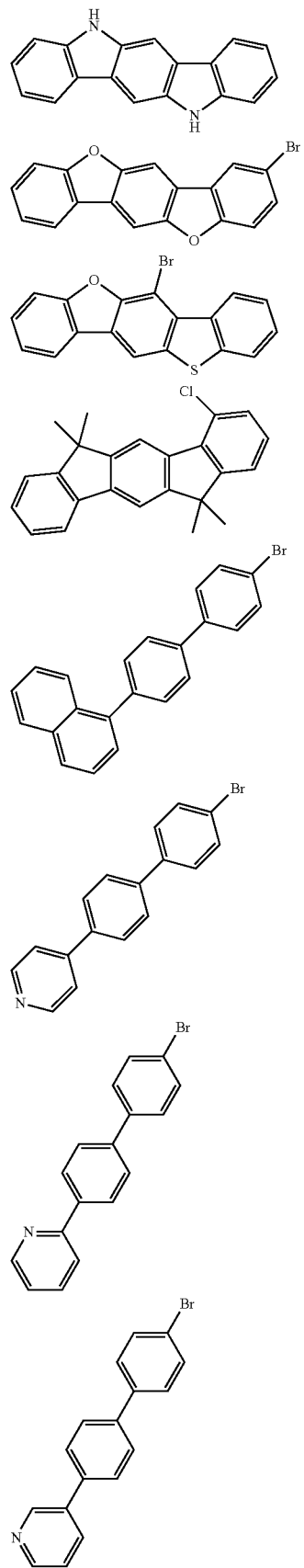
Sub1-117
Sub1-118
Sub1-119
Sub1-120
Sub1-121
Sub1-122
Sub1-123
Sub1-124
TABLE 1-continued
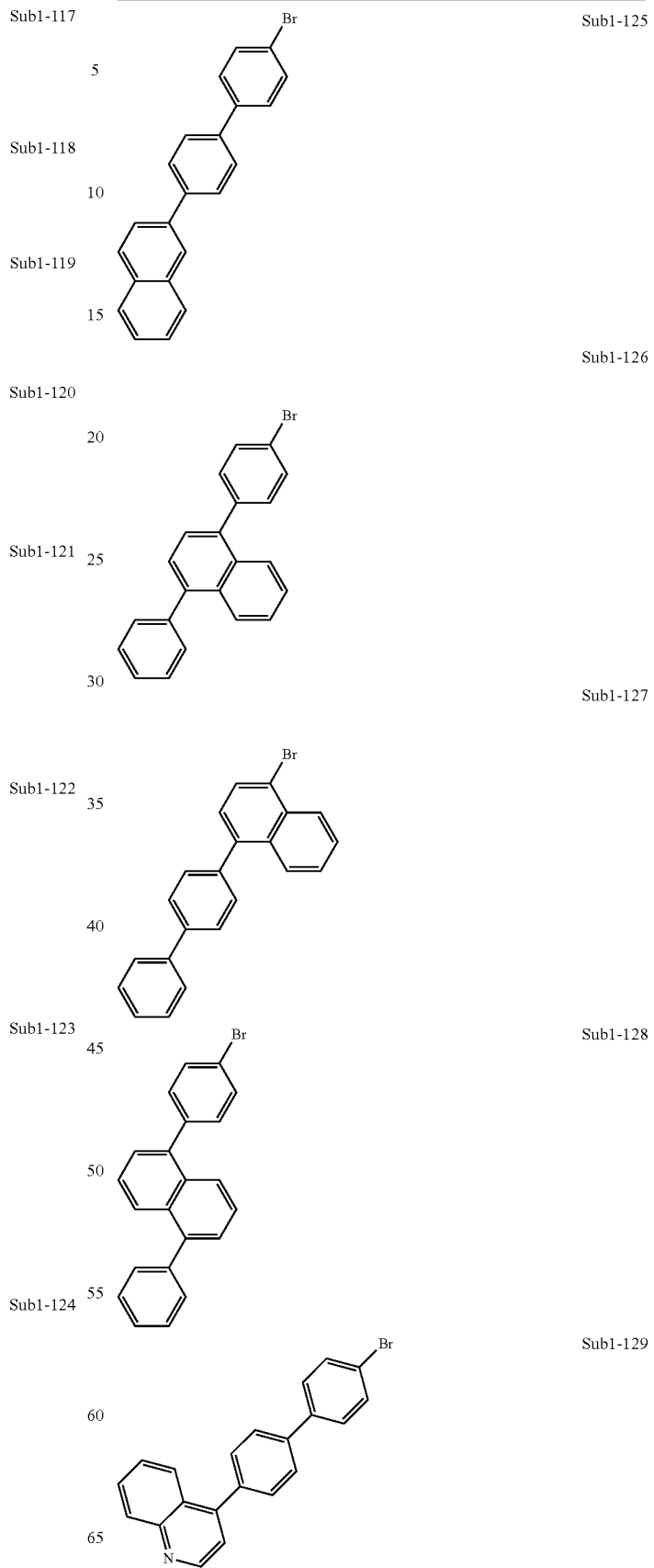
Sub1-125
Sub1-126
Sub1-127
Sub1-128
Sub1-129

TABLE 1-continued
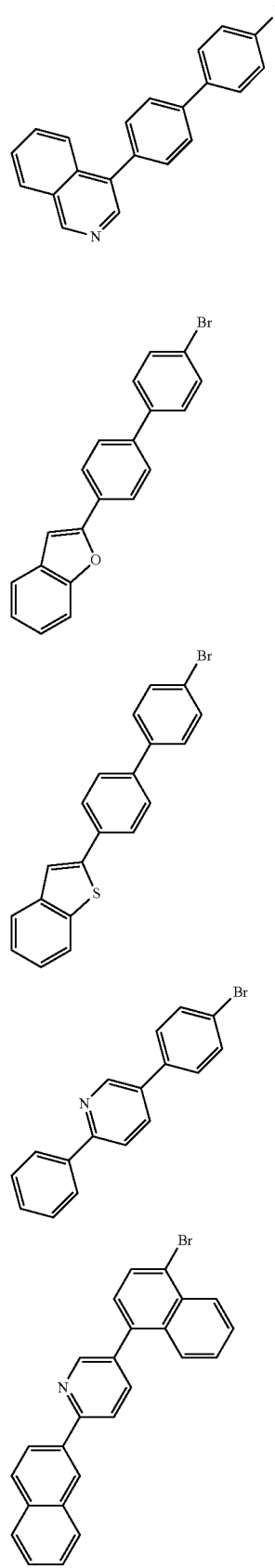
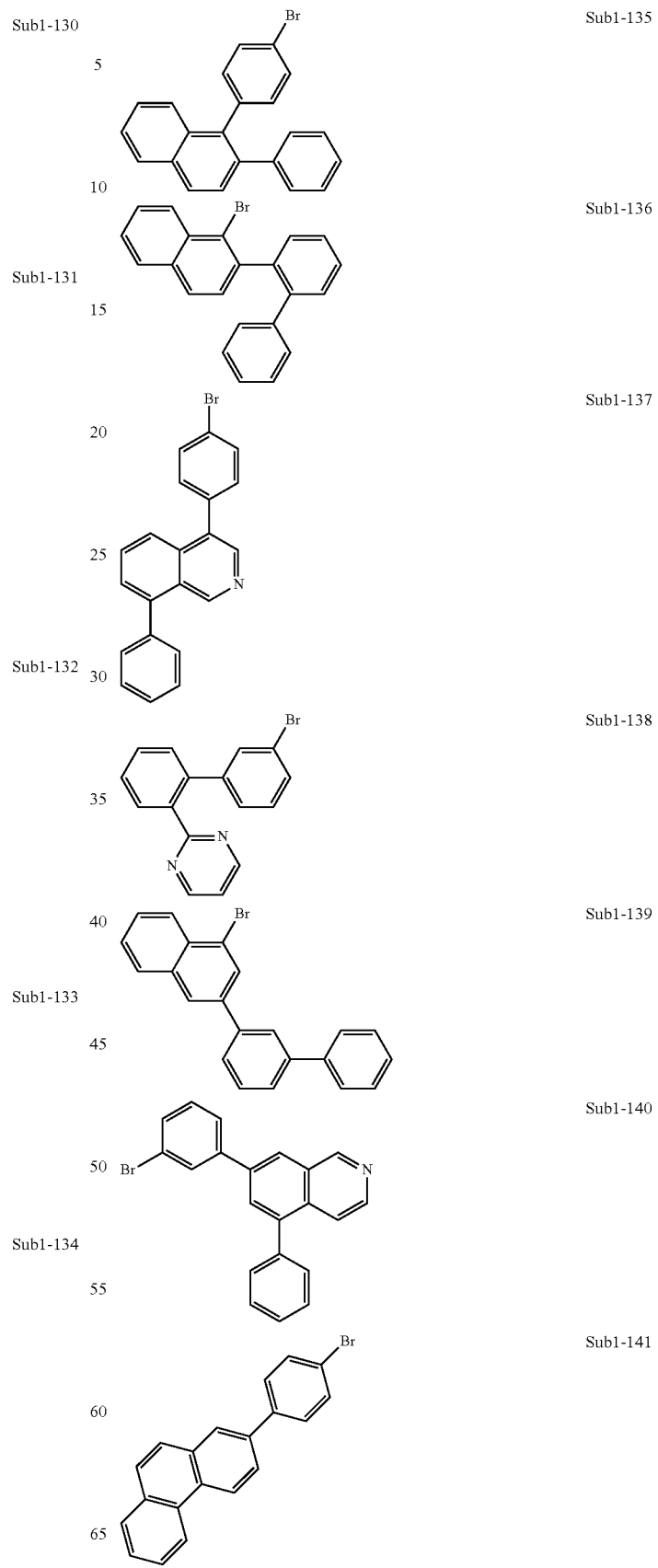

TABLE 1-continued
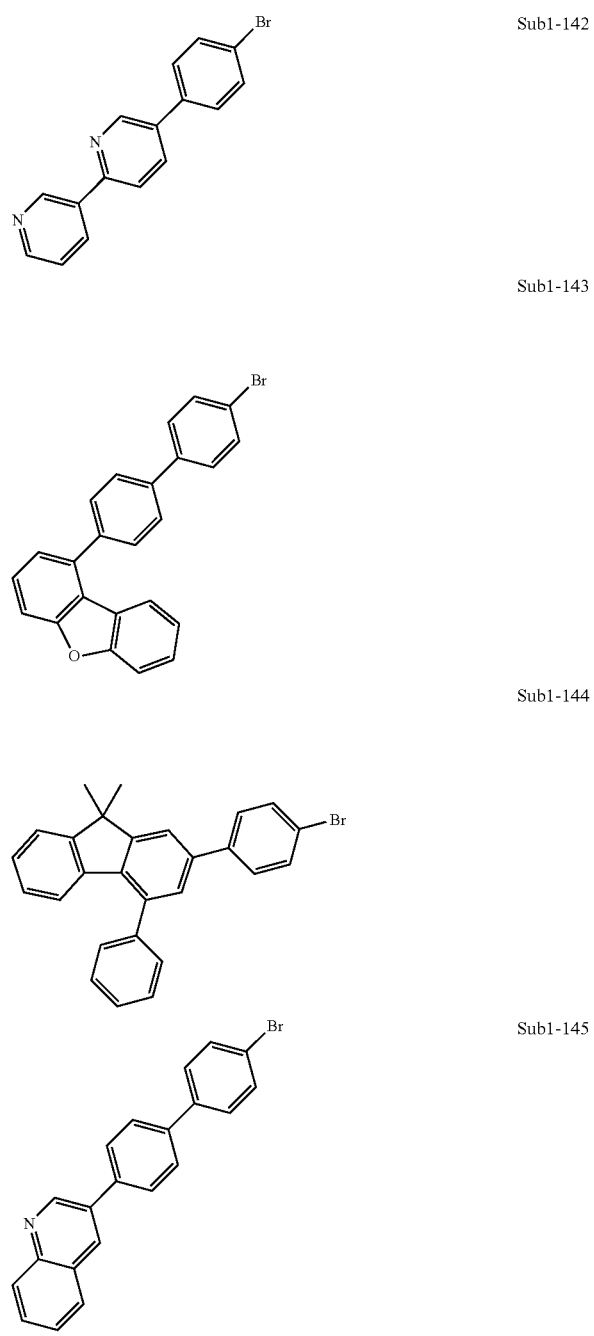
Sub1-142
Sub1-143
Sub1-144
Sub1-145
TABLE 1-continued
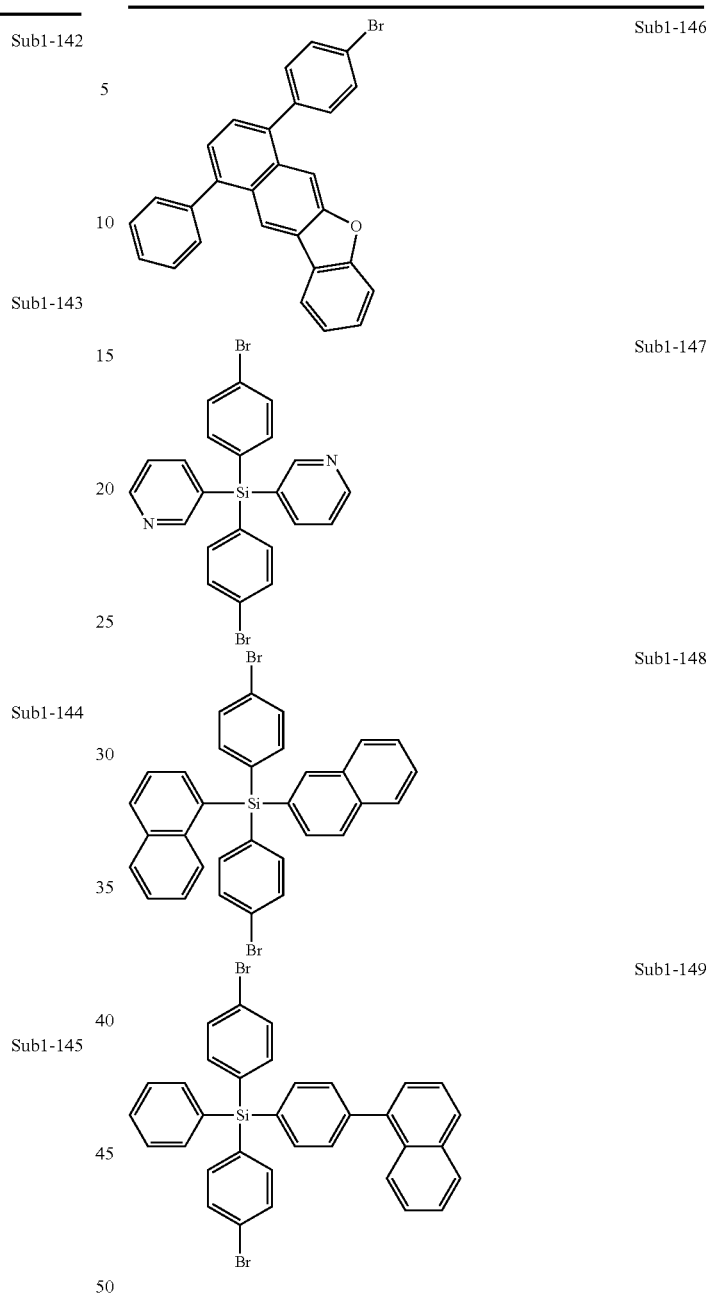
Sub1-146
Sub1-147
Sub1-148
Sub1-149
II. Synthesis of Sub2
1. Synthesis Example of Sub2-12
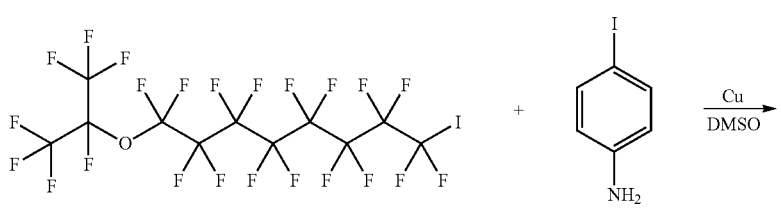

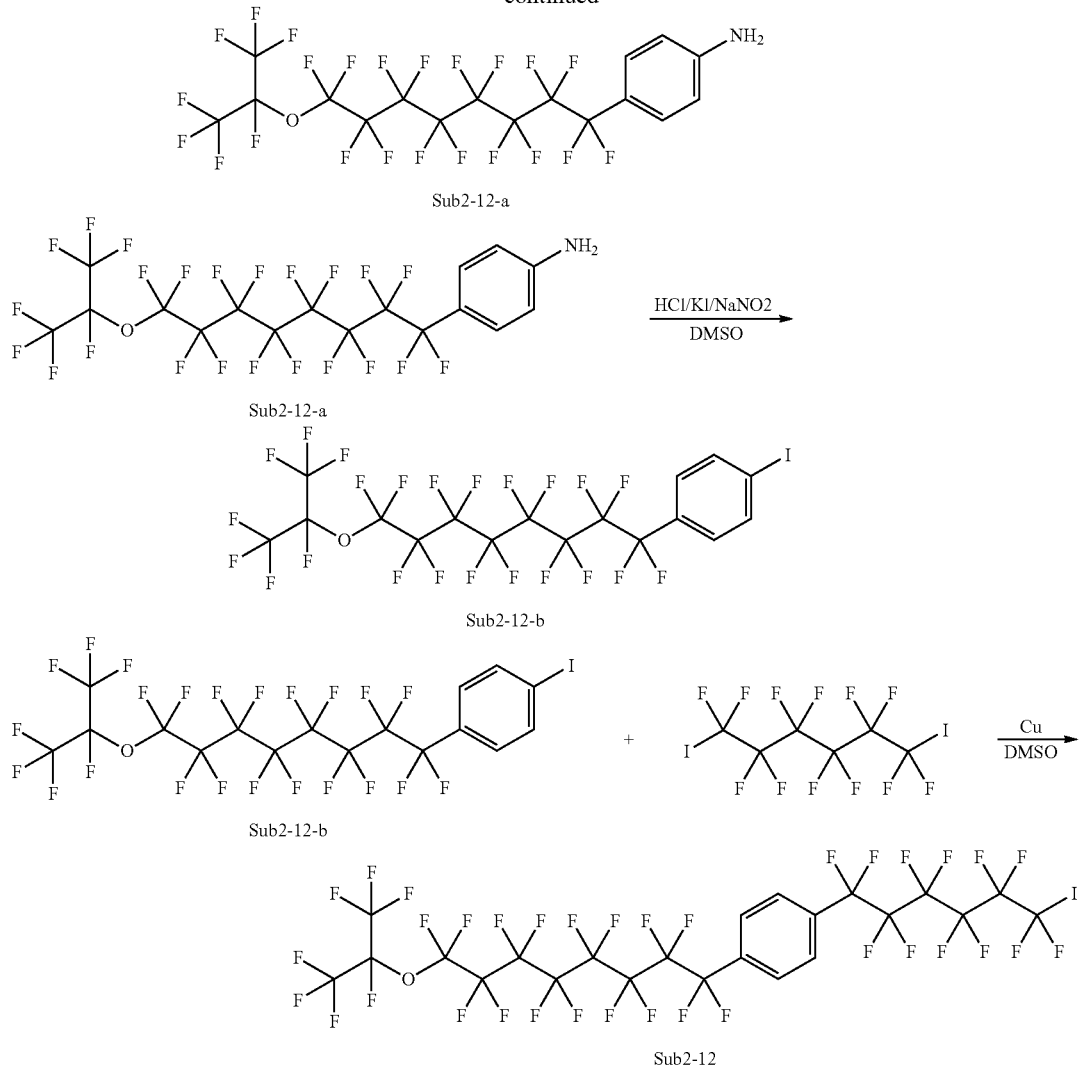

Sub2-12-a

Sub2-12-a

Sub2-12-b

Sub2-12-b

Sub2-12

(1) Synthesis Example of Sub2-12-a

In a round-bottom flask, 4-iodoaniline (30.0 g, 137 mmol), Cu (34.8 g, 548 mmol) and DMSO (274 mL) were added and dissolved at 70° C., followed by stirring for 30 minutes. After that, 1,1,2,2,3,3,4,4,5,5,6,6,7,7,8,8-hexadecafluoro-1-iodo-8-((perfluoropropan-2-yl)oxy)octane (117 g, 164 mmol) was slowly added dropwise over 1 hour, followed by stirring at 120° C. for 24 hours. When the reaction was completed, distilled water was added and the resulting solid was filtered under reduced pressure. After that, the filtrate was extracted with ethyl acetate, and the organic layer was dried over MgSO₄ and concentrated, and the resulting compound was separated by a silica gel column to obtain 63.0 g (yield: 68%) of the product.

(2) Synthesis Example of Sub2-12-b

The synthesized Sub2-12-a (50.0 g, 73.8 mmol) and 35% HCl (6.84 mL, 222 mmol) were added to a round-bottom flask and stirred for 1 hour. Then, after cooling with an ice bath, an aqueous solution in which NaNO₂ (7.13 g, 103 mmol) was dissolved was added dropwise for 30 minutes, and KI (17.2 g, 103 mmol) dissolved in distilled water (60 mL) was additionally added dropwise. After adding THF (80 mL), the mixture was stirred at room temperature overnight. When the reaction is complete, neutralize with aqueous NaOH solution and extract with diethylether, the organic layer was dried over MgSO₄ and concentrated, and the resulting compound was separated by a silica gel column to obtain 47.0 g (yield: 81%) of the product.

(3) Synthesis Example of Sub2-12

The synthesized Sub2-12-b (40.0 g, 50.8 mmol), Cu (7.10 g, 112 mmol) and DMSO (102 mL) were added to a round-bottom flask and dissolved at 70° C., followed by stirring for 30 minutes. After that, 1,1,2,2,3,3,4,4,5,5,6,6-dodecafluoro-1,6-diiodohexane (33.7 g, 60.9 mmol) was slowly added dropwise for 1 hour and stirred at 120° C. for 24 hours. When the reaction was completed, distilled water was added and the resulting solid was filtered under reduced pressure. After that, the filtrate was extracted with ethyl acetate, the organic layer was dried over MgSO₄, concentrated, and the resulting compound was separated by a silica gel column to obtain 11.0 g (yield: 20%) of the product.

2. Synthesis Example of Sub2-13

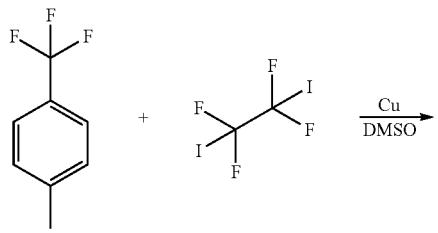

Sub2-13

1-iodo-4-(trifluoromethyl)benzene (40.0 g, 147 mmol), Cu (20.6 g, 324 mmol), 1,1,2,2-tetrafluoro-1,2-diiodoethane (62.4 g, 176 mmol), DMSO (294 mL) were used for the synthesis of Sub2-12 to obtain 9.3 g (yield: 17%) of the product.

3. Synthesis Example of Sub2-15

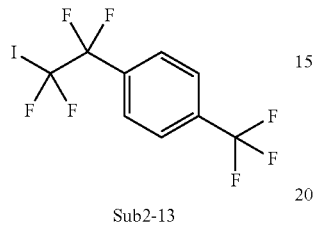

Sub2-15

1-iodo-4-(perfluorohexyl)benzene (40.0 g, 76.6 mmol), Cu (10.7 g, 169 mmol), 1,1,2,2-tetrafluoro-1,2-diiodoethane (32.5 g, 92.0 mmol), DMSO (153 mL) were used for the synthesis of Sub2-12 to obtain 9.1 g (yield: 19%) of the product.

4. Synthesis Example of Sub2-16

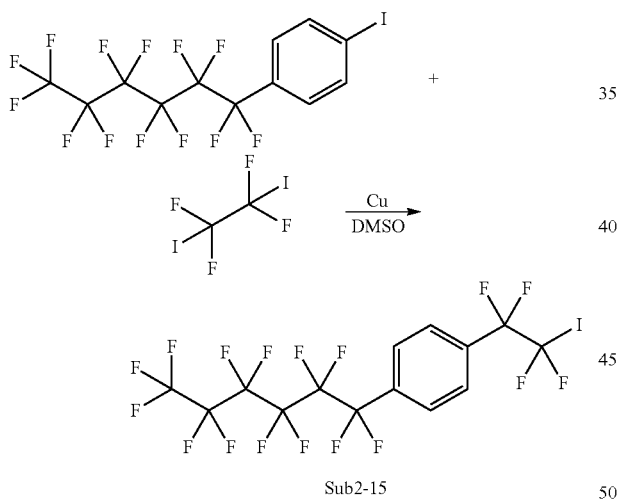

Sub2-16

1-iodo-4-(perfluorohexyl)benzene (40.0 g, 76.6 mmol), Cu (10.7 g, 169 mmol), 1,1,2,2,3,3,4,4,5,5,6,6-dodecafluoro-1,6-diiodohexane (50.9 g, 92.0 mmol), DMSO (153 mL) were used for the synthesis of Sub2-12 to obtain 13.2 g (yield: 21%) of the product.

Meanwhile, the compound belonging to Sub2 may be a compound as follows, but is not limited thereto, and Table 2 shows FD-MS values or CAS # of the following compounds. In the case of known compounds in Table 2, it is indicated by CAS #, and in the case of unknown compounds, it is indicated by FD-MS.

TABLE 2

| compound | CAS# or FD-MS |
| --- | --- |
| Sub2-1 | CAS#: 355-43-1 |
| Sub2-2 | CAS#: 355-58-0 |
| Sub2-3 | CAS#: 507-63-1 |
| Sub2-4 | CAS#: 423-62-1 |
| Sub2-5 | CAS#: 213014-41-6 |
| Sub2-6 | CAS#: 1146953-90-3 |
| Sub2-7 | CAS#: 2043-57-4 |
| Sub2-8 | CAS#: 677-69-0 |
| Sub2-9 | CAS#: 375-51-9 |
| Sub2-10 | CAS#: 212563-43-4 |
| Sub2-11 | CAS#: 25080-19-7 |
| Sub2-12 | m/z = 1087.87($C_{23}H_4F_{35}IO$ = 1088.13) |
| Sub2-13 | m/z = 371.92($C_9H_4F_7I$ = 372.02) |
| Sub2-14 | CAS#: 155367-62-7 |
| Sub2-15 | m/z = 621.91($C_{14}H_4F_{17}I$ = 622.06) |
| Sub2-16 | m/z = 821.9($C_{18}H_4F_{25}I$ = 822.09) |
| Sub2-17 | CAS#: 7057-81-0 |
| Sub2-18 | CAS#: 678-39-7 |
| Sub2-19 | m/z = 499.99($C_{10}H_3F_{19}O$ = 500.1) |
| Sub2-20 | CAS#: 1803004-25-2 |

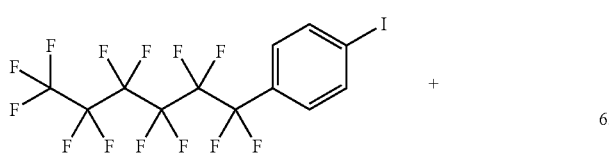

TABLE 2-continued

| | |
|---|---|
| 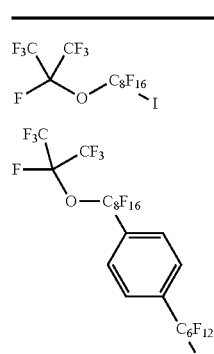 | Sub2-11 |
| | Sub2-12 |
| 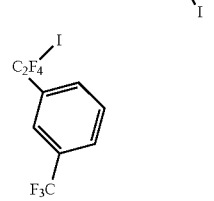 | Sub2-13 |
| | Sub2-14 |
| 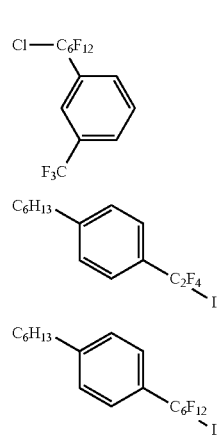 | Sub2-15 |
| | Sub2-16 |
| | Sub2-17 |
| | Sub2-18 |
| 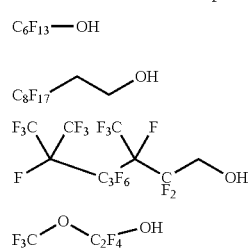 | Sub2-19 |
| | Sub2-20 |

III. Synthesis of Sub 3

1. Synthesis Example of Sub3-1

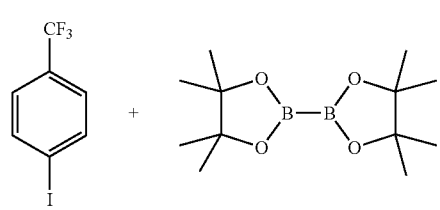

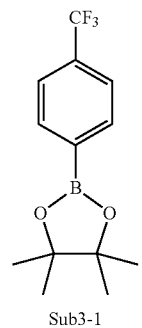

Put 1-Iodo-4-(trifluoromethyl)benzene (5.0 g, 18.4 mmol) in a round-bottom flask, Bis(pinacolato)diboron (4.9 g, 19.3 mmol), Pd$_2$(dba)$_3$ (0.51 g, 0.55 mmol), x-phos (0.53 g, 1.10 mmol), KOAc (3.6 g, 36.8 mmol) and Toluene (61 mL) were added and refluxed at 120° C. When the reaction was completed, the reaction solution was concentrated and separated through a silica gel column to obtain 3.9 g (yield: 79%) of the product.

2. Synthesis Example of Sub3-2

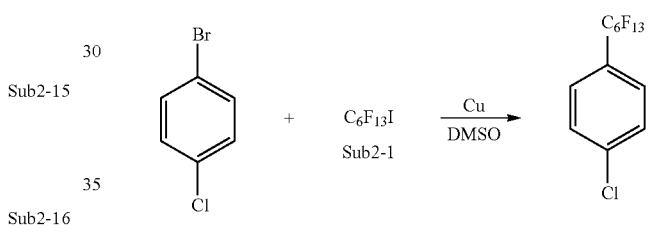

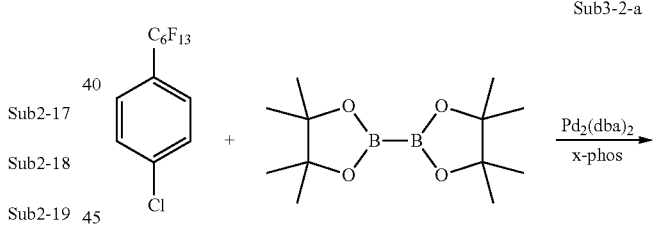

(1) Synthesis Example of Sub3-2-a

In a round flask, the synthesized 1-bromo-4-chlorobenzene (30.0 g, 157 mmol), Cu (39.8 g, 627 mmol) and DMSO (313 mL) were added and dissolved at 70° C., followed by stirring for 30 minutes. Then, Sub2-1 (76.9 g, 172 mmol)

was slowly added dropwise for 1 hour, followed by stirring at 120° C. for 24 hours. When the reaction was completed, distilled water was added and the resulting solid was filtered under reduced pressure. After that, the filtrate was extracted with ethyl acetate and the organic layer was dried over $MgSO_4$ and concentrated, and the resulting compound was separated by a silica gel column and recrystallized to obtain 50.7 g (yield: 75%) of the product.

(2) Synthesis Example of Sub3-2

The synthesized Sub3-2-a (50.7 g, 118 mmol), Bis(pinacolato)diboron (31.4 g, 124 mmol), $Pd_2(dba)_3$ (3.24 g, 3.54 mmol), x-phos (3.37 g, 7.07 mmol), KOAc (23.1 g, 236 mmol), and Toluene (393 mL) were used for the synthesis of Sub3-1, 49.9 g (yield: 81%) of the product was obtained.

3. Synthesis Example of Sub3-7

(1) Synthesis Example of Sub3-7-a 3-bromo-3'-chloro-1,1'-biphenyl (10.0 g, 37.4 mmol), Cu (9.5 g, 145 mmol), DMSO (75 mL) and Sub2-1 (18.3 g, 41.1 mmol) were used for the synthesis of Sub3-2-a to obtain 14.6 g (yield: 77%) of the product.

(2) Synthesis Example of Sub3-7

The obtained Sub3-7-a (14.6 g, 28.9 mmol), Bis(pinacolato)diboron (7.7 g, 30.3 mmol), $Pd_2(dba)_3$ (0.79 g, 0.87 mmol), x-phos (0.83 g, 1.73 mmol), KOAc (5.7 g, 57.7 mmol) and Toluene (96 mL) were used for the synthesis of Sub3-1, 13.8 g (yield: 80%) of the product was obtained.

4. Synthesis Example of Sub3-15

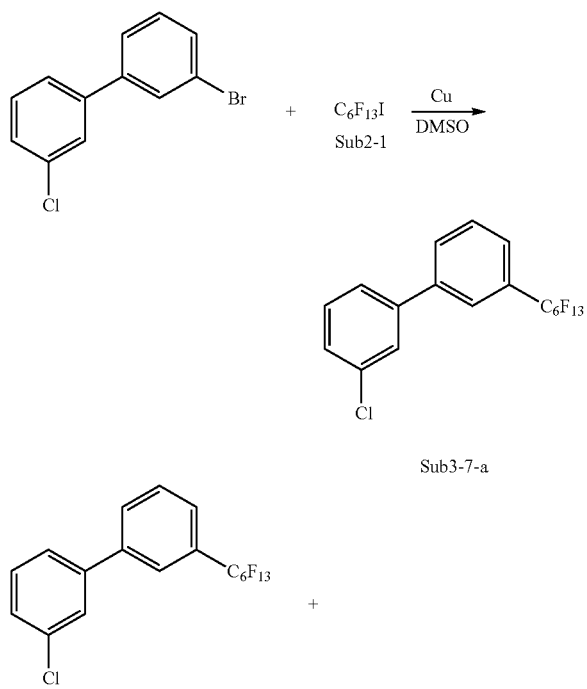

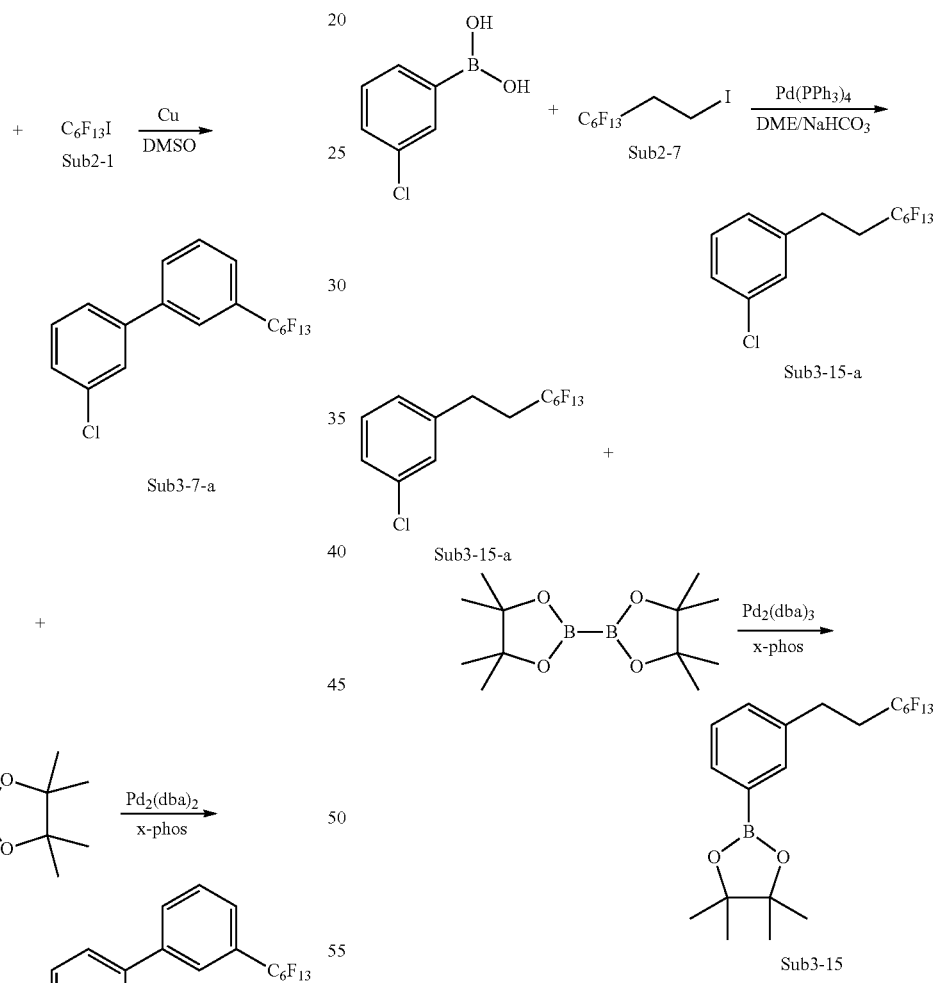

(1) Synthesis Example of Sub3-15-a

Put (3-chlorophenyl)boronic acid (8.0 g, 51.2 mmol), 1,1,1,1,1,1,1,1,1,1,1,1,1-tridecafluoro-8-iodo-1λ$^{16}$-octa-1,3,5-triyne (26.7 g, 56.3 mmol) in a round-bottom flask and dissolve it with DME (ethylene glycol dimethyl ether) (256 mL) and 1N $NaHCO_3$ aqueous solution (128 mL). After adding $Pd(PPh_3)_4$ (3.55 g, 3.07 mmol), the mixture was stirred under reflux for 5 hours. When the reaction is complete, the organic layer is cooled to room temperature, extracted with diethyl ether and brine, and the remaining moisture is removed from the obtained organic layer with $MgSO_4$. Then, the obtained organic layer was filtered under reduced pressure to obtain 17.7 g of a product (yield: 76%) through a silica gel column.

(2) Synthesis Example of Sub3-15

The synthesized Sub3-15-a (17.7 g, 38.7 mmol), Bis(pinacolato)diboron (10.3 g, 40.6 mmol), $Pd_2(dba)_3$ (1.06 g, 1.16 mmol), x-phos (1.11 g, 2.32 mmol), KOAc (7.6 g, 77.3 mmol) and Toluene (129 mL) were used for the synthesis of Sub3-1, 16.9 g (yield: 79%) of the product was obtained.

5. Synthesis Example of Sub3-23

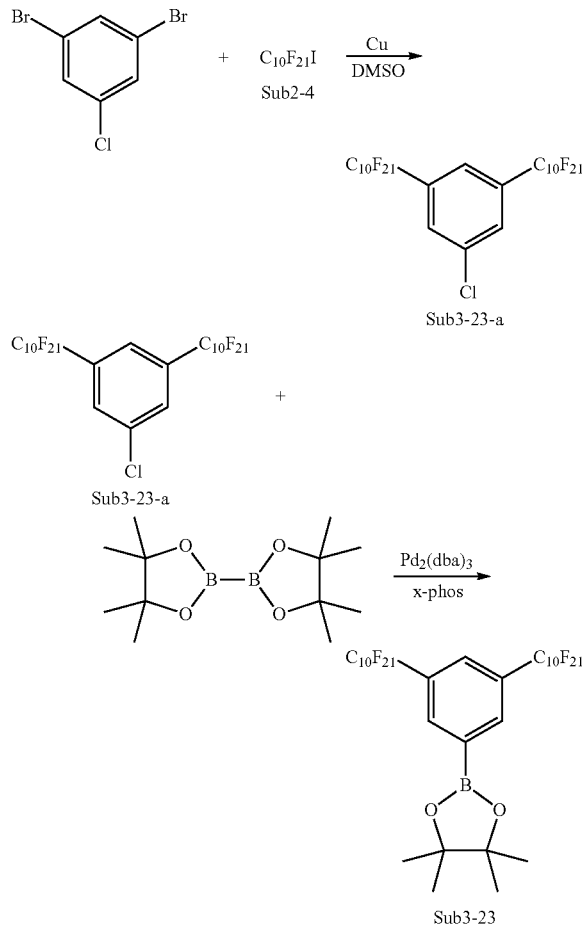

Sub3-23

(1) Synthesis Example of Sub3-23-a 1,3-dibromo-5-chlorobenzene (30.0 g, 111 mmol), Cu (56.4 g, 888 mmol), DMSO (222 mL) and Sub2-4 (158 g, 244 mmol) were used for the synthesis of Sub3-2-a to obtain 99.8 g (yield: 78%) of the product.

(2) Synthesis Example of Sub3-23

The obtained Sub3-23-a (99.8 g, 86.9 mmol), Bis(pinacolato)diboron (23.2 g, 91.2 mmol), $Pd_2(dba)_3$ (2.39 g, 2.61 mmol), x-phos (2.49 g, 5.21 mmol), KOAc (17.1 g, 174 mmol) and Toluene (290 mL) were used for the synthesis of Sub3-1, 84.5 g (yield: 78%) of the product was obtained.

Meanwhile, the compound belonging to Sub3 may be a compound as follows, but is not limited thereto, and Table 3 shows FD-MS values of the following compounds.

TABLE 3

| compound | FD-MS |
|---|---|
| Sub3-1 | m/z = 272.12($C_{13}H_{16}BF_3O_2$ = 272.07) |
| Sub3-2 | m/z = 522.10($C_{18}H_{16}BF_{13}O_2$ = 522.11) |
| Sub3-3 | m/z = 622.1($C_{20}H_{16}BF_{17}O_2$ = 622.13) |
| Sub3-4 | m/z = 522.10($C_{18}H_{16}BF_{13}O_2$ = 522.11) |
| Sub3-5 | m/z = 722.09($C_{22}H_{16}BF_{21}O_2$ = 722.14) |
| Sub3-6 | m/z = 722.09($C_{22}H_{16}BF_{21}O_2$ = 722.14) |
| Sub3-7 | m/z = 598.13($C_{24}H_{20}BF_{13}O_2$ = 598.21) |
| Sub3-8 | m/z = 572.12($C_{22}H_{18}BF_{13}O_2$ = 572.17) |
| Sub3-9 | m/z = 372.11($C_{15}H_{16}BF_7O_2$ = 372.09) |
| Sub3-10 | m/z = 422.11($C_{16}H_{16}BF_9O_2$ = 422.10) |
| Sub3-11 | m/z = 572.10($C_{19}H_{16}BF_{15}O_2$ = 572.12) |
| Sub3-12 | m/z = 794.05($C_{22}H_{12}BF_{25}O_2$ = 794.11) |
| Sub3-13 | m/z = 536.12($C_{19}H_{18}BF_{13}O_2$ = 536.14) |
| Sub3-14 | m/z = 550.13($C_{20}H_{20}BF_{13}O_2$ = 550.17) |
| Sub3-15 | m/z = 550.13($C_{20}H_{20}BF_{13}O_2$ = 550.17) |
| Sub3-16 | m/z = 566.13($C_{20}H_{20}BF_{13}O_3$ = 566.17) |
| Sub3-17 | m/z = 438.10($C_{16}H_{16}BF_9O_3$ = 438.10) |
| Sub3-18 | m/z = 404.10($C_{15}H_{16}BF_7O_4$ = 404.09) |
| Sub3-19 | m/z = 898.12($C_{30}H_{20}BF_{25}O_2$ = 898.26) |
| Sub3-20 | m/z = 840.07($C_{24}H_{15}BF_{26}O_2$ = 840.15) |
| Sub3-21 | m/z = 940.07($C_{26}H_{15}BF_{30}O_2$ = 940.17) |
| Sub3-22 | m/z = 1040.06($C_{28}H_{15}BF_{34}O_2$ = 1040.18) |
| Sub3-23 | m/z = 1240.05($C_{32}H_{15}BF_{42}O_2$ = 1240.21) |
| Sub3-24 | m/z = 916.11($C_{30}H_{19}BF_{26}O_2$ = 916.25) |
| Sub3-25 | m/z = 992.14($C_{36}H_{23}BF_{26}O_2$ = 992.35) |
| Sub3-26 | m/z = 896.14($C_{28}H_{23}BF_{26}O_2$ = 896.26) |
| Sub3-27 | m/z = 1068.09($C_{30}H_{19}BF_{34}O_2$ = 1068.24) |
| Sub3-28 | m/z = 1268.08($C_{34}H_{19}BF_{42}O_2$ = 1268.27) |
| Sub3-29 | m/z = 1372.03($C_{34}H_{15}BF_{46}O_4$ = 1372.23) |
| Sub3-30 | m/z = 1200.08($C_{32}H_{19}BF_{38}O_4$ = 1200.25) |
| Sub3-31 | m/z = 692.16($C_{30}H_{23}BF_{14}O_2$ = 692.30) |
| Sub3-32 | m/z = 636.11($C_{21}H_{18}BF_{17}O_2$ = 636.16) |
| Sub3-33 | m/z = 841.07($C_{23}H_{14}BF_{26}NO_2$ = 841.14) |
| Sub3-34 | m/z = 1140.06($C_{30}H_{15}BF_{38}O_2$ = 1140.20) |
| Sub3-35 | m/z = 1040.06($C_{28}H_{15}BF_{34}O_2$ = 1040.18) |
| Sub3-36 | m/z = 940.07($C_{26}H_{15}BF_{30}O_2$ = 940.17) |

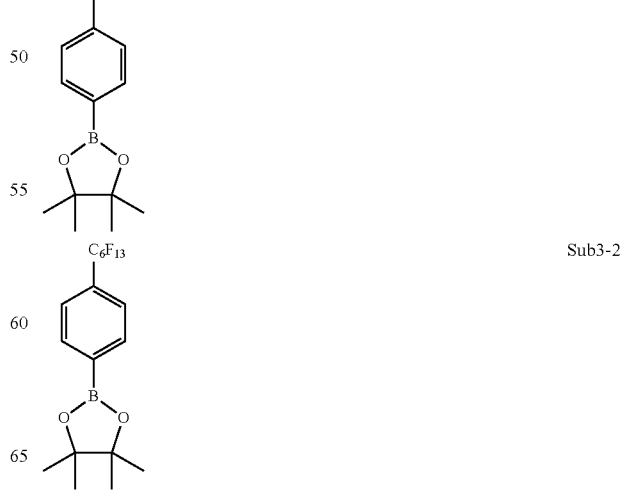

Sub3-1

Sub3-2

TABLE 3-continued
| | |
|---|---|
| 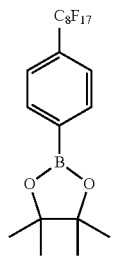 | Sub3-3 |
| 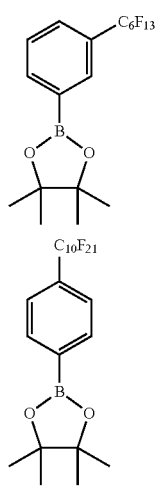 | Sub3-4 |
| | Sub3-5 |
| 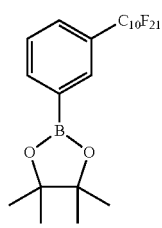 | Sub3-6 |
| 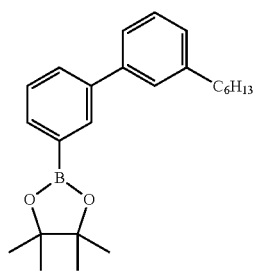 | Sub3-7 |
| 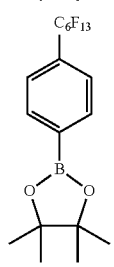 | Sub3-8 |
TABLE 3-continued
| | |
|---|---|
| 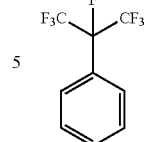 | Sub3-9 |
| 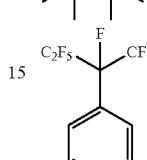 | Sub3-10 |
| 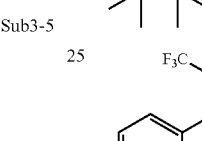 | Sub3-11 |
| 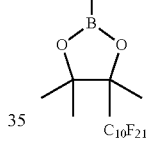 | Sub3-12 |
| 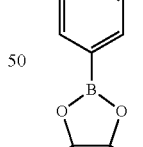 | Sub3-13 |
| 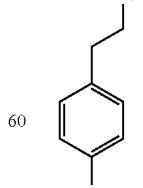 | Sub3-14 |

TABLE 3-continued
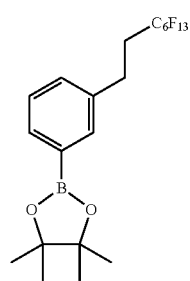 Sub3-15
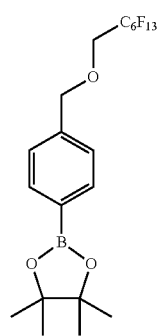 Sub3-16
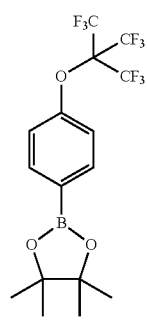 Sub3-17
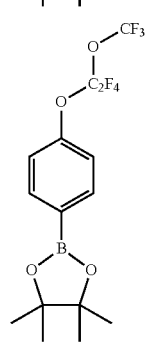 Sub3-18
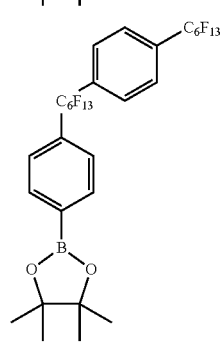 Sub3-19
TABLE 3-continued
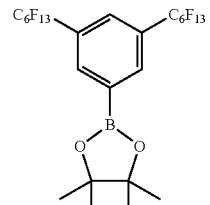 Sub3-20
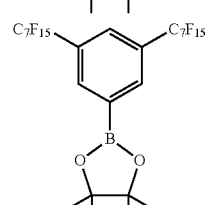 Sub3-21
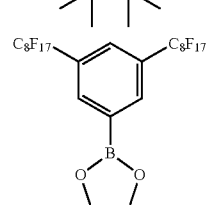 Sub3-22
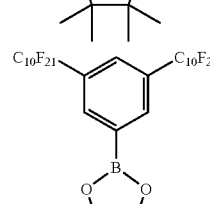 Sub3-23
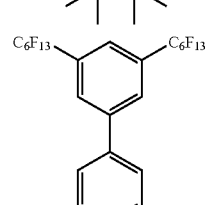 Sub3-24
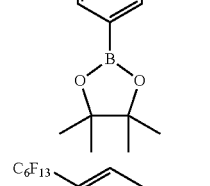 Sub3-25
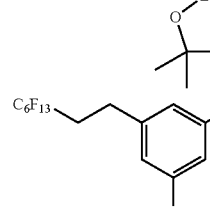 Sub3-26

TABLE 3-continued
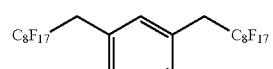 Sub3-27
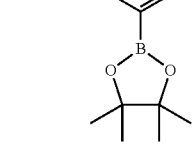 Sub3-28
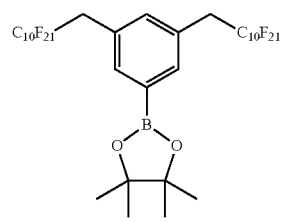 Sub3-29
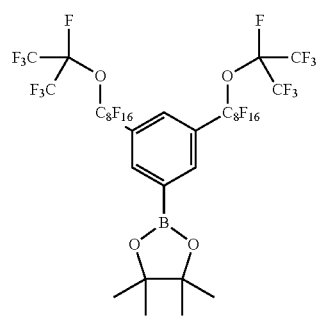 Sub3-30
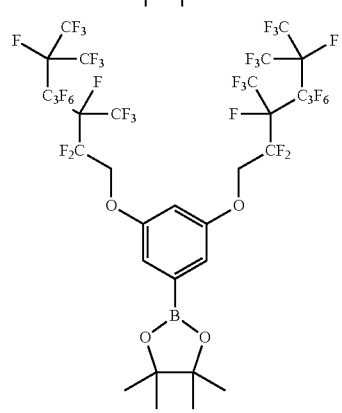 Sub3-31
TABLE 3-continued
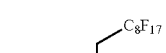 Sub3-32
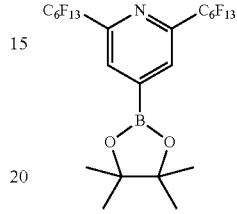 Sub3-33
Sub3-34
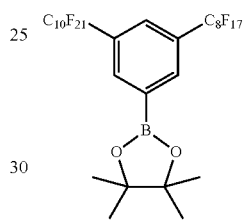 Sub3-35
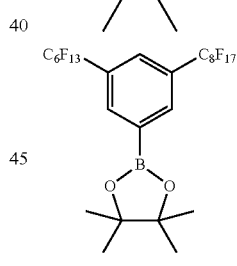 Sub3-36
IV. Synthesis of Final Product
1. Synthesis Example of P1-1
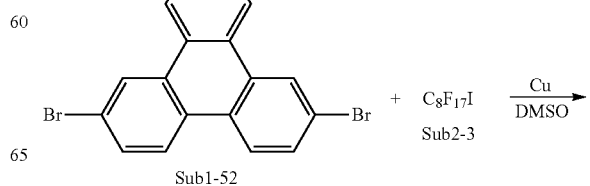

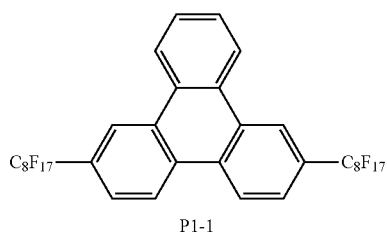

P1-1

Sub1-52 (3.0 g, 7.77 mmol), Cu (4.0 g, 62.2 mmol) and DMSO (16 mL) were placed in a round flask and dissolved at 70° C., followed by stirring for 30 minutes. Then, Sub2-3 (9.3 g, 17.1 mmol) was slowly added dropwise over 1 hour, followed by stirring at 120° C. for 24 hours. When the reaction was completed, distilled water was added and the resulting solid was filtered under reduced pressure. After that, the filtrate was extracted with ethyl acetate, the organic layer was dried over MgSO$_4$, concentrated, and the resulting compound was separated by a silica gel column and recrystallized to obtain 6.6 g (yield: 80%) of the product.

2. Synthesis Example of P1-22

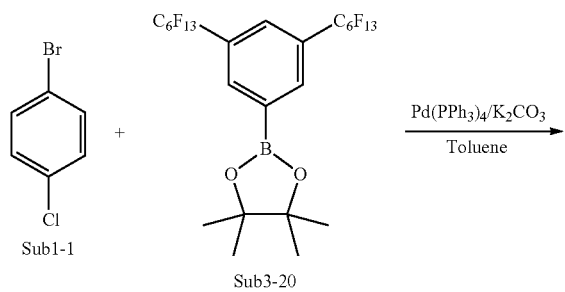

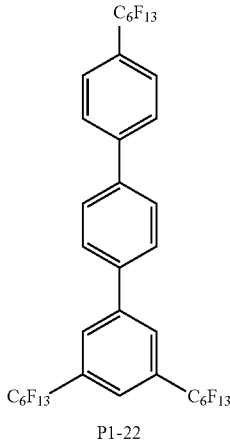

P1-22

(1) Synthesis Example of Inter1-22

After dissolving Sub1-1 (1.0 g, 5.22 mmol) in Toluene (17 mL) in a round flask, Sub3-20 (4.39 g, 5.22 mmol), K$_2$CO$_3$ (2.17 g, 15.7 mmol) and Pd(PPh$_3$)$_4$ (0.12 g, 0.10 mmol) were added and stirred at 120° C. When the reaction was completed, the product was separated by silica gel column and recrystallized to obtain 3.53 g (yield: 82%) of the product.

(2) Synthesis Example of P1-22

After dissolving the synthesized Inter1-22 (3.0 g, 3.64 mmol) in Toluene (12 mL) in a round flask, Sub3-2 (1.9 g, 3.64 mmol), K$_2$CO$_3$ (1.5 g, 10.9 mmol) and Pd(PPh$_3$)$_4$ (0.08 g, 0.07 mmol) were added and stirred at 120° C. When the reaction was completed, the product was separated by silica gel column and recrystallized to obtain 3.41 g (yield: 79%) of the product.

3. Synthesis Example of P1-23

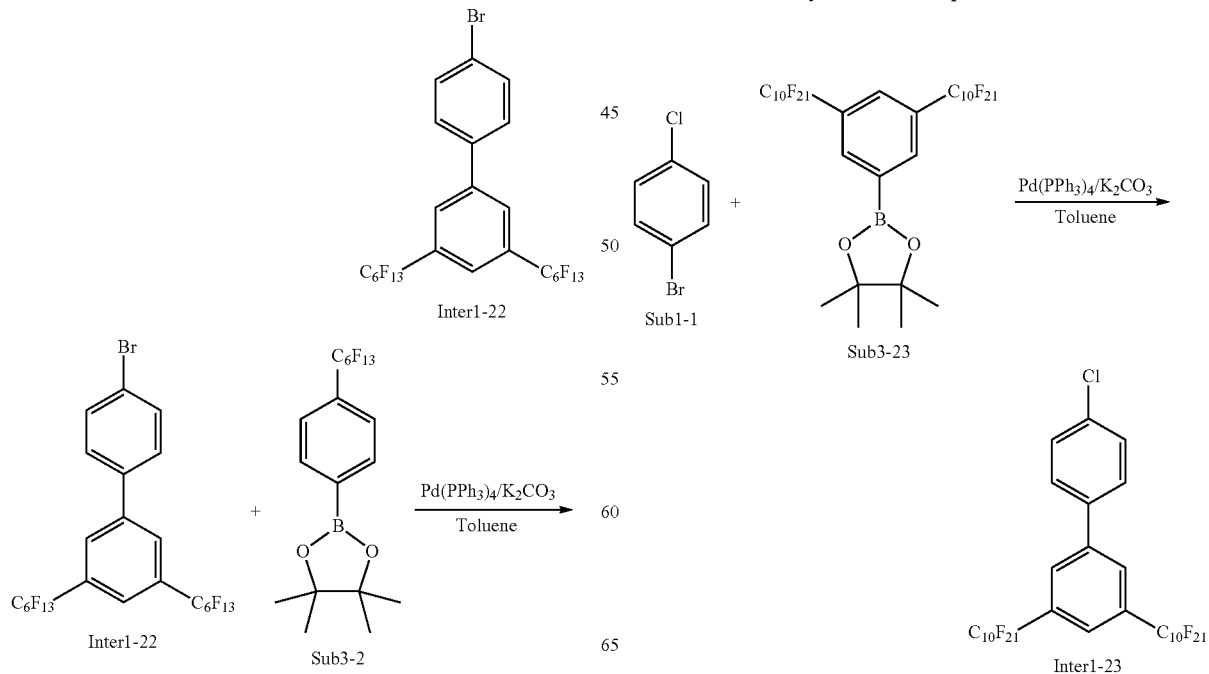

-continued

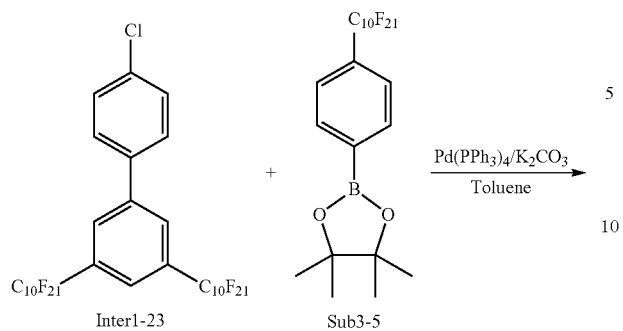

(1) Synthesis Example of Inter1-23

Sub1-1 (1.0 g, 5.22 mmol), Sub3-23 (7.1 g, 5.75 mmol), $K_2CO_3$ (2.2 g, 15.7 mmol), $Pd(PPh_3)_4$ (0.12 g, 0.10 mmol), Toluene (17.4 mL) were obtained through the synthesis of Inter1-22, 4.4 g (yield: 69%) of the product was obtained.

(2) Synthesis Example of P1-23

The obtained Inter1-23 (4.4 g, 3.60 mmol), Sub3-5 (2.86 g, 3.96 mmol), $K_2CO_3$ (1.49 g, 10.8 mmol), $Pd(PPh_3)_4$ (0.08 g, 0.07 mmol), Toluene (12 mL) were synthesized by P1-22 to obtain 4.9 g (yield: 76%) of the product.

4. Synthesis Example of P1-34

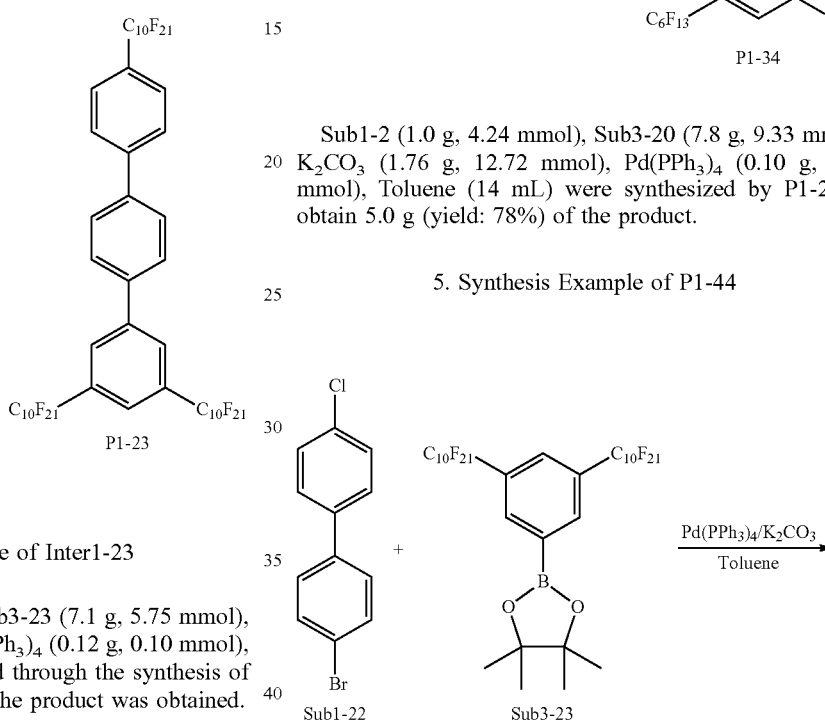

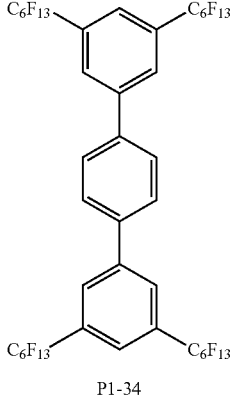

Sub1-2 (1.0 g, 4.24 mmol), Sub3-20 (7.8 g, 9.33 mmol), $K_2CO_3$ (1.76 g, 12.72 mmol), $Pd(PPh_3)_4$ (0.10 g, 0.08 mmol), Toluene (14 mL) were synthesized by P1-22 to obtain 5.0 g (yield: 78%) of the product.

5. Synthesis Example of P1-44

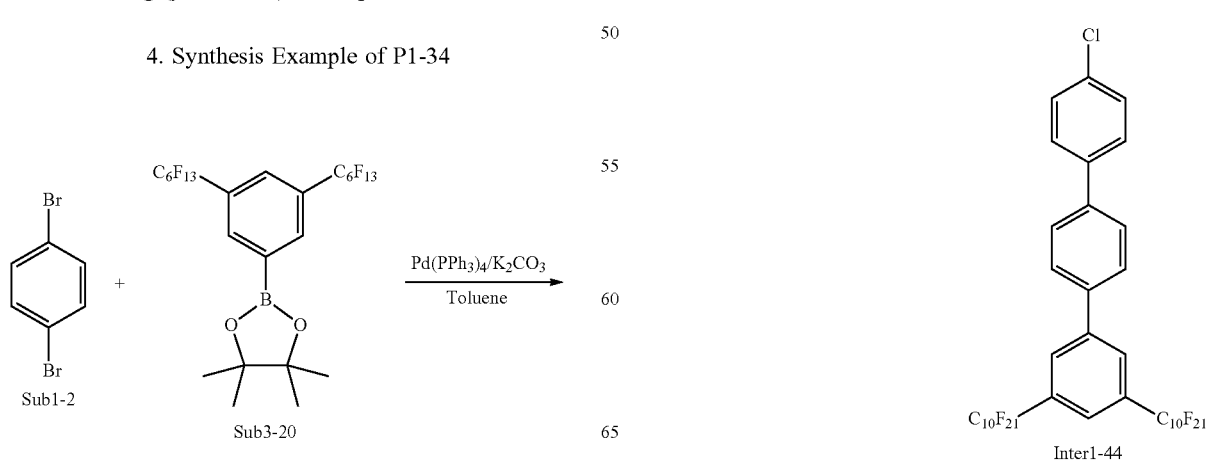

143
-continued

144

6. Synthesis Example of P1-46

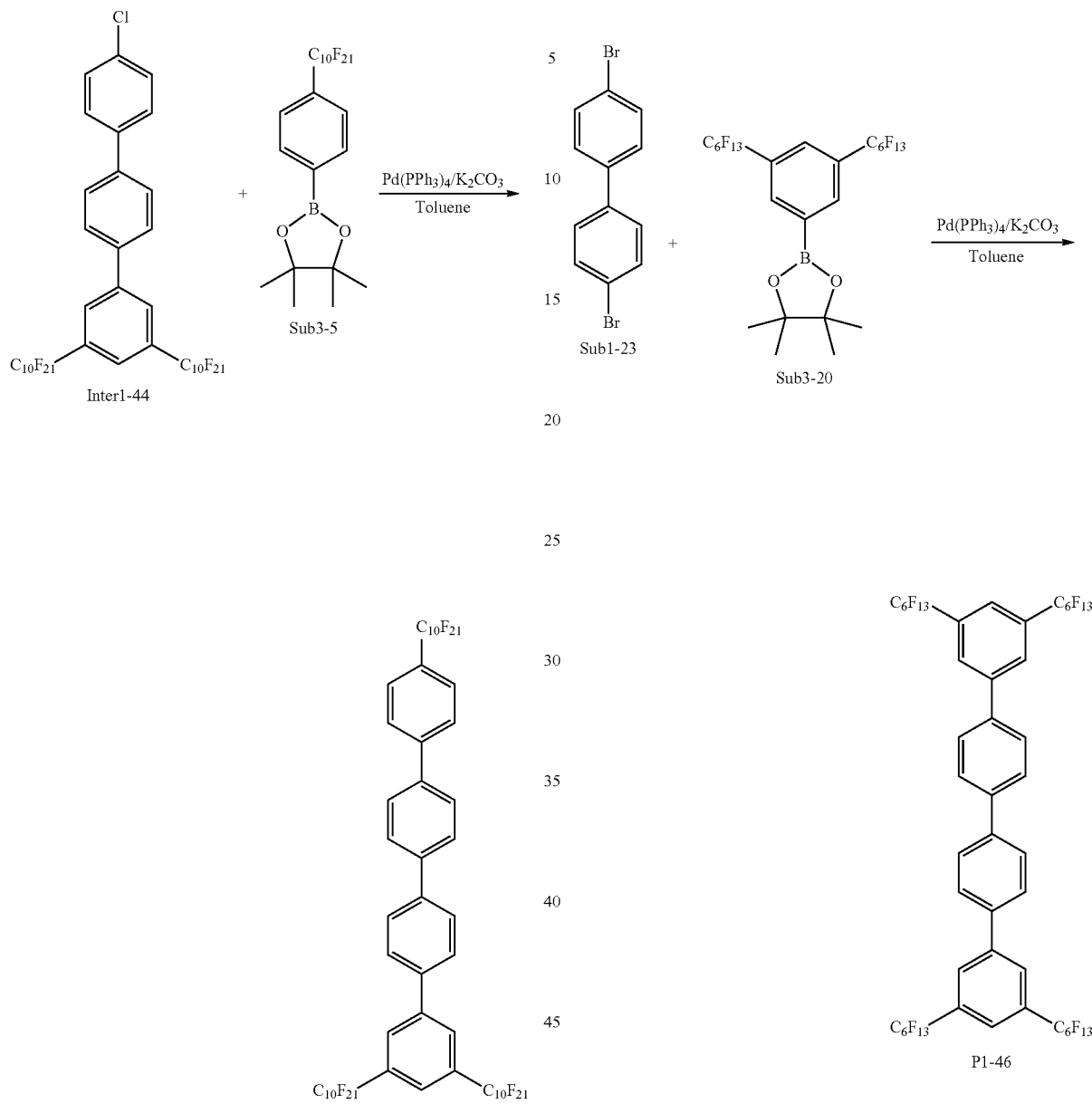

(1) Synthesis Example of Inter1-44

Sub1-22 (1.0 g, 3.74 mmol), Sub3-23 (5.1 g, 4.11 mmol), $K_2CO_3$ (1.6 g, 11.21 mmol), $Pd(PPh_3)_4$ (0.09 g, 0.07 mmol), Toluene (13 mL) were synthesized by P1-22 to obtain 3.3 g (yield: 67%) of the product.

(2) Synthesis Example of P1-44

The obtained Inter-44 (3.3 g, 2.51 mmol), Sub3-5 (2.0 g, 2.76 mmol), $K_2CO_3$ (1.0 g, 7.52 mmol), $Pd(PPh_3)_4$ (0.06 g, 0.05 mmol), Toluene (8.4 mL) were synthesized by P1-22 to obtain 3.6 g (yield: 77%) of the product.

Sub1-23 (1.0 g, 3.21 mmol), Sub3-20 (5.9 g, 7.05 mmol), $K_2CO_3$ (1.3 g, 9.62 mmol), $Pd(PPh_3)_4$ (0.07 g, 0.06 mmol), Toluene (11 mL) were synthesized by P1-22 to obtain 4.6 g (yield: 79%) of the product.

7. Synthesis Example of P1-50

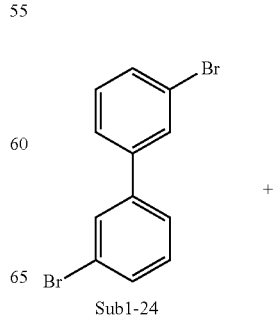

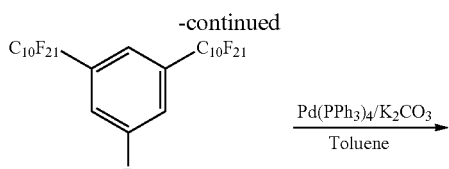
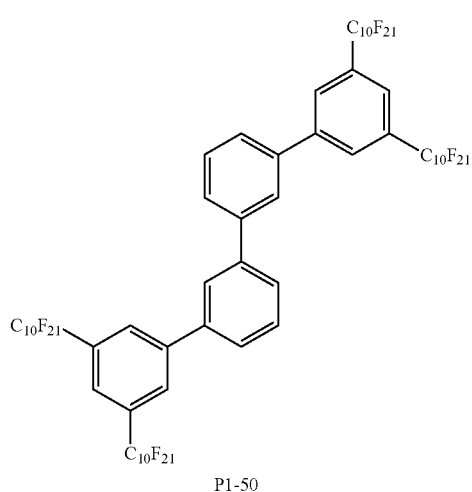
P1-50
Sub1-24 (1.0 g, 3.21 mmol), Sub3-23 (8.8 g, 7.05 mmol), K₂CO₃ (1.3 g, 9.62 mmol), Pd(PPh₃)₄ (0.07 g, 0.06 mmol), Toluene (11 mL) were synthesized by P1-22 to obtain 5.3 g (yield: 70%) of the product.
8. Synthesis Example of P1-52
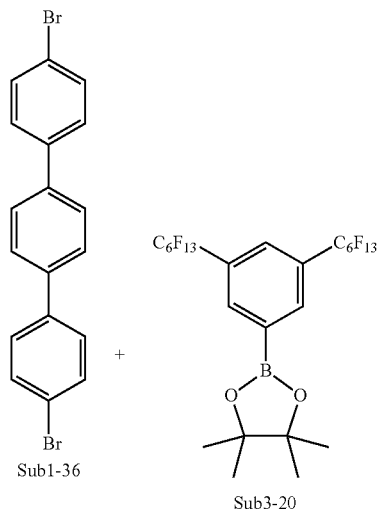
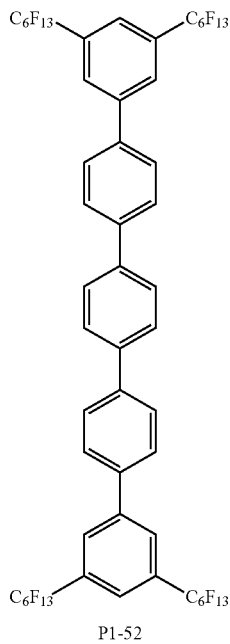
P1-52
Sub1-36 (1.0 g, 2.58 mmol), Sub3-20 (4.8 g, 5.67 mmol), K₂CO₃ (1.1 g, 7.73 mmol), Pd(PPh₃)₄ (0.06 g, 0.05 mmol), Toluene (8.6 mL) were synthesized by P1-22 to obtain 3.1 g (yield: 73%) of the product.
9. Synthesis Example of P1-55
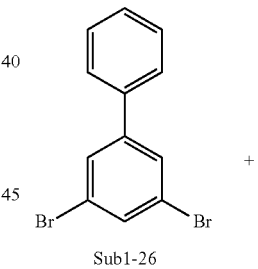
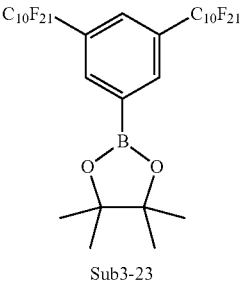

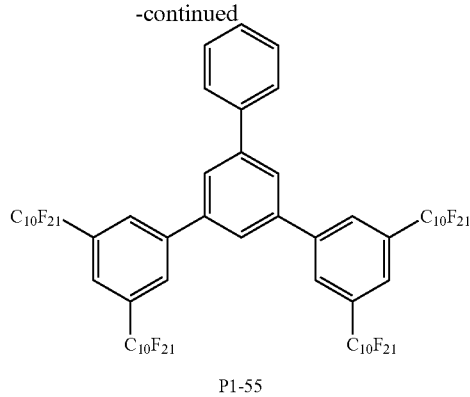

P1-55

Sub1-26 (1.0 g, 3.21 mmol), Sub3-23 (8.8 g, 7.05 mmol), K₂CO₃ (1.3 g, 9.62 mmol), Pd(PPh₃)₄ (0.07 g, 0.06 mmol), Toluene (11 mL) were synthesized by P1-22 to obtain 5.5 g (yield: 72%) of the product.

10. Synthesis Example of P1-61

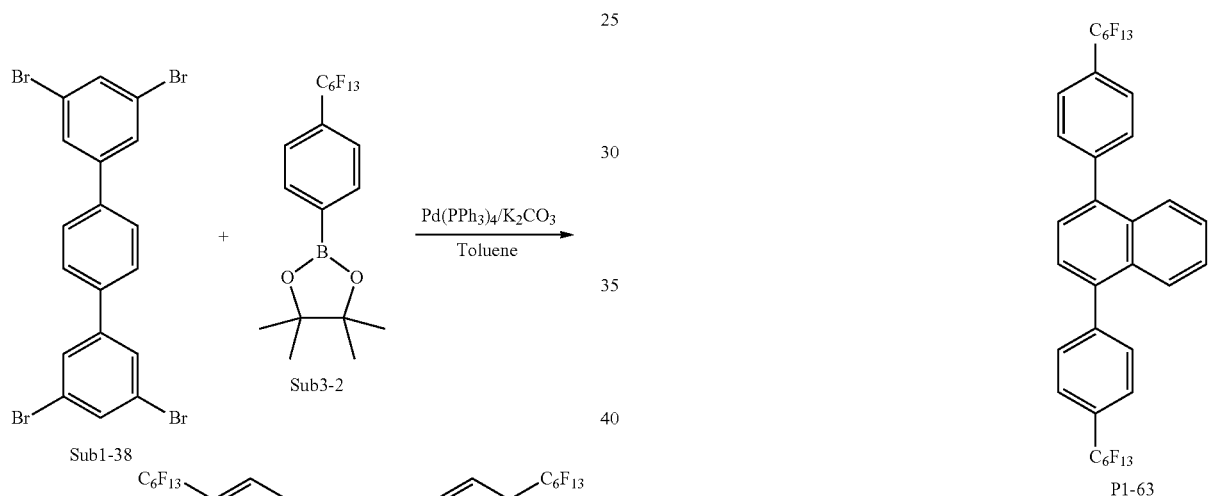

P1-61

Sub1-38 (2.0 g, 3.66 mmol), Sub3-2 (8.4 g, 16.1 mmol), K₂CO₃ (3.0 g, 22.0 mmol), Pd(PPh₃)₄ (0.08 g, 0.07 mmol), Toluene (12 mL) were synthesized by P1-22 to obtain 3.8 g (yield: 58%) of the product.

11. Synthesis Example of P1-63

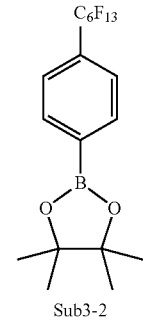

P1-63

Sub1-41 (2.0 g, 6.99 mmol), Sub3-2 (8.0 g, 15.4 mmol), K₂CO₃ (2.90 g, 21.0 mmol), Pd(PPh₃)₄ (0.16 g, 0.14 mmol), Toluene (23 mL) were synthesized by P1-22 to obtain 4.8 g (yield: 75%) of the product.

12. Synthesis Example of P1-65

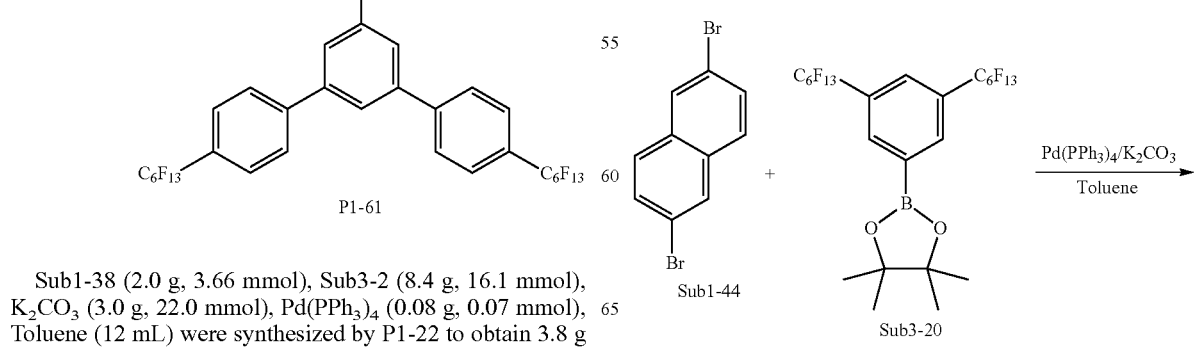

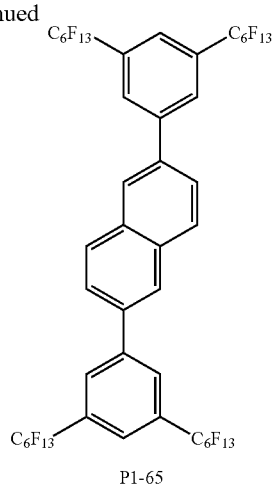

P1-65

Sub1-44 (1.0 g, 3.50 mmol), Sub3-20 (6.5 g, 7.69 mmol), K₂CO₃ (1.45 g, 10.5 mmol), Pd(PPh₃)₄ (0.08 g, 0.07 mmol), Toluene (12 mL) were synthesized by P1-22 to obtain 4.1 g (yield: 76%) of the product.

13. Synthesis Example of P1-67

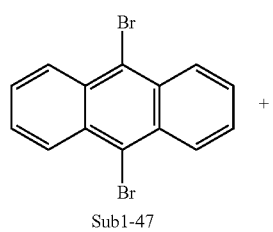

Sub1-47

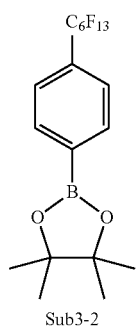

Sub3-2

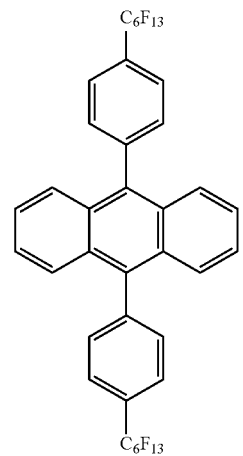

P1-67

Sub1-47 (2.0 g, 5.95 mmol), Sub3-2 (6.8 g, 13.1 mmol), K₂CO₃ (2.5 g, 17.9 mmol), Pd(PPh₃)₄ (0.14 g, 0.12 mmol), Toluene (20 mL) were synthesized by P1-22 to obtain 4.4 g (yield: 77%) of the product.

14. Synthesis Example of P1-69

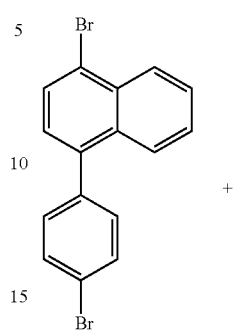

Sub1-45

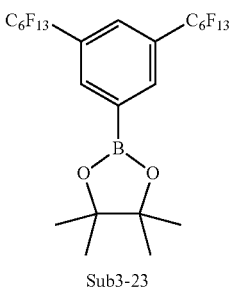

Sub3-23

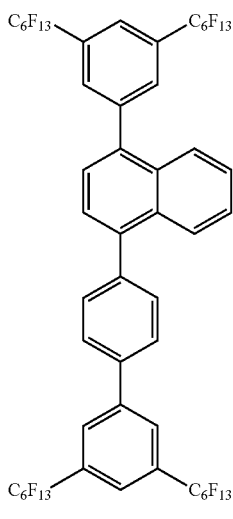

P1-69

Sub1-45 (1.0 g, 2.76 mmol), Sub3-23 (7.6 g, 6.08 mmol), K₂CO₃ (1.2 g, 8.29 mmol), Pd(PPh₃)₄ (0.06 g, 0.06 mmol), Toluene (9.2 mL) were synthesized by P1-22 to obtain 4.8 g (yield: 71%) of the product.

15. Synthesis Example of P1-71

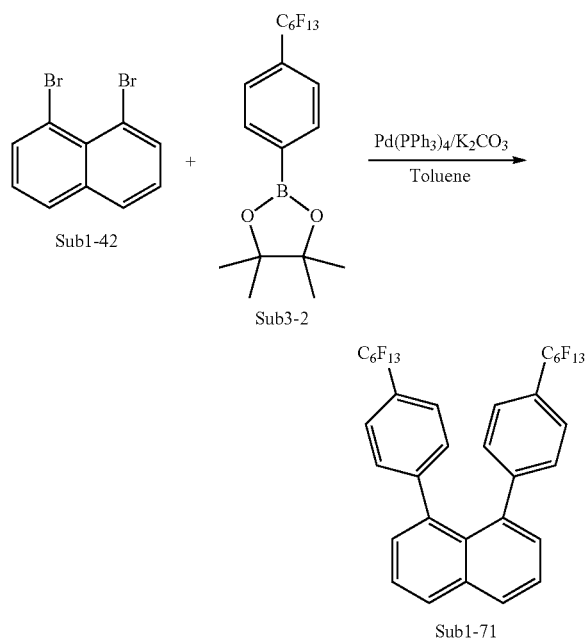

Sub1-42 (2.0 g, 6.99 mmol), Sub3-2 (8.0 g, 15.4 mmol), K$_2$CO$_3$ (2.9 g, 21.0 mmol), Pd(PPh$_3$)$_4$ (0.16 g, 0.14 mmol), Toluene (23 mL) were synthesized by P1-22 to obtain 4.7 g (yield: 74%) of the product.

16. Synthesis Example of P1-73

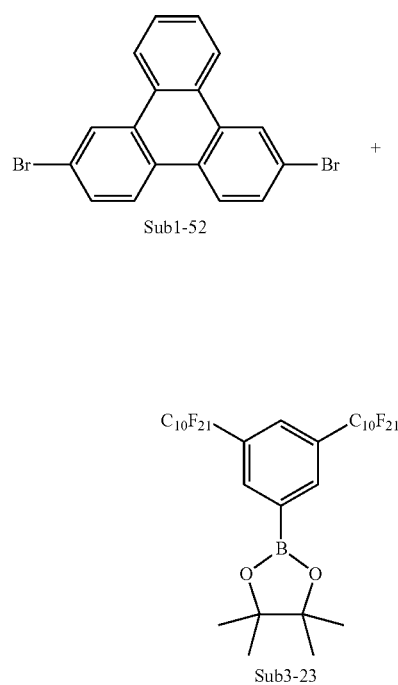

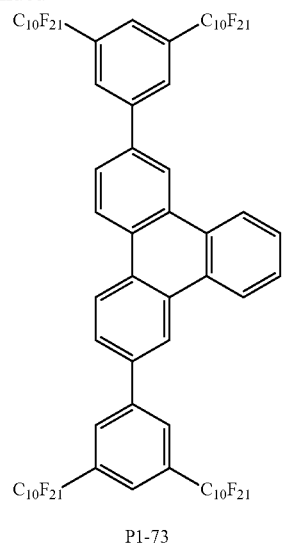

P1-73

Sub1-52 (0.8 g, 2.07 mmol), Sub3-23 (5.7 g, 4.56 mmol), K$_2$CO$_3$ (0.86 g, 6.22 mmol), Pd(PPh$_3$)$_4$ (0.05 g, 0.04 mmol), Toluene (6.9 mL) were synthesized by P1-22 to obtain 3.9 g (yield: 76%) of the product.

17. Synthesis Example of P2-1

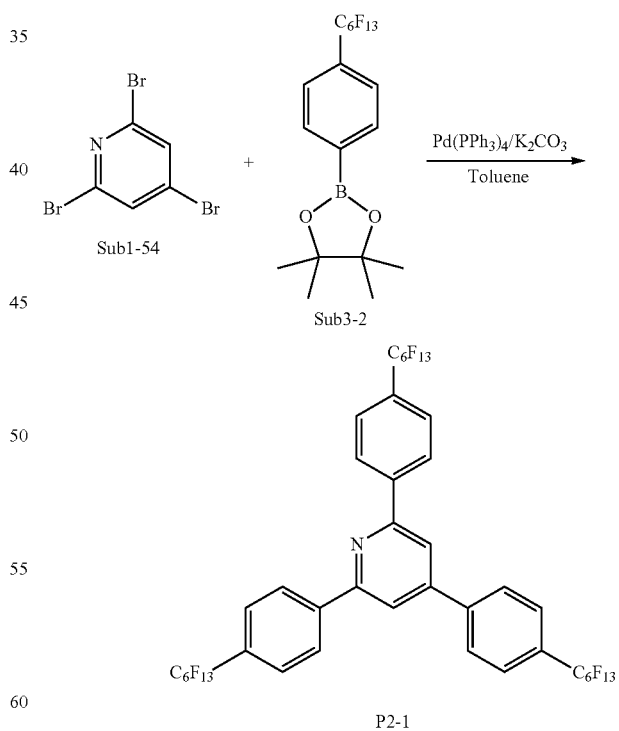

Sub1-54 (2.0 g, 6.33 mmol), Sub3-2 (10.9 g, 20.9 mmol), K$_2$CO$_3$ (5.3 g, 38.0 mmol), Pd(PPh$_3$)$_4$ (0.15 g, 0.13 mmol), Toluene (21 mL) were synthesized by P1-22 to obtain 4.9 g (yield: 61%) of the product.

18. Synthesis Example of P2-2

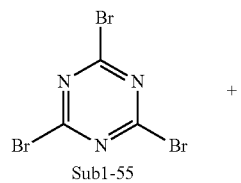 Sub1-55 +

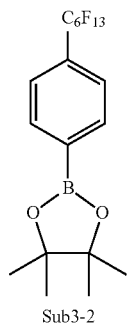 Sub3-2

Pd(PPh₃)₄/K₂CO₃ / Toluene →

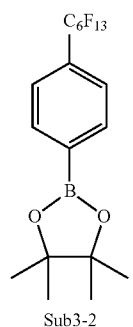 Sub3-2

Pd(PPh₃)₄/K₂CO₃ / Toluene →

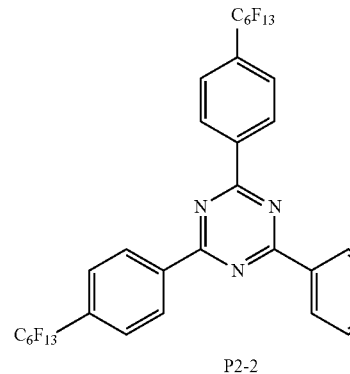 P2-2

Sub1-55 (1.0 g, 3.15 mmol), Sub3-2 (5.42 g, 10.4 mmol), K₂CO₃ (1.3 g, 9.44 mmol), Pd(PPh₃)₄ (0.07 g, 0.06 mmol), Toluene (11 mL) were synthesized by P1-22 to obtain 3.1 g (yield: 78%) of the product.

19. Synthesis Example of P3-2

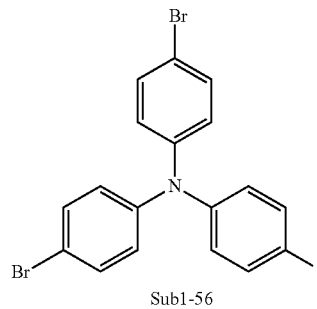 Sub1-56 +

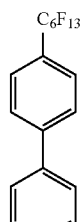 Sub3-2

Pd(PPh₃)₄/K₂CO₃ / Toluene →

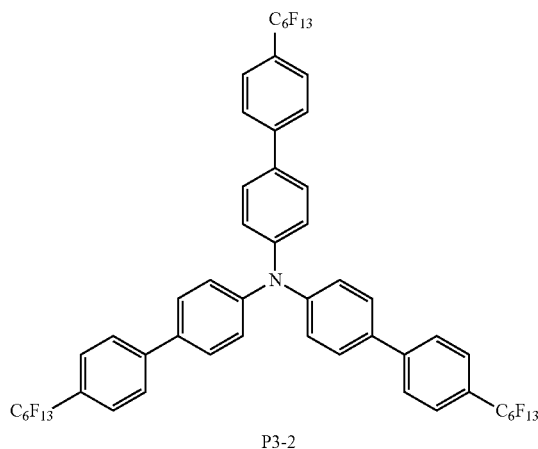 P3-2

Sub1-56 (2.0 g, 4.15 mmol), Sub3-2 (7.2 g, 13.7 mmol), K₂CO₃ (3.4 g, 24.9 mmol), Pd(PPh₃)₄ (0.10 g, 0.08 mmol), Toluene (14 mL) were synthesized by P1-22 to obtain 3.6 g (yield: 61%) of the product.

20. Synthesis Example of P3-4

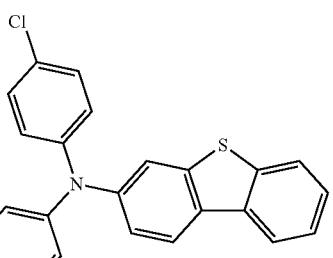 Sub1-58

C₁₀F₂₁I  Sub2-4    Cu / DMSO →

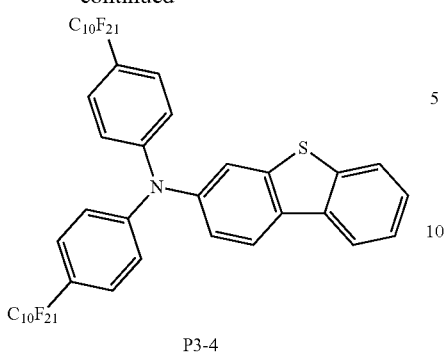

P3-4

The synthesized Sub1-58 (1.5 g, 3.58 mmol), Cu (1.8 g, 28.6 mmol), Sub2-4 (5.1 g, 7.88 mmol), DMSO (7 mL) were used for the synthesis of P1-1 to obtain 3.8 g (yield: 76%) of the product.

21. Synthesis Example of P3-5

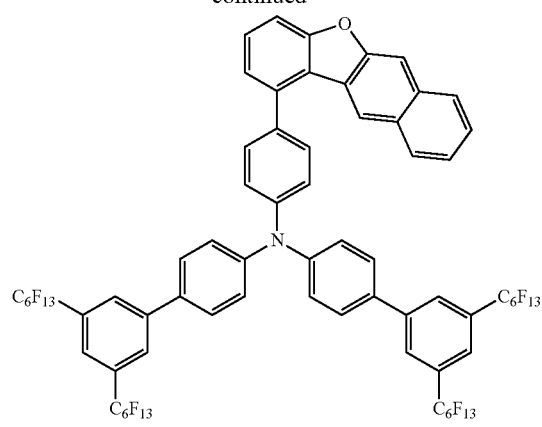

P3-5

Sub1-59 (2.0 g, 3.23 mmol), Sub3-20 (6.0 g, 7.10 mmol), K$_2$CO$_3$ (1.34 g, 9.69 mmol), Pd(PPh$_3$)$_4$ (0.07 g, 0.06 mmol), Toluene (11 mL) were synthesized by P1-22 to obtain 4.1 g (yield: 68%) of the product.

22. Synthesis Example of P4-2

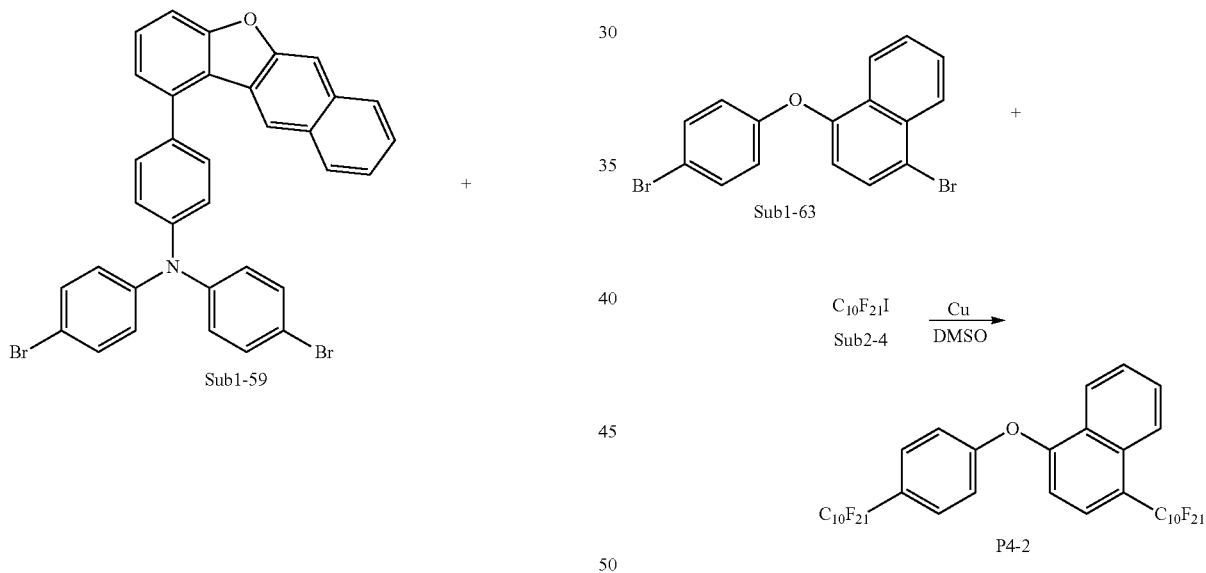

The synthesized Sub1-63 (1.5 g, 3.97 mmol), Cu (2.0 g, 31.7 mmol), Sub2-4 (5.6 g, 8.73 mmol), DMSO (8 mL) were used for the synthesis of P1-1 to obtain 3.6 g (yield: 72%) of the product.

23. Synthesis Example of P4-4

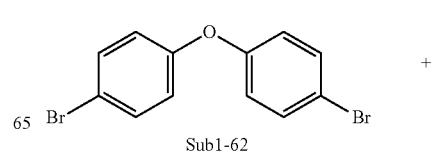

Sub1-62

157
-continued

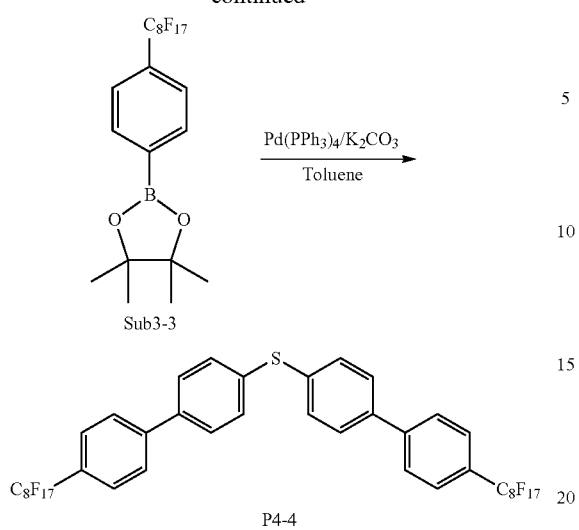

Sub1-62 (2.0 g, 6.10 mmol), Sub3-3 (8.4 g, 13.4 mmol), K₂CO₃ (2.5 g, 18.3 mmol), Pd(PPh₃)₄ (0.14 g, 0.12 mmol), Toluene (20 mL) were used for the synthesis of P1-22 to obtain 5.2 g (yield: 73%) of the product.

24. Synthesis Example of P5-3

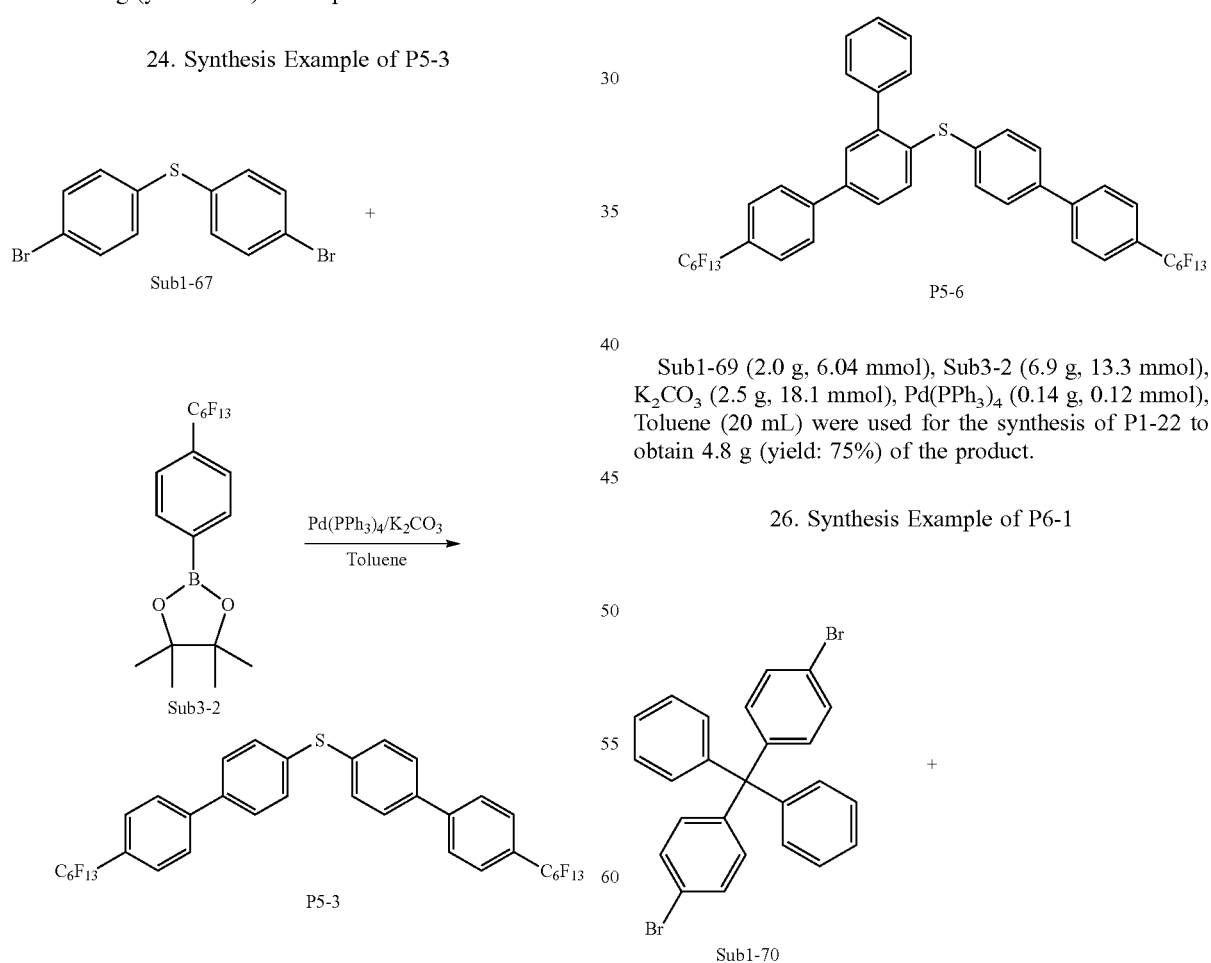

Sub1-67 (2.0 g, 5.81 mmol), Sub3-2 (6.7 g, 12.8 mmol), K₂CO₃ (2.4 g, 17.4 mmol), Pd(PPh₃)₄ (0.13 g, 0.12 mmol), Toluene (19 mL) were used for the synthesis of P1-22 to obtain 4.5 g (yield: 72%) of the product.

158
25. Synthesis Example of P5-6

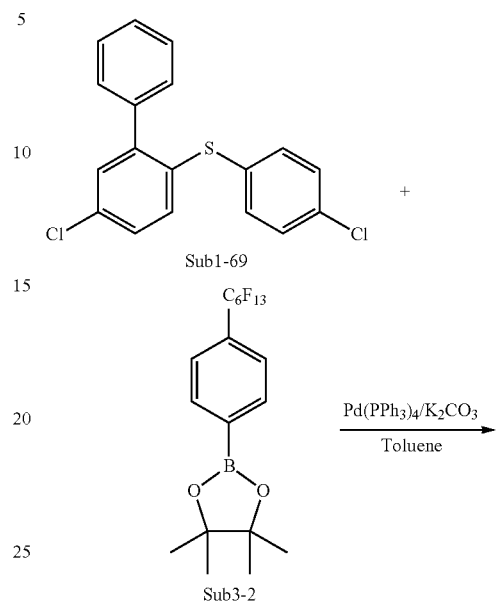

Sub1-69 (2.0 g, 6.04 mmol), Sub3-2 (6.9 g, 13.3 mmol), K₂CO₃ (2.5 g, 18.1 mmol), Pd(PPh₃)₄ (0.14 g, 0.12 mmol), Toluene (20 mL) were used for the synthesis of P1-22 to obtain 4.8 g (yield: 75%) of the product.

26. Synthesis Example of P6-1

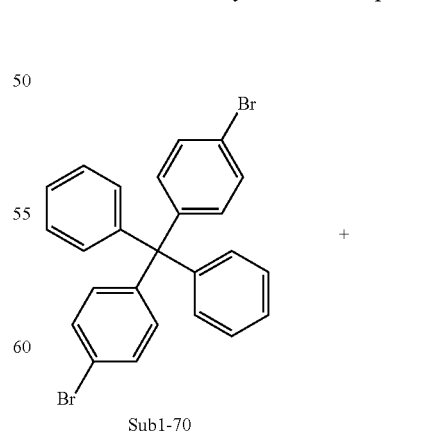

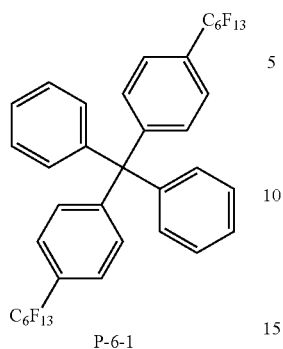
P-6-1
Sub1-70 (3.0 g, 6.27 mmol), Cu (3.2 g, 50.2 mmol), Sub2-1 (6.2 g, 13.8 mmol), DMSO (13 mL) were used for the synthesis of P1-1 to obtain 4.9 g (yield: 81%) of the product.
27. Synthesis Example of P6-4
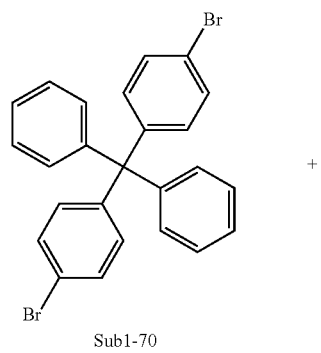
Sub1-70
+
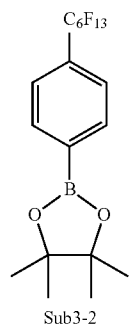
Sub3-2
Pd(PPh₃)₄/K₂CO₃
Toluene
→
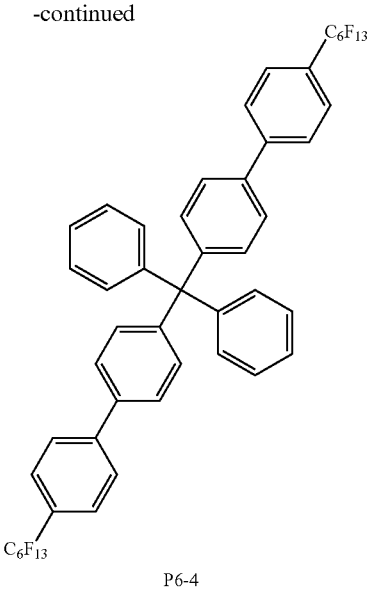
P6-4
Sub1-70 (2.0 g, 4.18 mmol), Sub3-2 (4.8 g, 9.20 mmol), K₂CO₃ (1.7 g, 12.6 mmol), Pd(PPh₃)₄ (0.10 g, 0.08 mmol), Toluene (14 mL) were used for the synthesis of P1-22 to obtain 3.3 g (yield: 72%) of the product.
28. Synthesis Example of P7-1
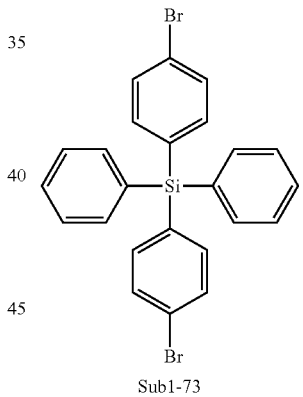
Sub1-73
+ C₆F₁₃I   Cu
  Sub2-1  DMSO →
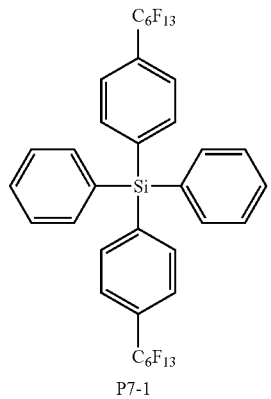
P7-1

Sub1-73 (3.0 g, 6.07 mmol), Cu (3.1 g, 48.6 mmol), Sub2-1 (6.0 g, 13.4 mmol), DMSO (12 mL) were used for the synthesis of P1-1 to obtain 4.4 g (yield: 75%) of the product.

29. Synthesis Example of P7-4

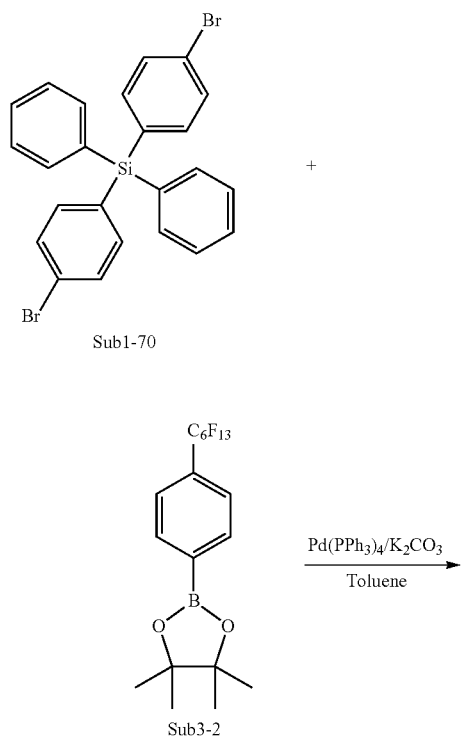

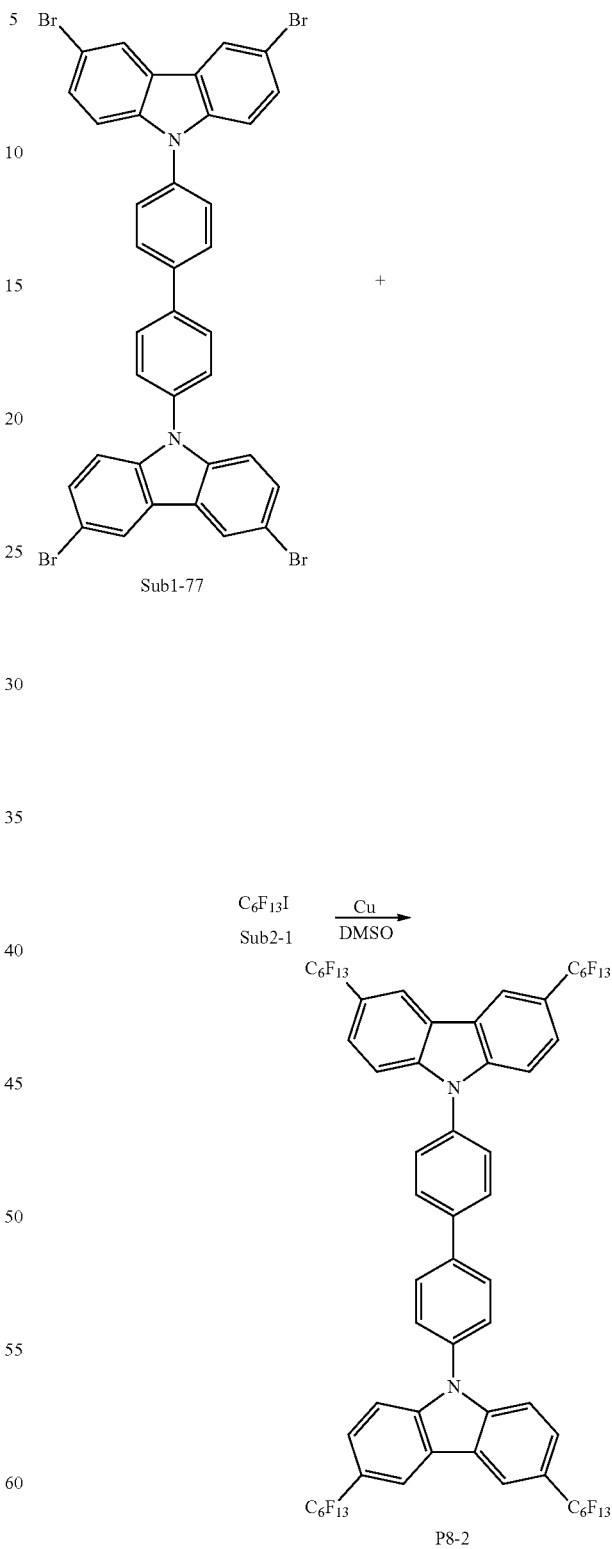

Sub1-73 (2.0 g, 4.05 mmol), Sub3-2 (4.7 g, 8.90 mmol), K$_2$CO$_3$ (1.68 g, 12.1 mmol), Pd(PPh$_3$)$_4$ (0.09 g, 0.08 mmol), Toluene (14 mL) were used for the synthesis of P1-22 to obtain 3.5 g (yield: 76%) of the product.

30. Synthesis Example of P8-2

Sub1-77 (3.0 g, 3.75 mmol), Cu (2.9 g, 45.0 mmol), Sub2-1 (7.4 g, 16.5 mmol), DMSO (7 mL) were used for the synthesis of P1-1 to obtain 3.4 g (yield: 52%) of the product.

31. Synthesis Example of P8-3

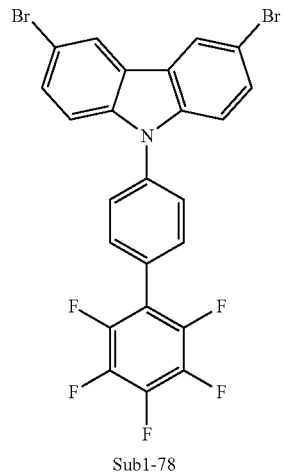

Sub1-78

+

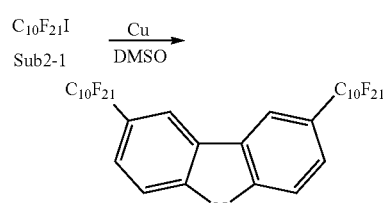

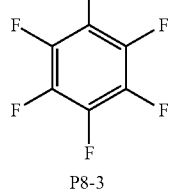

P8-3

The synthesized Sub1-78 (2.0 g, 3.53 mmol), Cu (1.8 g, 28.2 mmol), Sub2-4 (5.0 g, 7.76 mmol), DMSO (7 mL) were used for the synthesis of P1-1 to obtain 3.9 g (yield: 77%) of the product.

32. Synthesis Example of P9-3

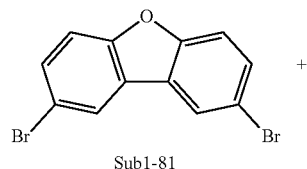

Sub1-81

+

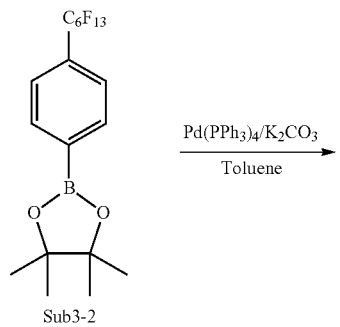

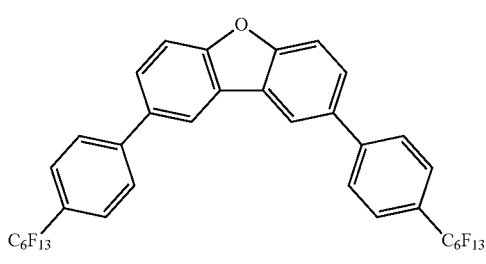

P9-3

Sub1-81 (2.0 g, 6.14 mmol), Sub3-2 (7.1 g, 13.5 mmol), K$_2$CO$_3$ (2.5 g, 18.4 mmol), Pd(PPh$_3$)$_4$ (0.14 g, 0.12 mmol), Toluene (21 mL) were used for the synthesis of P1-22 to obtain 4.3 g (yield: 73%) of the product.

33. Synthesis Example of P9-4

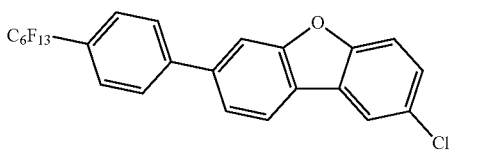

Sub1-83

Sub2-1

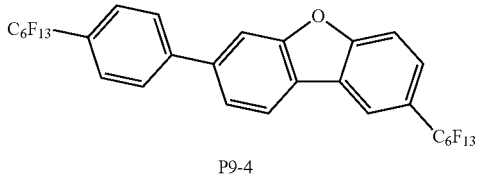

P9-4

The synthesized Sub1-83 (3.0 g, 5.03 mmol), Cu (2.6 g, 40.2 mmol), Sub2-1 (2.3 g, 5.03 mmol), DMSO (10 mL) were used for the synthesis of P1-1 to obtain 3.6 g (yield: 82%) of the product.

34. Synthesis Example of P9-6
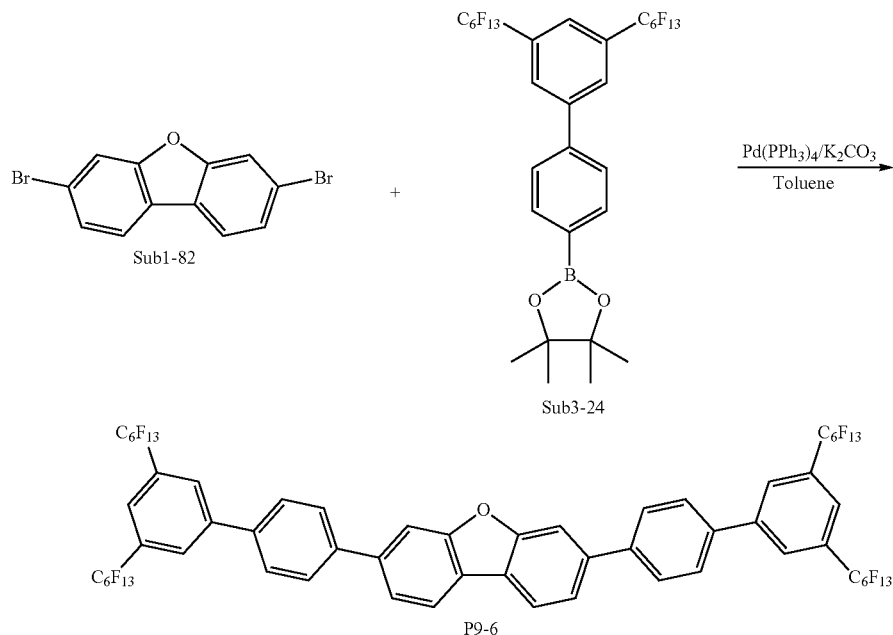
Sub1-82 (1.0 g, 3.07 mmol), Sub3-24 (6.2 g, 6.75 mmol), K$_2$CO$_3$ (1.3 g, 9.20 mmol), Pd(PPh$_3$)$_4$ (0.07 g, 0.06 mmol), Toluene (10 mL) were used for the synthesis of P1-22 to obtain 3.8 g (yield: 71%) of the product.
35. Synthesis Example of P10-1
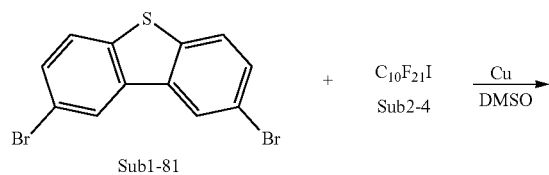
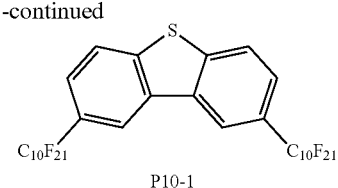
Sub1-81 (3.0 g, 8.77 mmol), Cu (4.5 g, 70.2 mmol), Sub2-4 (12.5 g, 19.3 mmol), DMSO (18 mL) were used for the synthesis of P1-1 to obtain 8.2 g (yield: 77%) of the product.
36. Synthesis Example of P10-5
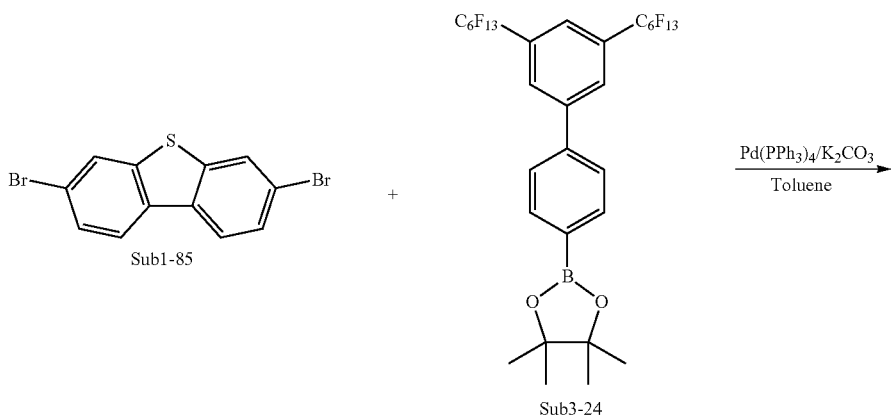

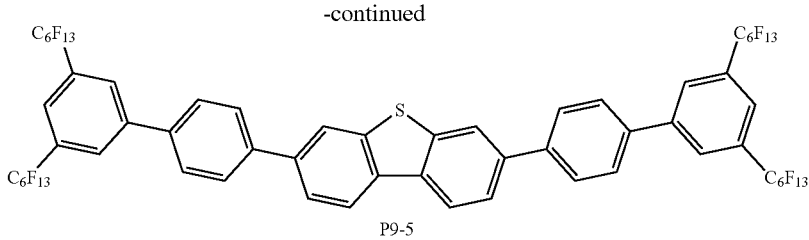

P9-5

Sub1-85 (1.0 g, 2.92 mmol), Sub3-24 (5.9 g, 6.43 mmol), K₂CO₃ (1.2 g, 8.77 mmol), Pd(PPh₃)₄ (0.07 g, 0.06 mmol), Toluene (10 mL) were used for the synthesis of P1-22 to obtain 3.6 g (yield: 70%) of the product.

37. Synthesis Example of P11-2

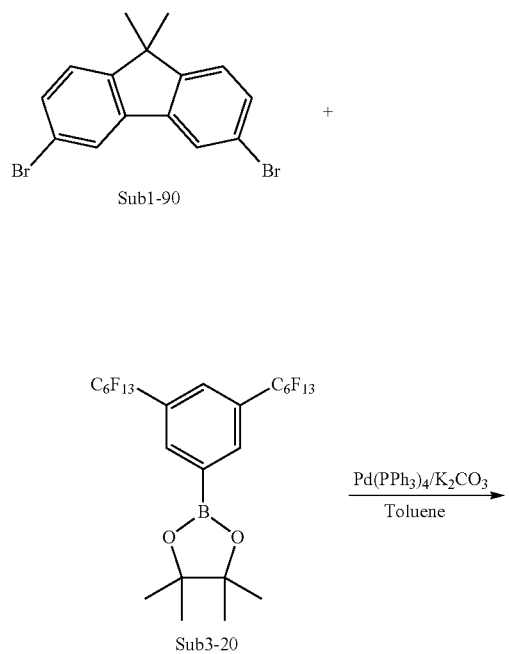

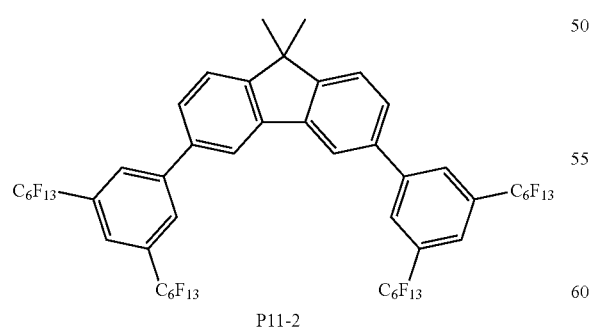

P11-2

Sub1-90 (1.0 g, 2.84 mmol), Sub3-20 (5.3 g, 6.25 mmol), K₂CO₃ (1.2 g, 8.52 mmol), Pd(PPh₃)₄ (0.07 g, 0.06 mmol), Toluene (10 mL) were used for the synthesis of P1-22 to obtain 3.4 g (yield: 73%) of the product.

38. Synthesis Example of P11-4

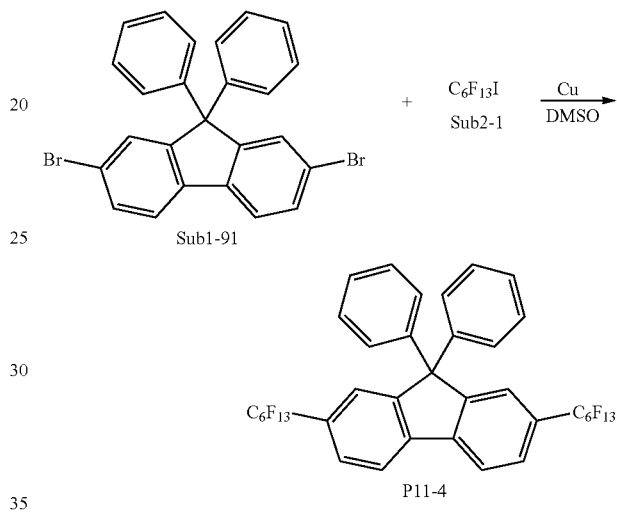

P11-4

Sub1-91 (3.0 g, 6.30 mmol), Cu (3.2 g, 50.4 mmol), Sub2-1 (6.2 g, 13.9 mmol), DMSO (13 mL) were used for the synthesis of P1-1 to obtain 4.8 g (yield: 80%) of the product.

39. Synthesis Example of P11-6

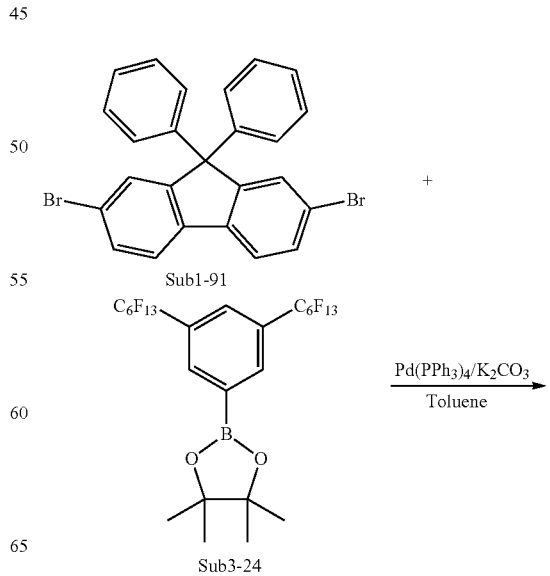

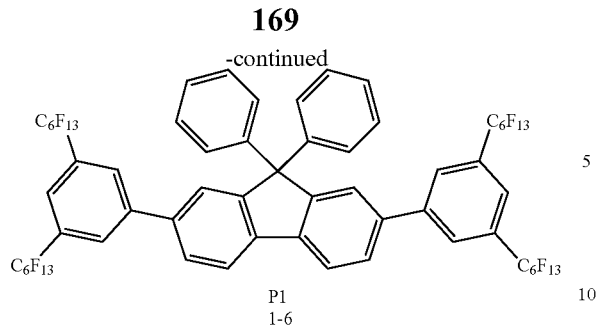

P1 1-6

Sub1-91 (2.0 g, 4.20 mmol), Sub3-20 (7.8 g, 9.24 mmol), K₂CO₃ (1.7 g, 12.6 mmol), Pd(PPh₃)₄ (0.10 g, 0.08 mmol), Toluene (14 mL) were used for the synthesis of P1-22 to obtain 5.2 g (yield: 71%) of the product.

40. Synthesis Example of P11-10

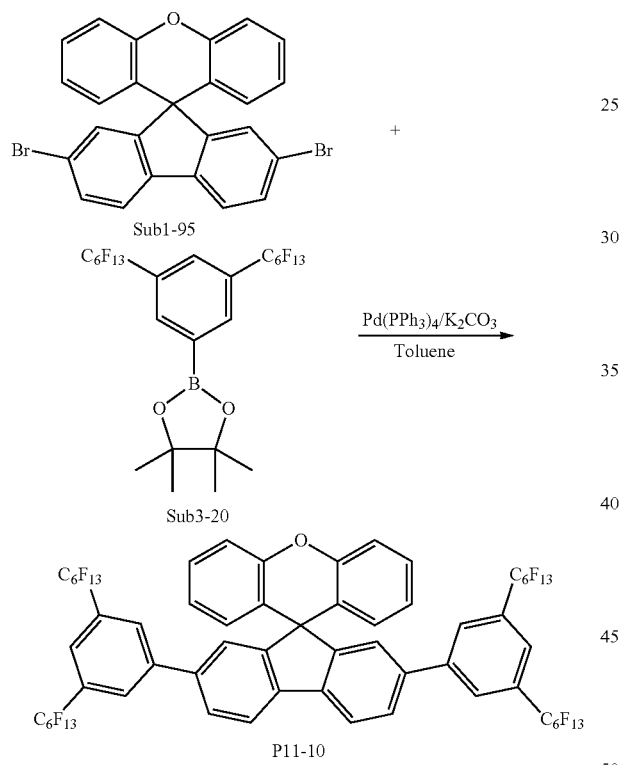

P11-10

Sub1-95 (2.0 g, 4.08 mmol), Sub3-20 (7.5 g, 8.98 mmol), K₂CO₃ (1.7 g, 12.2 mmol), Pd(PPh₃)₄ (0.09 g, 0.08 mmol), Toluene (14 mL) were used for the synthesis of P1-22 to obtain 4.9 g (yield: 68%) of the product.

41. Synthesis Example of P12-1

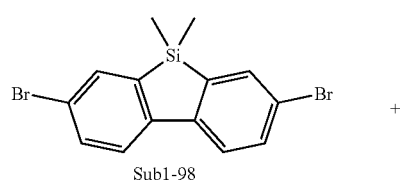

Sub1-98

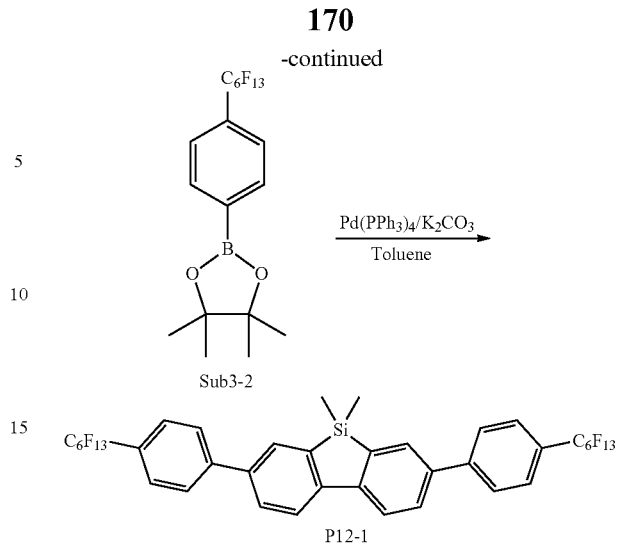

P12-1

Sub1-98 (2.0 g, 5.43 mmol), Sub3-2 (6.2 g, 12.0 mmol), K₂CO₃ (2.3 g, 16.3 mmol), Pd(PPh₃)₄ (0.13 g, 0.11 mmol), Toluene (18 mL) were used for the synthesis of P1-22 to obtain 4.0 g (yield: 73%) of the product.

42. Synthesis Example of P13-3

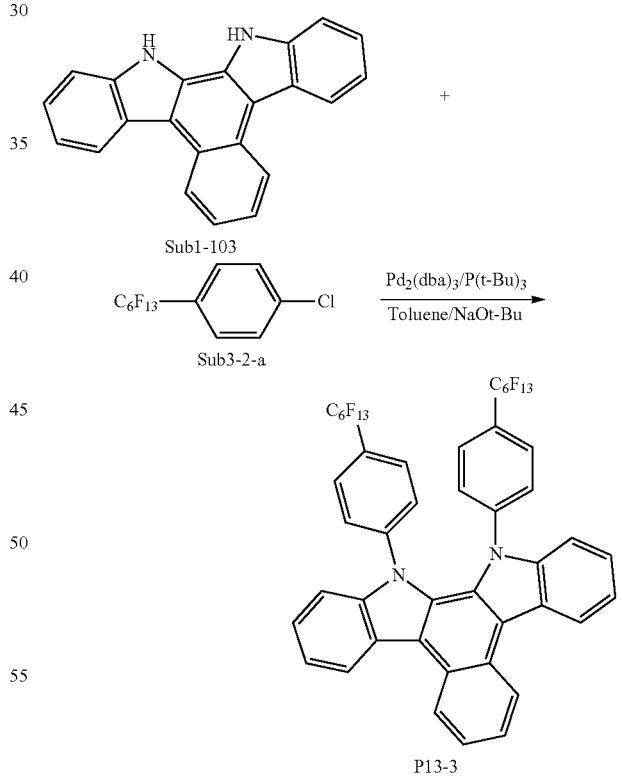

P13-3

Sub1-103 (2.0 g, 6.5 mmol), Toluene (33 mL), Sub3-2-a (6.2 g, 14.4 mmol), Pd₂(dba)₃ (0.18 g, 0.20 mmol), P(t-Bu)₃ (0.08 g, 0.39 mmol), NaOt-Bu (2.5 g, 26.1 mmol) were added to a round bottom flask and stirred at 120° C. When the reaction was completed, the mixture was extracted with CH₂Cl₂ and water, and the organic layer was dried over MgSO₄ and concentrated. Then, the resulting compound was recrystallized after applying a silica gel column to obtain 5.1 g (yield: 72%) of the product.

43. Synthesis Example of P14-4

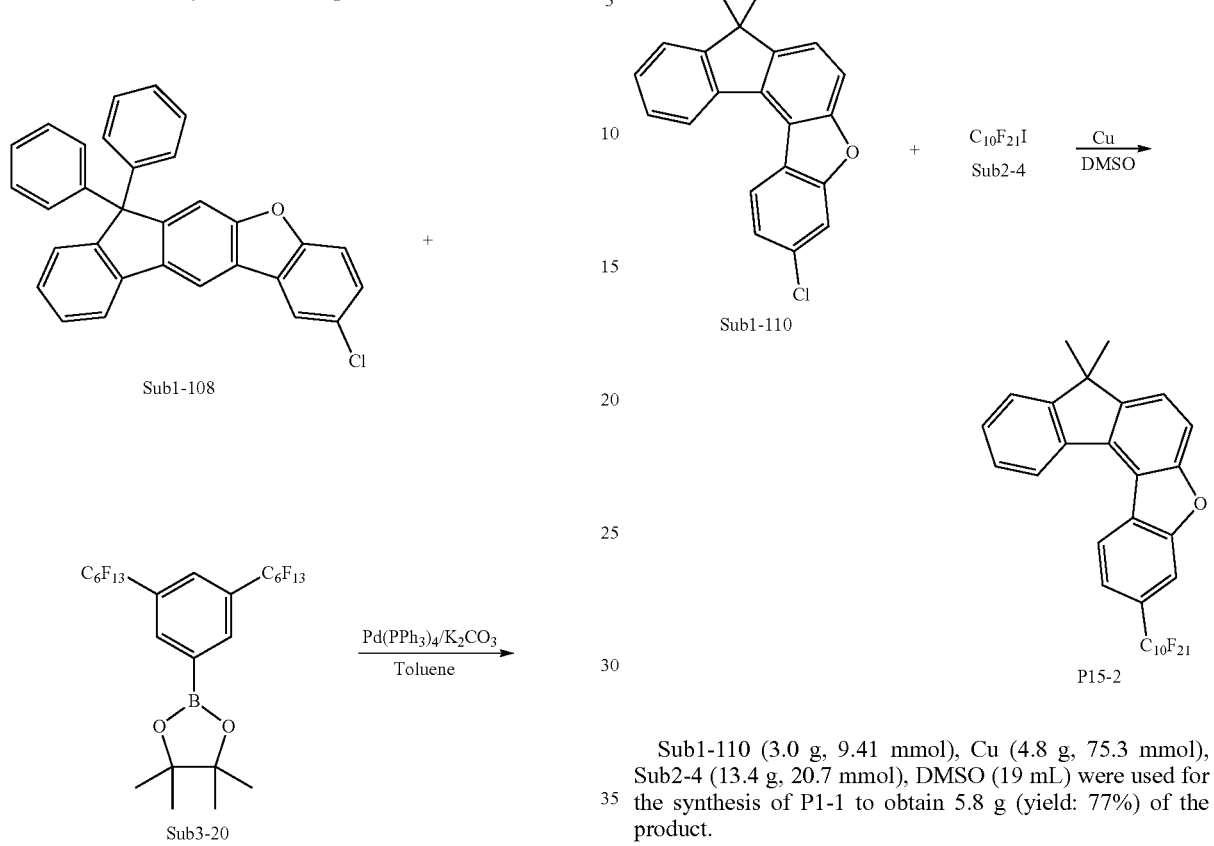

Sub1-108 (2.0 g, 4.52 mmol), Sub3-20 (4.2 g, 4.97 mmol), K$_2$CO$_3$ (1.9 g, 13.6 mmol), Pd(PPh$_3$)$_4$ (0.10 g, 0.09 mmol), Toluene (15 mL) were used for the synthesis of P1-22 to obtain 4.0 g (yield: 79%) of the product.

44. Synthesis Example of P15-2

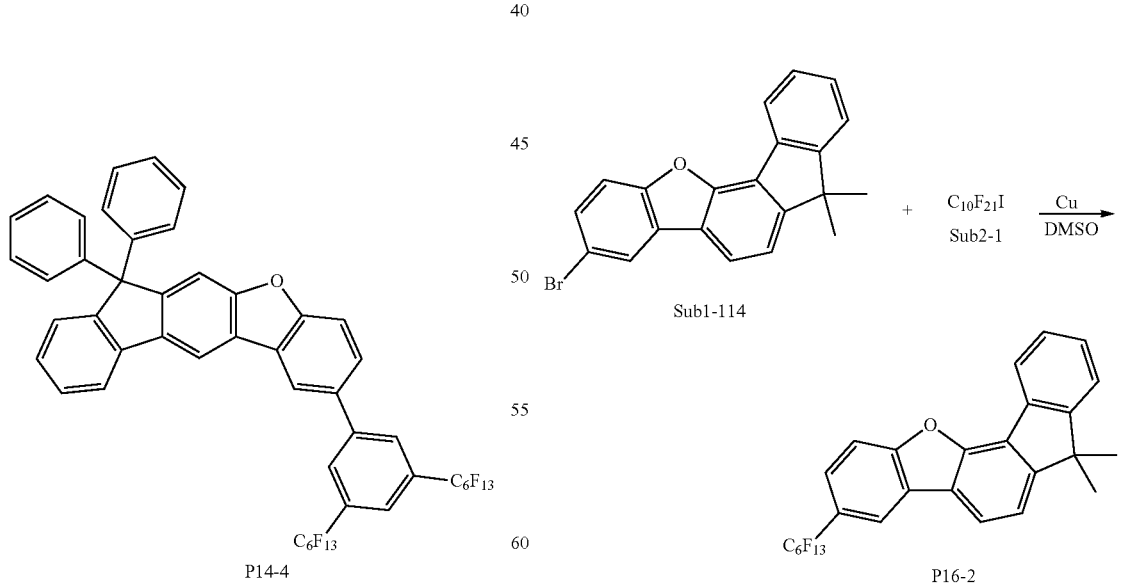

Sub1-110 (3.0 g, 9.41 mmol), Cu (4.8 g, 75.3 mmol), Sub2-4 (13.4 g, 20.7 mmol), DMSO (19 mL) were used for the synthesis of P1-1 to obtain 5.8 g (yield: 77%) of the product.

45. Synthesis Example of P16-2

Sub1-114 (3.0 g, 8.26 mmol), Cu (4.2 g, 66.1 mmol), Sub2-1 (11.7 g, 18.2 mmol), DMSO (17 mL) were used for the synthesis of P1-1 to obtain 3.7 g (yield: 75%) of the product.

46. Synthesis Example of P17-1

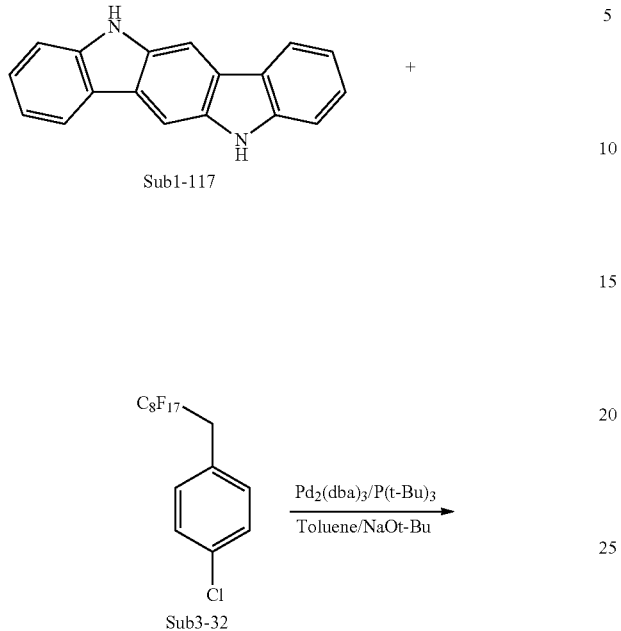

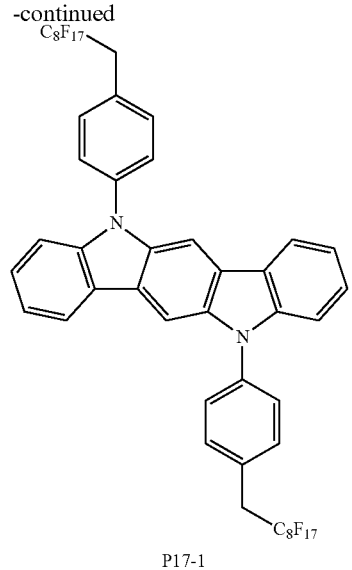

Sub1-117 (2.0 g, 7.80 mmol), Sub3-32 (9.3 g, 17.2 mmol), Pd$_2$(dba)$_3$ (0.21 g, 0.23 mmol), P(t-Bu)$_3$ (0.09 g, 0.47 mmol), NaOt-Bu (3.0 g, 31.2 mmol), Toluene (39 mL) were used for the synthesis of P13-3 to obtain 7.3 g (yield: 74%) of the product. FD-MS values of compounds P1-1 to P17-4 of the present invention prepared according to the above synthesis examples are shown in Table 4.

TABLE 4

| compound | FD-MS | compound | FD-MS |
| --- | --- | --- | --- |
| P1-1 | m/z = 1064.02($C_{34}H_{10}F_{34}$ = 1064.4) | P1-2 | m/z = 1190.00($C_{32}H_8F_{42}$ = 1190.35) |
| P1-3 | m/z = 1266.03($C_{38}H_{12}F_{42}$ = 1266.45) | P1-4 | m/z = 1785.98($C_{46}H_9F_{63}N_2$ = 1786.49) |
| P1-5 | m/z = 1707.95($C_{42}H_7F_{63}$ = 1708.42) | P1-6 | m/z = 2225.91($C_{52}H_6F_{84}$ = 2226.49) |
| P1-7 | m/z = 548.08($C_{24}H_{13}F_{13}$ = 548.35) | P1-8 | m/z = 748.07($C_{28}H_{13}F_{21}$ = 748.38) |
| P1-9 | m/z = 648.07($C_{26}H_{13}F_{17}$ = 648.36) | P1-10 | m/z = 753.10($C_{28}H_8D_5F_{21}$ = 753.41) |
| P1-11 | m/z = 564.08($C_{24}H_{13}F_{13}O$ = 564.35) | P1-12 | m/z = 692.10($C_{28}H_{17}F_{17}O$ = 692.42) |
| P1-13 | m/z = 866.05($C_{30}H_{12}F_{26}$ = 866.38) | P1-14 | m/z = 1266.03($C_{38}H_{12}F_{42}$ = 1266.45) |
| P1-15 | m/z = 796.07($C_{29}H_{14}F_{22}O$ = 796.39) | P1-16 | m/z = 938.11($C_{34}H_{20}F_{26}O$ = 938.49) |
| P1-17 | m/z = 966.05($C_{32}H_{12}F_{30}$ = 966.40) | P1-18 | m/z = 1392.07($C_{48}H_{18}F_{42}$ = 1392.60) |
| P1-19 | m/z = 1482.08($C_{54}H_{20}F_{42}O$ = 1482.69) | P1-20 | m/z = 978.18($C_{38}H_{28}F_{26}$ = 978.60) |
| P1-21 | m/z = 1002.03($C_{32}H_{10}F_{32}$ = 1002.38) | P1-22 | m/z = 1184.02($C_{36}H_{11}F_{39}$ = 1184.42) |
| P1-23 | m/z = 1783.99($C_{48}H_{11}F_{63}$ = 1784.52) | P1-24 | m/z = 1820.07($C_{50}H_7D_8F_{63}$ = 1820.62) |
| P1-25 | m/z = 1960.05($C_{62}H_{19}F_{63}$ = 1960.73) | P1-26 | m/z = 2016.02($C_{64}H_{19}F_{63}S$ = 2016.82) |
| P1-27 | m/z = 1261.05($C_{41}H_{14}F_{39}N$ = 1261.51) | P1-28 | m/z = 909.98($C_{28}H_4F_{30}$ = 910.29) |
| P1-29 | m/z = 938.01($C_{30}H_8F_{30}$ = 938.35) | P1-30 | m/z = 1266.03($C_{38}H_{12}F_{42}$ = 1266.45) |
| P1-31 | m/z = 894.08($C_{32}H_{16}F_{26}$ = 894.44) | P1-32 | m/z = 1358.05($C_{44}H_{16}F_{42}O$ = 1358.54) |
| P1-33 | m/z = 1783.99($C_{48}H_{11}F_{63}$ = 1784.52) | P1-34 | m/z = 1502.00($C_{42}H_{10}F_{52}$ = 1502.46) |
| P1-35 | m/z = 2301.94($C_{58}H_{10}F_{84}$ = 2302.58) | P1-36 | m/z = 1574.05($C_{46}H_{18}F_{52}O$ = 1574.57) |
| P1-37 | m/z = 1573.96($C_{42}H_6F_{56}$ = 1574.42) | P1-38 | m/z = 1634.09($C_{52}H_{22}F_{52}$ = 1634.66) |
| P1-39 | m/z = 134.03($C_{58}H_{18}F_{52}S$ = 1734.76) | P1-40 | m/z = 2055.03($C_{61}H_{17}F_{68}N$ = 2055.71) |
| P1-41 | m/z = 1142.07($C_{40}H_{16}F_{34}$ = 1142.51) | P1-42 | m/z = 1010.07($C_{37}H_{15}F_{29}$ = 1010.48) |
| P1-43 | m/z = 1110.06($C_{39}H_{15}F_{33}$ = 1110.50) | P1-44 | m/z = 1860.02($C_{54}H_{15}F_{63}$ = 1860.61) |
| P1-45 | m/z = 1977.04($C_{61}H_{18}F_{63}NO$ = 1977.72) | P1-46 | m/z = 1578.03($C_{48}H_{14}F_{52}$ = 1578.56) |
| P1-47 | m/z = 1778.01($C_{52}H_{14}F_{60}$ = 1778.59) | P1-48 | m/z = 1690.15($C_{56}H_{36}F_{52}$ = 1690.77) |
| P1-49 | m/z = 1819.12($C_{66}H_{25}F_{52}N$ = 1819.85) | P1-50 | m/z = 2377.98($C_{64}H_{14}F_{84}$ = 2378.68) |
| P1-51 | m/z = 2377.98($C_{64}H_{14}F_{84}$ = 2378.68) | P1-52 | m/z = 1654.06($C_{54}H_{18}F_{52}$ = 1654.65) |
| P1-53 | m/z = 2110.09($C_{66}H_{26}F_{68}$ = 2110.83) | P1-54 | m/z = 2454.01($C_{70}H_{18}F_{84}O$ = 2454.78) |
| P1-55 | m/z = 2377.98($C_{64}H_{14}F_{84}$ = 2378.68) | P1-56 | m/z = 1668.04($C_{54}H_{16}F_{52}O$ = 1668.64) |
| P1-57 | m/z = 2036.04($C_{62}H_{19}F_{67}$ = 2036.73) | P1-58 | m/z = 2088.11($C_{72}H_{27}F_{63}$ = 2088.91) |
| P1-59 | m/z = 2088.11($C_{72}H_{27}F_{63}$ = 2088.91) | P1-60 | m/z = 3641.99($C_{102}H_{24}F_{126}$ = 3643.11) |
| P1-61 | m/z = 1806.12($C_{66}H_{26}F_{52}$ = 1806.85) | P1-62 | m/z = 3382.13($C_{114}H_{38}F_{104}$ = 3383.39) |
| P1-63 | m/z = 916.07($C_{34}H_{14}F_{26}$ = 916.44) | P1-64 | m/z = 1316.04($C_{42}H_{14}F_{42}$ = 1316.51) |
| P1-65 | m/z = 1552.01($C_{46}H_{12}F_{52}$ = 1552.52) | P1-66 | m/z = 916.07($C_{34}H_{14}F_{26}$ = 916.44) |
| P1-67 | m/z = 966.08($C_{38}H_{16}F_{26}$ = 966.50) | P1-68 | m/z = 1584.04($C_{50}H_{15}F_{51}$ = 1584.59) |
| P1-69 | m/z = 2427.99($C_{68}H_{16}F_{84}$ = 2428.74) | P1-70 | m/z = 2427.99($C_{68}H_{16}F_{84}$ = 2428.74) |
| P1-71 | m/z = 916.07($C_{34}H_{14}F_{26}$ = 916.44) | P1-72 | m/z = 1316.04($C_{42}H_{14}F_{42}$ = 1316.51) |
| P1-73 | m/z = 2451.99($C_{70}H_{16}F_{84}$ = 2452.76) | P1-74 | m/z = 2478.01($C_{72}H_{18}F_{84}$ = 2478.80) |
| P1-75 | m/z = 2665.94($C_{70}H_{14}F_{92}O_4$ = 2666.73) | P1-76 | m/z = 1584.04($C_{50}H_{15}F_{51}$ = 1584.59) |
| P1-77 | m/z = 2322.03($C_{66}H_{22}F_{76}O_4$ = 2322.78) | P1-78 | m/z = 2458.04($C_{70}H_{22}F_{84}$ = 2458.81) |
| P1-79 | m/z = 942.08($C_{36}H_{16}F_{26}$ = 942.48) | P1-80 | m/z = 992.10($C_{40}H_{18}F_{26}$ = 992.54) |

TABLE 4-continued

| compound | FD-MS | compound | FD-MS |
|---|---|---|---|
| P1-81 | m/z = 943.08($C_{35}H_{15}F_{26}N$ = 943.47) | P1-82 | m/z = 943.08($C_{35}H_{15}F_{26}N$ = 943.47) |
| P1-83 | m/z = 943.08($C_{35}H_{15}F_{26}N$ = 943.47) | P1-84 | m/z = 943.08($C_{35}H_{15}F_{26}N$ = 943.47) |
| P1-85 | m/z = 992.10($C_{40}H_{18}F_{26}$ = 992.54) | P1-86 | m/z = 992.10($C_{40}H_{18}F_{26}$ = 992.54) |
| P1-87 | m/z = 992.10($C_{40}H_{18}F_{26}$ = 992.54) | P1-88 | m/z = 992.10($C_{40}H_{18}F_{26}$ = 992.54) |
| P1-89 | m/z = 993.09($C_{39}H_{17}F_{26}N$ = 993.53) | P1-90 | m/z = 993.09($C_{39}H_{17}F_{26}N$ = 993.53) |
| P1-91 | m/z = 982.08($C_{38}H_{16}F_{26}O$ = 982.50) | P1-92 | m/z = 998.06($C_{38}H_{16}F_{26}S$ = 998.56) |
| P1-93 | m/z = 943.08($C_{35}H_{15}F_{26}N$ = 943.47) | P1-94 | m/z = 1242.10($C_{48}H_{20}F_{34}$ = 1242.63) |
| P1-95 | m/z = 1192.09($C_{44}H_{18}F_{34}$ = 1192.57) | P1-96 | m/z = 1192.09($C_{44}H_{18}F_{34}$ = 1192.57) |
| P1-97 | m/z = 1193.08($C_{43}H_{17}F_{34}N$ = 1193.56) | P1-98 | m/z = 1144.06($C_{38}H_{14}F_{34}N_2$ = 1144.49) |
| P1-99 | m/z = 1392.07($C_{48}H_{18}F_{42}$ = 1392.60) | P1-100 | m/z = 1393.07($C_{47}H_{17}F_{42}N$ = 1393.59) |
| P1-101 | m/z = 1366.06($C_{46}H_{16}F_{42}$ = 1366.57) | P1-102 | m/z = 1344.05($C_{42}H_{14}F_{42}N_2$ = 1344.52) |
| P1-103 | m/z = 1432.07($C_{50}H_{18}F_{42}O$ = 1432.63) | P1-104 | m/z = 1358.13($C_{51}H_{24}F_{38}$ = 1358.69) |
| P1-105 | m/z = 1193.08($C_{43}H_{17}F_{34}N$ = 1193.56) | P1-106 | m/z = 1182.10($C_{48}H_{20}F_{30}O$ = 1182.6) |
| P1-107 | m/z = 802.13(C35H21F19 = 802.52) | P1-108 | m/z = 752.14(C34H21F17 = 752.51) |
| P1-109 | m/z = 916.14(C38H23F23 = 916.57) | P1-110 | m/z = 884.14(C37H22F22 = 884.55) |
| P1-111 | m/z = 934.13(C38H22F24 = 934.56) | P1-112 | m/z = 1098.14(C42H24F30 = 1098.61) |
| P1-113 | m/z = 850.12(C35H21F19O3 = 850.52) | P1-114 | m/z = 800.12(C34H21F17O3 = 800.51) |
| P1-115 | m/z = 964.13(C38H23F23O3 = 964.56) | P1-116 | m/z = 932.13(C37H22F22O3 = 932.54) |
| P1-117 | m/z = 998.11(C38H22F24O4 = 998.55) | P1-118 | m/z = 1162.12(C42H24F30O4 = 1162.6) |
| P1-119 | m/z = 1238.07(C42H18F36O2 = 1238.55) | P1-120 | m/z = 1238.07(C42H18F36O2 = 1238.55) |
| P1-121 | m/z = 1738.04(C52H18F56O2 = 1738.62) | P1-122 | m/z = 1278.05(C42H14F40 = 1278.51) |
| P2-1 | m/z = 1261.05($C_{41}H_{14}F_{39}N$ = 1261.51) | P2-2 | m/z = 1263.04($C_{39}H_{12}F_{39}N_3$ = 1263.48) |
| P2-3 | m/z = 949.03($C_{30}H_{11}F_{28}NO_2$ = 949.38) | | |
| P3-1 | m/z = 1799.00($C_{48}H_{12}F_{63}N$ = 1799.53) | P3-2 | m/z = 1427.13($C_{54}H_{24}F_{39}N$ = 1427.73) |
| P3-3 | m/z = 1172.17($C_{52}H_{26}F_{26}N_2$ = 1172.75) | P3-4 | m/z = 1387.03($C_{44}H_{15}F_{42}NS$ = 1387.60) |
| P3-5 | m/z = 1885.13($C_{70}H_{27}F_{52}NO$ = 1885.91) | P3-6 | m/z = 2028.16($C_{69}H_{32}F_{60}N_2$ = 2028.93) |
| P3-7 | m/z = 1925.04($C_{58}H_{18}F_{63}N$ = 1925.69) | P3-8 | m/z = 1401.11($C_{52}H_{22}F_{39}N$ = 1401.69) |
| P4-1 | m/z = 1205.99($C_{32}H_{8}F_{42}O$ = 1206.35) | P4-2 | m/z = 1256.01($C_{36}H_{10}F_{42}O$ = 1256.41) |
| P4-3 | m/z = 1349.92($C_{32}F_{50}O$ = 1350.27) | P4-4 | m/z = 1158.07($C_{40}H_{16}F_{34}O$ = 1158.51) |
| P4-5 | m/z = 1350.16($C_{55}H_{28}F_{34}O$ = 1350.77) | P4-6 | m/z = 2446.06($C_{66}H_{26}F_{84}O_2$ = 2446.8) |
| P5-1 | m/z = 1221.97($C_{32}H_{8}F_{42}S$ = 1222.41) | P5-2 | m/z = 1271.98($C_{36}H_{10}F_{42}S$ = 1272.47) |
| P5-3 | m/z = 974.06($C_{36}H_{16}F_{26}S$ = 974.54) | P5-4 | m/z = 1074.09($C_{44}H_{20}F_{26}S$ = 1074.66) |
| P5-5 | m/z = 1074.09($C_{44}H_{20}F_{26}S$ = 1074.66) | P5-6 | m/z = 1050.09($C_{42}H_{20}F_{26}S$ = 1050.64) |
| P6-1 | m/z = 956.10($C_{37}H_{18}F_{26}$ = 956.51) | P6-2 | m/z = 866.22($C_{49}H_{31}F_{13}$ = 866.77) |
| P6-3 | m/z = 1056.13($C_{45}H_{22}F_{26}$ = 1056.63) | P6-4 | m/z = 1108.16($C_{49}H_{26}F_{26}$ = 1108.71) |
| P6-5 | m/z = 945.24($C_{52}H_{32}F_{13}N_3$ = 945.83) | | |
| P7-1 | m/z = 972.08($C_{36}H_{18}F_{26}Si$ = 972.58) | P7-2 | m/z = 1124.14($C_{48}H_{26}F_{26}Si$ = 1124.78) |
| P7-3 | m/z = 1124.14($C_{48}H_{26}F_{26}Si$ = 1124.78) | P7-4 | m/z = 1124.14($C_{48}H_{26}F_{26}Si$ = 1124.78) |
| P7-5 | m/z = 1760.08($C_{60}H_{24}F_{52}Si$ = 1760.85) | P7-6 | m/z = 2162.05($C_{66}H_{22}F_{68}N2Si$ = 2162.89) |
| P7-7 | m/z = 2260.09($C_{76}H_{28}F_{68}Si$ = 2261.04) | P7-8 | m/z = 2186.11($C_{76}H_{30}F_{64}Si$ = 2187.06) |
| P8-1 | m/z = 1279.02($C_{38}H_{11}F_{42}N$ = 1279.45) | P8-2 | m/z = 1756.08($C_{60}H_{20}F_{52}N_2$ = 1756.75) |
| P8-3 | m/z = 1445.01($C_{44}H_{10}F_{47}N$ = 1445.5) | P8-4 | m/z = 1211.02($C_{42}H_{9}F_{36}N$ = 1211.48) |
| P8-5 | m/z = 1543.21($C_{58}H_{35}F_{42}N$ = 1543.86) | | |
| P9-1 | m/z = 1203.97($C_{32}H_{6}F_{42}O$ = 1204.33) | P9-2 | m/z = 956.06($C_{36}H_{14}F_{26}O$ = 956.47) |
| P9-3 | m/z = 956.06($C_{36}H_{14}F_{26}O$ = 956.47) | P9-4 | m/z = 880.03($C_{30}H_{10}F_{26}O$ = 880.37) |
| P9-5 | m/z = 1896.13($C_{72}H_{28}F_{52}O$ = 1896.93) | P9-6 | m/z = 1744.07($C_{60}H_{20}F_{52}O$ = 1744.74) |
| P9-7 | m/z = 1056.06($C_{38}H_{14}F_{30}O$ = 1056.48) | | |
| P10-1 | m/z = 1219.95($C_{32}H_{6}F_{42}S$ = 1220.39) | P10-2 | m/z = 972.04($C_{36}H_{14}F_{26}S$ = 972.53) |
| P10-3 | m/z = 896.01($C_{30}H_{10}F_{26}S$ = 896.43) | P10-4 | m/z = 1912.11($C_{72}H_{28}F_{52}S$ = 1912.99) |
| P10-5 | m/z = 1760.05($C_{60}H_{20}F_{52}S$ = 1760.80) | P10-6 | m/z = 1198.12($C_{54}H_{24}F_{26}S$ = 1198.80) |
| P10-7 | m/z = 735.13($C_{36}H_{14}D_{5}F_{13}S$ = 735.62) | | |
| P11-1 | m/z = 982.11($C_{39}H_{20}F_{26}$ = 982.55) | P11-2 | m/z = 1618.06($C_{51}H_{18}F_{52}$ = 1618.62) |
| P11-3 | m/z = 2418.01($C_{67}H_{18}F_{84}$ = 2418.75) | P11-4 | m/z = 954.08($C_{37}H_{16}F_{26}$ = 954.49) |
| P11-5 | m/z = 1354.06($C_{45}H_{16}F_{42}$ = 1354.56) | P11-6 | m/z = 1742.09($C_{61}H_{22}F_{52}$ = 1742.76) |
| P11-7 | m/z = 1278.10($C_{48}H_{21}F_{35}O$ = 1278.64) | P11-8 | m/z = 952.07($C_{37}H_{14}F_{26}$ = 952.48) |
| P11-9 | m/z = 954.08($C_{37}H_{16}F_{26}$ = 954.49) | P11-10 | m/z = 1756.07($C_{61}H_{20}F_{52}$ = 1756.75) |
| P11-11 | m/z = 1772.05($C_{61}H_{20}F_{52}S$ = 1772.81) | P11-12 | m/z = 1831.12($C_{67}H_{25}F_{52}N$ = 1831.86) |
| P12-1 | m/z = 998.09($C_{38}H_{20}F_{26}Si$ = 998.62) | P12-2 | m/z = 998.09($C_{38}H_{20}F_{26}Si$ = 998.62) |
| P12-3 | m/z = 1370.04($C_{44}H_{16}F_{42}Si$ = 1370.63) | | |
| P13-1 | m/z = 1213.13($C_{54}H_{25}F_{26}NS$ = 1213.82) | P13-2 | m/z = 986.02($C_{36}H_{12}F_{26}OS$ = 986.51) |
| P13-3 | m/z = 1094.12($C_{46}H_{20}F_{26}N_2$ = 1094.64) | P13-4 | m/z = 848.18($C_{45}H_{26}F_{14}O$ = 848.68) |
| P14-1 | m/z = 817.07($C_{36}H_{13}F_{18}NO$ = 817.48) | P14-2 | m/z = 892.15($C_{49}H_{25}F_{13}S$ = 892.78) |
| P14-3 | m/z = 652.07($C_{30}H_{13}F_{13}O_2$ = 652.41) | P14-4 | m/z = 1120.13($C_{49}H_{22}F_{26}O$ = 1120.67) |
| P15-1 | m/z = 776.15($C_{40}H_{21}F_{13}N_2$ = 776.60) | P15-2 | m/z = 802.08($C_{31}H_{15}F_{21}O$ = 802.43) |
| P15-3 | m/z = 622.03($C_{25}H_{11}F_{13}O_2S$ = 622.40) | P15-4 | m/z = 853.16($C_{41}H_{24}F_{17}N$ = 853.62) |
| P16-1 | m/z = 985.04($C_{36}H_{13}F_{26}NS$ = 985.53) | P16-2 | m/z = 602.09($C_{27}H_{15}F_{13}O$ = 602.40) |
| P16-3 | m/z = 734.04($C_{34}H_{15}F_{13}S_2$ = 734.59) | P16-4 | m/z = 628.14($C_{30}H_{21}F_{13}$ = 628.48) |
| P17-1 | m/z = 1272.12($C_{48}H_{22}F_{34}N_2$ = 1272.66) | P17-2 | m/z = 576.04($C_{24}H_{9}F_{13}O_2$ = 576.31) |
| P17-3 | m/z = 986.02($C_{36}H_{12}F_{26}OS$ = 986.51) | P17-4 | m/z = 628.14($C_{30}H_{21}F_{13}$ = 628.48) |

Light Transmittance Measurement

[Example 1]: Comparison of Light Transmittance According to the Type of Metal Patterning Layer First, on a glass substrate, a N-([1,1'-biphenyl]-4-yl)-9,9-dimethyl-N-(4-(9-phenyl-9H-carbazol-3-yl)phenyl)-9H-fluoren-2-amine (hereinafter abbreviated as C-1) film was vacuum-deposited as an organic layer to form a thickness of 100 nm. On the organic layer, the compound P1-22 of the present invention was vacuum-deposited to a thickness of 10 nm to form an electrode patterning layer. Then, after vacuum deposition of Yb as an electron injection layer on the electrode patterning layer, a cathode was deposited with Mg and Ag in a weight of 1:9. Then, as a capping layer, N4,N4'-diphenyl-N4,N4'-bis(9-phenyl-9H-carbazol-3-yl)-[1,1'-biphenyl]-4,4'-diamine (hereinafter abbreviated as D-1) was deposited to a thickness of 70 nm to prepare a sample required for measurement of light transmittance.

[Example 2] to [Example 10]

A light transmittance sample was prepared in the same manner as in Example 1, except that the compound of the present invention described in Table 5 was used instead of the compound P1-22 of the present invention as a material for the metal (electrode) patterning layer.

Comparative Example 1

A light transmittance sample was prepared in the same manner as in Example 1, except that the metal (electrode) patterning layer was not used.

Comparative Example 2

A light transmittance sample was prepared in the same manner as in Example 1, except that Comparative compound A was used instead of the compound P1-22 of the present invention as a material for the metal (electrode) patterning layer. [Comparative compound A]

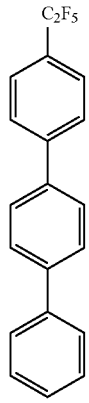

The light transmittance samples of Examples and Comparative Examples prepared as described above were measured for light transmittance at 550 nm, which is a visible light region, with Perkinelmer's Lambda 365 UV/VIS Spectrometer measuring equipment, wherein the measurement results are shown in Table 5. Also, the fluorine content of a material for the metal (electrode) patterning layer is shown in Table 5. The results of Table 5 were prepared based on the light transmittance measurement result graph of FIG. 5.

TABLE 5

| | compound | Fluorine content (%) | light transmittance (%) | T (%) |
|---|---|---|---|---|
| comparative example 1 | — | 0.00% | 69.13~72.38 | 100% |
| comparative example 2 | comparative compound A | 13.16% | 50.16 | 73% |
| example 1 | P1-22 | 45.35% | 95.50 | 139% |
| example 2 | P1-34 | 50.00% | 95.11 | 138% |
| example 3 | P1-46 | 45.61% | 95.03 | 137% |
| example 4 | P1-63 | 35.14% | 93.80 | 130% |
| example 5 | P1-65 | 47.27% | 95.45 | 132% |
| example 6 | P1-71 | 35.14% | 92.73 | 128% |
| example 7 | P1-73 | 49.41% | 92.20 | 130% |
| example 8 | P1-80 | 30.95% | 95.99 | 132% |
| example 9 | P1-81 | 33.77% | 96.89 | 133% |
| example 10 | P7-1 | 32.10% | 93.40 | 129% |

Referring to the results of Table 5, it was confirmed that the light transmittance was less than 90% when Comparative Example 1 without using a metal patterning layer and Comparative Compound A, which was a compound having a small intramolecular fluorine content, were used, and in the case of Examples 1 to 10 using the compound of the present invention having an intramolecular fluorine content of 30% or more, the light transmittance was 90% or more.

In particular, in the case of Comparative Example 1, as a result of comparative evaluation with Comparative Example 2 and Examples 1 to 10, it was confirmed that the light transmittance was 69.13% to 72.38% for each lot. Also, it was confirmed that Comparative Compound A having an intramolecular fluorine content of 13.16% had lower light transmittance than Comparative Example 1 without a material containing intramolecular fluorine.

The light transmittance for each lot of Comparative Example 1 was slightly different, and as a result of T % to correct this (After calculating the light transmittance of Comparative Example 1 as 100% for each lot, the difference in light transmittance with the compound of the present invention is shown), it was found that the light transmittance increased by 28% to 39% when the compound of the present invention was used than in Comparative Example 1.

Light transmittance is used to determine the amount of electrode material present on a surface in relation to the coating of an electrode (electrically conductive material). This is because the electrode material contains a metal, and an electrically conductive material such as a metal attenuates and/or absorbs light. Therefore, when the light transmittance exceeds 90% in the visible region of the electromagnetic spectrum, the surface can be considered to be substantially free of an electrically conductive material.

Therefore, as a result of measuring the light transmittance of the sample prepared in the present invention, when using the compound of the present invention having an intramolecular fluorine content of 20% or more as shown in Table 5, it was found that Yb, which is a metal used as the electron injection layer, and Ag, and Mg, which is used as a cathode, were not deposited on the compound of the present invention.

In order to confirm the above contents, the cross-sections of the samples of Comparative Examples 1 and Example 3 were checked using a scanning electron microscope (SEM), which is an analysis equipment capable of observing the surface of a metal type, as shown in FIG. 4. (FE-SEM: JEOL's JMS6701F)

As shown in (a) of FIG. 4, it can be seen that a thin white thin film is formed between the organic layer (lower part) and the capping layer (upper part), and as shown in (b) of FIG. 4, it was confirmed that a thin film was not formed between the organic layer and the metal patterning layer (lower part) and the capping layer (upper part).

[Example 11] Comparison of Light Transmittance According to the Presence or Absence of Metal in the Electron Injection Layer and the Type of Metal in the Electrode First, a C-1 film as an organic layer was vacuum-deposited on a glass substrate to form a thickness of 100 nm. On the organic layer, the compound P1-46 of the present invention was vacuum-deposited to a thickness of 10 nm to form a metal patterning layer. Then, after vacuum deposition of Yb as an electron injection layer on the metal patterning layer, a cathode was deposited with Mg and Ag in a weight of 1:9. After that, as a capping layer, D-1 was deposited to a thickness of 70 nm to prepare a sample.

Comparative Example 3

An organic electronic element was manufactured in the same manner as in Example 11, except that the metal patterning layer was not used.

[Example 12] Sample without Yb, the Electron Injection Layer Metal

First, a C-1 film as an organic layer was vacuum-deposited on a glass substrate to form a thickness of 100 nm. On the organic layer, the compound P1-46 of the present invention was vacuum-deposited to a thickness of 10 nm to form a metal patterning layer. Then, Mg and Ag were deposited in a weight of 1:9 on the metal patterning layer as a cathode. Then, as a capping layer, D-1 was deposited to a thickness of 70 nm to manufacture an organic electronic element.

[Comparative Example 4] Sample without Yb, the Electron Injection Layer Metal

An organic electronic element was manufactured in the same manner as in Example 12, except that the metal patterning layer was not used.

[Example 13] Sample Using Only Ag Electrode (Cathode)

First, a C-1 film as an organic layer was vacuum-deposited on a glass substrate to form a thickness of 100 nm. On the organic layer, the compound P1-46 of the present invention was vacuum-deposited to a thickness of 10 nm to form a metal patterning layer. Then, after vacuum deposition of Yb as an electron injection layer on the metal patterning layer, Ag was deposited as a cathode. Then, as a capping layer, D-1 was deposited to a thickness of 70 nm to manufacture an organic electronic element.

[Comparative Example 5] Sample Using Only Ag Electrode (Cathode)

An organic electronic element was manufactured in the same manner as in Example 13, except that the metal patterning layer was not used.

The light transmittance samples of Examples and Comparative Examples prepared as described above were measured for light transmittance in the visible ray region of 550 nm with Perkinelmer's Lambda 365 UV/VIS Spectrometer measuring equipment, and the measurement results are shown in Table 6.

TABLE 6

| | Compound | Electron injection layer | Cathode | light transmittance | T (%) |
|---|---|---|---|---|---|
| Comparative example 3 | — | Yb | Mg:Ag | 73.73 | 100% |
| Example 11 | P1-46 | Yb | Mg:Ag | 95.63 | 130% |
| Comparative example 4 | — | — | Mg:Ag | 66.17 | 100% |
| Example 12 | P1-46 | — | Mg:Ag | 96.68 | 146% |
| Comparative example 5 | — | Yb | Ag | 72.01 | 100% |
| Example 13 | P1-46 | Yb | Ag | 97.23 | 135% |

The results of Table 6 were prepared based on the light transmittance measurement result graph of FIG. 6. Table 6 compares the light transmittance of Comparative Example 3, Comparative Example 4, and Comparative Example 5 without using a metal patterning layer and Examples 11, 12, and 13 using the inventive compound P1-46 having an intramolecular fluorine content of 30% or more, to find out whether electrode patterning is possible according to the presence or absence of the electron injection layer metal and the electrode patterning change according to the type of metal of the cathode.

Comparative Examples 3 and Example 11 were evaluated as a reference for the case where the electron injection layer metal Yb and the cathode electrode metal Mg were not used. When the compound P1-46 of the present invention having an intramolecular fluorine content of 30% or more was used for the metal patterning layer, it was confirmed that the light transmittance was 95.63%.

As a result of performing Comparative Examples 4 and Example 12 to confirm the patterning performance of the metal of the cathode except for Yb, which is the metal used as the electron injection layer, in the absence of Yb, the electron injection layer metal, the light transmittance of Example 12 using the compound of the present invention was 96.68% (T %: 146%), and it was confirmed that the light transmittance (16% increase in T %) was higher than in Example 11, which is the case with the electron injection layer.

Also, in order to investigate the patterning performance according to the type of metal of the anode, Comparative Examples 5 and Example 13 using only Ag for the anode were compared with Comparative Examples 3 and 11, which are comparative groups. When only Ag was used for the cathode, the light transmittance of the device using the compound of the present invention for the metal patterning layer was 135% (T %), confirming that the light transmittance was increased by 5% compared to Example 11.

Example 14

First, a C-1 film as an organic layer was vacuum-deposited on a glass substrate to form a thickness of 100 nm. On the organic layer, the compound P1-22 of the present invention was vacuum-deposited to a thickness of 3 nm to form a metal patterning layer. Then, after vacuum deposition of Yb as an electron injection layer on the metal patterning layer, a cathode was deposited with Mg and Ag in a weight of 1:9. After that, as a capping layer, D-1 was deposited to a thickness of 70 nm to prepare a sample.

[Example 15] to [Example 25]

A sample was prepared in the same manner as in Example 14, except that the compound of the present invention described in Table 7 and the thickness described in Table 7 were used instead of the compound P1-22 of the present invention as a material for the metal patterning layer.

Comparative Example 6

A sample was prepared in the same manner as in Example 14, except that the metal patterning layer was not used.

The light transmittance samples of Examples and Comparative Examples prepared as described above were measured for light transmittance in the visible ray region of 550 nm with Perkinelmer's Lambda 365 UV/VIS Spectrometer measuring equipment, and the measurement results are shown in Table 7.

TABLE 7

| | compound | Thickness of the metal patterning layer | light transmittance | T (%) |
|---|---|---|---|---|
| Comparative example 6 | — | | 69.13~72.38 | 100% |
| Example 14 | P1-22 | 3 nm | 95.01 | 139% |
| Example 15 | | 5 nm | 96.14 | 140% |
| Example 16 | | 10 nm | 95.50 | 139% |
| example 17 | P1-34 | 3 nm | 96.37 | 139% |
| example 18 | | 5 nm | 95.93 | 139% |
| example 19 | | 10 nm | 95.11 | 138% |
| example 20 | P1-46 | 3 nm | 96.31 | 139% |
| example 21 | | 5 nm | 96.00 | 139% |
| example 22 | | 10 nm | 95.03 | 137% |
| example 23 | P1-65 | 3 nm | 96.60 | 133% |
| example 24 | | 5 nm | 96.47 | 133% |
| example 25 | | 10 nm | 95.45 | 132% |

The results of Table 7 were prepared based on the light transmittance measurement result graph of FIG. 7. Table 7 was performed to confirm the change in light transmittance according to the thickness of the metal patterning layer using the compound of the present invention. In the case of Comparative Example 6, the light transmittance results for each lot of Comparative Examples used in the evaluation of each material described in Examples 14 to 25 were described in the range (69.13% to 72.38%), and the light transmittance measured for each lot was calculated as 100% (T %), and the light transmittance of the example thereof was described as T %.

In Examples 14 to 25, when the compound of the present invention was used as a metal patterning layer having a thickness of 3 nm, 5 nm, and 10 nm, respectively, it was confirmed that there was no significant difference in the light transmittance of 95.01% to 96.47% (T % 132% to 140%). This will prevent problems such as performance degradation due to variations in deposition thickness that may occur in the deposition process when the compound of the present invention is used as a material for metal patterning.

Example 26

In order to measure the contact angle, a sample was prepared by vacuum-depositing the compound P1-34 of the present invention to a thickness of 50 nm on a glass substrate.

[Example 27] to [Example 34]

A sample was prepared in the same manner as in Example 26, except that the compound of the present invention described in Table 8 was used instead of the compound P1-34 of the present invention on a glass substrate.

Comparative Example 7

It proceeded in the same manner as in Example 26, except that C-1 was used instead of compound P1-34 of the present invention.

The contact angles of the samples of Comparative Example 7 and Examples 26 to 34 prepared in this way were measured with a DSA25 contact angle measuring device manufactured by KRUSS, and the measurement results are shown in Table 8.

TABLE 8

| | compound | contact angle (°) |
|---|---|---|
| comparative example 7 | C-1 | 83.2 |
| example 26 | P1-34 | 103.6 |
| example 27 | P1-46 | 116.4 |
| example 28 | P1-63 | 109.6 |
| example 29 | P1-65 | 116.1 |
| example 30 | P1-71 | 117.0 |
| example 31 | P1-73 | 118.2 |
| example 32 | P1-80 | 117.3 |
| example 33 | P1-81 | 111.7 |
| example 34 | P7-1 | 111.1 |

Referring to Table 8, it can be seen that the contact angle of the C-1 material, which does not contain fluorine and has low light transmittance, is 83.2°, on the contrary, it was confirmed that all of the contact angles of the compounds of the present invention having a light transmittance of 90% or more were 100° or more (103.6 to 118.2). The results of Table 8 are judged to show the reason why the compound of the present invention having high light transmittance (90% or more) is suitable for metal patterning.

In general, adhesion is explained by the solid surface energy through wetting angle or the contact angle and wettability. Mostly, the larger the contact angle is, the smaller the wettability becomes, due to this, when the adhesiveness becomes small, it has a low solid surface energy. This is because, if the surface tension of the liquid is large, the pulling force between them becomes large, making it difficult to spread on the surface of the solid.

The above can also be confirmed through the following Young's Equation.

The following relationship is established between the interfacial tension and the contact angle.

$$gLV\cos\theta = gSV - gSL \qquad \text{(Equation 1)}$$

gSL: interfacial tension between solid and liquid,
gSV: the interfacial tension between the solid surface and the liquid vapor,
gLV: interfacial tension between liquid and liquid vapor
Equation (1) is expressed as follows in the equation for the work of adhesion, Wa presented by Dupre.

$$Wa = gS + gLV - gSL = gS + gLV + (gLV \cos \theta - gSV) = (gS - gSV) + gLV(1 + \cos \theta) \quad \text{(Equation 2)}$$

gS in Equation (2) is the surface tension of the solid itself, and since gS and gSV are generally considered to be the same at a small low surface energy, Equation 2 is summarized as follows.

$$Wa = gLV(1 + \cos \theta) \quad \text{(Equation 3)}$$

According to Equation 3, if the contact angle is 0°, it is completely wet because cos 0°=1, on the other hand, if the contact angle is 180°, cos 180°=−1, so it is not wet at all.

Therefore, as the contact angle goes from 90° to 0°, it gets closer to cos θ=1, which increases the wettability and adhesiveness, whereas as it goes from 90° to 180°, it approaches cos θ=−1, which decreases the wettability and adhesiveness.

When the compound of the present invention is used as a material for metal patterning, it is determined that the adhesion of the metal (electrode) is reduced due to the low surface energy of the compound of the present invention, and the light transmittance is high.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

INDUSTRIAL APPLICABILITY

According to the present invention, it is possible to manufacture an organic device having excellent device characteristics of high luminance, high light emission and long lifespan, and thus has industrial applicability.

What is claimed is:

1. A fluorinated compound represented by Formula (2-12):

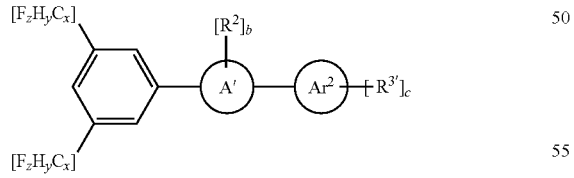

Formula (2-12)

wherein:
1) 1) $Ar^2$ is a $C_6$-$C_{30}$ aryl group; or a $C_2$-$C_{30}$ heterocyclic group including at least one heteroatom of O, N, S, Si or P;
2) A' is a $C_6$-$C_{30}$ arylene group;
3) $R^4$ is selected from the group consisting of a $C_6$-$C_{30}$ aryl group; a fluorenyl group; a $C_2$-$C_{30}$ heterocyclic group including at least one heteroatom of O, N, S, Si or P; a $C_1$-$C_{20}$ alkyl group; and a $C_1$-$C_{20}$ alkoxyl group; or $R^4$ may be bonded to each other to form a ring,
4) $R^{3'}$ is selected from the group consisting of hydrogen; deuterium; a $C_6$-$C_{30}$ aryl group; fluorenyl group; a $C_2$-$C_{30}$ heterocyclic group including at least one heteroatom of O, N, S, Si or P; a $C_1$-$C_{20}$ alkyl group; and a $C_1$-$C_{20}$ alkoxyl group; and $R^{3'}$ may be bonded to each other to form a ring,
5) b and c are each independently an integer of 0 to 10,
6) x is an integer from 2 to 15, and y+z is an integer of 2x+1,
7) wherein the aryl group, the arylene group, the heterocyclic group, the fluorenyl group, the alkyl group, the alkoxyl group and a ring formed by bonding adjacent groups to each other may be further substituted with one or more substituents selected from the group consisting of each deuterium; halogen; a $C_1$-$C_{20}$ alkyl group; $C_2$-$C_{20}$ alkenyl group; $C_6$-$C_{20}$ aryl group; $C_6$-$C_{20}$ aryl group substituted with deuterium; $C_6$-$C_{20}$ aryl group substituted with halogen; and $C_2$-$C_{20}$ heterocyclic group, wherein the substituents may be bonded to each other to form a ring.

2. The fluorinated compound of claim 1, wherein the compound represented by Formula (2-12) is any one of the following compounds:

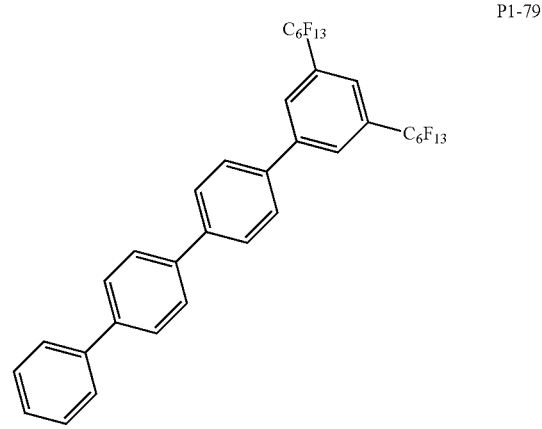

P1-79

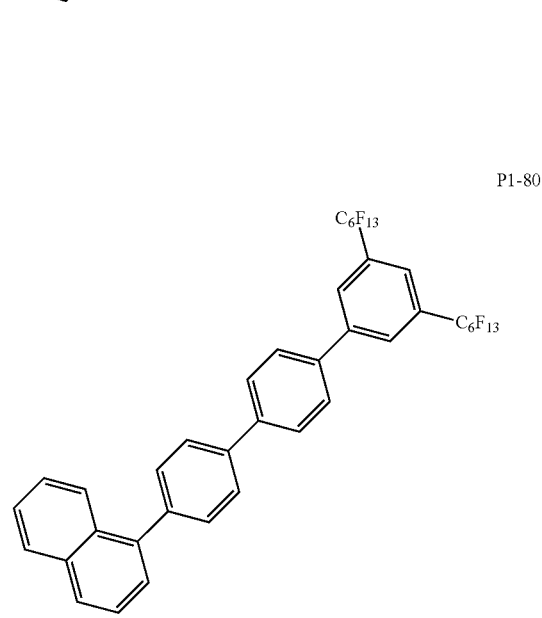

P1-80

P1-81
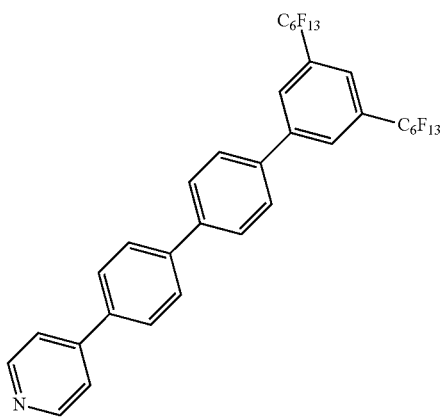
P1-82
P1-83
P1-85
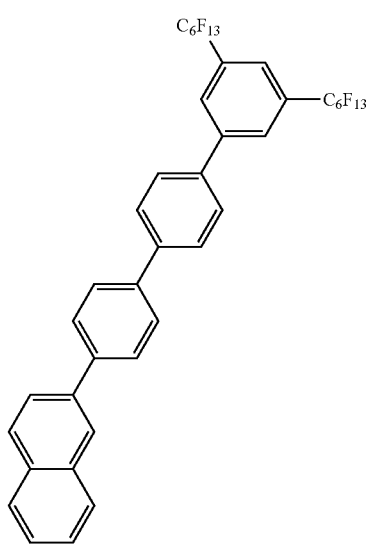
P1-86
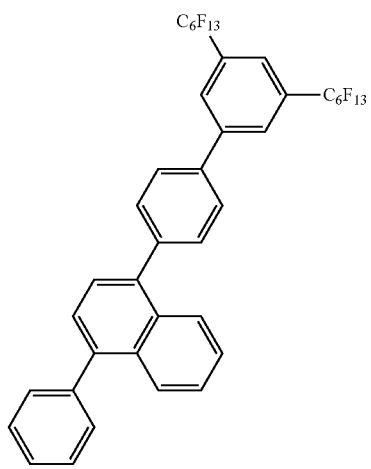
P1-87
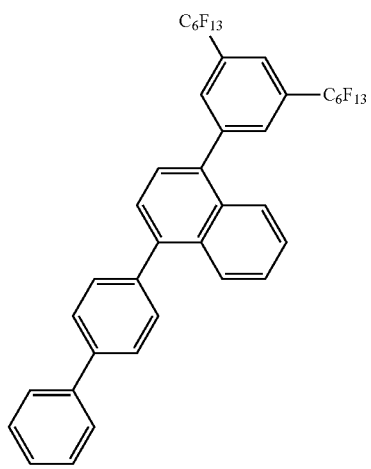

P1-88
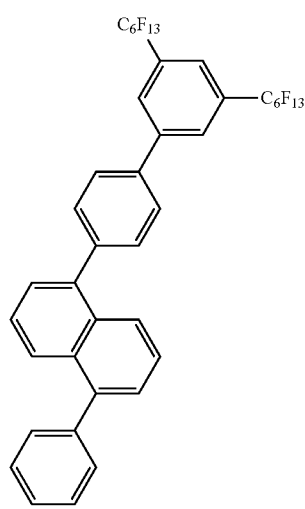
P1-89
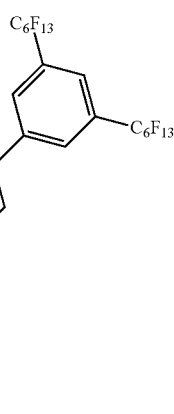
P1-90
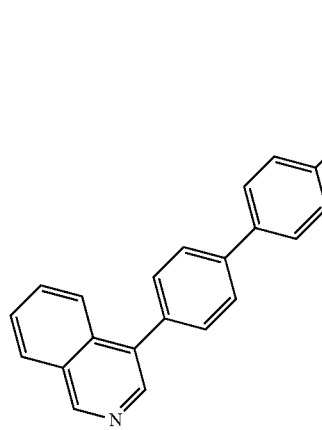
P1-91
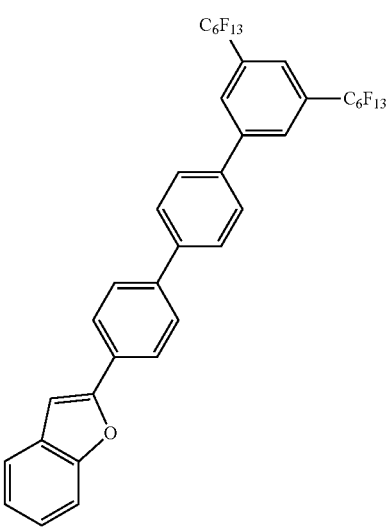
P1-92
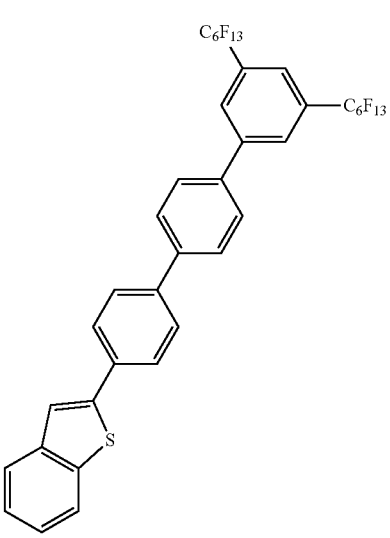
P1-93
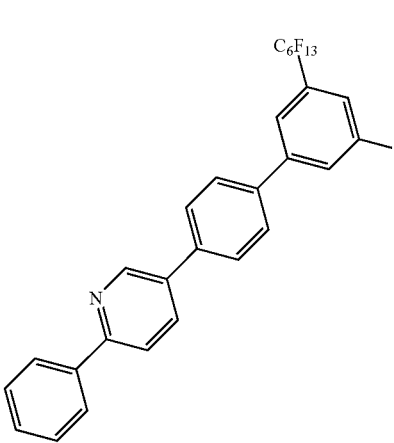

P1-94 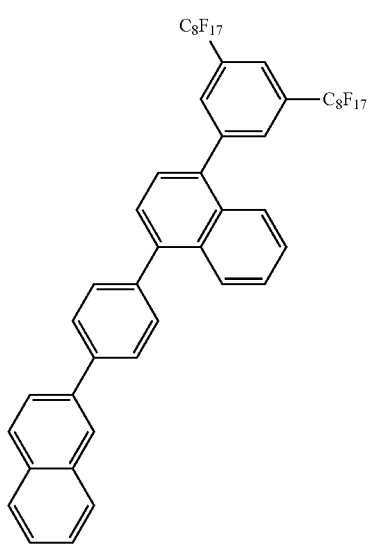
P1-95 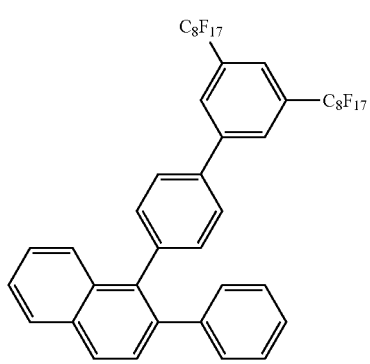
P1-96 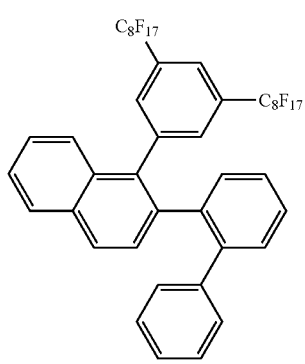
P1-97 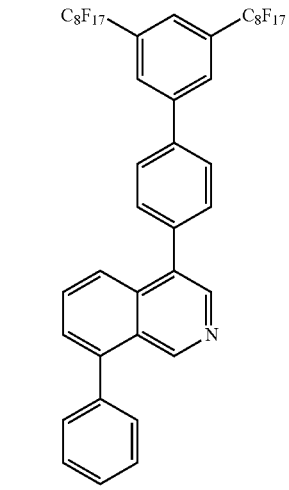
P1-98 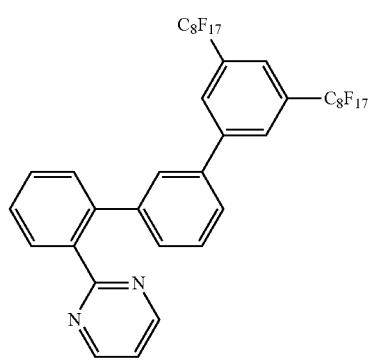
P1-99 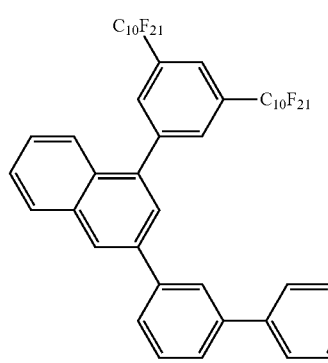
P1-100 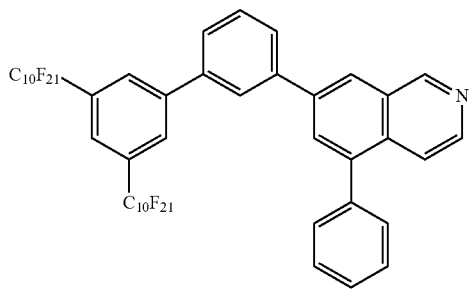

-continued

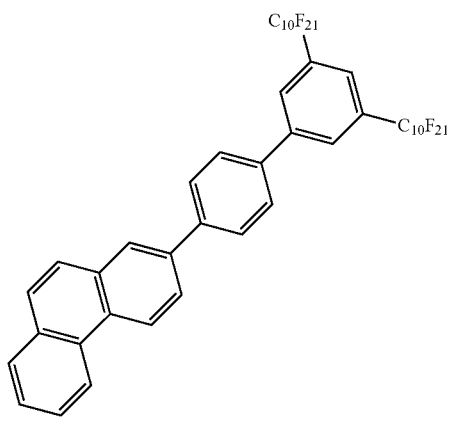

P1-101

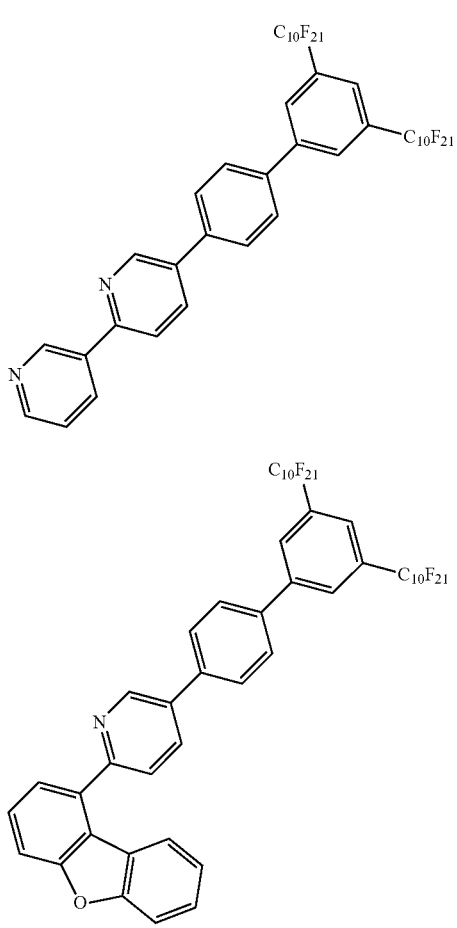

P1-102

P1-103

P1-104

-continued

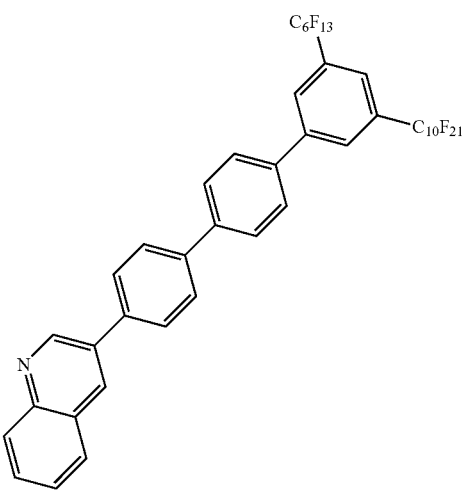

P1-105

P1-106

3. The fluorinated compound of claim 1, wherein the fluorine content of the compound represented by Formula (2-12) is 30% to 80%.

4. The fluorinated compound of claim 1, wherein the contact angle of the compound represented by Formula (2-12) is 90° to 180°.

5. The fluorinated compound of claim 1, wherein the contact angle of the compound represented by Formula (2-12) is 90° to 150°.

6. An organic electronic element comprising an anode; a non-light emitting region; and a light emitting region; wherein the non-light emitting region comprises at least one organic material layer on the anode, and a metal patterning layer on the organic material layer, and wherein, on the organic material layer, the light emitting region comprises a metal; a metal electrode; or metal and metal electrodes; and wherein the metal patterning layer is represented by Formula (2-12) according to claim 1 and has an intramolecular fluorine content of 30% or more.

7. The organic electronic element of claim 6, wherein the metal in the metal patterning using the compound represented by Formula (2-12) comprises Ag.

8. The organic electronic element of claim 6, wherein the metal in the metal patterning using the compound represented by Formula (2-12) comprises Ag or Mg.

9. The organic electronic element of claim 6, wherein a mixture of two or more different compounds represented by Formula (2-12) is used.

10. An electronic device comprising: a display device comprising the organic electronic element of claim 6; and a control unit for driving the display device.

11. The electronic device according to claim 10, wherein the organic electronic element is selected from the group consisting of an organic electroluminescent device, an organic transistor, a monochromatic lighting device, and a quantum dot display device.

12. A composition for metal patterning comprising any one of the fluorinated compounds according to Formula (2-12) of claim 1, or two or more of the compounds having different structures from each other.

* * * * *